(12) United States Patent
Qiu et al.

(10) Patent No.: US 12,054,493 B2
(45) Date of Patent: *Aug. 6, 2024

(54) HEPATITIS B ANTIVIRAL AGENTS

(71) Applicant: ENANTA PHARMACEUTICALS, INC., Watertown, MA (US)

(72) Inventors: Yao-Ling Qiu, Andover, MA (US); Xuri Gao, Newtonville, MA (US); Wei Li, Lexington, MA (US); Hui Cao, Belmont, MA (US); Meizhong Jin, Wellesley, MA (US); Jorden Kass, Arlington, MA (US); Xiaowen Peng, Sudbury, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 628 days.

This patent is subject to a terminal disclaimer.

(21) Appl. No.: 17/143,326

(22) Filed: Jan. 7, 2021

(65) Prior Publication Data
US 2021/0230176 A1 Jul. 29, 2021

Related U.S. Application Data

(60) Continuation of application No. 16/715,602, filed on Dec. 16, 2019, now Pat. No. 10,934,306, which is a
(Continued)

(51) Int. Cl.
*C07D 493/08* (2006.01)
*A61K 31/167* (2006.01)
(Continued)

(52) U.S. Cl.
CPC .......... *C07D 493/08* (2013.01); *A61K 31/167* (2013.01); *A61K 31/18* (2013.01); *A61K 31/196* (2013.01); *A61K 31/215* (2013.01); *A61K 31/223* (2013.01); *A61K 31/277* (2013.01); *A61K 31/325* (2013.01); *A61K 31/335* (2013.01); *A61K 31/336* (2013.01); *A61K 31/341* (2013.01); *A61K 31/351* (2013.01); *A61K 31/357* (2013.01); *A61K 31/365* (2013.01); *A61K 31/39* (2013.01); *A61K 31/401* (2013.01); *A61K 31/41* (2013.01); *A61K 31/415* (2013.01); *A61K 31/416* (2013.01); *A61K 31/4164* (2013.01); *A61K 31/421* (2013.01); *A61K 31/426* (2013.01); *A61K 31/439* (2013.01); *A61K 31/44* (2013.01); *A61K 31/4402* (2013.01); *A61K 31/4409* (2013.01); *A61K 31/4425* (2013.01); *A61K 31/445* (2013.01); *A61K 31/4545* (2013.01); *A61K 31/5377* (2013.01); *A61K 31/655* (2013.01); *C07B 59/001* (2013.01); *C07C 235/56* (2013.01); *C07C 311/53* (2013.01); *C07C 317/32* (2013.01); *C07C 317/44* (2013.01); *C07C 323/42* (2013.01); *C07C 323/62* (2013.01); *C07D 207/16* (2013.01); *C07D 211/54* (2013.01); *C07D 213/52* (2013.01); *C07D 213/81* (2013.01); *C07D 213/89* (2013.01); *C07D 231/12* (2013.01); *C07D 233/64* (2013.01); *C07D 257/04* (2013.01); *C07D 261/02* (2013.01); *C07D 261/08* (2013.01); *C07D 261/20* (2013.01); *C07D 263/52* (2013.01); *C07D 277/26* (2013.01); *C07D 295/088* (2013.01); *C07D 303/26* (2013.01); *C07D 303/34* (2013.01);
(Continued)

(58) Field of Classification Search
None
See application file for complete search history.

(56) References Cited

U.S. PATENT DOCUMENTS 3,385,756 A 5/1968 Early et al.
3,975,532 A 8/1976 Miller et al.
(Continued)

FOREIGN PATENT DOCUMENTS

CL 1999000690 4/1999
CN 102093320 A 6/2011
(Continued)

OTHER PUBLICATIONS

PubChemCID 69233333. Retrieved from the internet on Jan. 8, 2024, https://pubchem.ncbi.nlm.nih.gov/compound/69233333. (Year: 2024).*
(Continued)

*Primary Examiner* — Amy C Bonaparte
*Assistant Examiner* — Lauren Wells
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

X-A-Y-L-R  (I)

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

10 Claims, No Drawings

Related U.S. Application Data continuation of application No. 16/194,608, filed on Nov. 19, 2018, now Pat. No. 10,538,532, which is a division of application No. 15/450,125, filed on Mar. 6, 2017, now Pat. No. 10,179,792.

(60) Provisional application No. 62/337,675, filed on May 17, 2016, provisional application No. 62/304,671, filed on Mar. 7, 2016.

(51) Int. Cl.

| | | |
|---|---|---|
| A61K 31/18 | (2006.01) | |
| A61K 31/196 | (2006.01) | |
| A61K 31/215 | (2006.01) | |
| A61K 31/223 | (2006.01) | |
| A61K 31/277 | (2006.01) | |
| A61K 31/325 | (2006.01) | |
| A61K 31/335 | (2006.01) | |
| A61K 31/336 | (2006.01) | |
| A61K 31/341 | (2006.01) | |
| A61K 31/351 | (2006.01) | |
| A61K 31/357 | (2006.01) | |
| A61K 31/365 | (2006.01) | |
| A61K 31/39 | (2006.01) | |
| A61K 31/401 | (2006.01) | |
| A61K 31/41 | (2006.01) | |
| A61K 31/415 | (2006.01) | |
| A61K 31/416 | (2006.01) | |
| A61K 31/4164 | (2006.01) | |
| A61K 31/421 | (2006.01) | |
| A61K 31/426 | (2006.01) | |
| A61K 31/439 | (2006.01) | |
| A61K 31/44 | (2006.01) | |
| A61K 31/4402 | (2006.01) | |
| A61K 31/4409 | (2006.01) | |
| A61K 31/4425 | (2006.01) | |
| A61K 31/445 | (2006.01) | |
| A61K 31/4545 | (2006.01) | |
| A61K 31/5377 | (2006.01) | |
| A61K 31/655 | (2006.01) | |
| C07B 59/00 | (2006.01) | |
| C07C 235/56 | (2006.01) | |
| C07C 311/53 | (2006.01) | |
| C07C 317/32 | (2006.01) | |
| C07C 317/44 | (2006.01) | |
| C07C 323/42 | (2006.01) | |
| C07C 323/62 | (2006.01) | |
| C07D 207/16 | (2006.01) | |
| C07D 211/54 | (2006.01) | |
| C07D 213/52 | (2006.01) | |
| C07D 213/81 | (2006.01) | |
| C07D 213/89 | (2006.01) | |
| C07D 231/12 | (2006.01) | |
| C07D 233/64 | (2006.01) | |
| C07D 257/04 | (2006.01) | |
| C07D 261/02 | (2006.01) | |
| C07D 261/08 | (2006.01) | |
| C07D 261/20 | (2006.01) | |
| C07D 263/52 | (2006.01) | |
| C07D 277/26 | (2006.01) | |
| C07D 295/088 | (2006.01) | |
| C07D 303/26 | (2006.01) | |
| C07D 303/34 | (2006.01) | |
| C07D 307/32 | (2006.01) | |
| C07D 307/33 | (2006.01) | |
| C07D 309/08 | (2006.01) | |
| C07D 313/04 | (2006.01) | |
| C07D 317/72 | (2006.01) | |
| C07D 327/10 | (2006.01) | |
| C07D 401/04 | (2006.01) | |
| C07D 451/04 | (2006.01) | |
| C07D 493/04 | (2006.01) | |

(52) U.S. Cl.
CPC ......... *C07D 307/32* (2013.01); *C07D 307/33* (2013.01); *C07D 309/08* (2013.01); *C07D 313/04* (2013.01); *C07D 317/72* (2013.01); *C07D 327/10* (2013.01); *C07D 401/04* (2013.01); *C07D 451/04* (2013.01); *C07D 493/04* (2013.01); *C07B 2200/05* (2013.01); *C07B 2200/07* (2013.01); *C07C 2601/04* (2017.05); *C07C 2601/08* (2017.05); *C07C 2601/14* (2017.05); *C07C 2601/16* (2017.05); *C07C 2601/18* (2017.05); *C07C 2602/44* (2017.05); *C07C 2602/46* (2017.05); *C07C 2603/74* (2017.05)

(56) References Cited

U.S. PATENT DOCUMENTS

| | | |
|---|---|---|
| 4,285,946 A | 8/1981 | Kampe et al. |
| 4,507,481 A | 3/1985 | Davidson et al. |
| 5,510,387 A | 4/1996 | Leonidov et al. |
| 5,656,644 A | 8/1997 | Adams et al. |
| 6,498,165 B1 | 12/2002 | Armstrong et al. |
| 6,503,913 B1 | 1/2003 | Goldmann et al. |
| 6,525,069 B1 | 2/2003 | Ko et al. |
| 6,667,342 B1 | 12/2003 | Clarke et al. |
| 7,232,825 B2 | 6/2007 | Chen et al. |
| 7,312,214 B2 | 12/2007 | Qiao et al. |
| 7,411,003 B1 | 8/2008 | Liu et al. |
| 7,615,569 B2 | 11/2009 | Fulp et al. |
| 7,741,494 B2 | 6/2010 | Bressi et al. |
| 8,101,643 B2 | 1/2012 | Qiu et al. |
| 8,202,876 B2 | 6/2012 | Albaugh et al. |
| 8,420,823 B2 | 4/2013 | Sato et al. |
| 9,447,086 B2 | 9/2016 | Liu et al. |
| 9,498,479 B2 | 11/2016 | Zhang et al. |
| 9,573,941 B2 | 2/2017 | Liu et al. |
| 9,617,252 B2 | 4/2017 | Liu |
| 9,845,325 B2 | 12/2017 | Fu et al. |
| 9,938,301 B2 | 4/2018 | He et al. |
| 10,179,131 B2 | 1/2019 | Qiu et al. |
| 10,179,792 B2 | 1/2019 | Qiu et al. |
| 10,189,846 B2 | 1/2019 | Qiu et al. |
| 10,253,030 B2 | 4/2019 | He et al. |
| 10,428,070 B2 | 10/2019 | Qiu et al. |
| 10,538,532 B2 | 1/2020 | Qiu et al. |
| 10,640,511 B2 | 5/2020 | Qiu et al. |
| 10,723,733 B2 | 7/2020 | Qiu et al. |
| 10,729,688 B2 | 8/2020 | Qiu et al. |
| 10,934,306 B2 * | 3/2021 | Qiu ...................... A61K 31/167 |
| 10,952,978 B2 | 3/2021 | Qiu et al. |
| 11,198,693 B2 | 12/2021 | Panarese et al. |
| 11,596,611 B2 * | 3/2023 | Qiu ...................... C07D 491/107 |
| 2002/0068838 A1 | 6/2002 | Demassey et al. |
| 2003/0232842 A1 | 12/2003 | Goldmann et al. |
| 2004/0082619 A1 | 4/2004 | Tada et al. |
| 2004/0209930 A1 | 10/2004 | Carboni et al. |
| 2005/0113450 A1 | 5/2005 | Thorarensen et al. |
| 2005/0203119 A1 | 9/2005 | Ono et al. |
| 2006/0100233 A1 | 5/2006 | Villa et al. |
| 2007/0219239 A1 | 9/2007 | Mjalli et al. |
| 2007/0225373 A1 | 9/2007 | Chen et al. |
| 2009/0023740 A1 | 1/2009 | Fulp et al. |
| 2009/0036420 A1 | 2/2009 | Galley et al. |
| 2009/0118268 A1 | 5/2009 | Riedl et al. |
| 2011/0009622 A1 | 1/2011 | Jitsuoka et al. |
| 2011/0165118 A1 | 7/2011 | Chan et al. |

(56) References Cited

U.S. PATENT DOCUMENTS

| | | |
|---|---|---|
| 2011/0281950 A1 | 11/2011 | Baiocchi et al. |
| 2012/0009142 A1 | 1/2012 | Karp et al. |
| 2013/0251673 A1 | 9/2013 | Hartman et al. |
| 2013/0267517 A1 | 10/2013 | Guo et al. |
| 2013/0309196 A1 | 11/2013 | Link et al. |
| 2014/0206666 A1 | 7/2014 | Guo et al. |
| 2014/0343032 A1 | 11/2014 | Guo et al. |
| 2014/0357858 A1 | 12/2014 | Ushioda et al. |
| 2015/0005295 A1 | 1/2015 | Hachéet al. |
| 2015/0038515 A1 | 2/2015 | Cuconati et al. |
| 2015/0119362 A1 | 4/2015 | Gurney et al. |
| 2015/0133428 A1 | 5/2015 | Velaparthi et al. |
| 2015/0152073 A1 | 6/2015 | Hartman et al. |
| 2015/0152096 A1 | 6/2015 | Zhang et al. |
| 2015/0197493 A1 | 7/2015 | Hartman et al. |
| 2015/0210682 A1 | 7/2015 | Han et al. |
| 2015/0252057 A1 | 9/2015 | Zhu et al. |
| 2015/0266890 A1 | 9/2015 | Vandyck et al. |
| 2015/0274653 A1 | 10/2015 | Vandyck et al. |
| 2016/0115149 A1 | 4/2016 | Vandyck et al. |
| 2016/0185777 A1 | 6/2016 | Hartman et al. |
| 2016/0206616 A1 | 7/2016 | Zhang et al. |
| 2016/0237078 A9 | 8/2016 | Guo et al. |
| 2016/0264562 A1 | 9/2016 | Liu et al. |
| 2016/0264563 A1 | 9/2016 | Ren et al. |
| 2016/0289212 A1 | 10/2016 | Gao et al. |
| 2016/0296515 A1 | 10/2016 | Han et al. |
| 2016/0332996 A1 | 11/2016 | Gao et al. |
| 2016/0347746 A1 | 12/2016 | Zhang |
| 2017/0014408 A1 | 1/2017 | Gao et al. |
| 2017/0022150 A1 | 1/2017 | Gao et al. |
| 2017/0197986 A1 | 7/2017 | He et al. |
| 2017/0217974 A1 | 8/2017 | Gao et al. |
| 2017/0240548 A1 | 8/2017 | Fu et al. |
| 2017/0253609 A1 | 9/2017 | Gao et al. |
| 2017/0354641 A1 | 12/2017 | Bastian et al. |
| 2017/0355701 A1 | 12/2017 | Qiu et al. |
| 2017/0355712 A1 | 12/2017 | Campbell et al. |
| 2018/0134723 A1 | 5/2018 | Tets et al. |
| 2018/0312507 A1 | 11/2018 | Fu et al. |
| 2018/0312512 A1 | 11/2018 | He et al. |
| 2019/0060258 A1 | 2/2019 | Qiu et al. |
| 2019/0084994 A1 | 3/2019 | Qiu et al. |
| 2019/0119288 A1 | 4/2019 | Qiu et al. |
| 2019/0144448 A1 | 5/2019 | Kotschy et al. |
| 2019/0144449 A1 | 5/2019 | Kotschy et al. |
| 2019/0177316 A1 | 6/2019 | Qiu et al. |
| 2019/0177320 A1 | 6/2019 | Qiu et al. |
| 2019/0224188 A1 | 7/2019 | Panarese et al. |
| 2019/0298865 A1 | 10/2019 | Cuthbertson et al. |
| 2019/0321360 A1 | 10/2019 | Qiu et al. |
| 2019/0337903 A1 | 11/2019 | Khan |
| 2020/0095258 A1 | 3/2020 | Panarese et al. |
| 2020/0165249 A1 | 5/2020 | Panarese et al. |
| 2021/0079014 A1 | 3/2021 | Panarese et al. |
| 2023/0241012 A1 | 8/2023 | Qiu et al. |

FOREIGN PATENT DOCUMENTS

| | | |
|---|---|---|
| CN | 103889953 A | 6/2014 |
| CN | 106810548 A | 6/2017 |
| CN | 106928215 A | 7/2017 |
| CN | 106928245 A | 7/2017 |
| CN | 108727378 A | 11/2018 |
| DE | 10109856 A1 | 9/2002 |
| EP | 2280001 A1 | 2/2011 |
| JP | 2010526151 A | 7/2010 |
| JP | 2012526820 A | 11/2012 |
| JP | 2013507350 A | 3/2013 |
| JP | 2014523901 A | 9/2014 |
| JP | 2015506927 A | 3/2015 |
| JP | 2015531773 A | 11/2015 |
| JP | 2015533782 A | 11/2015 |
| JP | 2016509591 A | 3/2016 |
| WO | 8702367 A2 | 4/1987 |
| WO | 9504046 A1 | 2/1995 |
| WO | 0168641 A1 | 9/2001 |
| WO | 0168647 A1 | 9/2001 |
| WO | 2004018414 A2 | 3/2004 |
| WO | 2004052852 A1 | 6/2004 |
| WO | 2006033995 A2 | 3/2006 |
| WO | 2006067446 A1 | 6/2006 |
| WO | 2008093614 A1 | 8/2008 |
| WO | 2008120759 A1 | 10/2008 |
| WO | 2009131065 A1 | 10/2009 |
| WO | 2009158473 A1 | 12/2009 |
| WO | 2010012442 A2 | 2/2010 |
| WO | 2010123139 A1 | 10/2010 |
| WO | 2011088561 A1 | 7/2011 |
| WO | 2013006394 A1 | 1/2013 |
| WO | 2013096744 A1 | 6/2013 |
| WO | 2013130703 A2 | 9/2013 |
| WO | 2013144129 A1 | 10/2013 |
| WO | 2013163404 A1 | 10/2013 |
| WO | 2013181584 A2 | 12/2013 |
| WO | 2014033170 A1 | 3/2014 |
| WO | 2014106019 A2 | 7/2014 |
| WO | 2014184350 A1 | 11/2014 |
| WO | 2014184365 A1 | 11/2014 |
| WO | 2015005295 A1 | 1/2015 |
| WO | 2015074546 A1 | 5/2015 |
| WO | 2015108631 A1 | 7/2015 |
| WO | 2015109130 A1 | 7/2015 |
| WO | 2015113990 A1 | 8/2015 |
| WO | 2015173164 A1 | 11/2015 |
| WO | 2016016370 A1 | 2/2016 |
| WO | 2016023877 A1 | 2/2016 |
| WO | 2016025933 A2 | 2/2016 |
| WO | 2016071215 A1 | 5/2016 |
| WO | 2016089990 A1 | 6/2016 |
| WO | 2016107832 A1 | 7/2016 |
| WO | 2016128335 A1 | 8/2016 |
| WO | 2016177655 A1 | 11/2016 |
| WO | 2017013046 A1 | 1/2017 |
| WO | 2017017042 A1 | 2/2017 |
| WO | 2017017043 A1 | 2/2017 |
| WO | 2017061466 A1 | 4/2017 |
| WO | 2017140821 A1 | 8/2017 |
| WO | 2017153919 A1 | 9/2017 |
| WO | 2017205115 A1 | 11/2017 |
| WO | 2017216391 A1 | 12/2017 |
| WO | 2017216685 A1 | 12/2017 |
| WO | 2017216686 A1 | 12/2017 |
| WO | 2018001944 A1 | 1/2018 |
| WO | 2018001952 A1 | 1/2018 |
| WO | 2018019297 A1 | 2/2018 |
| WO | 2018022282 A1 | 2/2018 |
| WO | 2018047109 A1 | 3/2018 |
| WO | 2018073753 A1 | 4/2018 |
| WO | 2018083081 A1 | 5/2018 |
| WO | 2018083106 A1 | 5/2018 |
| WO | 2018083136 A1 | 5/2018 |
| WO | 2018085619 A1 | 5/2018 |
| WO | 2018087345 A1 | 5/2018 |
| WO | 2018130152 A1 | 7/2018 |
| WO | 2018144605 A1 | 8/2018 |
| WO | 2018154466 A1 | 8/2018 |
| WO | 2018161960 A1 | 9/2018 |
| WO | 2018181883 A1 | 10/2018 |
| WO | 2018196805 A1 | 11/2018 |
| WO | 2018198079 A1 | 11/2018 |
| WO | 2018219356 A1 | 12/2018 |
| WO | 2019069293 A1 | 4/2019 |
| WO | 2019097479 A1 | 5/2019 |
| WO | 2019100735 A1 | 5/2019 |
| WO | 2019110352 A1 | 6/2019 |
| WO | 2019123285 A1 | 6/2019 |

(56) References Cited

FOREIGN PATENT DOCUMENTS

| WO | 2019129681 A1 | 7/2019 |
|---|---|---|
| WO | 2019166951 A1 | 9/2019 |

OTHER PUBLICATIONS

PubChemCID 18378621. Retrieved from the Internet on Jan. 8, 2024, https://pubchem.ncbi.nlm.nih.gov/#query=18378621. (Year: 2024).*
Blaszykowski, C. et al., "A Palladium-Catalyzed Alkylation/Direct Arylation Synthesis of Nitrogen-Containing Heterocycles", J. Org. Chem., 73(5), Feb. 9, 2008, 1888-1897.
Patani, G. A., et al., "Bioisosterism: A Rational Approach in Drug Design", Chem. Rev., 96, 1996, 3147-3176
CAS registry No. 1011646-53-9; Entry Date Apr. 3, 2008.
CAS registry No. 1011895-54-7; Entry Date: Apr. 3, 2008.
CAS registry No. 1011949-47-5; Entry Date: Apr. 3, 2008.
CAS registry No. 1011949-58-8; Entry Date: Apr. 3, 2008.
Chemical Abstract Service STN CAplus [online database], Accession No. 2003:1014580. (Year: 2003).
Chemical Abstract Service STN Database Registry No. 1578268-77-5 [online][Entered STN: Apr. 1, 2014].
Chemical Abstracts Registry No. 1026741-09-2, indexed in the Registry file on Jun. 9, 2008.
Chemical Abstracts Registry No. 115280-56-3, indexed in the Registry file on STN CAS Online Jul. 16, 1988.
Chemical Abstracts Registry No. 1269203-67-9, indexed in the Registry file on STN CAS Online Mar. 21, 2011.
Chemical Abstracts Registry No. 1350251-34-1, indexed in the Registry file on STN CAS Online Dec. 7, 2011.
Chemical Abstracts Registry No. 397288-41-1, indexed in the Registry file on Mar. 1, 2002.
Chemical Abstracts Registry No. 792901-47-4, indexed in the Registry file on STN CAS Online Dec. 6, 2004.
Chemical Abstracts Registry No. 92555-24-3, indexed in the Registry file on Dec. 17, 1984.
Chemical Abstracts Registry No. 950067-32-0, indexed in the Registry file on Oct. 10, 2007.
PubChem CID 57036978, National Center for Biotechnology Information. PubChem Compound Database; CID=57036978, https://pubchem.ncbi.nlm.nih.gov/compound/57036978 (accessed May 19, 2017), create date Jun. 13, 2012.
PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.
PubChem CI D 10194182, National Center for Biotechnology Information. PubChem Compound Database; CI 0=10194182, https://pubchem.ncbi.nlm.nih.gov/compound/10194182 (accessed May 19, 2017), create date Oct. 25, 2006.
PubChem, CID 90713021, Create Date: Mar. 16, 2015.
Pubchem—'428' Create Date: Sep. 11, 2005 (Sep. 11, 2005) Date Accessed: Jun. 17, 2016.
PUBCHEM-CID 23201920, Create Date: Dec. 5, 2007, p. 3.
PUBCHEM-CID 63186259, Create Date: Oct. 22, 2012 (Oct. 22, 2012) p. 3.
PUBCHEM-SID 15224030 Deposit Date: Oct. 25, 2006.
Pubchem-57224610 ('610') Create Date: Jun. 14, 2012 (Jun. 14, 2012) Date Accessed: Jun. 17, 2016.
CAS Abstract and Indexed Compounds WO 01/68647 (2001).
PubChem SID 79456770 CID 10880307, 2009.
"(3 'R,4R)-3-[(E)-But-2-enyl]-3'-(2-chloro-4-fluorophenyl)-4'-[1-(difluoromethyl)pyrazol-3-yl]-1'-(1,3-thiazol-2-yl)spiro[1,3-oxazolidine-4,6'-5, 7-dihydro-3H-pyrrolo[1,2-c] pyrimidine]-2-one", PubChem, CID: 138722908, Retrieved from the Internet <URL: https://pubchem.ncbi.nlm.nih.gov/compound/138722908>, 2019, 1-10.
"8-Tert-butyl-4-[(1 E)-1-(difluoromethoxy)buta-1,3-dienyl]-5-ethyl-12-oxo-6, 9-diazatricyclo[7.4.0.02,6]trideca-1(13),2,4, 10-tetraene-11-carboxylic acid", PubChem-CID-134460393, CreateDate: Jun. 23, 2018 (Jun. 23, 2018), p. 2, Fig.
"N-[4-(cyanomethyl)phenyl]-5-(hexyhydro-1-H-azepine-1-yl)sulfonyl]-2-methoxy-benzamid e", Database Registry [Online] Chemical Abstracts Service, Columbus, Ohio, US; May 6, 2011 (May 6, 2011), XP55358935, accession No. RN: 1291044-81-9.
Ballatore, C. et al., "Carboxylic Acid (Bio)Isosteres in Drug Design", ChemMedChem., vol. 8, No. 3, 2013, 385-395.
Chowshury, C. et al., "A rapid and facile method for the general synthesis of 3-aryl substituted 4,5,6,7-tetrahydro[1,2,3]triazolo[1,5-a]pyrazines and their ring fused analogues", Organic & Biomolecular Chemistry, vol. 9, 2011, 5856-5862.
Clark, M. T. et al., "5-(alkylsulfonyl)salicylanilides as Potential Dental Antiplaque Agent", Journal of Medicinal Chemistry, 29(1), 1986, 25-29.
Das, J. et al., "Discovery of 2-Amino-heteroaryl-benzothiazole-6-anilides as Potent p56lck Inhibitors", Biorganic & Medicinal Chemistry Letters, 13, 2003, 2587-2590.
El-Hamouly, W. S. et al., "Synthesis and Antimicrobial Activity of New 3, 4-Dihydropyrimidinones", International Journal of Pharmaceutical Sciences and Research, vol. 2, 2011, 1054-1062.
Flachner, B. et al., "Rapid in silico selection of an MCHR1 antagonists' focused library from multi-million compounds' repositories: biological evaluation", Med. Chem. Res., 23, 2014, 1234-1247.
Janetka, J. W. et al., "Discovery of a novel class of 2-ureido thiophene carboxamide checkpoint kinase inhibitors", Bioorganic & Medicinal Chemistry Letters, 18, 2008, 4242-4248.
Li, X. et al., ACS Medicinal Chemistry Letters, 8, 2017, 969-974.
Noguchi, Chiemi et al., "G to A Hypermutation of Hepatitis B Virus", Hepatology, vol. 41, No. 3, 2005, 2005, 626-633.
Qiu, Z. et al., "Design and Synthesis of Orally Bioavailable 4-Methyl Heteroaryldihydropyrimidine Based Hepatitis B Virus (HBV) Capsid Inhibitors", Journal of Medicinal Chemistry, 2016.
Stachulski, A. V. et al., "Thiazolides as Novel Antiviral Agensts. 1. Inhibition of Hepatitis B Virus Replication", J. Med. Chem., 54, May 9, 2011, 4119-4132.
Teuber, Hans et al., "Simple indolo[2,3-a]quinolizine synthesis", Tetrahedron Letters, vol. 5 (7), pp. 325-329, 1964.
Wu, et al., Toxicology, 236, 2007, 1-6.
Yang, et al., "Enzyme-mediated hydrolytic activation of prodrugs", Acta Pharmaceutica Sinica B., vol. 1(3), Sep. 9, 2011, 143-159.

* cited by examiner

HEPATITIS B ANTIVIRAL AGENTS

RELATED APPLICATIONS

This application is a continuation of U.S. application Ser. No. 16/715,602, filed on Dec. 16, 2019, which is a continuation application of U.S. application Ser. No. 16/194,608, filed on Nov. 19, 2018, now U.S. Pat. No. 10,538,532, issued on Jan. 21, 2020, which is a divisional of U.S. application Ser. No. 15/450,125, filed on Mar. 6, 2017, now U.S. Pat. No. 10,179,792, issued on Jan. 15, 2019, which claims the benefit of U.S. Provisional Application Nos. 62/304,671, filed on Mar. 7, 2016, and 62/337,675, filed on May 17, 2016. The entire teachings of the above applications are incorporated herein by reference.

TECHNICAL FIELD

The present invention relates generally to novel antiviral agents. Specifically, the present invention relates to compounds which can inhibit the protein(s) encoded by hepatitis B virus (HBV) or interfere with the function of the HBV life cycle, compositions comprising such compounds, methods for inhibiting HBV viral replication, methods for treating or preventing HBV infection, and processes for making the compounds.

BACKGROUND OF THE INVENTION

HBV infection remains a major public health problem, affecting approximately 2 billion people worldwide. Among them, 350 million people worldwide and 1.4 million in the US develop a chronic infection, which can lead to chronic persistent hepatitis, liver cirrhosis, and hepatocellular carcinoma (HCC). Every year 500,000 to 1 million people die from the end stage of liver diseases caused by HBV infection.

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent HCC. Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid or core protein (CP) plays essential roles in HBV replication. The predominant biological function of capsid protein is to act as a structural protein to encapsidate pre-genomic RNA and form immature capsid particles, which spontaneously self-assemble from many copies of core dimers in the cytoplasm. Capsid protein also regulates viral DNA synthesis through different phosphorylation status of its C-terminal phosphorylation sites. Also, capsid protein might facilitate the nuclear translocation of viral relaxed circular genome by means of the nuclear localization signals located in the Arginine-rich domain of the C-terminal region of capsid protein. In the nucleus, as a component of viral cccDNA minichromosome, capsid protein could play a structural and regulatory role in the functionality of cccDNA minichromosomes. Capsid protein also interacts with viral large envelope protein in endoplasmic reticulum (ER) and triggers the release of intact viral particles from hepatocytes.

Capsid related anti-HBV inhibitors have been reported. For example, phenylpropen-amide derivatives, including compounds named AT-61 and AT-130 (Feld J. et al. Antiviral Res. 2007, 76, 168), and a class of thiazolidin-4-ones from Valeant (WO2006/033995), have been shown to inhibit pregenomic RNA (pgRNA) packaging. Heteroaryldihydropyrimi-dines or HAPs were discovered in a tissue culture-based screening (Weber et al., Antiviral Res. 2002, 54, 69). These HAP analogs act as synthetic allosteric activators and are able to induce aberrant capsid formation that leads to degradation of the core protein. A subclass of sulphamoylarylamides shows activity against HBV (WO2013/006394, WO2013/096744, and WO2014/184365). It was also shown that the small molecule bis-ANS acts as a molecular 'wedge' and interferes with normal capsid-protein geometry and capsid formation (Zlotnick A. et al. J. Virol. 2002, 4848).

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds.

Compounds of the present invention inhibit the protein(s) encoded by hepatitis B virus (HBV) or interfere with the life cycle of HBV and are also useful as antiviral agents. In addition, the present invention includes the process for the preparation of the said compounds.

In its principal aspect, the present invention provides a compound of Formula (I):

$$X\text{-}A\text{-}Y\text{-}L\text{-}R \qquad (I)$$

or a pharmaceutically acceptable salt thereof, wherein:
  X and Y are each independently selected from optionally substituted aryl or optionally substituted heteroaryl; in one embodiment one of X and Y is optionally substituted phenyl; in another embodiment, both X and Y are optionally substituted phenyl;
  A is selected from the group consisting of —NHC(O)—,

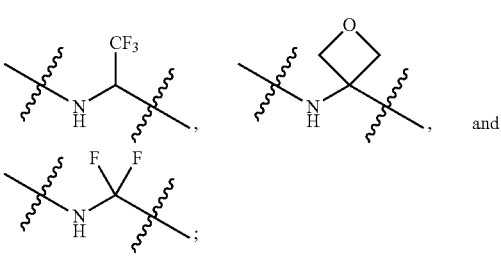

preferably A is —NHC(O)—;

L is S(O)$_2$, S(O), S or O;

R is connected to L via a carbon atom and is independently selected from the group consisting of optionally substituted —C$_1$-C$_{10}$ alkyl, optionally substituted —C$_2$-C$_{10}$ alkenyl, optionally substituted —C$_2$-C$_{10}$ alkynyl, optionally substituted aryl, optionally substituted heteroaryl, optionally substituted —C$_3$-C$_{12}$ cycloalkyl, optionally substituted —C$_3$-C$_{12}$ cycloalkenyl, optionally substituted 3- to 12-membered heterocyclic; in one embodiment, R is optionally substituted —C$_5$-C$_{12}$ cycloalkyl or optionally substituted 5- to 12-membered heterocyclic, each optionally substituted with one or more of the following: fused rings, one or more spiro rings or one or more bridging ring moieties. In another embodiment, R is optionally substituted C$_3$—C$_{12}$ cycloalkyl-C$_1$-C$_6$-alkyl-, optionally substituted C$_3$-C$_{12}$ cycloalkenyl-C$_1$-C$_6$-alkyl-, or optionally substituted 3- to 12-membered heterocyclic-C$_1$-C$_6$-alkyl-.

Each preferred group stated above can be taken in combination with one, any or all other preferred groups.

DETAILED DESCRIPTION OF THE INVENTION

In one embodiment of the present invention is a compound of Formula (I) described above, or a pharmaceutically acceptable salt thereof.

In certain embodiments, the present invention relates to compounds of Formula (I), and their pharmaceutically acceptable salts thereof, wherein X is optionally substituted phenyl. In certain embodiments, X is phenyl substituted with one or more substituents, such as 1, 2, 3, 4 or 5 substituents. Preferably the substituents are independently selected from halogen, CN, optionally substituted —C$_1$-C$_3$ alkoxy, optionally substituted —C$_1$-C$_3$ alkyl, and optionally substituted —C$_3$-C$_6$ cycloalkyl. In certain embodiments, X is phenyl substituted with one or more substituents independently selected from fluoro, chloro, bromo, difluoromethyl, trifluoromethyl, CN and cyclopropyl. In certain embodiments, X is selected from the groups below:

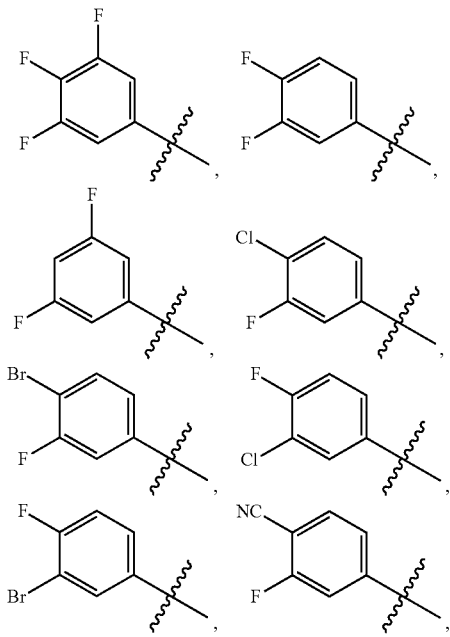

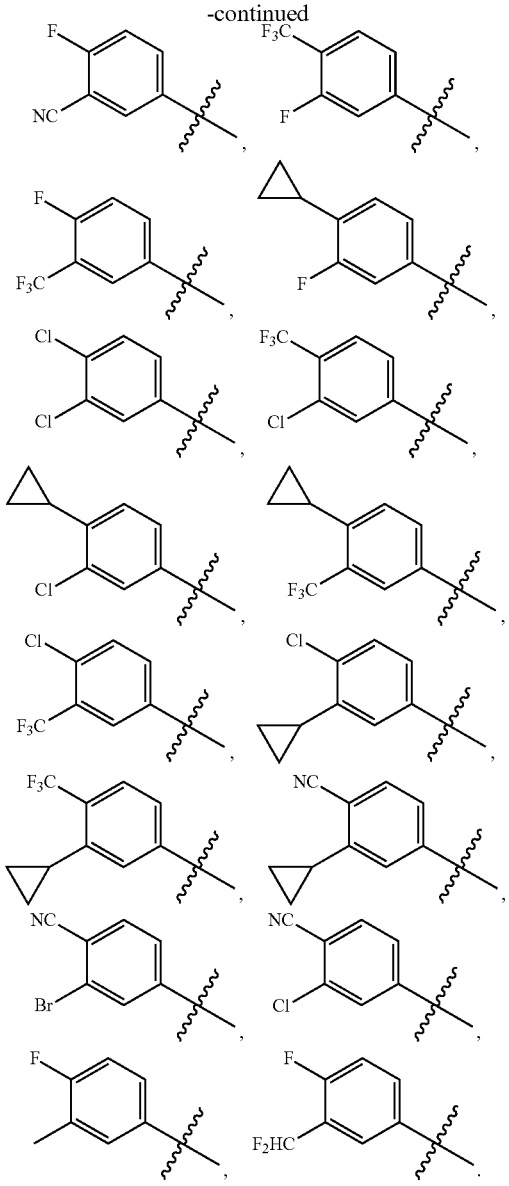

In certain embodiments, the present invention relates to compounds of Formula (I), and pharmaceutically acceptable salts thereof, wherein X is optionally substituted monocyclic heteroaryl. In certain embodiments, the present invention relates to compounds of Formula (I) or, and pharmaceutically acceptable salts thereof, wherein X is optionally substituted thiophenyl, optionally substituted thiazolyl, optionally substituted pyridyl, or optionally substituted pyrimidinyl.

In certain embodiments, the present invention relates to compounds of Formula (I), and pharmaceutically acceptable salts thereof, wherein X is optionally substituted bicyclic heteroaryl. In certain embodiments, the present invention relates to compounds of Formula (I), and pharmaceutically acceptable salts thereof, wherein X is optionally substituted 5/6 bicyclic heteroaryl and is connected to A through either a carbon or nitrogen atom, preferably a carbon atom, of the 6-membered ring of said 5/6 bicyclic heteroaryl. In certain embodiments, the present invention relates to compounds of Formula (I), and pharmaceutically acceptable salts thereof, wherein X is optionally substituted benzimidazolyl, benzothiazolyl, benzoxazolyl, indazolyl, quinolyl, isoquinolyl or quinazolyl.

In certain embodiments, the present invention relates to compounds of Formula (I), and pharmaceutically acceptable salts thereof, wherein Y is optionally substituted phenyl. In certain embodiments, the present invention relates to compounds of Formula (I), and pharmaceutically acceptable salts thereof, wherein Y is phenyl substituted with halogen, CN, optionally substituted —C$_1$-C$_3$ alkoxy, optionally substituted —C$_1$-C$_3$ alkyl, and optionally substituted —C$_3$-C$_6$ cycloalkyl. In certain embodiments, the present invention relates to compounds of Formula (I), and pharmaceutically acceptable salts thereof, wherein Y is optionally substituted 1,3-phenylene, for example

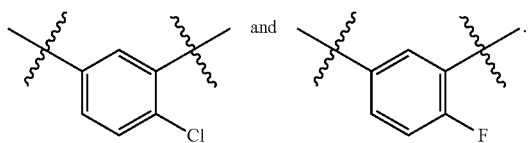 [SMILES: *c1ccc(Cl)c(*)c1 ; *c1ccc(F)c(*)c1]

In certain embodiments, the present invention relates to compounds of Formula (I), and pharmaceutically acceptable salts thereof, wherein Y is optionally substituted 2,4-pyrrolylene, for example

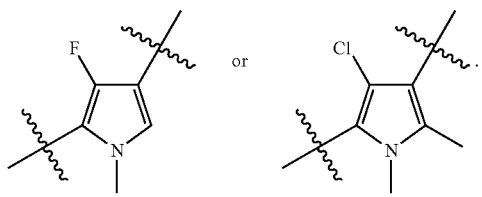

In certain embodiments, the present invention relates to compounds of Formula (I), and pharmaceutically acceptable salts thereof, wherein Y is optionally substituted monocyclic heteroaryl. In certain embodiments, the present invention relates to compounds of Formula (I) and pharmaceutically acceptable salts thereof, wherein Y is optionally substituted thiophenyl, optionally substituted thiazolyl, optionally substituted pyrrolyl, optionally substituted pyrazolyl, optionally substituted imidazolyl, optionally substituted pyridyl, or optionally substituted pyrimidinyl. In certain embodiments, the present invention relates to compounds of Formula (I) and pharmaceutically acceptable salts thereof, wherein Y is pyrrolyl optionally substituted with halogen, CN and optionally substituted —C$_1$-C$_3$ alkyl.

In certain embodiments, the present invention relates to compounds of Formula (I), and pharmaceutically acceptable salts thereof, wherein Y is optionally substituted bicyclic heteroaryl. In certain embodiments, the present invention relates to compounds of Formula (I), and pharmaceutically acceptable salts thereof, wherein Y is optionally substituted 5/6 bicyclic heteroaryl and is connected to A through either a carbon or nitrogen atom of the 5-membered ring of said 5/6 bicyclic heteroaryl. In certain embodiments, the present invention relates to compounds of Formula (I), and pharmaceutically acceptable salts thereof, wherein Y is optionally substituted benzimidazolyl, benzothiazolyl, benzoxazolyl, indazolyl, quinolyl, isoquinolyl or quinazolyl.

In certain embodiments, the present invention relates to compounds of Formula (I), and pharmaceutically acceptable salts thereof, wherein X and Y are each independently optionally substituted monocyclic heteroaryl.

In certain embodiments, the present invention relates to compounds of Formula (I), and pharmaceutically acceptable salts thereof, wherein X is optionally substituted phenyl and Y is optionally substituted monocyclic heteroaryl.

In certain embodiments, the present invention relates to compounds of Formula (I), and pharmaceutically acceptable salts thereof, wherein X is optionally substituted monocyclic heteroaryl and Y is optionally substituted phenyl.

In certain embodiments, the present invention relates to compounds of Formula (I), and pharmaceutically acceptable salts thereof, wherein X and Y are each independently phenyl or monocyclic heteroaryl, each optionally substituted with 1- to 3-substituents selected from the group consisting of halogen, CN, optionally substituted methyl, optionally substituted methoxy, and optionally substituted cyclopropyl.

In certain embodiments, the present invention relates to compounds of Formula (I), and pharmaceutically acceptable salts thereof, wherein X and Y are each independently selected from the group consisting of optionally substituted phenyl, optionally substituted thiophenyl, optionally substituted pyridyl, and optionally substituted pyrimidyl.

In certain embodiments, the present invention relates to compounds of Formula (I), and pharmaceutically acceptable salts thereof, wherein X and Y are each independently optionally substituted phenyl. In certain embodiments, the present invention relates to compounds of Formula (I), and pharmaceutically acceptable salts thereof, wherein X is optionally substituted phenyl and Y is optionally substituted pyrrolyl.

In certain embodiments, the present invention relates to compounds of Formula (I), and pharmaceutically acceptable salts thereof, wherein A is —NHC(O)—.

In certain embodiments, the present invention relates to compounds of Formula (I), and pharmaceutically acceptable salts thereof, wherein A is —NHC(O)—,

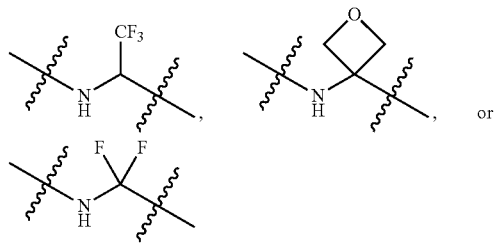

and the said nitrogen of —NHC(O)—,

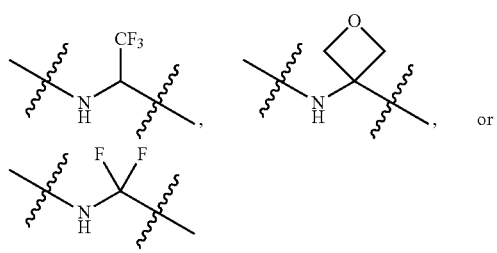

is connected to X.

In certain embodiments, the present invention relates to compounds of Formula (I), and pharmaceutically acceptable salts thereof, wherein A is —NHC(O)—,

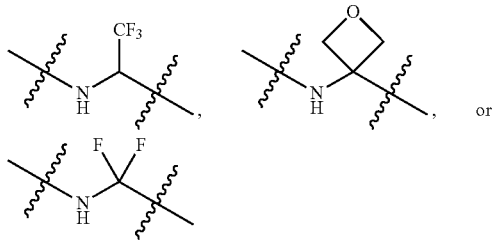

and the said nitrogen of —NHC(O)—,

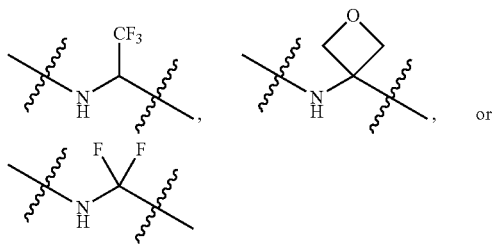

is connected to Y.

In certain embodiments, the present invention relates to compounds of Formula (I), and pharmaceutically acceptable salts thereof, wherein L is $S(O)_2$.

In certain embodiments, the present invention relates to compounds of Formula (I), and pharmaceutically acceptable salts thereof, wherein L is S(O).

In certain embodiments, the present invention relates to compounds of Formula (I), and pharmaceutically acceptable salts thereof, wherein L is S.

In certain embodiments, the present invention relates to compounds of Formula (I), and pharmaceutically acceptable salts thereof, wherein L is O.

In certain embodiments, the present invention relates to compounds of Formula (I), and pharmaceutically acceptable salts thereof, wherein R is optionally substituted —$C_1$-$C_{10}$ alkyl, optionally substituted —$C_2$-$C_{10}$ alkenyl, or optionally substituted —$C_2$-$C_{10}$ alkynyl.

In certain embodiments, the present invention relates to compounds of Formula (I), and pharmaceutically acceptable salts thereof, wherein R is optionally substituted aryl or optionally substituted heteroaryl.

In certain embodiments, the present invention relates to compounds of Formula (I), and pharmaceutically acceptable salts thereof, wherein R is optionally substituted —$C_3$-$C_{12}$ cycloalkyl or optionally substituted 3- to 12-membered heterocyclic.

In certain embodiments, the present invention relates to compounds of Formula (I), and pharmaceutically acceptable salts thereof, wherein R is optionally substituted $C_3$-$C_{12}$ cycloalkyl-$C_1$-$C_6$-alkyl-, optionally substituted $C_3$-$C_{12}$ cycloalkenyl-$C_1$-$C_6$-alkyl-, or optionally substituted 3- to 12-membered heterocyclic-$C_1$-$C_6$-alkyl-.

In certain embodiments, the present invention relates to compounds of Formula (I), and pharmaceutically acceptable salts thereof, wherein R is optionally substituted —$C_5$-$C_{12}$ cycloalkyl or optionally substituted 5- to 12-membered heterocyclic, each optionally substituted with one or more fused rings.

In certain embodiments, the present invention relates to compounds of Formula (I), and pharmaceutically acceptable salts thereof, wherein R is optionally substituted —$C_5$-$C_{12}$ cycloalkyl or optionally substituted 5- to 12-membered heterocyclic, each optionally substituted with one or more spiro rings.

In certain embodiments, the present invention relates to compounds of Formula (I), and pharmaceutically acceptable salts thereof, wherein R is optionally substituted —$C_5$-$C_{12}$ cycloalkyl or optionally substituted 5- to 12-membered, each optionally comprising a bridging moiety.

In certain embodiments, the present invention relates to compounds of Formula (I), and pharmaceutically acceptable salts thereof, wherein R is —$C(R_{10})_3$,

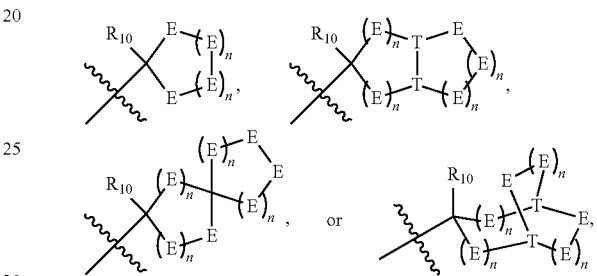

wherein n at each occurrence is independently selected from 0, 1, 2, or 3; T at each occurrence is independently selected from $C(R_{10})$ and N; E at each occurrence is independently selected from —$C(R_{10})_2$—, —$N(R_{10})$—, O, S, S(O), and $S(O)_2$; wherein $R_{10}$ at each occurrence is independently selected from the group consisting of hydrogen, halo, —CN, —$NO_2$, optionally substituted —$C_1$-$C_6$ alkyl, optionally substituted —$C_2$-$C_5$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, optionally substituted heteroaryl, and —$L_1$-$R_1$; wherein $L_1$ is —O—, —S—, —$NR_1$—, —C(O)—, —C(O)O—, —OC(O)—, —$C(O)N(R_1)$—, —$N(R_1)C(O)$—, —$OC(O)N(R_1)$—, —$N(R_1)C(O)O$—, —$N(R_1)C(O)N(R_1)$—, —S(O)—, —$S(O)_2$—, —$S(O)_2N(R_1)$—, —$N(R_1)S(O)_2$—; $R_1$ at each occurrence is independently selected from the group consisting of hydrogen, optionally substituted —$C_1$-$C_6$ alkyl, optionally substituted —$C_2$-$C_8$ alkenyl, optionally substituted —$C_2$-$C_8$ alkynyl, optionally substituted —$C_3$-$C_5$ cycloalkyl, optionally substituted 3- to 8-membered heterocyclic, optionally substituted aryl, and optionally substituted heteroaryl.

In certain embodiments, each $R_{10}$ is independently selected from hydrogen, halo, hydroxy, protected hydroxy, —CN, —$NO_2$, amino, protected amino, optionally substituted —$C_1$-$C_6$ alkyl, optionally substituted —$C_1$-$C_6$ alkoxy, optionally substituted aryl, optionally substituted heteroaryl and —O-(hydroxy prodrug group). In certain embodiments, the hydroxy prodrug group is phosphate or sulfamate. In certain embodiments, the said hydroxy prodrug group is an acyl group derived from an amino acid, preferably an α-amino acid.

In certain embodiments, two adjacent $R_{10}$ groups are taken together with the carbon or nitrogen atoms to which they are attached to form an olefinic or iminic double-bond or a fused ring. In certain embodiments, two geminal $R_{10}$ groups together form an oxo, an optionally substituted olefin, an optionally substituted oxime, or a spiro ring. In certain embodiments, two remote $R_{10}$ groups are taken together with the atoms to which they are attached and any intervening atoms to form a bridging moiety.

In certain embodiments, the present invention relates to compounds of Formula (I), and pharmaceutically acceptable salts thereof, wherein R is optionally substituted $(CH_2)_{0-4}$—$C(R_{10})_3$,

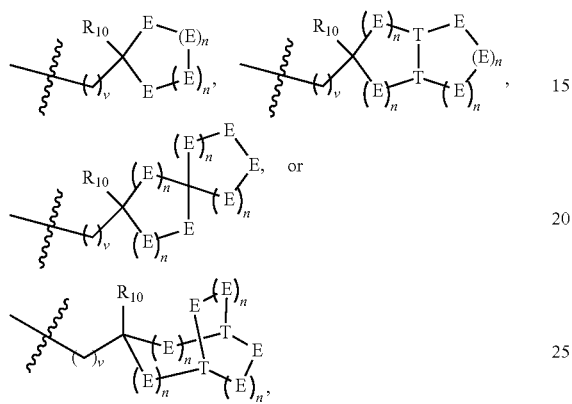

or wherein n, E, T and $R_{10}$ are previously defined; v is selected from 1, 2, 3 or 4. In certain embodiments, each $R_{10}$ is independently selected from hydrogen, halo, hydroxy, protected hydroxy, —CN, —NO$_2$, amino, protected amino, optionally substituted —C$_1$-C$_6$ alkyl, optionally substituted —C$_1$-C$_6$ alkoxy, optionally substituted aryl, optionally substituted heteroaryl and —O-(hydroxy prodrug group). In certain embodiments, the hydroxy prodrug group is phosphate or sulfamate. In certain embodiments, the said hydroxy prodrug group is an acyl group derived from an amino acid, preferably an α-amino acid. In certain embodiments, two adjacent $R_{10}$ groups are taken together with the carbon or nitrogen atoms to which they are attached to form an olefinic double-bond, an iminic double bond or a fused carbocyclic or heterocyclic ring. In certain embodiments, two geminal $R_{10}$ groups together form an oxo, an optionally substituted olefin, an optionally substituted oxime, or a spiro ring. In certain embodiments, two remote $R_{10}$ groups are taken together with the atoms to which they are connected and any intervening atoms to form a bridging moiety.

In certain embodiments, R is selected from the groups below, and is optionally substituted:

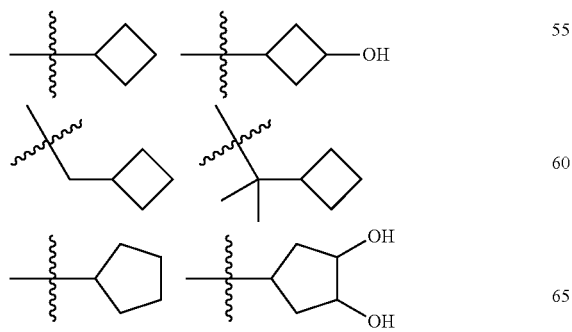

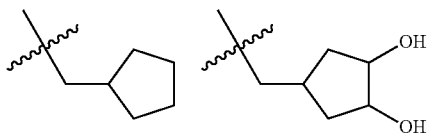

In certain embodiments, R is selected from the groups set forth below, and is optionally substituted:

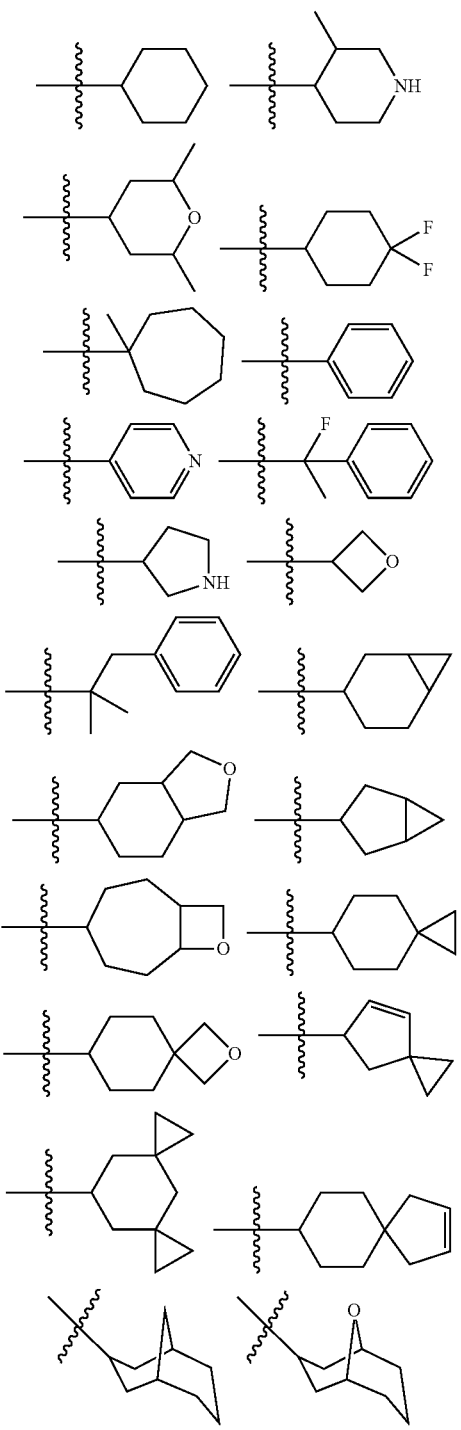

-continued

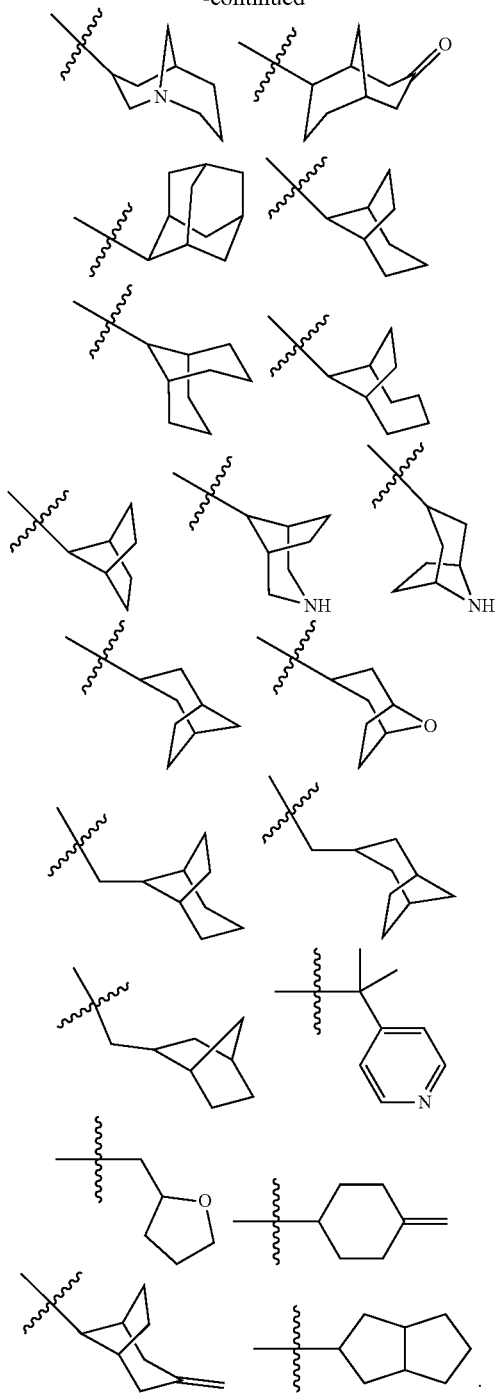

In certain embodiments, R is selected from the groups below, and is optionally substituted.

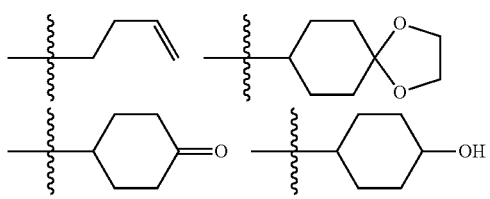

-continued

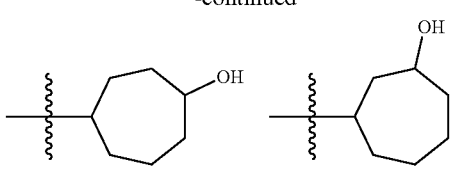

In another embodiment, the compound of Formula (I) is represented by Formula (Ia), (Ib), (Ic), or (Id) or a pharmaceutically acceptable salt thereof:

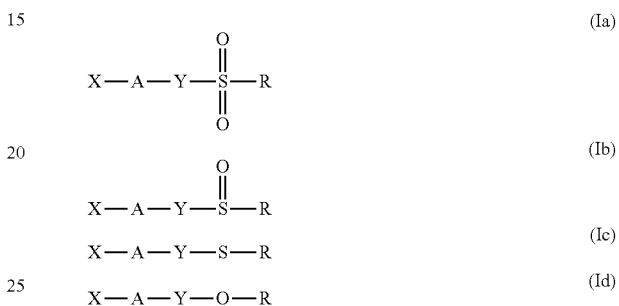

wherein X, A, Y, and R are as previously defined.

In another embodiment, the compound of Formula (I) is represented by Formula (IIa), (IIb), (IIc), (IId), (IIe), (IIf), (IIg), or (IIh), or a pharmaceutically acceptable salt thereof:

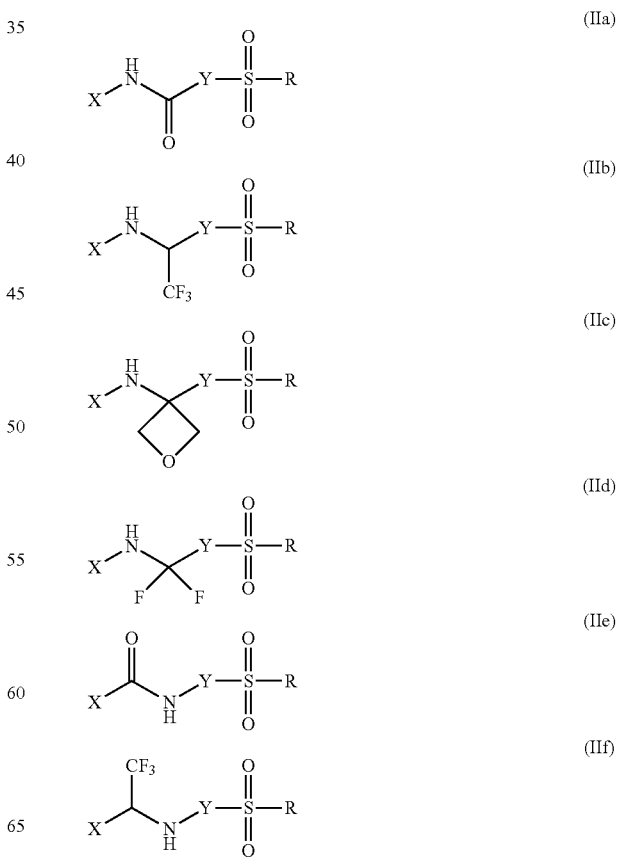

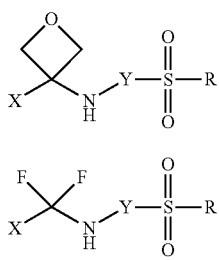
(IIg)

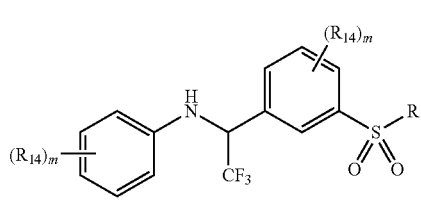
(IIh)

wherein X, Y, and R are as previously defined.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X and Y are each independently optionally substituted phenyl or optionally substituted monocyclic heteroaryl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, X and Y are each independently optionally substituted phenyl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X is optionally substituted phenyl and Y is optionally substituted 5-membered heteroaryl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X is optionally substituted 5-membered heteroaryl and Y is optionally substituted phenyl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X is optionally substituted phenyl and Y is optionally substituted pyrrolyl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X and Y are each independently optionally substituted phenyl, optionally substituted naphthyl, optionally substituted pyridyl, optionally substituted pyrimidinyl, optionally substituted thiophenyl, optionally substituted pyrrolyl, optionally substituted thiazolyl, optionally substituted thiadiazolyl, optionally substituted oxazolyl, optionally substituted isoxazolyl, optionally substituted oxadiazolyl, optionally substituted imidiazolyl, optionally substituted pyrazolyl, optionally substituted triazolyl, or optionally substituted quinolinyl.

In another embodiment, the compound of Formula (I) is represented by Formula (IIIa), (IIIb), (IIIc), or (IIId), or a pharmaceutically acceptable salt thereof:

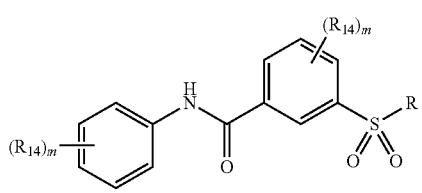
(IIIa)

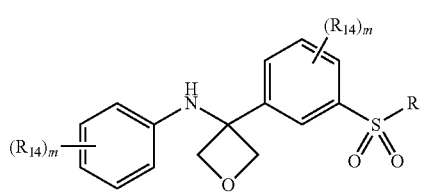
(IIIb)

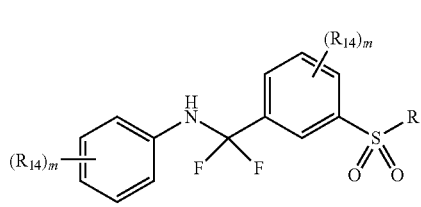
(IIIc)

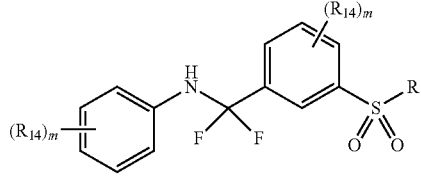
(IIId)

wherein m at each occurrence is independently 0, 1, 2, 3 or 4; $R_{14}$ at each occurrence is independently selected from the group consisting of hydroxy, protected hydroxy, halogen, —CN, —NO$_2$, optionally substituted amino, N$_3$, optionally substituted aryl, optionally substituted heteroaryl, optionally substituted —C$_1$-C$_6$ alkyl, optionally substituted —C$_2$-C$_8$ alkenyl, optionally substituted —C$_2$-C$_5$ alkynyl, optionally substituted —C$_3$-C$_8$ cycloalkyl, optionally substituted 3- to 8-membered heterocyclic, optionally substituted —C$_1$-C$_6$ alkoxy, —C(O)$_2$—C$_1$-C$_6$ alkyl, —C(O)NH—C$_1$-C$_6$ alkyl, and —C(O)—C$_1$-C$_6$ alkyl; and R is as previously defined.

In another embodiment, the compound of Formula (I) is represented by Formula (IIIa-1), (IIIb-1), (IIIc-1), or (IIId-1), or a pharmaceutically acceptable salt thereof:

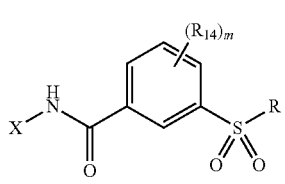
(IIIa-1)

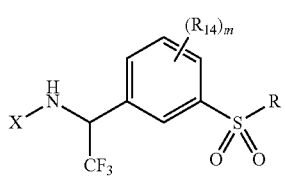
(IIIb-1)

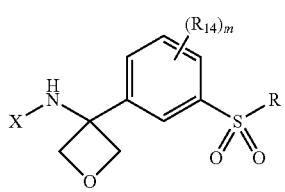
(IIIc-1)

-continued (IIId-1)
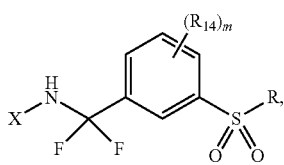

wherein X, R, $R_{14}$, and m are as previously defined.

In another embodiment, the compound of Formula (I) is represented by Formula (IIIa-2), (IIIb-2), (IIIc-2), or (IIId-2), or a pharmaceutically acceptable salt thereof:

(IIIa-2)
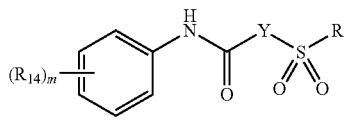

(IIIb-2)
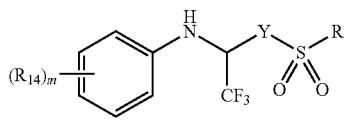

(IIIc-2)
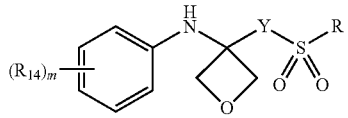

(IIId-2)
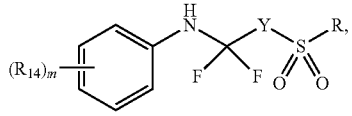

wherein Y, R, $R_{14}$, and m are as previously defined.

In another embodiment, the compound of Formula (I) is represented by Formula (IVa), (IVb), (IVc), (IVd), or (IVe) or a pharmaceutically acceptable salt thereof:

(IVa)
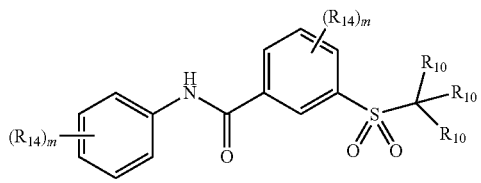

(IVb)
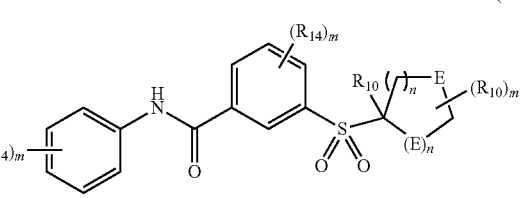

(IVc)
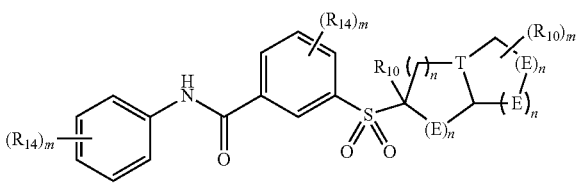

(IVd)
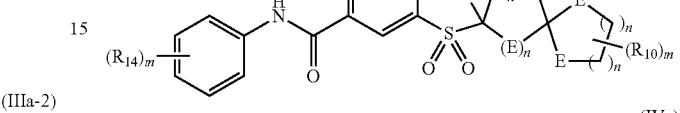

(IVe)
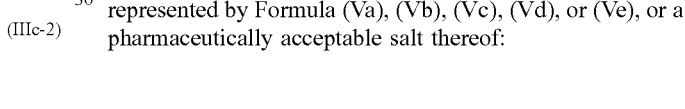

wherein E, T, m, n, $R_{10}$, and $R_{14}$ are as previously defined.

In another embodiment, the compound of Formula (I) is represented by Formula (Va), (Vb), (Vc), (Vd), or (Ve), or a pharmaceutically acceptable salt thereof:

(Va)
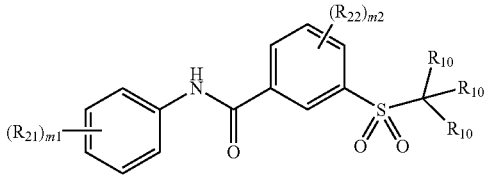

(Vb)
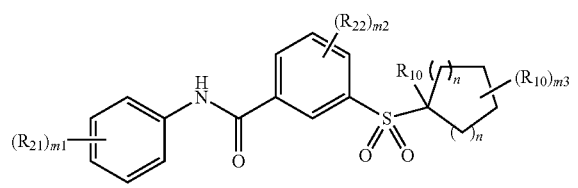

(Vc)
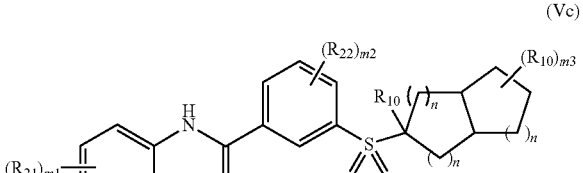

(Vd)
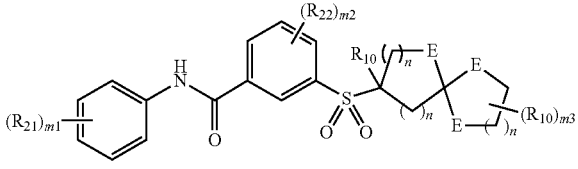

-continued (Ve)

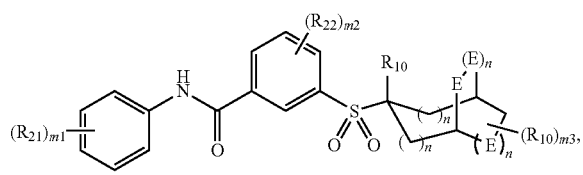

wherein m1 at each occurrence is independently 1, 2, or 3; m2 at each occurrence is independently 0, 1, or 2; m3 at each occurrence is independently 0, 1, 2, or 3; $R_{21}$ at each occurrence is independently selected from the group consisting of halogen, CN, optionally substituted —$C_1$-$C_6$ alkyl, optionally substituted —$C_1$-$C_6$ alkoxy, and optionally substituted $C_3$-$C_8$ cycloalkyl; $R_{22}$ at each occurrence is independently selected from the group consisting of halogen, CN, optionally substituted —$C_1$-$C_6$ alkyl, and optionally substituted —$C_1$-$C_6$ alkoxy; E, n, and $R_{10}$ are as previously defined.

In another embodiment, the compound of Formula (I) is represented by Formula (Vf), (Vg), (Vh), or (Vj), or a pharmaceutically acceptable salt thereof:

(Vf)

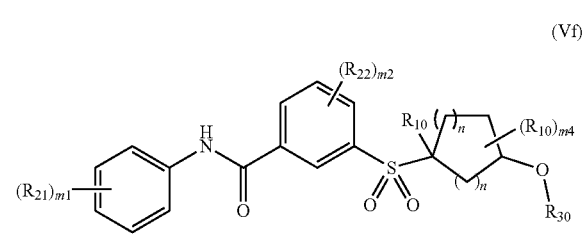

(Vg)

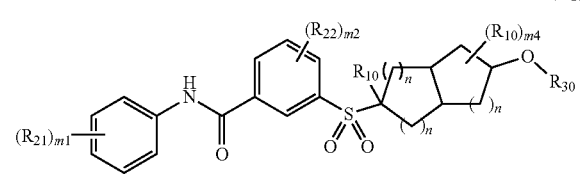

(Vh)

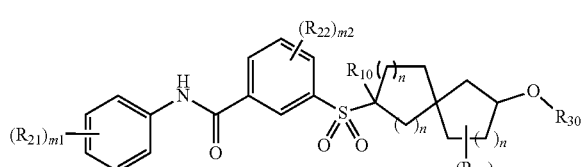

(Vj)

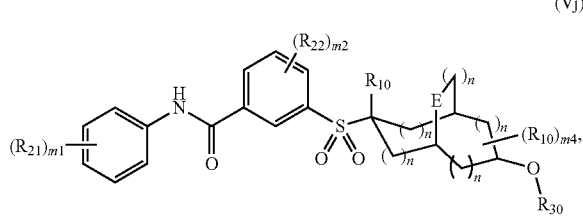

wherein m4 at each occurrence is independently 0, 1, or 2; $R_{30}$ is hydrogen, optionally substituted —$C_1$-$C_6$ alkyl, a hydroxy protecting group or a hydroxy prodrug group; m1, m2, n, E, $R_{10}$, $R_{21}$, and $R_{22}$ are as previously defined. In certain embodiments, $R_{30}$ is phosphate or sulfamate. In certain embodiments, $R_{30}$ is an acyl group derived from an amino acid, preferably an α-amino acid.

In another embodiment, the compound of Formula (I) is represented by Formula (VIa), (VIb), (VIc), (VId), (VIe), or (VIf), or a pharmaceutically acceptable salt thereof:

(VIa)

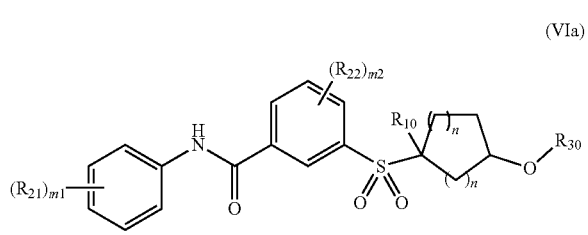

(VIb)

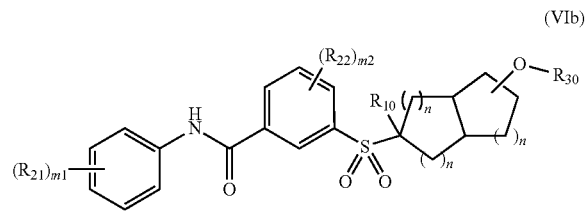

(VIc)

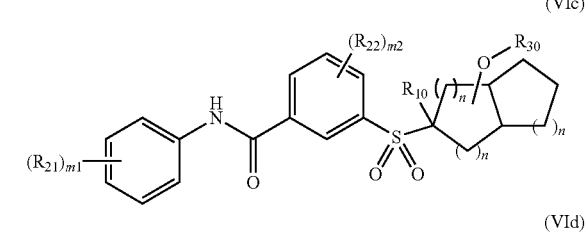

(VId)

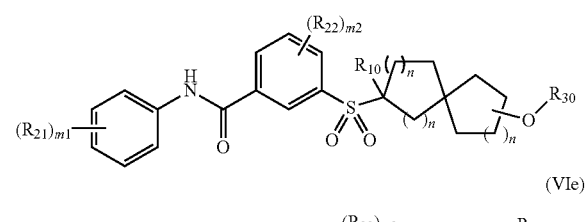

(VIe)

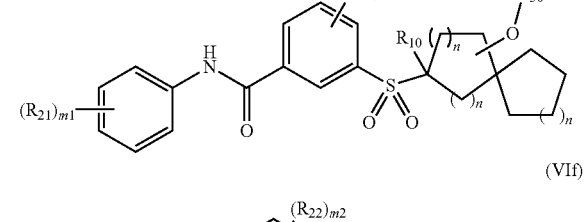

(VIf)

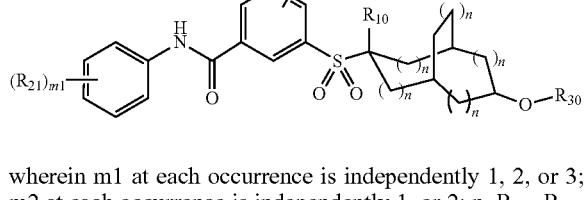

wherein m1 at each occurrence is independently 1, 2, or 3; m2 at each occurrence is independently 1, or 2; n, $R_{21}$, $R_{22}$, and $R_{30}$ are as previously defined. In certain embodiments, $R_{30}$ is phosphate or sulfamate. In certain embodiments, $R_{30}$ is an acyl group derived from an amino acid, preferably an α-amino acid.

In another embodiment, the compound of Formula (I) is represented by Formula (VIa), (VIb), (VIc), (VId), (VIe), or (VIf), or a pharmaceutically acceptable salt thereof, wherein m1 at each occurrence is independently 2 or 3; m2 at each occurrence is 1; n at each occurrence is independently 0, 1, or 2; $R_{21}$ is halogen, CN, optionally substituted methyl, optionally substituted methoxy, and optionally substituted cyclopropyl; $R_{22}$ is halogen, CN, optionally substituted methyl, and optionally substituted methoxy; $R_{30}$ is acyl group derived from an amino acid. In certain embodiments, $R_{30}$ is acyl group derived from an α-amino acid having an aliphatic side-chain. In certain embodiments, $R_{30}$ is acyl group derived from alaline or valine.

In another embodiment, the compound of Formula (I) is represented by Formula (VIIa), (VIIb), (VIIc), (VIId), or (VIIe), or a pharmaceutically acceptable salt thereof:

(VIIa)

(VIIb)

(VIIc)

(VIId)

(VIIe)

wherein m1, m3, n, E, $R_{10}$, $R_{21}$, and $R_{22}$ are as previously defined.

In another embodiment, the compound of Formula (I) is represented by Formula (VIIa-1), (VIIb-1), (VIIc-1), (VIId-1), or (VIIe-1), or a pharmaceutically acceptable salt thereof:

(VIIa-1)

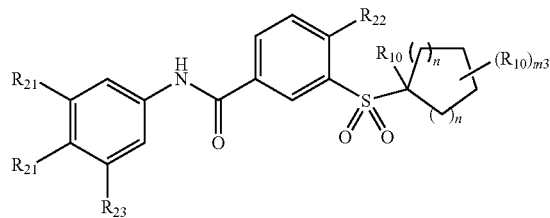
(VIIb-1)

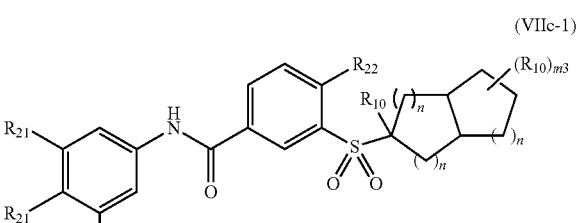
(VIIc-1)

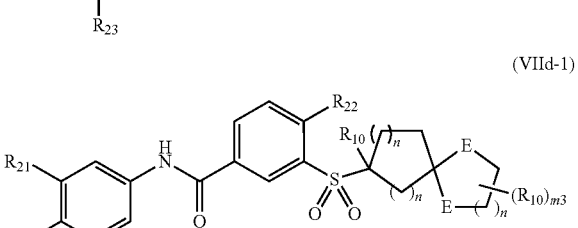
(VIId-1)

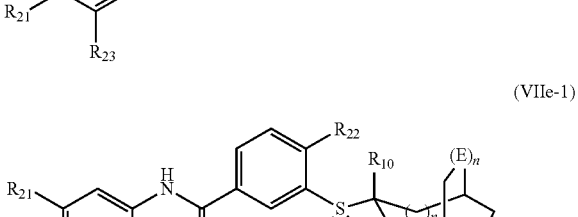
(VIIe-1)

wherein $R_{23}$ at each occurrence is independently selected from the group consisting of hydrogen, halogen, CN, optionally substituted —$C_1$-$C_6$ alkyl, optionally substituted —$C_1$-$C_6$ alkoxy, and optionally substituted $C_3$-$C_8$ cycloalkyl; m3, n, E, $R_{10}$, $R_{21}$, and $R_{22}$ are as previously defined.

In another embodiment, the compound of Formula (I) is represented by Formula (VIIa-2), (VIIb-2), (VIIc-2), or (VIId-2), or a pharmaceutically acceptable salt thereof:

(VIIa-2)

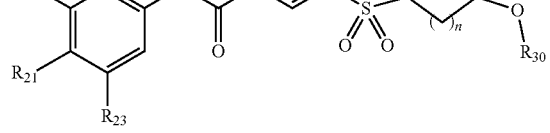

-continued

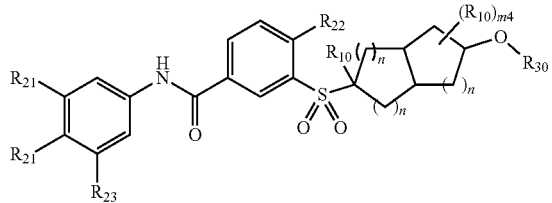
(VIIb-2)

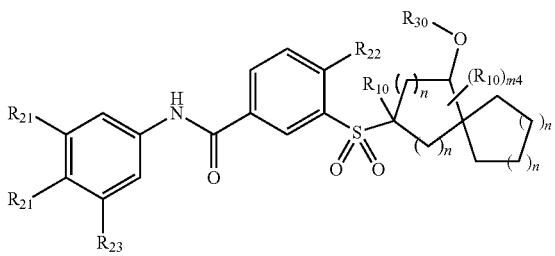
(VIIc-2)

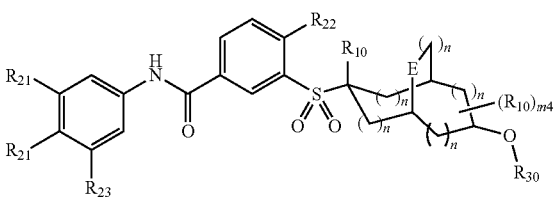
(VIId-2)

wherein m4, n, E, $R_{10}$, $R_{11}$, $R_{21}$, $R_{22}$, $R_{23}$, and $R_{30}$ are as previously defined. In certain embodiments, $R_{30}$ is hydrogen. In certain embodiments, $R_{30}$ is acyl group derived from an amino acid, preferably an α-amino acid.

In another embodiment, the compound of Formula (I) is represented by Formula (VIIa-2), (VIIb-2), (VIIc-2), or (VIId-2), or a pharmaceutically acceptable salt thereof, wherein n at each occurrence is independently 0, 1, or 2; $R_{21}$ at each occurrence is independently halogen, CN, methyl, methoxy, or cyclopropyl; $R_{22}$ is halogen, CN, methyl, or methoxy; $R_{23}$ or halogen; $R_{10}$ is halogen, hydroxyl, or optionally substituted $C_1$-$C_3$ alkyl; $R_{30}$ is hydrogen or acyl group derived from an amino acid. In certain embodiments, $R_{21}$ at each occurrence is fluorine. In certain embodiments, $R_{22}$ is fluorine or chlorine. In certain embodiments, $R_{10}$ is halogen, hydroxyl, hydroxymethyl, fluoromethyl, trifluoromethyl, or methoxymethyl. In certain embodiments, $R_{23}$ is fluorine. In certain embodiments, $R_{30}$ is an acyl group derived from alaline or valine.

In another embodiment, the compound of Formula (I) is represented by Formula (VIIIa), (VIIIb), (VIIIc), or (VIIId), or a pharmaceutically acceptable salt thereof:

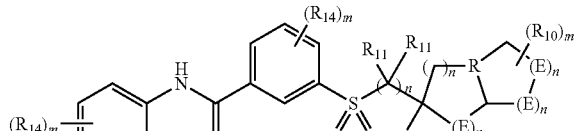
(VIIIb)

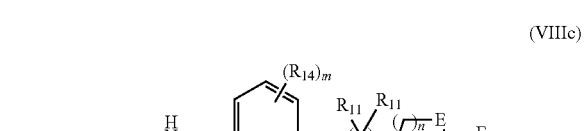
(VIIIc)

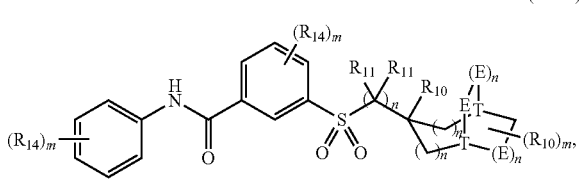
(VIIId)

wherein $R_1$ at each occurrence is independently selected from the group consisting of hydrogen, halogen, hydroxy, protected hydroxy, —CN, amino, protected amino, optionally substituted aryl, optionally substituted heteroaryl, optionally substituted —$C_1$-$C_6$ alkyl, optionally substituted —$C_2$-$C_5$ alkenyl, optionally substituted —$C_2$-$C_8$ alkynyl, optionally substituted —$C_3$-$C_5$ cycloalkyl, optionally substituted 3- to 8-membered heterocyclic, optionally substituted —$C_1$-$C_6$ alkoxy, optionally substituted —NH—$C_1$-$C_6$ alkyl, optionally substituted —N($C_1$-$C_6$ alkyl)$_2$, —$CO_2$H, optionally substituted —$C(O)_2$—$C_1$-$C_6$ alkyl, optionally substituted —C(O)NH—$C_1$-$C_6$ alkyl, and optionally substituted —C(O)—$C_1$-$C_6$ alkyl; m, n, E, T, $R_{10}$ and $R_{14}$ are as previously defined. In certain embodiments, the preferred $R_{11}$ groups include hydrogen, halogen, hydroxy, protected hydroxy, protected amino, optionally substituted aryl, optionally substituted heteroaryl, —$CO_2$H, optionally substituted —$C_1$-$C_6$ alkyl, optionally substituted NHC(O)$_2$-$C_1$-$C_6$ alkyl, and optionally substituted —$C_1$-$C_6$ alkoxy. In certain embodiments, $R_1$ is optionally substituted —$C_1$-$C_6$ alkyl, optionally substituted aryl, optionally substituted heteroaryl, and optionally substituted —$C_1$-$C_6$ alkoxy.

In another embodiment, the compound of Formula (I) is represented by Formula (VIIIa-1), (VIIIb-1), (VIIIc-1), or (VIIId-1), or a pharmaceutically acceptable salt thereof:

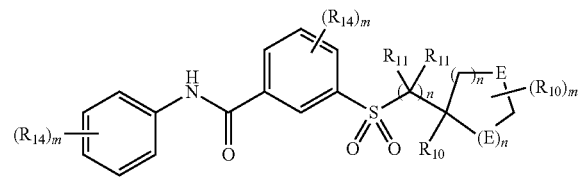
(VIIIa)

(VIIIa-1)

(VIIIb-1)

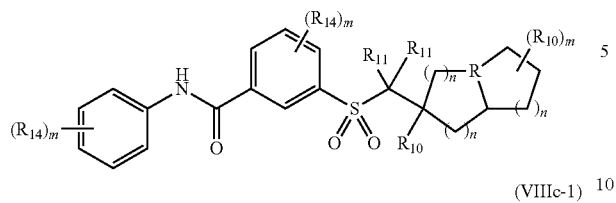

(VIIIc-1)

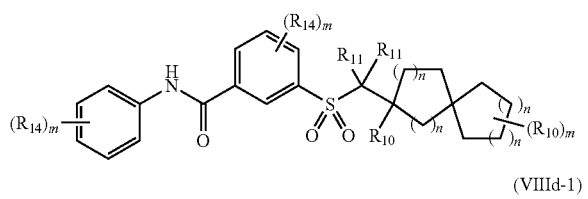

(VIIId-1)

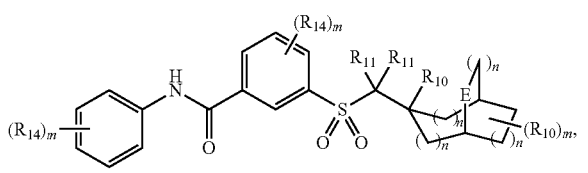

wherein m, n, E, $R_{10}$, $R_1$, and $R_{14}$ are as previously defined.

In another embodiment, the compound of Formula (I) is represented by Formula (IXa), (IXb), (IXc), or (IXd), or a pharmaceutically acceptable salt thereof:

(IXa)

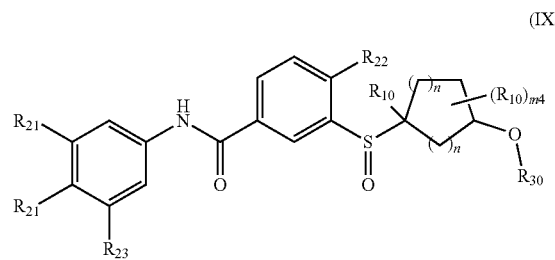

(IXb)

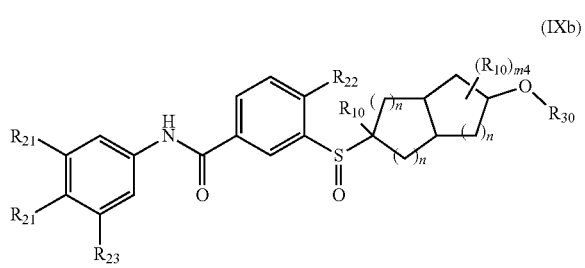

(IXc)

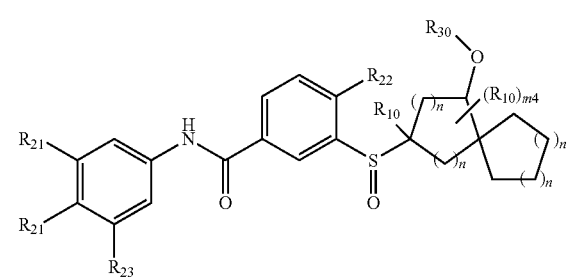

(IXd)

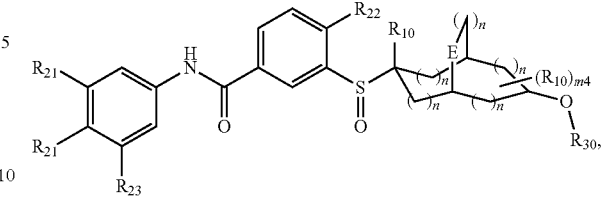

wherein m4, n, $R_{10}$, Rn, $R_{21}$, $R_{22}$, $R_{23}$, and $R_{30}$ are as previously defined.

In another embodiment, the compound of Formula (I) is represented by Formula (Xa), (Xb), (Xc), or (Xd), or a pharmaceutically acceptable salt thereof:

(Xa)

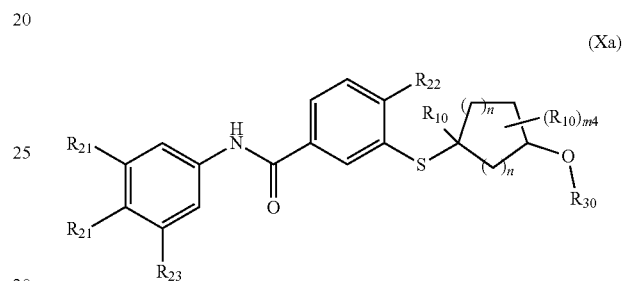

(Xb)

(Xc)

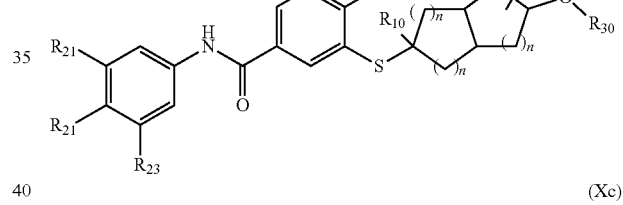

(Xd)

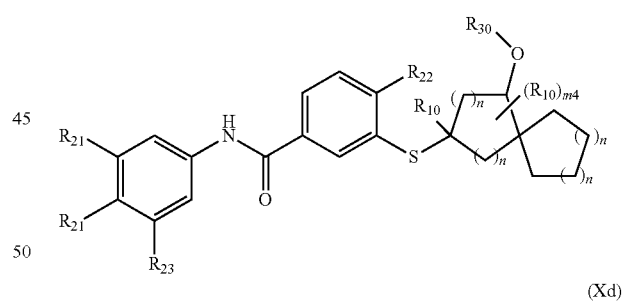

wherein m4, n, $R_{10}$, $R_1$, $R_{21}$, $R_{22}$, $R_{23}$, and $R_{30}$ are as previously defined.

In another embodiment, the compound of Formula (I) is represented by Formula (XIa), (XIb), (XIc), or (XId), or a pharmaceutically acceptable salt thereof:

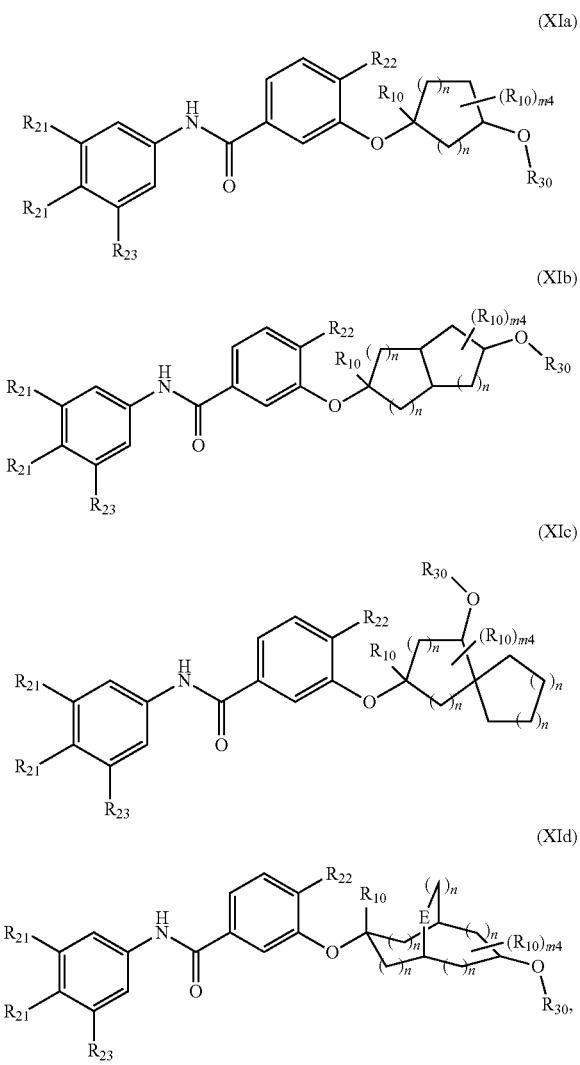

wherein m4, n, $R_{10}$, Rn, $R_{21}$, $R_{22}$, $R_{23}$, and $R_{30}$ are as previously defined.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one aspect, the compounds of the invention are useful in HBV treatment by disrupting, accelerating, reducing, delaying and/or inhibiting normal viral core protein functions including, but not limited to, direct or indirect interaction with viral relaxed circular (rc) DNA, cccDNA, or reverse transcriptase, direct or indirect interaction with host proteins such as histones or host partners such as kinase, capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, the compounds of the invention disrupt and/or modulate the interaction between core protein and viral rcDNA, cccDNA or reverse transcriptase during vial infectivity. In yet another embodiment, the compounds of the invention disrupt and/or modulate the interaction between core protein and host partners or proteins during vial infectivity. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein; or RNA interence (RNAi) or small interfering RNA (siRNA) such as ARC-520, ARC-521, ARB-1467, and ALN-HBV RNAi; or another core protein inhibitor or modulator; or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl) propyl]amino Imethyl)phenyl]acetate), GS-9620 (4-Amino-2-butoxy-8-[3-(1-pyrrolidinylmethyl)benzyl]-7,8-dihydro-6 (5H)-pteridinone), and RO6864018.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_5$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo [2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to mono-cyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The tem "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds.

Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino,-diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$-$C_1$-$C_{12}$ alkyl, —CO$_2$-$C_2$-$C_8$ alkenyl, —CO$_2$-$C_2$-$C_8$ alkynyl, CO$_2$-$C_3$-$C_{12}$-cycloalkyl, —CO$_2$-aryl, CO$_2$-heteroaryl, CO$_2$-heterocyloalkyl, —OCONH$_2$, —OCONH— $C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH— heteroaryl, -OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)— heteroaryl, —NHC(O)-heterocycloalkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH—heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, S(O)—$C_2$-$C_8$-alkynyl, —S(O)—$C_3$-$C_{12}$-cycloalkyl, —S(O)-aryl, —S(O)-heteroaryl, —S(O)—heterocycloalkyl, —$SO_2NH_2$, —$SO_2NH$—$C_1$-$C_{12}$-alkyl, —$SO_2NH$—$C_2$-$C_8$-alkenyl, —$SO_2NH$— $C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S— heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, Protective Groups in Organic Synthesis, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, Protective Groups in Organic Synthesis, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, 3, y, or 6 amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —$NR^u$-$G(S_c)$—$C(O)$-$Q^1$, wherein $Q^1$ is —$SR^v$, —$NR^vR^v$ or alkoxyl, $R^v$ is hydrogen or alkyl, $S_c$ is a side-chain of a naturally occurring or non-naturally occurring amino acid, G is $C_1$-$C_2$ alkyl, and $R^u$ is hydrogen; or $R^u$ and $S_c$ are taken together with the atoms to which they are attached to form a five-membered heterocyclic ring. In an embodiment, an amino acid derivative is provided as a substituent of compound described herein, wherein the substituent is —O—$C(O)$-$G(S_c)$—NH-$Q^2$, wherein $Q^2$ is hydrogen or alkoxyl, $S_c$ is a side-chain of a naturally occurring or non-naturally occurring amino acid and G is $C_1$-$C_2$ alkyl. In certain embodiments, $Q^2$ and $S_c$ are taken together with the atoms to which they are attached to form a five-membered heterocyclic ring. In certain embodiments, G is an optionally substituted methylene and $S_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Combination and Alternation Therapy for HBV

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combinations and are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phospho-nium Hexafluorophosphate; Brine for sodium chloride solution in water; BSA for N,O-bis-(trimethylsilyl)acetamide; CDI for carbonyldiimidazole; CH$_2$C$_2$ for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphos-phinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or (i-Pr)$_2$EtN for N,N,-diisopropylethyl amine; Dess-Martin periodinane for 1,1,1-tris(acetyloxy)-1,1-dihydro-1,2-benziodoxol-3-(1H)-one; DMAP for 4-dimethyl-amino-pyridine; DME for 1,2-dimethoxyethane; DMF for N,N-dimethylformamide; DMSO for dimethyl sulfoxide; DMT for di(β-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; Et$_2$O for diethyl ether; HATU for O-(7-azabenzotriazol-1-yl)-N,N,N',N',-tetramethyluronium Hexafluoro-phosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; MTBE for t-butyl methyl ether; NaN(TMS)$_2$ for sodium bis(trimethylsilyl)amide; NaCl for sodium chloride; NaH for sodium hydride; NaHCO$_3$ for sodium bicarbonate or sodium hydrogen carbonate; Na$_2$CO$_3$ for sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMO for N-methyl-morpholine N-oxide; NaIO$_4$ for sodium periodate; Ni for nickel; NSFI for N-fluorobenzene-sulfonimide; OH for hydroxyl; OsO$_4$ for osmium tetroxide; PTSA for p-toluenesulfonic acid; PPTS for pyridinium p-toluenesulfonate; TBAF for tetrabutylammonium fluoride; TEA or Et$_3$N for triethylamine; TES for triethylsilyl; TESCI for triethylsilyl chloride; TESOTf for triethylsilyl trifluoromethanesulfonate; TFA for trifluoroacetic acid; THE for tetrahydro-furan; TMEDA for N,N,N',N'-tetramethylethylene-diamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolylsulfonic acid; Pd for palladium; Ph for phenyl; POPd for dihydrogen dichlorobis(di-tert-butylphosphinito-κP)palladate(II); Pd$_2$(dba)$_3$ for tris(dibenzylideneacetone) dipalladium (O); Pd(PPh$_3$)$_4$ for tetrakis (triphenyl-phosphine)palladium (O); PdCl$_2$(PPh$_3$)$_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; or TMSCI for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

The compounds of the Formula I may be prepared via several different synthetic routes from a variety of optionally substituted phenyl, heteroaryl, or fused bicyclic aryl or heteroaryl precursors using the chemical transformations that are known to those skilled in the art. Strategistically, a compound of Formula I can be constructed to form the sulfonyl group at the right end followed by formation of group A at the left end. Alternatively, a compound of Formula I can be constructed to form the group A at the left end followed by formation of sulfonyl group at the right end. The preparation of sulfones can be realized by either oxidation of sulfide (reviewed by K. Schank, The Chemistry of Sulfones and Sulfoxides, Wiley, New York, 1988, Chap. 7) or alkylation/arylation of a low-valent sulfur species such as sulfinate salts (reviewed by G. Liu, C. Fan, J. Wu, Org. Biomol. Chem. 2015, 13, 1592). A sulfide can be synthesized from a thiol precursor via a nucleophilic substitution to an organic halide or sulfonate ester, or a nucleophilic addition to an epoxide, aziridine, or unsaturated substrate (reviewed by G. Solladie, Comprehensive Organic Synthesis, 1991, Vol 6, 133), or a radical addition of thiol to an unsaturated substrate. A sulfinate salt can be accessed either by reduction of a sulfonyl halide (reviewed by Schubart, R. Sulfinic Acids and Derivatives, Ullmann's Encyclopedia of Industrial Chemistry, 2000, 677) or by transition metal catalyzed reaction of aryl or hetero aryl halide (A. Shavnya, S. S. Coffey, A. C. Smith, V. Mascitti, Org. Lett., 2013, 15, 6226) or boronic acid (A. Shavnya, K. D. Hesp, V. Mascitti, A. C. Smith, Angew. Chem. Int. Ed., 2015, 54, 13571) with potassium metabisulfite. A sulfone compound may be further functionalized by deprotonation with a strong base followed by reaction of the resultant anion with an electrophile such as an organic halide, aldehyde, ketone, electrophilic halogenation reagent, or an unsaturated substrate such as a Michael addition acceptor; a tertiary sulfone may be prepared from a primary sulfone through a two-round sequential deprontonation and anionic nucleophilic reaction.

A amide bond can be formed either by reaction of an acid halide or anhydride with an amine or by the direct coupling of a carboxylic acid with an amine in the presence of a coupling reagent such as DCC, EDC, or HATU.

As illustrated in Scheme 1, wherein X, Y and R are as defined previously; $LG_1$, $LG_2$ at each occurrence are leaving groups and are each independently selected from halogen, tosylate, mesylate and triflate. In one approach, an optionally substituted aryl or heteroaryl amine 1-1 can react selectively with various acid chloride 1-2 in a solvent such as but not limited to toluene, tetrahydrofuran, dichloromethane or a mixture of thereof, optionally in the presence of a base such as but not limited to triethylamine, DIPEA, or pyridine, to provide a variety of amide intermediates 1-3. 1-3 is then treated with a reducing reagent such as but not limited to triphenylphosphine, $SnCl_2$, Sn/HCl, Zn/HCl, or Pd/HCOOH, to provide thiol intermediate 1-4, which reacts with intermediate 1-5 by a nucleophilic displacement fashion optionally in the presence of a base such as but not limited to potassium carbonate, sodium carbonate, triethylamine or DIPEA to afford a sulfide intermediate which is transformed to a compound of Formula IIa in a suitable solvent in the presence of a oxidizing reagent such as but not limited to hydrogen peroxide, meta-chloroperbenzoic acid, perbenzoic acid or tert-butyl peroxide. Alternatively, carboxylic ester 1-6 is converted to sulfone intermediate 1-7 using chemistry similar to that described above or by nucleophilic substitution with an organometallic agent (R-M, wherein M is a Mg- or Zn-species). 1-7 can be saponified with a base, such as but not limited to lithium hydroxide, sodium hydroxide, or potassium hydroxide, to yield carboxylic acid 1-8. The acid 1-8 can react with amine 1-1 in the presence of coupling reagent such as but not limited to DCC, EDC, or HATU, in a suitable solvent, optionally in the presence of a base such as but not limited to triethylamine, DIPEA, or pyridine, to yield the compound of Formula IIa.

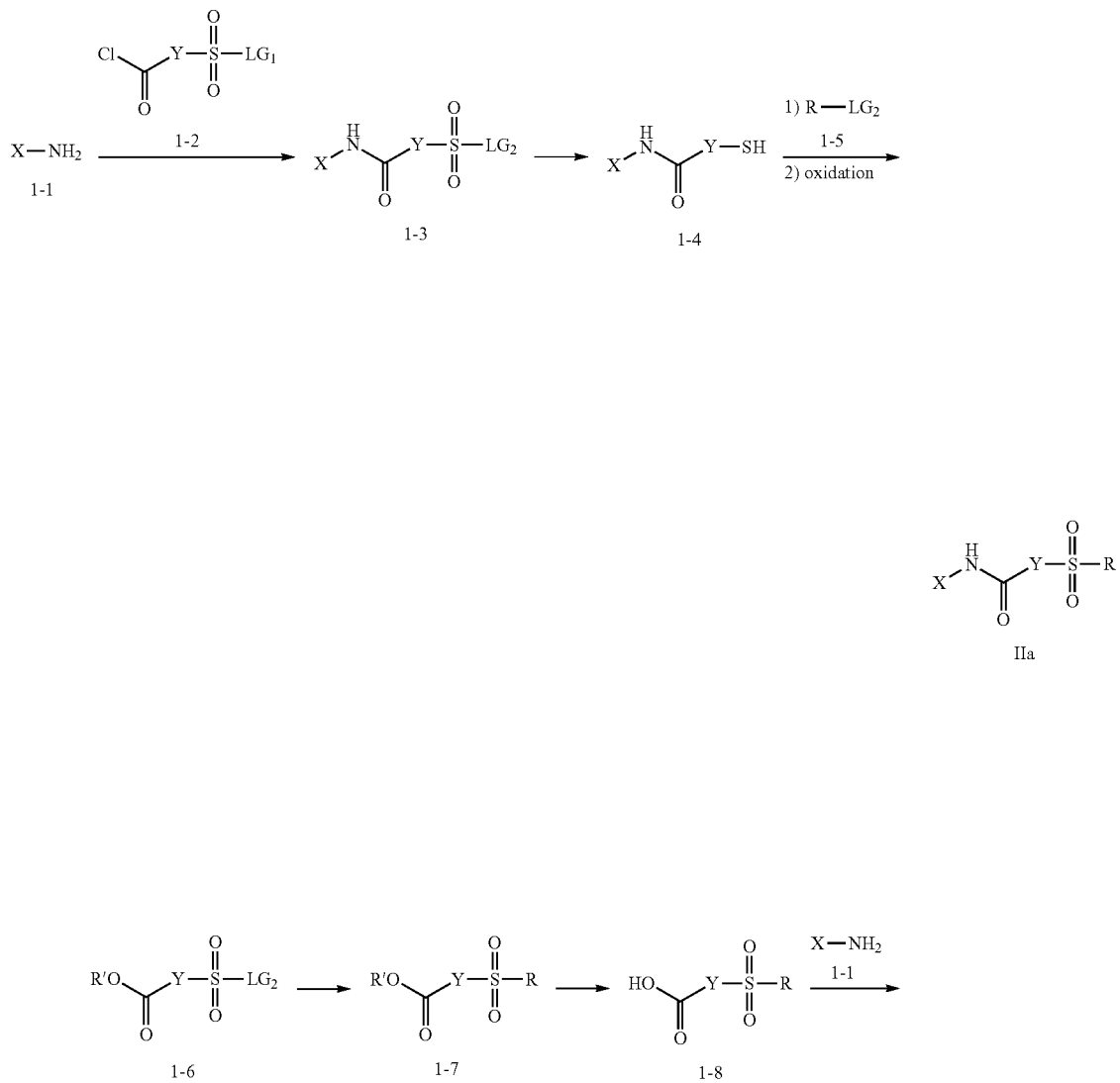

Scheme 1

The preparation of the compound of Formula IIb is described below in Scheme 2. An aldehyde 2-1 is reacted with TMSCF$_3$ to give a trifluoroethyl alcohol 2-2, which is converted to a triflate by reacting with Tf$_2$O in the presence of base such as DIPEA, followed by displacement with amine X—NH$_2$ to afford the compound of Formula IIb.

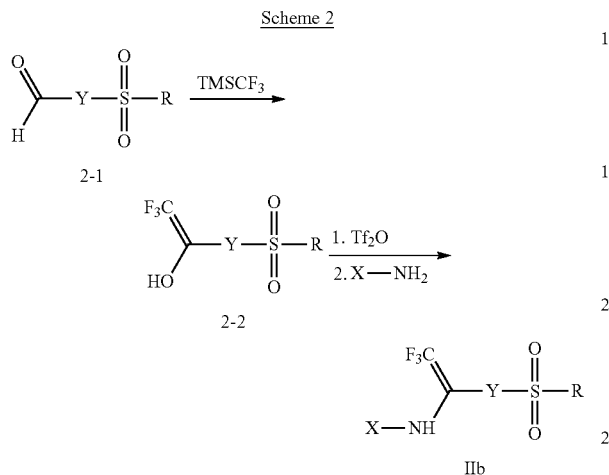

The synthesis of the compound of Formula IIc containing an aminooxetanyl moiety is exemplified in Scheme 3. An arylamine or heteroarylamine 3-1 is condensed with oxetan-3-one in the presence of an acid such as acetic acid or p-TsA to give imine 3-2, which is treated with a nucleophilic 3-3, wherein M$_1$ is an organometallic species including but not limited to that related to boronic acid/ester, organotin, organozinc, organolithium, or organomagesium moiety, to afford compound of formula IIc.

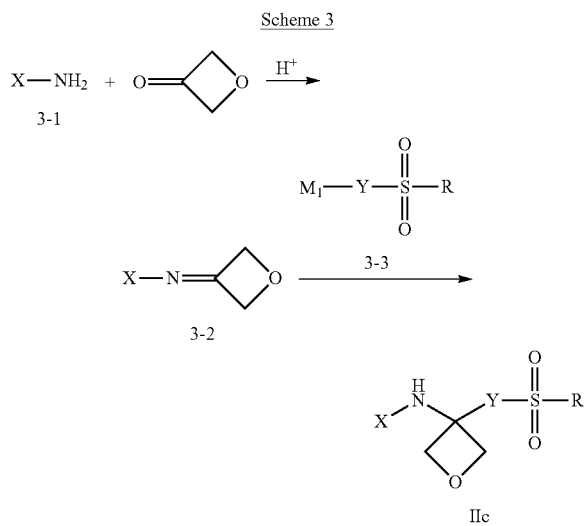

As shown in Scheme 4, the compound of Formula IId may be prepared from the compound of formula IIa. IIa may react with benzyl bromide in the presence of a base such as but not limited to NaH or LDA, to give compound 4-1, which is converted to a compound 4-2 by reacting with oxalyl chloride, followed by treatment with a fluorinating reagent such as but not limited to DAST, SF$_4$ or Et$_3$N—HF. Compound 4-2 may be treated with hydrogen gas in the presence a suitable catalyst such as but not limited to Pd/C, PtO$_2$, or Pd(OH)$_2$/C, to afford compound of Formula IId.

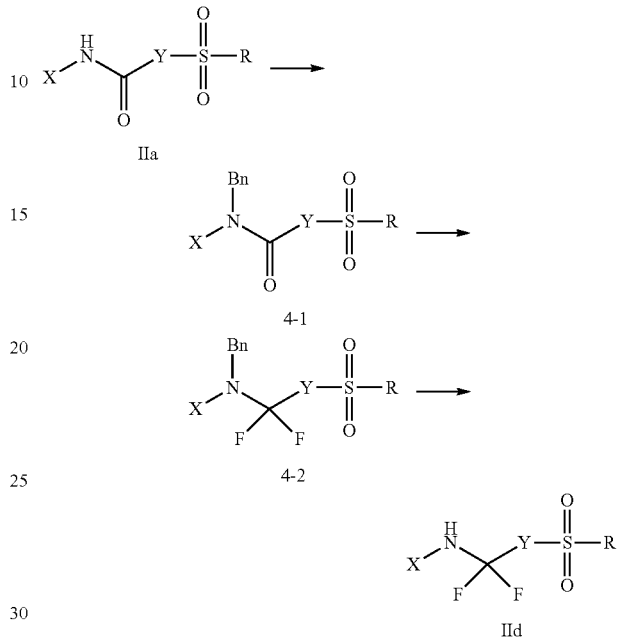

It will be appreciated that, with appropriate manipulation and protection of any chemical functionality, synthesis of compounds of Formula I is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

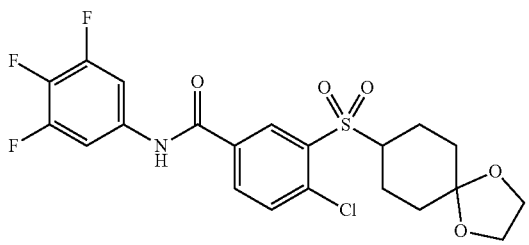 [SMILES: O=C(Nc1cc(F)c(F)c(F)c1)c1ccc(Cl)c(S(=O)(=O)C2CCC3(CC2)OCCO3)c1]

Step 1a. A mixture of 4-chloro-3-(chlorosulfonyl)-benzoic acid (0.86 g, 3.4 mmol) in SOCl$_2$ (5.0 mL) was heated to reflux overnight. It was concentrated to give the desire crude product, which was used for the next step directly.

Step 1b. The compound from Step 1a (0.91 g, 3.3 mmol) and 3,4,5-trifluoroaniline (0.49 g, 3.3 mmol) in toluene (10 mL) was stirred at 90° C. overnight. It was concentrated to give the crude desired compound, which was used for the next step directly.

Step 1c. The compound from Step 1b (0.89 g, 2.3 mmol) and triphenylphosphine (3.4 g, 13 mmol) in toluene (12 mL) was stirred at 80° C. for 4 h. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the desired compound as white solid (0.49 g, 71%). ESI-MS m/z=316.0, 318.0 [M−H]$^-$.

Step 1d. To a mixture of compound from Step 1c (0.49 g, 1.5 mmol) and potassium carbonate (0.43 g, 3.1 mmol) in DMF (7.0 mL) at rt was added 8-iodo-1,4-dioxaspiro[4.5]-decane (0.62 g, 2.3 mmol). It was stirred at rt overnight. It was diluted with ethyl acetate, filtered, and the filtrate was washed with water and brine. The organic was dried (Na$_2$SO$_4$), filtered and concentrated. The crude was chromatographed (silica, hexanes/EtOAc) to give the desired compound as white solid (0.63 g, 89%). ESI-MS m/z=456.1, 458.1 [M−H]$^-$.

Step 1e. A mixture of compound from Step 1d (0.63 g, 1.4 mmol) in DCM (30 mL) at 0° C. was treated with mCPBA (0.92 g 77%, 4.2 mmol) at rt overnight. It was diluted with ethyl acetate and washed with a mixture of sat. aqueous NaHCO$_3$, Na$_2$S$_2$O$_3$, and brine. The organic was dried (Na$_2$SO$_4$) and concentrated. The crude was chromatographed (silica hexanes/EtOAc) to give the title compound (0.56 g, 83%). ESI-MS m/z=488.05, 490.05 [M−H]-.

Example 2

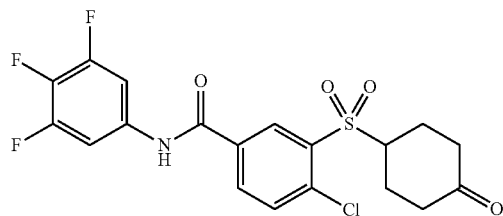 [SMILES: O=C1CCC(S(=O)(=O)c2cc(C(=O)Nc3cc(F)c(F)c(F)c3)ccc2Cl)CC1]

A stirred mixture of compound from Step 1e (0.56 g, 1.1 mmol) in acetone (15 mL) at rt was treated with 3 N aqueous HCl (3.5 mL, 10.5 mmol) at 50° C. for 30 minutes. It was diluted with ethyl acetate and washed with a sat. aqueous NaHCO$_3$ solution, brine. The organic layer was dried (Na$_2$SO$_4$) and concentrated. The crude was chromatographed (silica hexanes/EtOAc) to give the title compound (0.41 g, 80%). ESI-MS m/z=444.06, 446.06 [M−H]$^-$.

Example 3

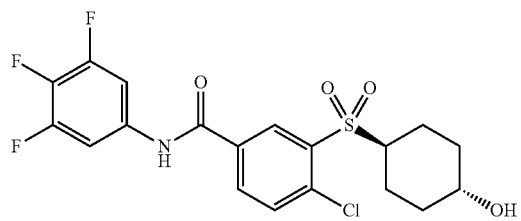 [SMILES: O=C(Nc1cc(F)c(F)c(F)c1)c1ccc(Cl)c(S(=O)(=O)[C@H]2CC[C@H](O)CC2)c1]

To a stirred mixture of compound from Example 2 (0.32 g, 0.72 mmol) in MeOH (10 mL) at 0° C. was added NaBH$_4$ (0.041 g, 1.1 mmol) and the mixture was stirred at 0° C. for 30 minutes. The reaction was quenched with aqueous NH$_4$Cl solution, and extracted with ethyl acetate and washed with water, brine. The organic was dried (Na$_2$SO$_4$) and concentrated. The residue was chromatographed (silica hexanes/EtOAc) to give the title compound (0.21 g, 65%). ESI-MS m/z=446.08, 448.08 [M−H]-.

Example 4

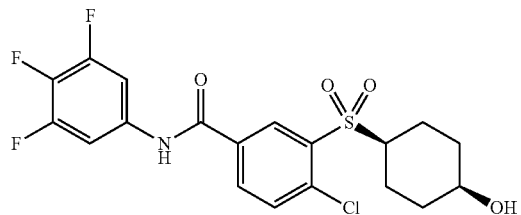 [SMILES: O=C(Nc1cc(F)c(F)c(F)c1)c1ccc(Cl)c(S(=O)(=O)[C@H]2CC[C@@H](O)CC2)c1]

The title compound (0.068 g, 21%) was isolated from the reaction of example 3. ESI-MS m/z=446.08, 448.08 [M−H]$^-$.

Example 5

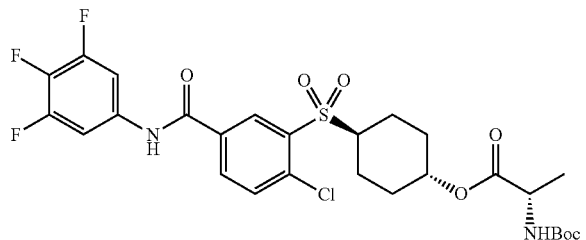 [SMILES: C[C@H](NC(=O)OC(C)(C)C)C(=O)O[C@H]1CC[C@H](S(=O)(=O)c2cc(C(=O)Nc3cc(F)c(F)c(F)c3)ccc2Cl)CC1]

A mixture of compound of Example 3 (0.10 g, 0.23 mmol) and (t-butoxycarbonyl)-L-alanine (0.066 g, 0.35 mmol) in DCM (6.0 mL) and DMF (0.50 mL) was treated with EDC (0.056 g, 0.29 mmol) and DMAP (0.057 g, 0.46 mmol) at rt overnight before being diluted with EtOAc and washed with water and brine. The organic was dried ($Na_2SO_4$) and concentrated. The crude was chromatographed (silica, hexanes/EtOAc) to give the title product (0.14 g, 95%). ESI-MS m/z=617.16, 619.16 [M−H]−.

Example 6

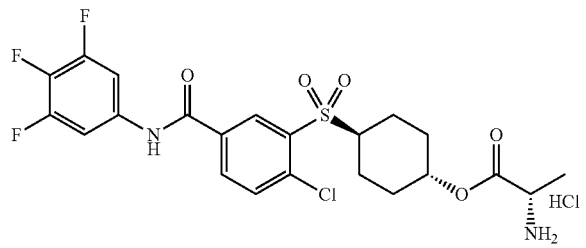 [SMILES: C[C@H](N)C(=O)O[C@H]1CC[C@H](S(=O)(=O)c2cc(C(=O)Nc3cc(F)c(F)c(F)c3)ccc2Cl)CC1 ; Cl]

The compound of Example 5 (0.11 g, 0.17 mmol) was treated with HCl in dioxane (4N, 2.0 mL) at 0° C. It was then slowly warmed up to rt in 30 min. The volatiles were removed to give the title compound as HCl salt (90 mg, 93%). ESI-MS m/z=519.17, 521.17 [M+H]+.

Example 7

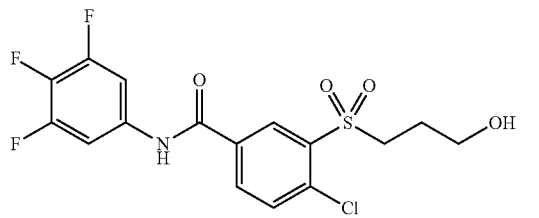 [SMILES: O=C(Nc1cc(F)c(F)c(F)c1)c1ccc(Cl)c(S(=O)(=O)CCCO)c1]

Step 7a. A solution of the compound from Step 1c (0.14 g, 0.44 mmol) in DMF was treated with $iPr_2NEt$ (0.23 g, 1.8 mmol) and 3-bromopropan-1-ol (0.15 g, 1.1 mmol) at rt for 5 minutes. It was diluted with ethyl acetate, washed with water, brine. The organics were dried ($Na_2SO_4$), filtered and concentrated. The crude was chromatographed (silica, hexanes/EtOAc) to give the desired compound as a white solid (0.14 g, 85%). ESI-MS m/z=376.0 [M+H]−.

Step 7b. A mixture of compound from Step 7a (87 mg, 0.23 mmol) in DCM/MeCN (2:1, 11 mL) at rt was treated with mCPBA (77% w/w, 0.16 g, 0.70 mmol) at rt overnight. It was diluted with ethyl acetate and washed with a mixture of sat. aqueous $NaHCO_3$, $Na_2S_2O_3$, and brine. The organics were dried ($Na_2SO_4$) and concentrated. The crude was chromatographed (silica hexanes/EtOAc) to give the title product (70 mg, 74%). ESI-MS m/z=408.0 [M+H].

Example 8

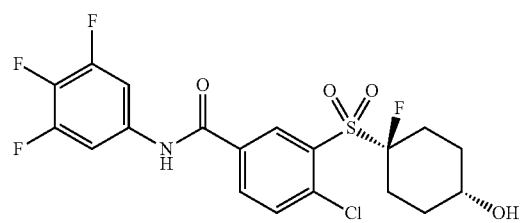 [SMILES: O=C(Nc1cc(F)c(F)c(F)c1)c1ccc(Cl)c(S(=O)(=O)[C@]2(F)CC[C@H](O)CC2)c1]

Step 8a. To a stirred mixture of compound from Example 3 (0.15 g, 0.34 mmol) and imidazole (0.057 g, 0.84 mmol) in DMF (3.0 mL) at rt was added TBSCl (0.06 g, 0.40 mmol). It was stirred at rt overnight. The reaction was diluted with ethyl acetate and it was washed with water, brine. The organic was dried ($Na_2SO_4$), filtered and concentrated. The crude was chromatographed (silica, hexanes/EtOAc) to give the desired compound as white solid (0.15 g, 79%). ESI-MS m/z=560.13, 562.13 [M−H]−.

Step 8b. To a stirred mixture of compound from Step 8a (0.070 g, 0.12 mmol) in THF (2 mL) at −78° C. was added LDA (1M in THF/hexanes, 0.31 mL, 0.31 mmol). After 30 min, N-fluorobenzenesulfonimide (0.049 g, 0.16 mmol) in THF (1 mL) was added. It was warmed up to −10° C. over 1 h and quenched with aqueous $NH_4Cl$. It was extracted with ethyl acetate and washed with water, brine. The organic was dried ($Na_2SO_4$) and concentrated. The crude was chromatographed (silica hexanes/EtOAc) to give a mixture of two diastereomers (0.049 g, 68%). ESI-MS m/z=578.13, 580.12 [M−H]−.

Step 8c. A stirred mixture of compound from Step 8b (0.039 g, 0.067 mmol) in MeOH (4 mL) was treated conc. HCl (5 drops) at 0° C. for 1 h and rt for 6 h. It was diluted with and washed with sat. aq. $NaHCO_3$, water and brine. The organic layer was dried ($Na_2SO_4$) and concentrated. The crude was chromatographed (silica hexanes/EtOAc) to give the title compound (0.012 g, 30%). ESI-MS m/z=464.03, 466.03 [M−H]−.

Example 9

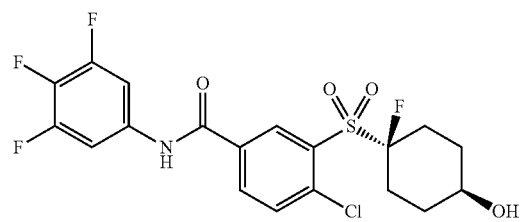 [SMILES: O=C(Nc1cc(F)c(F)c(F)c1)c1ccc(Cl)c(S(=O)(=O)[C@]2(F)CC[C@@H](O)CC2)c1]

The title compound (0.006 g, 15%) was isolated from step 8c. ESI-MS m/z=464.03, 466.03 [M−H]−.

Example 10

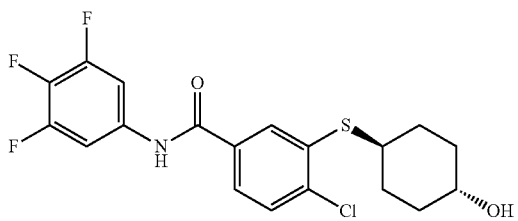 [SMILES: O=C(Nc1cc(F)c(F)c(F)c1)c1ccc(Cl)c(S[C@H]2CC[C@H](O)CC2)c1]

Step 10a. A stirred mixture of compound from Step 1c (0.79 g, 2.5 mmol) and trans-1-tert-butyldimethylsilyl-oxy-4-iodo-cyclohexane (1.1 g, 3.25 mmol) in DMF (10 mL) was treated with potassium carbonate (0.69 g, 5.0 mmol) at rt overnight. It was diluted with ethyl acetate, filtered, and the filtrate was washed with water, brine. The organic was dried ($Na_2SO_4$), filtered and concentrated. The crude was chromatographed (silica, hexanes/EtOAc) to give the desired compound as white solid (1.33 g, 56%). ESI-MS m/z=528.15, 530.14 [M−H]⁻.

Step 10b. A stirred mixture of compound from Step 10a (0.033 g, 0.062 mmol) in MeOH (4 mL) at 0° C. was treated with conc. HCl (5 drops) at 0° C. for 1 h and rt for 6 h. It was diluted with ethyl acetate and washed with sat. aq. $NaHCO_3$, water, brine. The organic was dried ($Na_2SO_4$) and concentrated. The crude product was chromatographed (silica hexanes/EtOAc) to give the title compound (0.025 g, 97%). ESI-MS m/z=414.06, 416.05 [M−H]⁻.

Example 14

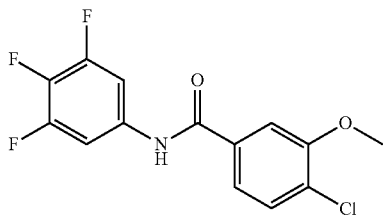 [SMILES: COc1cc(C(=O)Nc2cc(F)c(F)c(F)c2)ccc1Cl]

To a stirred solution of 4-chloro-3-methoxybenzoic acid (500 mg, 2.68 mmol), 3,4,5-trifluoroaniline (591 mg, 4.02 mmol) and HATU (1172 mg, 3.08 mmol) in DMF (3.0 ml) and DCM (15.00 ml) was added DIPEA (1.404 ml, 8.04 mmol) at 0° C. It was stirred at rt for 3 h before being diluted with EtOAC (30 mL) and washed with brine. The organic was dried and concentrated. The crude product was chromatographed (silica, EtOAc-hexanes) to give the title compound (Yield: 66%). ESI-MS m/z=314.07, 316.02 [M−H]⁻. ¹HNMR (400 MHz, Chloroform-d) δ 7.75 (s, 1H), 7.58-7.46 (m, 2H), 7.46-7.33 (m, 2H), 4.01 (s, 3H).

Example 16

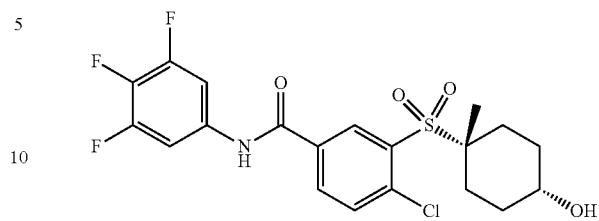

Step 16a. To a stirred mixture of compound from Step 8a (0.12 g, 0.22 mmol) in THF (3 mL) at −78° C. was added LDA (1M in THF/hexanes, 0.55 mL, 0.55 mmol). After 30 min, MeI (0.039 g, 0.28 mmol) in THF (1 mL) was added and it was warmed up to −10° C. over 1 h. It was quenched with aqueous $NH_4Cl$. It was extracted with ethyl acetate and washed with water, brine. The organic was dried ($Na_2SO_4$) and concentrated. The crude was chromatographed (silica, hexanes/EtOAc) to give the desired compounds as a mixture of diasteromers (0.089 g, 70%). ESI-MS m/z=578.13, 580.12 [M−H]⁻.

Step 16b. A stirred mixture of compound from Step 16a (0.089 g, 0.15 mmol) in MeOH (4 mL) at 0° C. was treated with conc. HCl (5 drops) at 0° C. for 1 h and rt for 6 h. It was diluted with ethyl acetate and washed with sat. aq. $NaHCO_3$, water, brine. The organic was dried ($Na_2SO_4$) and concentrated. The crude was chromatographed (silica hexanes/EtOAc) and purified by prep-HPLC using a C18 column and acetonitrile/water as eluent to give the title compound (0.014 g, 20%). ESI-MS m/z=460.07, 462.06 [M−H]⁻.

Example 17

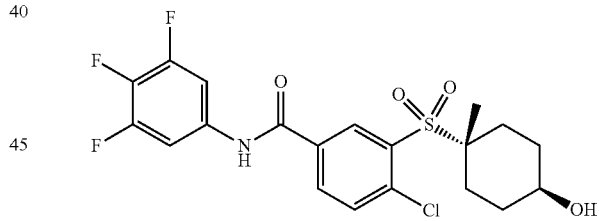

The title compound (0.025 g, 35%) was isolated from step 16b. ESI-MS m/z=460.06, 462.06 [M−H]⁻.

Example 18

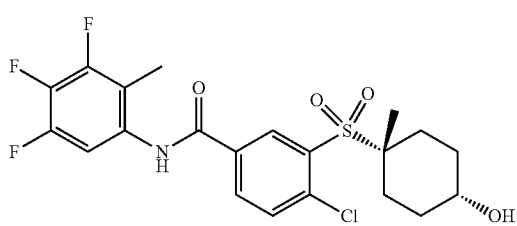 [SMILES: Cc1c(NC(=O)c2ccc(Cl)c(S(=O)(=O)[C@]3(C)CC[C@H](O)CC3)c2)cc(F)c(F)c1F]

The title compound (0.007 g, 9.5%) was isolated from step 16b. ESI-MS m/z=474.07, 476.07 [M−H]⁻.

Example 19

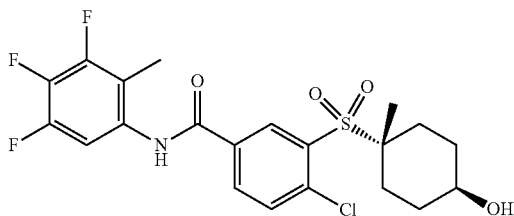 [SMILES: Cc1c(NC(=O)c2ccc(Cl)c(S(=O)(=O)[C@]3(C)CC[C@@H](O)CC3)c2)cc(F)c(F)c1F]

The title compound (0.009 g, 12%) was isolated from step 16b. ESI-MS m/z=474.08, 476.07 [M−H]⁻.

Example 20

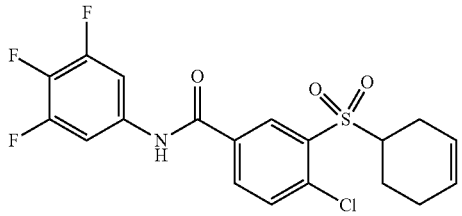 [SMILES: O=C(Nc1cc(F)c(F)c(F)c1)c1ccc(Cl)c(S(=O)(=O)C2CC=CCC2)c1]

A stirred mixture of compound from Example 4 (0.032 g, 0.071 mmol) in DCM (4 mL) at 0° C. was treated with DAST (81 mg, 0.50 mmol) at 0° C. for 1 h and rt for 16 h. It was diluted with ethyl acetate and washed with sat. aq. NaHCO₃, water, brine. The organic was dried (Na₂SO₄) and concentrated. The crude was chromatographed (silica hexanes/EtOAc) to give the title compound (0.0098 g, 32%). ESI-MS m/z=428.03 430.03 [M−H]⁻.

Example 21

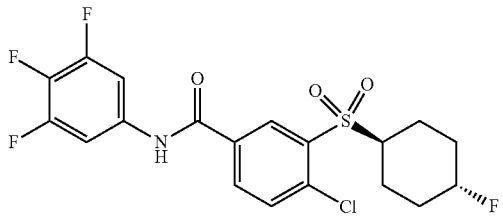 [SMILES: O=C(Nc1cc(F)c(F)c(F)c1)c1ccc(Cl)c(S(=O)(=O)[C@H]2CC[C@H](F)CC2)c1]

The compound (0.0038 g, 12%) was isolated in example 20. ESI-MS m/z=448.04, 450.04 [M−H]⁻.

Example 22

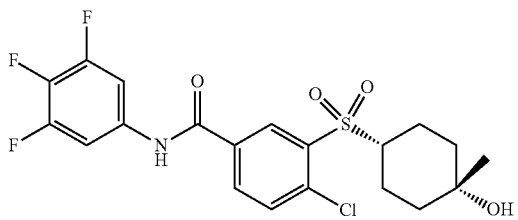 [SMILES: C[C@]1(O)CC[C@@H](S(=O)(=O)c2cc(C(=O)Nc3cc(F)c(F)c(F)c3)ccc2Cl)CC1]

Into a stirred solution of compound of Example 2 (0.045 g, 0.10 mmol) in THF (2.5 mL) at 0° C. was added methylmagnesium bromide (3M in diethyl ether, 0.13 mL, 0.40 mmol). After 1 h at rt, it was quenched with aqueous NH₄Cl. It was extracted with ethyl acetate and washed with water, brine. The organic was dried (Na₂SO₄) and concentrated. The residue was chromatographed (silica hexanes/EtOAc) to give the title compound (0.082 g, 18%). ESI-MS m/z=460.06, 462.06 [M−H]⁻.

Example 23

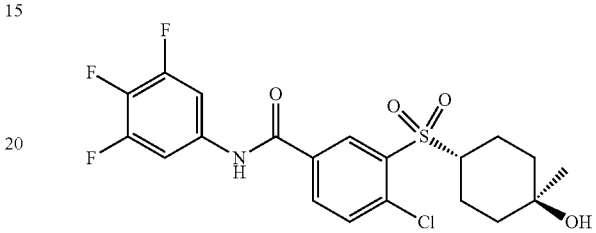

The title compound was isolated in example 22 (0.018 g, 39%) ESI-MS m/z=460.06, 462.06 [M−H]⁻.

Example 24

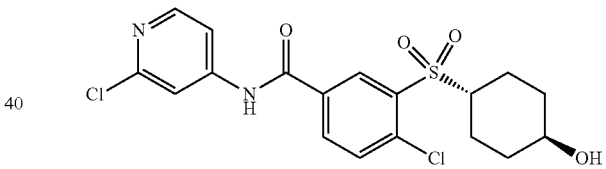

Step 24a. A stirred solution of methyl 3-((trans-4-((tert-butyldimethylsilyl)oxy)cyclohexyl)-sulfonyl)-4-chlorobenzoate (20.0 mg, 0.045 mmol) and 2-chloropyridin-4-amine (17.2 mg, 0.134 mmol) in toluene (0.8 ml) was added trimethylaluminum (2M in toluene, 0.067 ml, 0.134 mmol) at rt. It was then stirred at 90° C. for 2 h. It was diluted with EtOAc (20 mL), washed with sat. Rachelle's salt aqueous solution (10 mL). The organic was dried and concentrated. The crude was used for next step without further purification.

Step 24b. To a stirred solution of compound of step 24a (0.134 mmol at most) in MeOH (2 mL) was added HCl (4N in water, 0.2 ml) at 0° C. It was stirred at rt for 1 h before being diluted with EtOAc (20 mL), washed with aqueous Na₂S₂O₃ (10 mL), and brine (10 mL). The organic was dried and concentrated. The crude was chromatographed (silica, MeOH-DCM) to give the desired compound (79%). ESI-MS m/z=411.09, 413.06 [M−H]⁻. 1H NMR (400 MHz, Methanol-d4) δ 8.61 (d, J=2.3 Hz, 1H), 8.36-8.21 (m, 2H), 8.00 (d, J=1.9 Hz, 1H), 7.87 (d, J=8.4 Hz, 1H), 7.74 (dd, J=5.7, 1.9 Hz, 1H), 3.57 (qt, J=10.8, 3.9 Hz, 2H), 2.14-1.94 (m, 4H), 1.71 (qd, J=13.1, 3.5 Hz, 2H), 1.41-1.25 (m, 2H).

Example 25

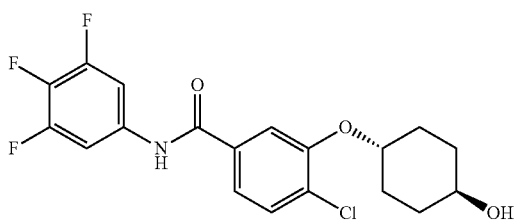 [SMILES: O=C(Nc1cc(F)c(F)c(F)c1)c1ccc(Cl)c(O[C@H]2CC[C@H](O)CC2)c1]

Step 25a. To a stirred solution of compound of example 14 (105 mg, 0.333 mmol) in DCM (5.00 ml) was added BBr$_3$ (0.499 ml, 0.499 mmol) at 0° C. It was slowly warmed up to rt and stirred at rt overnight. Additional BBr$_3$ (1.5 eq) was added at rt. It was stirred at rt for 3 h. Ice (10 g) was added. It was diluted with EtOAC (30 mL) and washed with brine. The organic was dried and concentrated. The crude was used for next step without further purification. ESI-MS m/z=300.02, 302.00 [M−H]$^-$.

Step 25b. To a stirred solution of triphenylphosphine (54.3 mg, 0.207 mmol) and cis-4-((tert-butyldimethylsilyl)oxy)cyclohexan-1-ol (38.2 mg, 0.166 mmol) in THF (2.00 ml) was added DIAD (0.032 ml, 0.166 mmol) at 0° C. It was stirred at 0° C. for 10 min, then 4-chloro-3-hydroxy-N-(3,4,5-trifluorophenyl)benzamide (25 mg, 0.083 mmol) was added to the mixture. The mixture was then stirred at rt for 2 h. Additional triphenylphosphine (54.3 mg, 0.207 mmol), DIAD (0.032 ml, 0.166 mmol) and cis-4-((tert-butyldimethylsilyl)oxy)cyclohexan-1-ol (38.2 mg, 0.166 mmol) was then added to the reaction mixture at rt. the resulting reaction mixture was stirred at rt overnight. The reaction mixture was concentrated to provide a crude product, which was purified by ISCO silica gel chromatography (eluent: 0→60% EtOAc in hexane) to give the desired compound (84%). ESI-MS m/z=512.23, 514.17 [M−H]$^-$.

Step 25c. To a stirred solution of compound of step 25b (26 mg, 0.051 mmol in MeOH (2.00 ml) was added aqueous HCl (4.0 M, 0.05 ml. It was stirred at rt for 1 h, then it was diluted with EtOAc, washed with aq. NaHCO$_3$(10 mL) and brine. The organic was dried and concentrated. The crude was chromatographed (silica, EtOAc-hexanes) to give the title compound (79%). $^1$H NMR (400 MHz, Methanol-d4) δ 7.68-7.56 (m, 3H), 7.56-7.43 (m, 2H), 4.56 (tt, J=8.5, 3.7 Hz,1H), 3.78 (tt, J=8.5, 3.8 Hz, 1H), 2.26-2.10 (m, 2H), 2.11-1.98 (m, 2H), 1.70-1.60 (m, 2H), 1.61-1.44 (m, 2H). ESI-MS m/z=398.11, 400.08 [M−H]$^-$.

Example 30

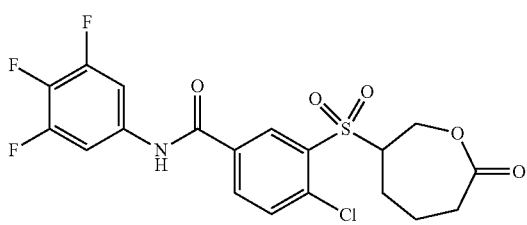 [SMILES: O=C1CCCC(S(=O)(=O)c2cc(C(=O)Nc3cc(F)c(F)c(F)c3)ccc2Cl)CO1]

Step 30a. Into a stirred solution of the compound from Step 1c (30 mg, 0.095 mmol) in MeOH (1.0 mL) at rt was added triethylamine (40 μL, 0.28 mmol) and cyclohex-2-en-1-one (18 mg, 0.19 mmol). It was stirred at rt for 2 h. It was concentrated and the residue was chromatographed (EtOAc/hexanes) to give the desired compound as white solid (35 mg, 89%), ESIMS m/z=414.06, 416.06 [M+H]*.

Step 30b. A stirred solution of the compound from Step 30a (35 mg, 0.084 mmol) in CH$_2$Cl$_2$ (4.2 mL) at rt was treated with mCPBA (purity: 77% w/w, 76 mg, 0.34 mmol) overnight. It was quenched with aqueous saturated Na$_2$S$_2$O$_3$. After 10 minutes, it was diluted and extracted with CH$_2$Cl$_2$. The combined organics were washed with brine, dried over Na$_2$SO$_4$, and concentrated. The crude was chromatographed (acetone/hexanes) to give the title product as while solid (10 mg, 26%), ESIMS m/z=460.02, 462.02 [M−H]$^-$.

Example 31

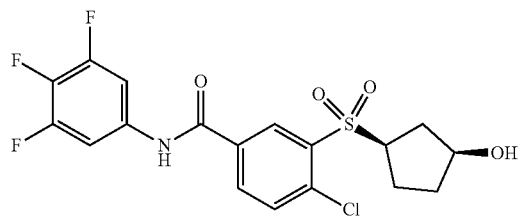 [SMILES: O=C(Nc1cc(F)c(F)c(F)c1)c1ccc(Cl)c(S(=O)(=O)[C@@H]2CC[C@H](O)C2)c1]

Step 31a. A stirred solution of the compound from Step 1c (30 mg, 0.095 mmol) in MeOH (0.93 mL) at rt was treated with triethylamine (39 μL, 0.28 mmol) and cyclopent-2-en-1-one (15 mg, 0.19 mmol) at rt for 2 hours before concentration. The residue was chromatographed (EtOAc/hexanes) to give the desired compound as white solid (37 mg), ESIMS m/z=400.04, 402.04 [M+H]$^+$.

Step 31b. A stirred solution of the compound from Step 31a (37 mg, 0.093 mmol) in CH$_2$Cl$_2$ (4.6 mL) at rt was treated with mCPBA (77% w/w, 83 mg, 0.37 mmol) overnight. It was quenched with aqueous saturated Na$_2$S$_2$O$_3$ for 10 minutes. After separation, the aqueous was extracted with CH$_2$C$_2$. The combined organics were washed with brine, dried over Na$_2$SO$_4$, concentrated, and the crude was chromatographed (acetone/hexanes) to give the desired compound as while solid (22 mg, 55%), ESIMS m/z=430.01, 430.01 [M−H]$^-$.

Step 31c. A stirred solution of the compound from Step 30b (13 mg, 0.030 mmol) in methanol (3.0 mL) at 0° C. was treated with NaBH$_4$ (1.7 mg, 0.045 mmol) for 3 hours. It was quenched by the aqueous saturated NH$_4$Cl, and extracted with CH$_2$Cl$_2$. The organics were washed with brine, dried over Na$_2$SO$_4$, concentrated, and the crude was chromatographed (acetone/hexanes) to give the title compound (11 mg, 86%) as while solid. ESIMS m/z=432.03, 434.03 [M−H]$^-$.

Example 37

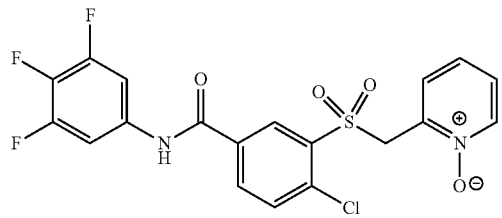 [SMILES: O=C(Nc1cc(F)c(F)c(F)c1)c1ccc(Cl)c(S(=O)(=O)Cc2cccc[n+]2[O-])c1]

Step 37a. To a stirred solution of the compound from Step Ic (40 mg, 0.13 mmol) in DMF (2.5 mL) at rt was added N-ethyl-N-isopropylpropan-2-amine (0.11 mL, 0.64 mmol) and 2-(bromomethyl)pyridine hydrobromide (48 mg, 0.19 mmol). It was stirred at rt for 5 minutes before being quenched with aq saturated NaHCO$_3$. The aqueous was extracted with EtOAc. The combined organics were washed with brine, dried over Na$_2$SO$_4$, concentrated, and the crude was chromatographed (EtOAc/hexanes) to give the desired compound (42 mg, 81%) as white solid, ESIMS m/z=409.04, 411.04 [M+H]$^+$.

Step 37b. A stirred solution of the compound from Step 37a (32 mg, 0.079 mmol) in CH$_2$Cl$_2$ (3.9 mL) at rt was treated with mCPBA (77% w/w, 70 mg, 0.31 mmol) at rt overnight. After being quenched with aq saturated Na$_2$S$_2$O$_3$ rt for 10 minutes, it was extracted with CH$_2$Cl$_2$. The combined organics were washed with brine, dried over Na$_2$SO$_4$, concentrated. The crude was chromatographed (acetone/hexanes) to give the title product as while solid (29 mg, 81%), ESIMS m/z=455.00, 457.00 [M−H]$^−$.

Example 39

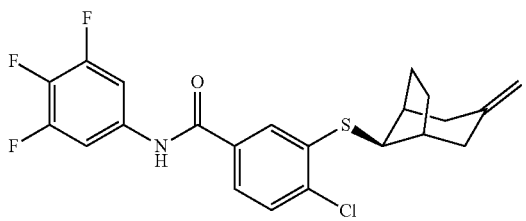

Step 39a. A mixture of 2-methylenepropane-1,3-diyl diacetate (2.69 g, 15.62 mmol), Pd(OAc)$_2$ (0.210 g, 0.937 mmol), Ph$_3$P (0.983 g, 3.75 mmol), and 1-(cyclopent-1-en-1-yl)pyrrolidine (3.19 ml, 21.86 mmol) in acetonitrile (89 ml) was heated to and remained at 65° C. for 18 hours. Water (45 ml) was added and the reaction mixture was stirred for 1 hour. Saturated brine was added and it was extracted with ethyl acetate. The organic phase was dried (Na$_2$SO$_4$), filtered and concentrated. The residue was chromatographed (silica, hexanes/EtOAc) to give the desired compound (1.53 g, 71.9% yield) as a colorless oil.

Step 39b. A solution of the compound from step 39a (477 mg, 3.50 mmol) in THF (18 mL) was cooled to −78° C. followed by addition of LiAlH$_4$ (1M in THF, 4.20 mL, 4.20 mmol). After being stirred for 30 minutes, it was quenched by water (0.5 mL), NaOH (1M, 0.5 mL) and water (1.5 mL). The organic was dried (Na$_2$SO$_4$), filtered over Celite and concentrated to give the crude desired compound (477 mg, 99%), which was used for the following step.

Step 39c. Into a solution of compound from step 39b (131 mg, 0.944 mmol) and Ph$_3$P (413 mg, 1.574 mmol) in THF (1.6 ml) was added DIAD (245 µl, 1.259 mmol) and 4-chloro-3-mercapto-N-(3,4,5-trifluorophenyl)benzamide (100 mg, 0.315 mmol). It was heated to and remained at 65° for 18 hours. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the title compound (60 mg, 0.137 mmol, 43.5% yield) as a white solid. ESI-MS m/z=436.08, 438.07[M−H]$^−$.

Example 44

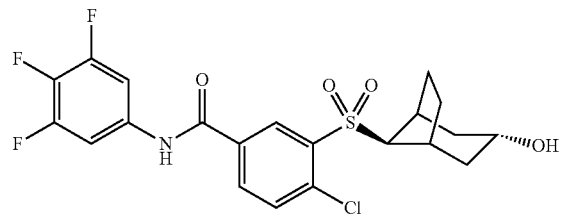 [SMILES: O=C(Nc1cc(F)c(F)c(F)c1)c1ccc(Cl)c(S(=O)(=O)[C@H]2C3CCC2C[C@@H](O)C3)c1]

Step 44a. A stream of ozone from an ozonizer was bubbled into a solution of compound from Step 39c (32 mg, 0.073 mmol) in DCM (2 ml) at −78° C. until blue color persisted; then oxygen was bubbled until the mixture is colorless. Dimethyl sulfide (1 mL, 13.52 mmol) was added; the mixture was warmed up to rt and stirred for 1 hour. MeOH (2 ml) then NaBH$_4$ (55.3 mg, 1.462 mmol) were added and the mixture was stirred for 2 hours. It was diluted with dichloromethane and then washed with H$_2$O and brine. The organic was dried (Na$_2$SO$_4$), filtered and concentrated to give the crude desired compounds which was used for next step without further purification.

Step 44b. A solution of the compounds from Step 44a (33 mg, 0.072 mmol) in DCM (2 ml) was treated with m-CPBA (77% w/w, 81 mg, 0.280 mmol) at rt for 18 hours. It was diluted with dichloromethane and then washed with NaHCO$_3$ and brine. The organic was dried with Na$_2$SO$_4$, filtered and concentrated. The crude was chromatographed (silica, ethyl acetate/hexanes) to give the title compound (8 mg, 23.4%) as a white solid. ESI-MS m/z=470.05, 472.05 [M−H]$^−$.

Example 49

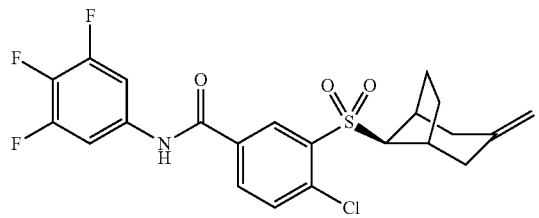

A solution of compound from Step 39c in ethanol (1 ml) was treated with ammonium molybdate tetrahydrate (2.8 mg, 2.28 µmol) and hydrogen peroxide (0.095 ml, 1.14 mmol) for 5 days at rt before additional ammonium molybdate tetrahydrate (2.82 mg, 2.284 µmol) and hydrogen peroxide (1 mL) were added. Saturated NaCl was added to the mixture followed by extraction with ethyl acetate. The combined organics were dried with Na$_2$SO$_4$, filtered and concentrated. The crude was chromatographed (silica, ethyl acetate/hexanes) to give the title compound (3 mg, 6.38 µmol, 28.0% yield) as a white solid. ESI-MS m/z=468.06, 470.06[M−H]$^−$.

Example 50

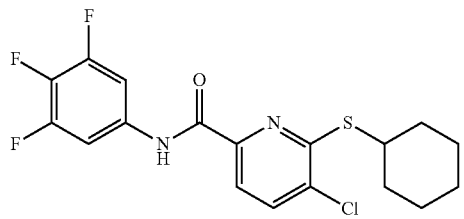 [SMILES: O=C(Nc1cc(F)c(F)c(F)c1)c1ccc(Cl)c(SC2CCCCC2)n1]

Step 50a. A solution of 3,4,5-trifluoroaniline (766 mg, 5.21 mmol) and 5,6-dichloropicolinic acid (500 mg, 2.60 mmol) in DMF (13 mL) was treated with HATU (1485 mg, 3.91 mmol) and Hunig's base (1.365 mL, 7.81 mmol) at rt for 1 hour. It was diluted with ethyl acetate and washed with $H_2O$ and saturated NaCl. The organic was dried with $Na_2SO_4$, filtered and concentrated. The crude product was chromatographed (silica, ethyl acetate/hexanes) to give the desired compound (696 mg, 2.168 mmol, 83% yield) as a white solid.

Step 50b. A solution of compound from step 50a (109 mg, 0.339 mmol) in DMF (1.7 ml) was treated with Hunig's base (119 μl, 0.679 mmol) and cyclohexanethiol (83 μl, 0.679 mmol) at 80° C. for 18 hours. It was diluted with ethyl acetate and washed with $H_2O$ and saturated NaCl. The organic was dried with $Na_2SO_4$, filtered and concentrated. The crude was chromatographed (silica, ethyl acetate/hexanes) to give the desired compound (6 mg, 0.015 mmol, 4.41% yield) as a white solid.

Step 50c. A mixture of compound from step 50b (6 mg, 0.015 mmol) and m-CPBA (77% w/w, 25.8 mg, 0.115 mmol) in DCM (1 ml) was stirred at rt for 2 hours then evaporated. The residue was chromatographed (silica, ethyl acetate/hexanes) to give the title compound (5 mg, 77%) as a white solid. ESI-MS m/z=431.06, 433.04[M−H]⁻.

Example 53

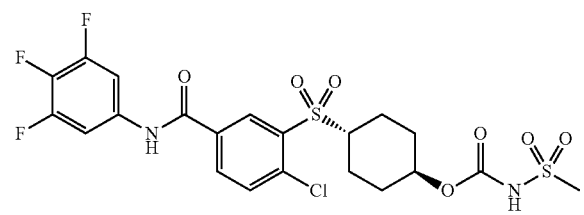 [SMILES: CS(=O)(=O)NC(=O)O[C@H]1CC[C@H](S(=O)(=O)c2cc(C(=O)Nc3cc(F)c(F)c(F)c3)ccc2Cl)CC1]

A stirred solution of compound from Example 3 (0.034 g, 0.076 mmol) in THF (0.5 mL) was treated with DIPEA (0.020 g, 0.15 mmol) and CDI (0.013 g, 0.084 mmol) for 16 h at rt. Methanesulfonamide (0.014 g, 0.15 mmol) in DMF (0.15 mL) and potassium carbonate (0.039 g, 0.28 mmol) were added. The mixture was heated at 65° C. for 16 h. It was diluted with ethyl acetate and washed with water, brine. The organic was dried ($Na_2SO_4$) and concentrated. The crude was purified by Prep-HPLC using a C18 column with acetonitrile/water as eluent to give the title compound (6.5 mg, 15%). ESI-MS m/z=567.02, 569.02 [M−H]⁻.

Example 54

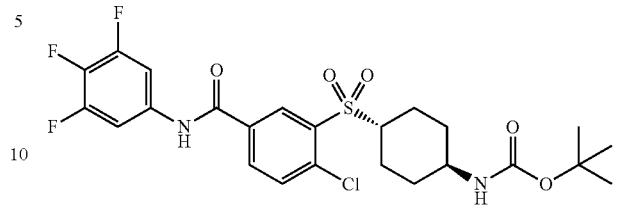

Step 54a. A stirred mixture of compound from Step 1c (0.64 g, 2.0 mmol) and cesium carbonate (0.78 g, 2.4 mmol) in DMF (7.0 mL) at rt was treated with tert-butyl cis-4-iodo (cyclohexyl)carbamate (0.98 g, 3.0 mmol) overnight. It was diluted with ethyl acetate and washed with water and brine. The organic was dried ($Na_2SO_4$), filtered and concentrated. The residue was chromatographed (silica, hexanes/EtOAc) to give the desired compound as white solid (0.48 g, 47%). ESI-MS m/z=513.12, 515.12 [M−H]⁻.

Step 54b. A stirred mixture of compound from Step 54a (0.19 g, 0.37 mmol) in DCM (10 mL) at 0° C. was added mCPBA (0.25 g 77%, 1.1 mmol). It was stirred at rt overnight. It was diluted with ethyl acetate and washed with a mixture of sat. aqueous $NaHCO_3$ solution, $Na_2S_2O_3$ solution, and brine. The organic was dried ($Na_2SO_4$) and concentrated. The crude was chromatographed (silica hexanes/EtOAc) to give the title compound (0.20 g, 76%). ESI-MS m/z=545.11, 547.11 [M−H]⁻.

Example 55

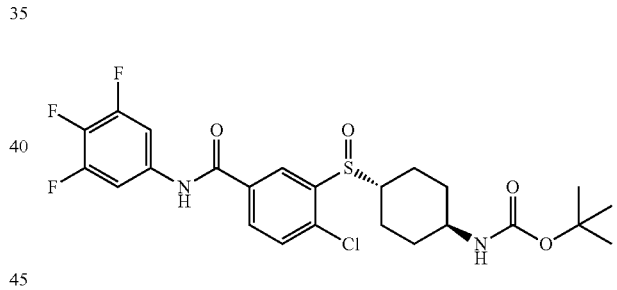

The title compound (0.041 g, 16%) was isolated from step 54b. ESI-MS m/z=529.11, 531.11 [M−H]⁻.

Example 60

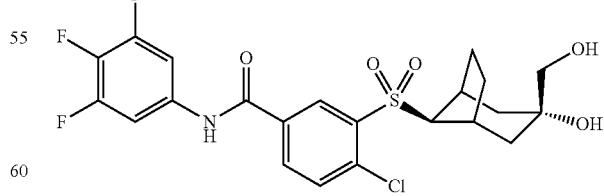

Method A: The compound from Step 39c (125 mg, 0.285 mmol) was dissolved in acetone (3.42 ml) and water (0.18 ml) at rt followed by addition of osmium tetroxide (2.5% in tBuOH, 0.179 ml, 0.014 mmol) and NMO (167 mg, 1.427 mmol). After 2 hours additional NMO (167 mg, 1.427 mmol) was added. It was stirred for another 2 hours before m-CPBA (77% w/w, 246 mg, 1.099 mmol) was added and stirring was continued for 18 hours. It was diluted with ethyl acetate and washed with NaHCO$_3$ and brine. The organic was dried (Na$_2$SO$_4$), filtered and concentrated. The crude was chromatographed (silica, ethyl acetate/hexanes) to give the title compound (97 mg, 0.192 mmol, 67.4% yield) as a white solid. ESI-MS m/z=502.09, 504.07[M−H]$^-$.

Method B: To the solution of the compound from step 138c (1.80 g, 3.81 mmol) in NMP (5 mL), m-CPBA (77 wt %, 2.14 g, 9.54 mmol) was added. It was stirred at rt for 20 hours before aq. NaS$_2$O$_3$ (3 mL) was added followed by aq. NaHCO$_3$(3 mL) and MeOH (5 mL). The white solid was collected under vacuum and washed with aq. NaHCO$_3$, water. This mixture was further recrystallized from MeOH to give the title compound (1.7 g, 87%). ESI-MS m/z=502.07, 504.07 [M−H]$^-$.

Example 61

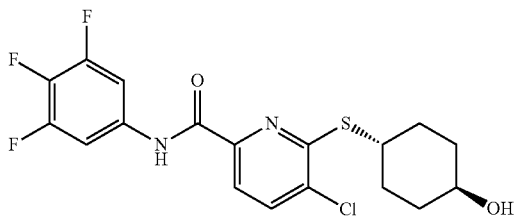 [SMILES: O=C(Nc1cc(F)c(F)c(F)c1)c1ccc(Cl)c(S[C@H]2CC[C@H](O)CC2)n1]

Step 61a. A mixture of the compound from Step 50a (100 mg, 0.311 mmol) and sodium hydrogensulfide (20.95 mg, 0.374 mmol) in DMF (1.6 ml) was stirred at rt for 2 hours before H$_2$O was added. It was extracted with ethyl acetate. The combined organics were dried with Na$_2$SO$_4$, filtered and concentrated. The residue was used for next step without purification.

Step 61b. A mixture of the compound from Step 61a (63 mg, 0.198 mmol), tert-butyl-(((1s,4s)-4-iodocyclohexyl)oxy)dimethylsilane (80 mg, 0.235 mmol), and potassium carbonate (54.6 mg, 0.395 mmol) in DMF (988 µl) was heated at 80° C. for 1 hour. It was diluted with ethyl acetate and washed with H$_2$O and saturated NaCl. The organic was dried with Na$_2$SO$_4$, filtered and concentrated. The crude was chromatographed (silica, ethyl acetate-hexanes) to give the desired compound (8 mg, 0.015 mmol, 7.81% yield) as a white solid.

Step 61c. A solution of the compound from Step 61b (8 mg, 0.015 mmol) in MeOH (1 ml) was treated with HCl (12M, 3.86 µl, 0.015 mmol) at rt for 1 hour. It was diluted with ethyl acetate and washed with saturated NaHCO$_3$ and saturated NaCl. The organic was dried with Na$_2$SO$_4$, filtered and concentrated. The crude was chromatographed (silica, ethyl acetate/hexanes) to give the title compound (6 mg, 0.014 mmol, 93% yield) as a white solid. ESI-MS m/z=415.05, 417.04[M−H]$^-$.

Example 62

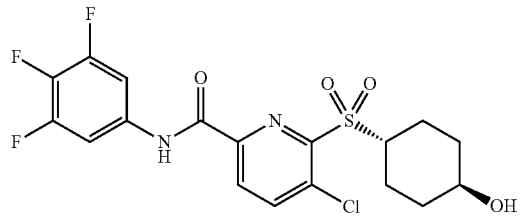 [SMILES: O=C(Nc1cc(F)c(F)c(F)c1)c1ccc(Cl)c(S(=O)(=O)[C@H]2CC[C@H](O)CC2)n1]

A mixture of the compound from Step 61c (6 mg, 0.014 mmol) and m-CPBA (77% w/w, 20 mg, 0.089 mmol) in DCM (1 ml) was stirred at rt for 1 hour. It was diluted with ethyl acetate and washed with saturated NaHCO$_3$ and saturated NaCl. The organic was dried with Na$_2$SO$_4$, filtered and concentrated. The crude was chromatographed (silica, ethyl acetate/hexanes) to give the title compound (3.5 mg, 54%) as a white solid. ESI-MS m/z=447.07, 449.04[M−H]$^-$.

Example 63

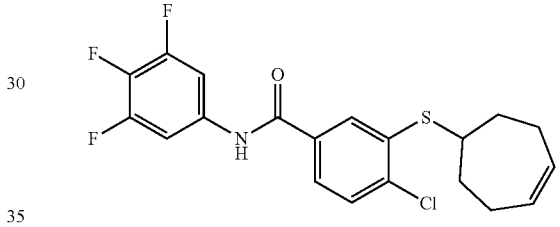

Step 63a. Into a stirred solution of pent-4-enal (5 g, 59.4 mmol) in THF (50 mL) was added a solution of but-3-en-1-ylmagnesium bromide (78 mL, 77.3 mmol) at −78° C. It was warmed up to and kept at rt for 1 hour and quenched with saturated NH$_4$Cl before partition (EtOAc/H$_2$O). The organic was dried (Na$_2$SO$_4$) and concentrated. The residue was chromatographed (silica, ethyl acetate/petroleum ether) to give the desired compound as yellow oil (6.1 g, 73.35%). HNMR (CDCl$_3$, σ): 5.91-5.75 (m, 2H), 5.15-4.95 (m, 4H), 3.71-3.60 (m 1H), 2.26-2.05 (m, 4H), 1.62-1.49 (m, 4H).

Step 63b. Into the solution of the compound of step 63a (5 g, 35.71 mmol) in DCM (120 mL) was added Grubb's 2"d-generation catalyst (910.71 mg, 1.07 mmol) at rt. It was stirred at rt for 16 hours before being concentrated. The crude was chromatographed (silica, ethyl acetate/petroleum ether) to give the desired compound as brown oil (2.4 g, 60.0%). HNMR (CDCl$_3$): 5.85-5.77 (m, 2H), 4.90-4.82 (m, 1H), 2.31-2.18 (m, 2H), 2.10-1.85 (m 4H), 1.55-1.35 (m, 2H).

Step 63c. A solution of compound from step 63b (2 g, 17.85 mmol), methylsulfonyl chloride (2.44 g, 21.42 mmol) and Et$_3$N (3.61 g, 35.7 mmol) in DCM (200 mL) was stirred for 1 hour at rt. It was diluted with H$_2$O and extracted with DCM. The organic was washed with aq. NaHCO$_3$, dried (Na$_2$SO$_4$) and concentrated. The residue was passed through a short column of silica to give the desired compound as yellow oil (3.2 g, 94.3%), which was used directly in next step without further purification.

Step 63d. A mixture of compounds from step 63c (72 mg, 0.37 mmol), example 1c (100 mg, 0.32 mmol) and K$_2$CO$_3$ (88 mg, 0.64 mmol) in DMF (3 mL) was stirred for 3 hours

Example 64

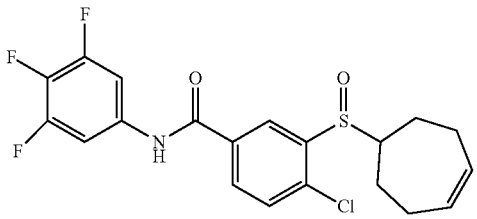 [SMILES: O=C(Nc1cc(F)c(F)c(F)c1)c1ccc(Cl)c(S(=O)C2CCC=CCC2)c1]

A solution of compound of example 63 (50 mg, 0.12 mmol) and m-CPBA (77% W/W, 22 mg, 0.1 mmol) in DCM (2 mL) was stirred for 3 hours at rt. It was concentrated and the residue was purified by Prep-HPLC (MeCN/H$_2$O, 0.1% FA) to give the title compound as white solid (2.1 mg, 4.1%). ESIMS m/z=427.90, 429.90 [M+H]$^+$; $^1$H-NMR (300 MHz, CDCl$_3$) δ 9.15(s, 1H), 8.19 (s, 1H), 8.09 (m, 1H), 7.54 (m, 3H), 5.77 (m, 2H), 3.08 (m, 1H), 2.21 (m, 5H), 1.75 (m, 1H), 1.55 (m, 2H).

Example 70

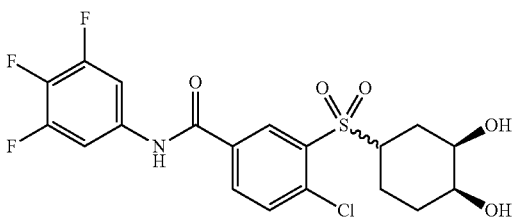 [SMILES: O=C(Nc1cc(F)c(F)c(F)c1)c1ccc(Cl)c(S(=O)(=O)C2CC[C@H](O)[C@H](O)C2)c1]

To a mixture of compound from Example 20 (0.022 g, 0.051 mmol) and NMO (0.024 g, 0.21 mmol) in acetone (2.5 mL) and water (0.3 mL) was added OsO$_4$ (2.5% in t-BuOH, 0.16 mL, 0.013 mmol). It was stirred at rt overnight before being diluted with ethyl acetate and washed with sat. aqueous Na$_2$S$_2$O$_3$ and brine. The organic was dried (Na$_2$SO$_4$) and concentrated. The crude was chromatographed (silica hexanes/EtOAc) to give the title compound as a 1:1 mixture of diastereomers (0.015 g, 63%). ESI-MS m/z=462.04, 464.04 [M–H]$^-$.

Example 71

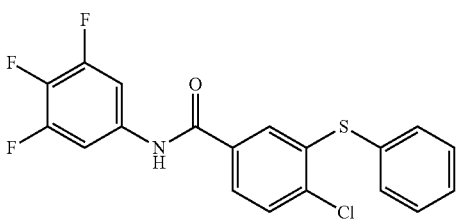 [SMILES: O=C(Nc1cc(F)c(F)c(F)c1)c1ccc(Cl)c(Sc2ccccc2)c1]

To a stirred solution of compound from step 1c (40 mg, 0.126 mmol) in 2-propanol (1.5 ml) at rt was added K$_2$CO$_3$ (52.2 mg, 0.378 mmol) and iodobenzene (51.4 mg, 0.252 mmol), followed by ethylene glycol (0.014 ml, 0.252 mmol) and copper(I) iodide (11.99 mg, 0.063 mmol). It was then heated to and kept at 60° C. for 3 days. After cooling, it was diluted with EtOAC (30 mL) and washed with brine. The organic was dried and concentrated. The residue was chromatographed (silica, EtOAc-hexanes) to give the title compound (38 mg, 77%). ESI-MS m/z=392.09, 394.08 [M–H]$^-$. $^1$HNMR (400 MHz, Methanol-d$_4$) δ 7.73 (dd, J=8.3, 2.2 Hz, 1H), 7.65-7.55 (m, 2H), 7.54-7.39 (m, 7H).

Example 72

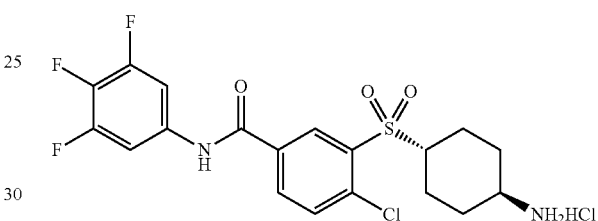

The compound of Example 54 (0.12 g, 0.22 mmol) was treated with HCl in dioxane (4N, 2.0 mL) at 0° C. It was then slowly warmed up to rt in 30 min. The volatiles were removed to give the title compound as HCl salt (0.10 g, 97%). ESI-MS m/z=445.06, 447.06 [M–H]$^-$.

Example 73

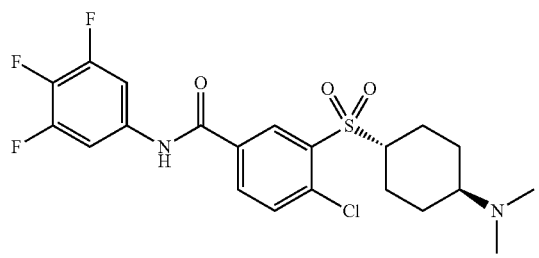 [SMILES: CN(C)[C@H]1CC[C@H](S(=O)(=O)c2cc(C(=O)Nc3cc(F)c(F)c(F)c3)ccc2Cl)CC1]

To a stirred mixture of compound of Example 72 (0.033 g, 0.068 mmol) and formaldehyde (37% in water, 0.057 g, 0.69 mmol) in MeOH (2 mL) was treated with NaBH$_3$CN (0.013 g, 0.21 mmol) at rt for 1 h. It was quenched with sat. aqueous NaHCO$_3$ and extracted with ethyl acetate then washed with water and brine. The organic was dried (Na$_2$SO$_4$) and concentrated. The crude was chromatographed (silica hexanes/EtOAc) to give the title compound (0.028 g, 86%). ESI-MS m/z=473.16, 475.16 [M–H]$^-$.

Example 75

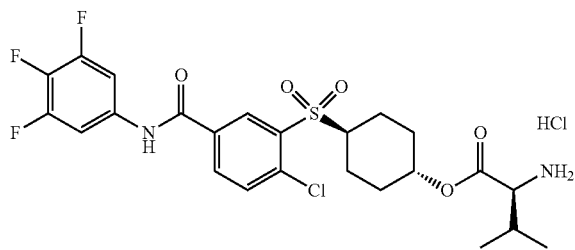 [SMILES: CC(C)[C@H](N)C(=O)O[C@H]1CC[C@H](S(=O)(=O)c2cc(C(=O)Nc3cc(F)c(F)c(F)c3)ccc2Cl)CC1 ; Cl]

A solution of compound from example 76 (135 mg, 0.209 mmol) in dioxane (2 ml) was treated with HCl (4M in dioxane, 2 mL, 65.8 mmol) at rt for 1 hour before additional HCl (4M in dioxane, 2 mL, 65.8 mmol) was added. It was heated to and kept at 50° C. for 2 hours. It was evaporated and lyophilized to give the title compound (110 mg, 0.189 mmol, 90%) as a white powder. ESI-MS m/z=545.11, 547.11[M–H]⁻.

Example 76

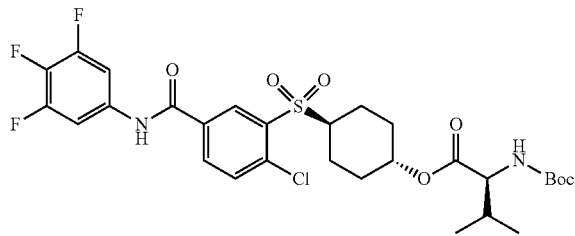 [SMILES: CC(C)[C@H](NC(=O)OC(C)(C)C)C(=O)O[C@H]1CC[C@H](S(=O)(=O)c2cc(C(=O)Nc3cc(F)c(F)c(F)c3)ccc2Cl)CC1]

A solution of the compound of example 3 (150 mg, 0.335 mmol) in DCM (3.04 ml) and DMF (0.30 ml) was treated with (tert-butoxycarbonyl)-L-valine (109 mg, 0.502 mmol), EDC (80 mg, 0.419 mmol) and DMAP (82 mg, 0.670 mmol) for 3 hours at rt. It was diluted with ethyl acetate and then washed with H₂O and saturated NaCl. The organic was dried with Na₂SO₄, filtered and concentrated. The crude was chromatographed (silica, ethyl acetate/hexanes) to give the title compound (175 mg, 0.270 mmol, 81% yield) as a white solid. ESI-MS m/z=645.17, 647.15 [M–H]⁻.

Example 77

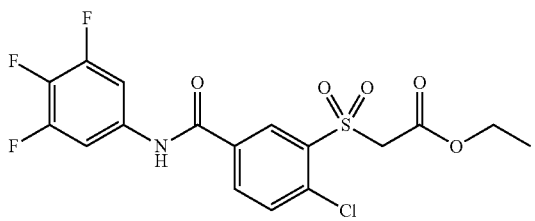 [SMILES: CCOC(=O)CS(=O)(=O)c1cc(C(=O)Nc2cc(F)c(F)c(F)c2)ccc1Cl]

Step 77a. To a stirred mixture of compound from Step 1c (0.93 g, 2.9 mmol) and cesium carbonate (1.1 g, 3.5 mmol) in DMF (10 mL) at rt was added ethyl 2-bromoacetate (0.51 g, 3.1 mmol). It was stirred at rt for 1 h. It was diluted with ethyl acetate and washed with water, brine. The organic was dried (Na₂SO₄), filtered and concentrated. The crude was chromatographed (silica, hexanes/EtOAc) to give the desired compound as white solid (1.1 g, 93%). ESI-MS m/z=402.02, 404.02 [M–H]⁻.

Step 77b. To a stirred mixture of compound from Step 77a (1.1 g, 2.7 mmol) in DCM (20 mL) at 0° C. was added mCPBA (77%, 1.8 g, 8.1 mmol). It was stirred at rt overnight. It was diluted with ethyl acetate and washed with a mixture of sat. aqueous NaHCO₃ solution, Na₂S₂O₃ solution, and brine. The organic was dried (Na₂SO₄) and concentrated. The crude was chromatographed (silica, hexanes/EtOAc) to give the title compound (1.1 g, 91%). ESI-MS m/z=473.16, 475.16 [M–H]⁻.

Example 78

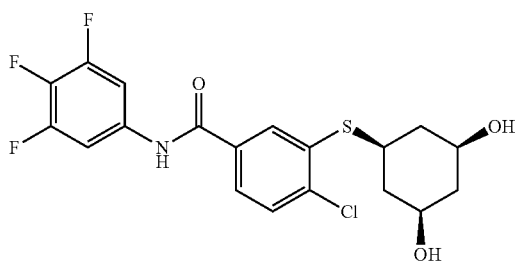 [SMILES: O=C(Nc1cc(F)c(F)c(F)c1)c1ccc(Cl)c(S[C@@H]2C[C@H](O)C[C@H](O)C2)c1]

Step 78a. (1s,3s,5s)-cyclohexane-1,3,5-triol (500 mg, 3.78 mmol) and carbon tetrabromide (1062 mg, 3.20 mmol) were dissolved in DMF (2 ml). Ph₃P (763 mg, 2.91 mmol) was added and the mixture was stirred at rt for 3 hours, then the reaction mixture was diluted with ethyl acetate and then washed with H₂O and saturated NaCl. The organic was dried with Na₂SO₄, filtered and concentrated. The crude was chromatographed (silica, methanol/dichloromethane) to give (1R,3S,5r)-5-bromocyclohexane-1,3-diol (78 mg, 13.74% yield) as a white solid.

Step 78b. A solution of compound of Step 78a (78 mg, 0.400 mmol) in DMF (2.0 ml) was treated with imidazole (109 mg, 1.600 mmol) and TBSCI (181 mg, 1.200 mmol) at rt for 18 hours. It was diluted with ethyl acetate and then washed with H₂O and saturated NaCl. The organic was dried with Na₂SO₄, filtered and concentrated. The crude was chromatographed (silica, ethyl acetate/hexanes) to give the desired compound (212 mg, 100%) as a colorless oil.

Step 78c. A mixture of compound from step Ic (59 mg, 0.186 mmol), K₂CO₃ (51.3 mg, 0.371 mmol) and compound from Step 78a (282 mg, 0.533 mmol) in DMF (929 μl) was heated at 80° C. for 3 hours. It was diluted with ethyl acetate and then washed with H₂O and saturated NaCl. The organic was dried with Na₂SO₄, filtered and concentrated. The crude was chromatographed (silica, ethyl acetate/hexanes) to give the desired compound (107 mg, 0.162 mmol, 87%) as a colorless oil.

Step 78d. A solution of the compound from Step 78c in MeOH (1620 μl) was treated with HCl (12M, 81 μl, 0.324 mmol) was stirred at rt for 1.5 hours. It was diluted with ethyl acetate and then washed with saturated NaHCO₃ and saturated NaCl. The organic was dried with Na₂SO₄, filtered and concentrated. The crude was chromatographed (silica, methanol/dichloromethane) to give the title compound (62 mg, 0.144 mmol, 89% yield) as a white solid. ESI-MS m/z=430.05, 432.05 [M–H]⁻.

Example 79

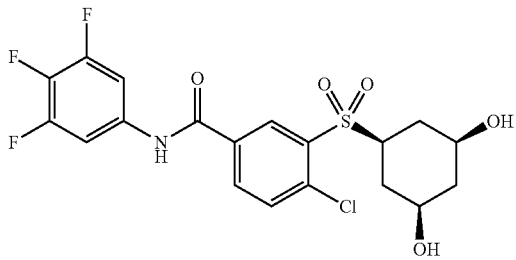 [SMILES: O=C(Nc1cc(F)c(F)c(F)c1)c1ccc(Cl)c(S(=O)(=O)[C@@H]2C[C@H](O)C[C@H](O)C2)c1]

A solution of the compound from Step 78d (47 mg, 0.109 mmol) in DCM (2 ml) and MeOH (2 ml) was treated with m-CPBA (77% w/w, 188 mg, 0.838 mmol) at rt for 3 hours. It was diluted with dichloromethane and then washed with saturated $NaHCO_3$ and saturated NaCl. The organic was dried ($Na_2SO_4$), filtered and concentrated. The crude was chromatographed (silica, methanol/dichloromethane) to give the title compound (24 mg, 47.5%) as a white solid. ESI-MS m/z=462.04, 464.04 [M−H]⁻.

Example 80

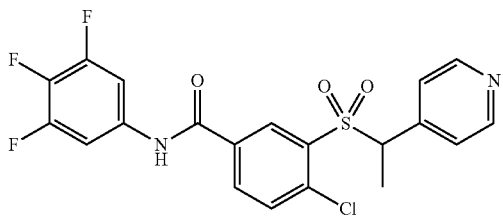 [SMILES: CC(c1ccncc1)S(=O)(=O)c1cc(C(=O)Nc2cc(F)c(F)c(F)c2)ccc1Cl]

Step 80a. A mixture of methyl 4-chloro-3-mercaptobenzoate (202 mg, 1.0 mmol), 4-(bromomethyl) pyridine hydrobromide (378 mg, 1.5 mmol) and DIPEA (0.53 L, 3 mmol) was stirred at rt overnight. It was concentrated and partitioned (EtOAc/$H_2O$). The organic was dried ($Na_2SO_4$) and concentrated. The residue was chromatographed (silica, ethyl acetate/hexanes) to give the desired compound as yellow solid (230 mg, 78%). ESIMS m/z=294.04, 296.04 [M+H]⁺.

Step 80b. Into a solution of compound of step 80a (210 mg, 0.715 mmol) in $CH_2Cl_2$ (8 mL) was added pTSA (204 mg, 1.08 mmol). It was stirred 3 hours before mCPBA (77%, 481 mg, 2.15 mmol) was added. It was further stirred for 16 hours at rt and concentrated. The residue was chromatographed (silica, ethyl acetate/hexanes) to give the desired compound as yellow solid (65 mg, 30%). ESIMS m/z=326.02, 328.02 [M+H]⁺.

Step 80c. Into a solution of freshly prepared LDA (0.26 mmol) in THF was added a solution of compound from 80b (65 mg, 0.2 mmol) at −78° C. It was stirred 15 minutes before MeI (0.04 mL, 0.6 mmol) was added. It was slowly warmed up to −30° C. in 2 hours before being quenched (aq. $NH_4Cl$). It was extracted with EtOAc and the organic was dried ($Na_2SO_4$), filtered and concentrated. The residue was chromatographed (silica, ethyl acetate/hexanes) to give the desired compound as yellow solid (35 mg, 52%). ESIMS m/z=340.11, 342.11[M+H]⁺.

Step 80d. Into a solution of compound from step 80c (25 mg, 0.074 mmol) and 3,4,5-trifluoroaniline (32.5 mg, 0.221 mmol) in toluene (2 mL) was added $Me_3Al$ (2.0 M in toluene, 0.15 mL, 0.30 mmol) at rt. It was heated at 90° C. for 1 h and cooled. Aq. sodium, potassium tartrate (5 mL) was added and it was stirred 2 hours before extraction with EtOAc. The organic was dried ($Na_2SO_4$), filtered and concentrated. The residue was chromatographed (silica, ethyl acetate/hexanes) to give the title compound as yellow solid (12 mg, 36%).

ESIMS m/z=455.09, 457.09 [M+H]⁺.

Example 81

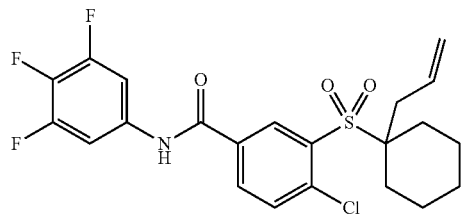 [SMILES: C=CCC1(S(=O)(=O)c2cc(C(=O)Nc3cc(F)c(F)c(F)c3)ccc2Cl)CCCCC1]

Into a solution of freshly prepared LDA (0.84 mmol) in THF was added a solution of compound of example 12 (121 mg, 0.28 mmol) at −78° C. It was stirred 20 minutes before allyl bromide (0.03 mL, 0.34 mmol) was added. It was slowly warmed up to −30° C. before being quenched (aq. $NH_4Cl$) and extracted with EtOAc. The organic was dried ($Na_2SO_4$), filtered and concentrated. The residue was chromatographed (silica, ethyl acetate/hexanes) to give the title compound as yellow solid (49 mg, 45%). ESIMS m/z=470.08, 472.08[M−H]⁻.

Example 82

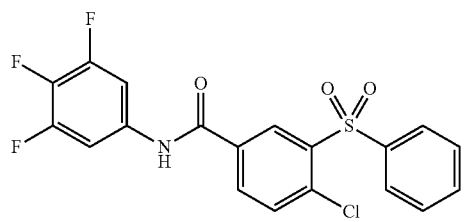 [SMILES: O=C(Nc1cc(F)c(F)c(F)c1)c1ccc(Cl)c(S(=O)(=O)c2ccccc2)c1]

Into a stirred solution of compound of example 71 (2 mg, 5.08 μmol) in DCM (1.0 ml) was added 3-chlorobenzoperoxoic acid (purity 77%, 3.98 mg, 0.018 mmol) at 0° C. It was then slowly warmed up to and kept at rt overnight. It was diluted with EtOAc, washed with aq.

$Na_2S_2O_3$, and brine. The organic was dried and concentrated. The crude was chromatographed (silica, EtOAc-hexanes) to give the title compound (1.8 mg, 83%). ESI-MS m/z=424.08, 426.07 [M−H]⁻. ¹HNMR (400 MHz, Methanol-d4) δ 8.78 (d, J=2.2 Hz, 1H), 8.07 (dd, J=8.3, 2.2 Hz, 1H), 7.96-7.86 (m, 2H), 7.66-7.59 (m, 2H), 7.56-7.49 (m, 4H).

Example 83

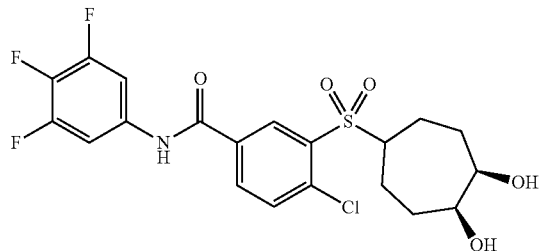 [SMILES: O=C(Nc1cc(F)c(F)c(F)c1)c1ccc(Cl)c(S(=O)(=O)C2CC[C@@H](O)[C@@H](O)CC2)c1]

OsO$_4$ (33 mg/mL, 0.02 mL) was added into a solution of compounds from example 63 (50 mg, 0.12 mmol) and NMO (58 mg, 0.50 mmol) in t-BuOH (1 mL). It was stirred overnight at rt and quenched (aq. Na$_2$S$_2$O$_3$), extracted with DCM. The organic was dried (Na$_2$SO$_4$), filtered and concentrated. The residue was purified by Prep-HPLC (MeCN/H$_2$O, 0.1% formic acid) to give the title compound as 1:1 diastereomeric mixture and white solid (19.7 mg, 34%). ESIMS m/z=475.85, 4477.85 [M−H]; $^1$H NMR (400 MHz, DMSO-d$_6$) δ 10.91 (s, 1H), 8.52 (m, 1H), 8.27 (m, 1H), 7.98 (m, 1H), 7.72 (m, 2H), 4.52 (d, J=4.2 Hz, 1H), 4.45 (d, J=3.8 Hz, 1H), 3.80 (m, 1H), 3.59 (m, 2H), 1.90 (m, 3H), 1.63 (m, 4H), 1.43 (m, 1H).

Example 84

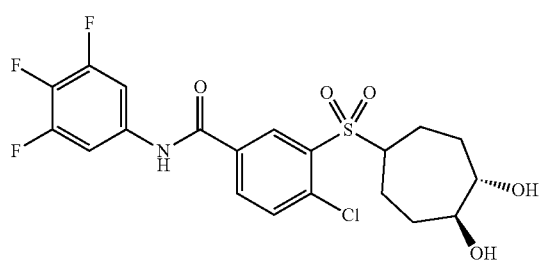 [SMILES: O=C(Nc1cc(F)c(F)c(F)c1)c1ccc(Cl)c(S(=O)(=O)C2CC[C@H](O)[C@@H](O)CC2)c1]

Step 84a. A solution of compound of example 63 (250 mg, 0.61 mmol) and mCPBA (629.52 mg, 3.66 mmol) in DCM (2 mL) was stirred for 16 hours at rt. It was concentrated and the residue was chromatographed (silica, ethyl acetate/petroleum ether) to give the desired compound as yellow solid (150 mg, 51.55%). ESIMS m/z=460.25, 462.25[M+H]$^+$.

Step 84b. A solution of compound from step 84a (50 mg, 0.11 mmol) in THE (3 mL) and H$_2$SO$_4$ (10% in water, 0.3 mL) was stirred for 4 hours at rt before the pH of the solution was adjusted to 8 with aq. NaHCO$_3$. It was extracted with EtOAc and the organic was dried (Na$_2$SO$_4$) and concentrated. The residue was purified by Flash-Prep-HPLC to give the title compound as white solid (16.9 mg, 32.2%). ESIMS m/z=476.20, 478.20 [M−H]$^-$.

Example 86

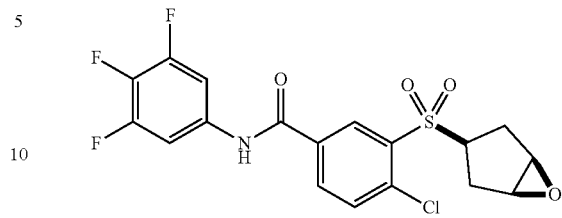

Step 86a. A stirred solution of cyclopent-3-en-1-ol (236 mg, 2.81 mmol) in CH$_2$Cl$_2$ (14 mL) was added triethylamine (0.59 mL, 4.21 mmol) and methanesulfonyl chloride (0.26 mL, 3.37 mmol) at 0° C., then warmed up to rt and stirred overnight. It was quenched with saturated NaHCO$_3$ aqueous solution, and extracted with CH$_2$Cl$_2$. The combined organics were washed with brine, dried over Na$_2$SO$_4$, concentrated. The crude was chromatographed (silica, EtOAc/hexanes) to give the desired compound (295 mg, 65%) as a colorless oil. 1H NMR, 400 MHz (CDCl$_3$): δ 5.77-5.71 (m, 2H), 5.38 (tt, J=6.6, 2.6 Hz, 1H), 3.02 (s, 3H), 2.86-2.75 (m, 2H), 2.72-2.62 (m, 2H).

Step 86b. A stirred solution of the compound from Step 1c (191 mg, 0.60 mmol) and the compound from Step 86a (195 mg, 1.2 mmol) in DMF (6.0 mL) was treated with K$_2$CO$_3$ (125 mg, 0.90 mmol) at rt overnight. It was diluted with EtOAc, washed with water and brine, dried over Na$_2$SO$_4$, and concentrated. The crude was chromatographed (EtOAc/hexanes) to give the desired compound (189 mg, 82%) as white solid. ESIMS m/z=383.03, 384.03 [M−H]$^-$.

Step 86c. To a stirred solution of the compound from Step 86b (70 mg, 0.18 mmol) in CH$_2$Cl$_2$ (6.1 mL) at rt was treated with mCPBA (77% w/w, 247 mg, 1.1 mmol) at rt overnight. It was quenched with aqueous saturated Na$_2$S$_2$O$_3$ and extracted with CH$_2$C$_2$. The combined organics were washed with brine, dried over Na$_2$SO$_4$, concentrated. The crude was chromatographed (acetone/hexanes) to give the title compound (14 mg, 18%) as white solid. ESIMS m/z=430.00, 432.00 [M−H]$^-$.

Example 87

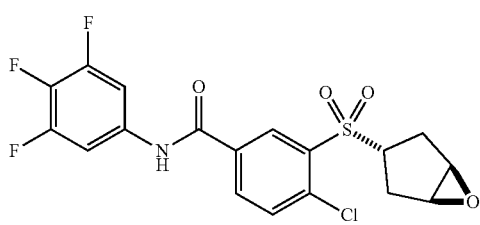

The title compound (37 mg, 47%) was isolated from step 86c as white solid. ESI-MS m/z=430.00, 432.00 [M−H]$^-$.

Example 88

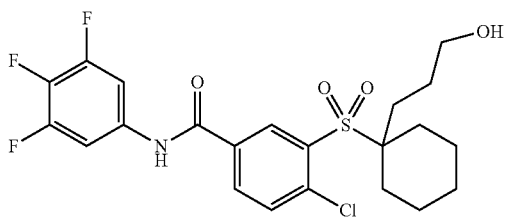 [SMILES: O=C(Nc1cc(F)c(F)c(F)c1)c1ccc(Cl)c(S(=O)(=O)C2(CCCO)CCCCC2)c1]

Into a solution of compound of example 81 (25 mg, 0.053 mmol) in THF (2 mL) was added BH$_3$·DMS (2.0 M in THF, 0.05 mL, 0.1 mmol) at rt. It was stirred for 3 hours before water was added, followed by NaBO$_3$·4H$_2$O (170 mg, 0.71 mmol). It was stirred 2 hours before being extracted with EtOAc and dried (Na$_2$SO$_4$). After filtration and concentration, the residue was chromatographed (silica, ethyl acetate/hexanes) to give the title compound as white solid (5 mg, 20%). ESIMS m/z=488.08, 490.08 [M–H]$^-$.

Example 89

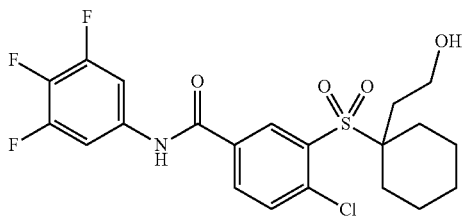 [SMILES: O=C(Nc1cc(F)c(F)c(F)c1)c1ccc(Cl)c(S(=O)(=O)C2(CCO)CCCCC2)c1]

Into a solution of compound of example 81 (25 mg, 0.053 mmol) in DCM (4 mL) was bubbled O3 at –78° C. for 15 minutes before raised to rt. Dimethylsulfide (2 mL) was added and it was stirred o/n before was concentrated. NaBH$_4$ (4 mg, 0.1 mmol) was added to the solution of this crude in EtOH (2 mL). It was stirred 2 hours at rt before aq NH$_4$Cl (2 mL) was added. It was partitioned (EtOAc/H$_2$O). The organic was dried (Na$_2$SO$_4$). After filtration and concentration, the residue was chromatographed (silica, ethyl acetate/hexanes) to give title compound as white solid (6 mg, 20%). ESIMS m/z=474.08, 476.07 [M–H]$^-$.

Example 90

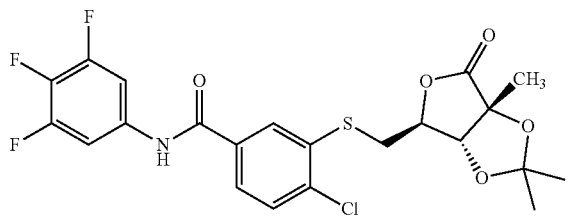 [SMILES: CC1(C)O[C@@H]2[C@@H](CSc3cc(C(=O)Nc4cc(F)c(F)c(F)c4)ccc3Cl)OC(=O)[C@]2(C)O1]

Step 90a. A solution of (3R,4R,5R)-3,4-dihydroxy-5-(hydroxymethyl)-3-methyldihydro-furan-2(3H)-one (0.5 g, 3.08 mmol) in acetonitrile (10 ml) was treated with 2,2-dimethoxy-propane (3.79 ml, 30.8 mmol) and pTSA (0.587 g, 3.08 mmol) at rt for 48 hours before being poured into aq NaHCO$_3$. It was diluted with ethyl acetate and then washed with H$_2$O and saturated NaCl. The organic was dried with Na$_2$SO$_4$, filtered and concentrated. The crude was chromatographed (silica, ethyl acetate/hexanes) to give the desired compound (438 mg, 70.2% yield) as a yellow gum.

Step 90b. A solution of the compound from Step 90a (438 mg, 2.166 mmol) in DCM (10.831 ml) was cooled to 0° C. followed by addition of Hunig's base (0.567 ml, 3.25 mmol) and MsCl (0.203 ml, 2.60 mmol) and stirred at rt for 3 hours. It was diluted with dichloromethane and then washed with H$_2$O and saturated NaCl. The organic was dried with Na$_2$SO$_4$, filtered and concentrated. The crude was chromatographed (silica, ethyl acetate/hexanes) to give the desired compound (596 mg, 98% yield) as a yellow gum.

Step 90c. A solution of the compound from step 1c (50 mg, 0.157 mmol) and the compound from Step 90b (88 mg, 0.315 mmol) in DMF (0.79 ml) was treated with K$_2$CO$_3$ (43.5 mg, 0.315 mmol) at 80° C. for 30 minutes. It was diluted with ethyl acetate and then washed with H$_2$O and saturated NaCl. The organic was dried with Na$_2$SO$_4$, filtered and concentrated. The crude was chromatographed (silica, ethyl acetate/hexanes) to give the title compound (78 mg, 99% yield) as a white solid. ESI-MS m/z=500.05, 502.05 [M–H]$^-$.

Example 91

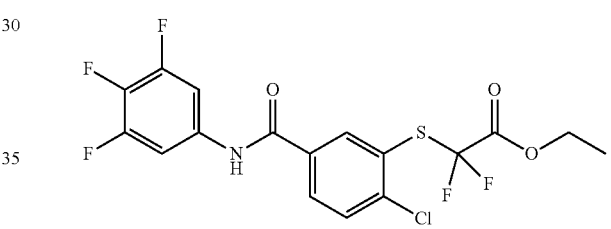

A stirred solution of the compound from step 1c (50 mg, 0.157 mmol) in DMF (2.0 ml) was treated with K$_2$CO$_3$ (47.9 mg, 0.346 mmol) and ethyl 2-bromo-2,2-difluoroacetate (96 mg, 0.472 mmol) at rt for 30 min. It was diluted with EtOAC (30 mL) and washed with brine. The organic was dried and concentrated. The crude was chromatographed (silica, EtOAc-hexanes) to give the title compound (50 mg, 72%). ESI-MS m/z=438.04, 440.00 [M–H]$^-$. $^1$HNMR (400 MHz, CDCl$_3$) δ 8.17 (d, J=2.1 Hz, 1H), 8.01-7.77 (m, 2H), 7.67 (d, J=8.3 Hz, 1H), 7.51-7.35 (m, 2H), 4.36 (q, J=7.1 Hz, 2H), 1.35 (t, J=7.1 Hz, 3H).

Example 92

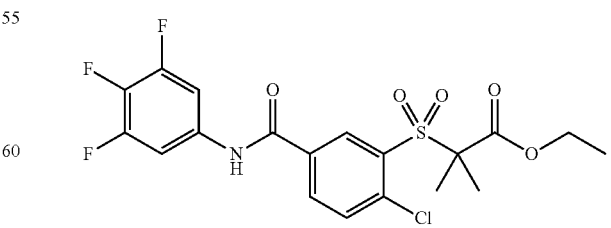

To a stirred mixture of compound of Example 77 (0.070 g, 0.16 mmol) and NaH (0.0096 g 60%, 0.24 mmol) in DMF (1.5 mL) at rt was added MeI (0.045 g, 0.24 mmol). It was stirred at rt for 16 h. It was quenched with sat. aqueous NH₄Cl. It was extracted with ethyl acetate and washed with water, brine. The organic was dried (Na₂SO₄) and concentrated. The crude was chromatographed (silica hexanes/EtOAc) to give the title compound (0.031 g, 43%), ESI-MS m/z=462.04, 464.04 [M−H]⁻.

Example 95

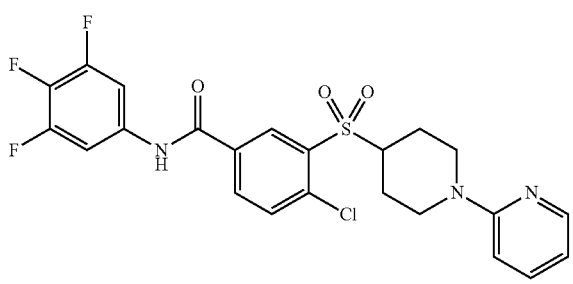 [SMILES: O=C(Nc1cc(F)c(F)c(F)c1)c1ccc(Cl)c(S(=O)(=O)C2CCN(c3ccccn3)CC2)c1]

Step 95a. A stirred solution of the compound from Step 1c (128 mg, 0.41 mmol) and tert-butyl 4-iodopiperidine-1-carboxylate (252 mg, 0.81 mmol) in DMF (4.0 mL) was treated with K₂CO₃ (112 mg, 0.81 mmol) at rt overnight. It was diluted with EtOAc, washed with water and brine, dried over Na₂SO₄, concentrated. The crude was chromatographed (silica, EtOAc/hexanes) to give the desired compound (195 mg, 96%) as colorless oil, ESIMS m/z=499.11, 501.11 [M+H]⁺.

Step 95b. A stirred solution of the compound from Step 95a (195 mg, 0.39 mmol) in CH₂C₁₂ (7.8 mL) was treated with mCPBA (77% w/w, 349 mg, 1.6 mmol) at rt overnight. It was quenched with saturated aq Na₂S₂O₃, and stirred at rt for 10 minutes. The aqueous was extracted with CH₂C₁₂. The combined organics were washed with brine, dried over Na₂SO₄, concentrated, and the crude was chromatographed (silica, acetone/hexanes) to give the desired compound as while solid (144 mg, 70%), ESIMS m/z=531.10, 533.10 [M−H]⁻.

Step 95c. A stirred solution of the compound from Step 95b (144 mg, 0.27 mmol) in CH₂C₁₂ (2.7 mL) was treated with TFA (0.62 mL, 8.1 mmol) at 0° C. for 3 hours. It was concentrated and the crude was used in next step directly. ESIMS m/z=433.06, 435.06 [M+H]⁺.

Step 95d. A stirred solution of the compound from Step 95c (33 mg, 0.077 mmol), N-ethyl-N-isopropylpropan-2-amine (0.14 ml, 0.77 mmol) and 2-fluoropyridine (75 mg, 0.77 mmol) in DMSO (1.5 mL) was heated at 140° C. for 3 hours under microwave. It was cooled to rt and diluted with EtOAc, washed with saturated NaHCO₃ solution and brine, dried over Na₂SO₄, concentrated. The crude was chromatographed (silica, EtOAc/hexanes) to give the title compound (2.1 mg, 5.3%) as a white solid. ESI-MS m/z=508.07, 510.07 [M−H]⁻.

Example 97

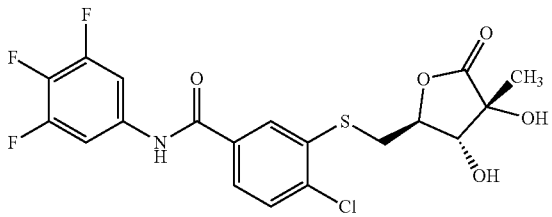 [SMILES: C[C@]1(O)C(=O)O[C@H](CSc2cc(C(=O)Nc3cc(F)c(F)c(F)c3)ccc2Cl)[C@H]1O]

A solution of compound from Step 90c (16 mg, 0.032 mmol) in HOAc (0.5 ml, 80% in H₂O) was treated with TFA (200 µl, 2.60 mmol) at 80° C. for 2 hours. The volatile was evaporated off and the residue was chromatographed (silica, methanol/dichloromethane) to give the title compound (9.5 mg, 64.5%) as white solid. ESIMS m/z=460.02, 462.02 [M−H]⁻.

Example 98

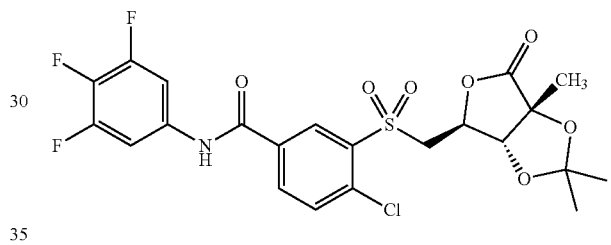

A solution of the compound from Step 90c (52 mg, 0.104 mmol) in DCM (518 µl) was treated with mCPBA (77% w/w, 89 mg, 0.399 mmol) at rt for 18 hours. It was diluted with ethyl acetate and then washed with saturated NaHCO₃ and saturated NaCl. The organic was dried with Na₂SO₄, filtered and concentrated. The crude product was chromatographed (silica, ethyl acetate/hexanes) to give the title product (35 mg, 63.3%) as a color solid. ESI-MS m/z=532.04, 534.04 [M−H]⁻.

Example 99

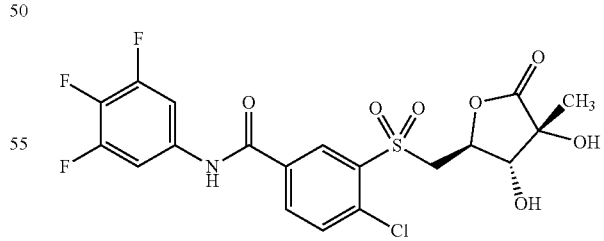

A solution of the compound of example 98 (25 mg, 0.047 mmol) in HOAc (0.5 ml) and water (125 µl) was treated with TFA (100 µl, 1.298 mmol) at 80° C. for 3 hours. It was evaporated and the residue was chromatographed (silica, methanol/dichloromethane) to give the title product (10.4 mg, 45.0%) as white solid. ESI-MS m/z=492.01, 494.01 [M−H]⁻.

Example 100

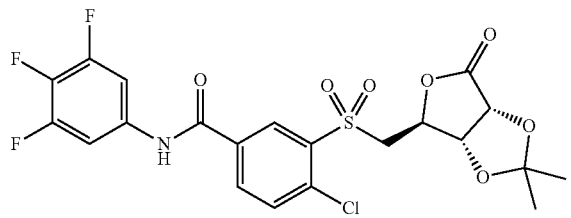 [SMILES: CC1(C)O[C@@H]2[C@@H](CS(=O)(=O)c3cc(C(=O)Nc4cc(F)c(F)c(F)c4)ccc3Cl)OC(=O)[C@@H]2O1]

Step 100a. A solution of (3aR,6R,6aR)-6-(hydroxymethyl)-2,2-dimethyldihydrofuro[3,4-d][1,3]dioxol-4(3aH)-one (250 mg, 1.329 mmol) in DCM (6.6 ml) was cooled to 0° C. before charging Hunig's base (348 µl, 1.993 mmol) and MsCl (124 µl, 1.594 mmol. It was stirred at rt for 18 hours before being diluted with ethyl acetate and washed with $H_2O$ and saturated NaCl. The organic was dried with $Na_2SO_4$, filtered and concentrated. The crude was chromatographed (silica, ethyl acetate/hexanes) to give the desired compound (298 mg, 84%) as a colorless oil.

Step 100b. A solution of the compound from step 1c (50 mg, 0.157 mmol) and the compound from Step 100a (84 mg, 0.315 mmol) in DMF (787 µl) was treated with $K_2CO_3$ (43.5 mg, 0.315 mmol) at 80° C. for 30 minutes. It was diluted with ethyl acetate and then washed with $H_2O$ and saturated NaCl. The organic was dried with $Na_2SO_4$, filtered and concentrated. The crude was chromatographed (silica, ethyl acetate/hexanes) to give the desired compound (37 mg, 48.2%) as white solid.

Step 100c. A solution of compound from Step 100b (37 mg, 0.076 mmol) in DCM was treated with mCPBA (77% w/w, 65.4 mg, 0.292 mmol) at rt for 18 hours. It was diluted with DCM and washed with aq. saturated $NaHCO_3$ and NaCl. The organic was dried with $Na_2SO_4$, filtered and concentrated. The crude was chromatographed (silica, ethyl acetate/hexanes) to give the title compound (28 mg, 71.0%) as white solid. ESI-MS m/z=518.10, 520.08 [M−H]⁻.

Example 101

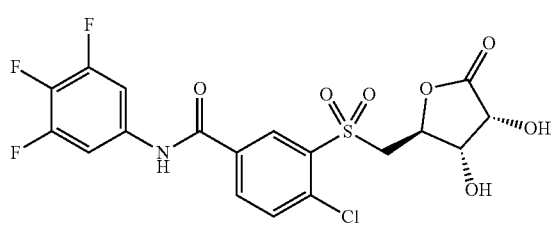 [SMILES: O=C(Nc1cc(F)c(F)c(F)c1)c1ccc(Cl)c(S(=O)(=O)C[C@H]2OC(=O)[C@H](O)[C@@H]2O)c1]

A solution of the compound from Step 100c (15 mg, 0.029 mmol) in HOAc (0.400 ml) and water (0.1 ml) was treated with TFA (0.1 ml, 1.298 mmol) at 80° C. for 2 hours. The volatile was evaporated off and the residue was chromatographed (silica, methanol/dichloromethane) to give the title compound (10 mg, 72.2%) as a white solid. ESI-MS m/z=477.99, 479.99 [M−H]⁻.

Example 103

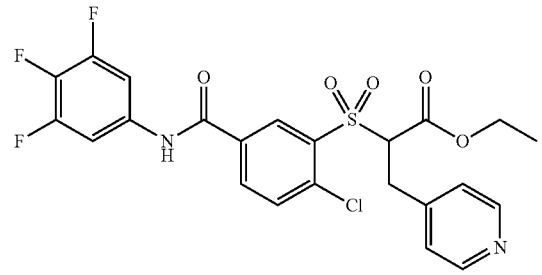 [SMILES: CCOC(=O)C(Cc1ccncc1)S(=O)(=O)c1cc(C(=O)Nc2cc(F)c(F)c(F)c2)ccc1Cl]

A stirred mixture of compound from Example 77 (0.050 g, 0.12 mmol) and NaH (60%, 9.2 mg 0.24 mmol) in DMF (1.5 mL) at rt was added 4-(bromomethyl) pyridine hydrobromide (0.029 g, 0.15 mmol). It was stirred at rt for 16 h and quenched with sat. aqueous $NH_4Cl$. It was extracted with ethyl acetate and washed with water, brine. The organic was dried ($Na_2SO_4$) and concentrated. The crude was chromatographed (silica, hexanes/EtOAc) to give the title compound (0.022 g, 36%). ESI-MS m/z=525.05, 527.05 [M−H]⁻.

Example 104

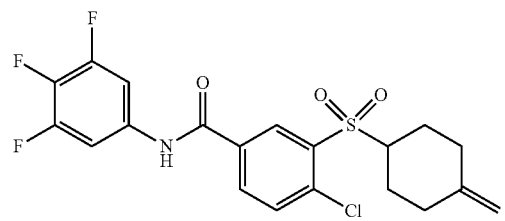 [SMILES: C=C1CCC(S(=O)(=O)c2cc(C(=O)Nc3cc(F)c(F)c(F)c3)ccc2Cl)CC1]

A suspension of methyltriphenylphosphonium bromide (0.45 g, 1.3 mmol) in THF (3 mL) was treated with n-BuLi (1.6 M in hexanes, 0.86 mL, 1.4 mmol) dropwisely at 0° C. for 30 min before the compound of Example 2 (0.22 g, 0.50 mmol) in THF (1 mL) was added. It was stirred at rt for 24 h, then quenched with sat. aqueous $NH_4Cl$. It was extracted with ethyl acetate and washed with water, brine. The organic was dried ($Na_2SO_4$) and concentrated. The crude was chromatographed (silica hexanes/EtOAc) to give the title compound (0.078 g, 35%). ESI-MS m/z=442.05, 444.05 [M−H]⁻.

Example 106

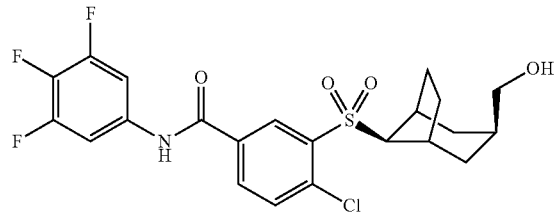 [SMILES: O=C(Nc1cc(F)c(F)c(F)c1)c1ccc(Cl)c(S(=O)(=O)[C@H]2C3CCC2C[C@H](CO)C3)c1]

Step 106a. Into a stirred solution of the compound from Step 39c (38 mg, 0.087 mmol) in THF (0.5 mL) at 0° C. was charged borane-methyl sulfide complex (2M, 0.087 mL, 0.174 mmol). It was stirred for 2 hours at rt. It was cooled to 0° C., water (0.2 mL) and then sodium perborate tetrahydrate (53.4 mg, 0.347 mmol) were added. It was stirred for 2 hours before warming to rt and being diluted with ethyl acetate and washed with H₂O and saturated NaCl. The organic was dried with Na₂SO₄, filtered and concentrated. The crude was chromatographed (silica, ethyl acetate/hexanes) to give the desired compound (24 mg, 60.7%) as a white solid.

Step 106b. A solution of compound from Step 106a (16 mg, 0.035 mmol) in DCM (1.3 ml) was treated with mCPBA (77% w/w, 30.3 mg, 0.135 mmol) at rt for 3 hours. It was charged with saturated NaHCO₃ and extracted with DCM. The organics were dried with Na₂SO₄, filtered and concentrated. The crude was chromatographed (silica, ethyl acetate/hexanes) to give the title compound (11.5 mg, 67.2%) as a white solid. ESI-MS m/z=486.09, 488.07 [M−H]⁻.

Example 107

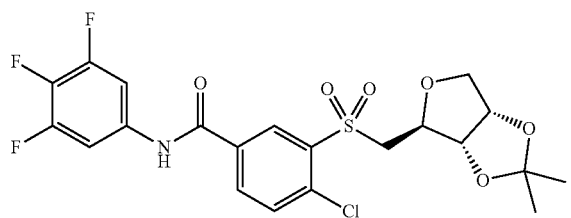 [SMILES: CC1(C)O[C@H]2[C@H](CO[C@@H]2CS(=O)(=O)c2cc(C(=O)Nc3cc(F)c(F)c(F)c3)ccc2Cl)O1]

Step 107a. A mixture of adonitol (1.00 g, 6.57 mmol) and pyridine hydrochloride (1.215 g, 10.52 mmol) was heated at 150° C. for 4 hours. After cooling, the crude was chromatographed (silica, EtOAc-MeOH) to give the desired compound (1.111 g, 97%) as a colorless gum.

Step 107b. A stirred solution of the compound from Step 107a (1.111 g, 6.38 mmol) in acetone (6.4 ml) was treated with 2,2-dimethoxypropane (3.14 ml, 25.5 mmol) and pTSA (3.03 g, 15.94 mmol) at rt for 18 hours. It was diluted with ethyl acetate and washed with saturated NaHCO₃ and saturated NaCl. The organic was dried with Na₂SO₄, filtered and concentrated. The crude was chromatographed (silica, ethyl acetate/hexanes) to give the desired compound (377 mg, 33.9%) as a light-yellow oil.

Step 107c. A solution of the compound from Step 107b (377 mg, 2.164 mmol) in DCM (10 mL) was treated with Hunig's base (0.567 mL, 3.25 mmol) and MsCl (0.202 mL, 2.60 mmol) at rt for 1 hour. It was diluted with DCM and washed with H₂O and saturated NaCl. The organic was dried (Na₂SO₄), filtered and concentrated. The crude was chromatographed (silica, ethyl acetate/hexanes) to give the desired compound (430 mg, 79%) as a yellow solid.

Step 107d. A mixture of the compounds from step 1c (50 mg, 0.157 mmol) and from Step 107c (79 mg, 0.315 mmol) and K₂CO₃ (43.5 mg, 0.315 mmol) in DMF (787 μl) was stirred at 80° C. for 1 hour. It was diluted with ethyl acetate and then washed with H₂O and saturated NaCl. The organic was dried (Na₂SO₄), filtered and concentrated. The crude was chromatographed (silica, ethyl acetate/hexanes) to give the desired compound (67 mg, 90%) as a white solid.

Step 107e. A solution of the compound from Step 107d (53 mg, 0.112 mmol) in DCM (2 ml) was treated with mCPBA (77% W/W, 96 mg, 0.43 mmol) at rt for 18 hours. Saturated NaHCO₃ was added and it was extracted with DCM. The combined organics were dried with Na₂SO₄, filtered and concentrated. The crude was chromatographed (silica, ethyl acetate/hexanes) to give the title product (17.7 mg, 31.3%). ESI-MS m/z=504.05, 506.05 [M−H]⁻.

Example 108

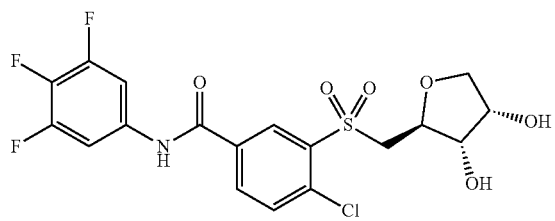 [SMILES: O=C(Nc1cc(F)c(F)c(F)c1)c1ccc(Cl)c(S(=O)(=O)C[C@H]2OC[C@H](O)[C@@H]2O)c1]

The title compound (16.4 mg, 31.5%) was isolated from step 107e. ESI-MS m/z=464.00, 466.06 [M−H]⁻.

Example 109

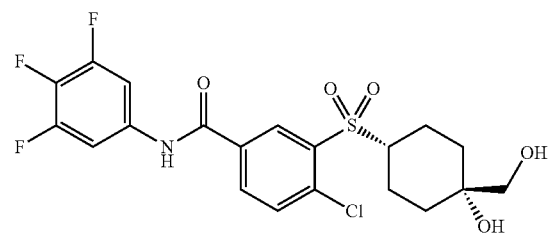 [SMILES: O=C(Nc1cc(F)c(F)c(F)c1)c1ccc(Cl)c(S(=O)(=O)[C@H]2CC[C@](O)(CO)CC2)c1]

To a stirred mixture of compound of Example 104 (0.052 g, 0.12 mmol) and NMO (0.048 g, 0.41 mmol) in acetone (3.5 mL) and water (0.4 mL) was added OsO₄ (2.5% in t-BuOH, 0.15 mL, 0.012 mmol). It was stirred at rt overnight. It was diluted with ethyl acetate and washed with sat. aqueous Na₂S₂O₃ and brine. The organic was dried (Na₂SO₄) and concentrated. The crude was chromatographed (silica, hexanes/EtOAc) and purified by prep-HPLC to give the title compound (0.015 g, 27%), ESI-MS m/z=476.05, 478.05 [M−H]⁻.

Example 110

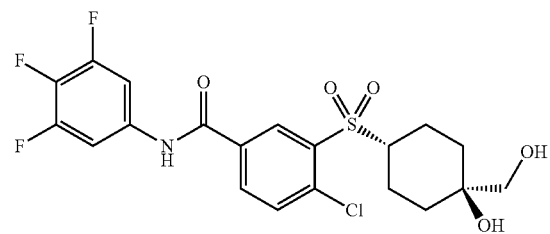 [SMILES: O=C(Nc1cc(F)c(F)c(F)c1)c1ccc(Cl)c(S(=O)(=O)[C@H]2CC[C@@](O)(CO)CC2)c1]

The title compound (0.035 g, 62%) was isolated from example 109. ESI-MS m/z=476.05, 478.05 [M−H]⁻.

Example 111

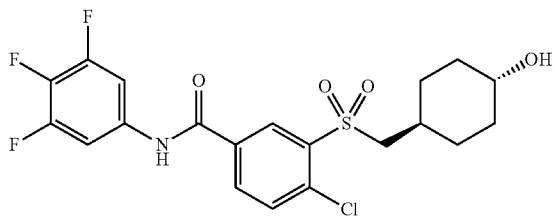 [SMILES: O=C(Nc1cc(F)c(F)c(F)c1)c1ccc(Cl)c(S(=O)(=O)C[C@H]2CC[C@H](O)CC2)c1]

Step 111a. Into a stirred mixture of 4-(hydroxymethyl)cyclohexan-1-ol (0.13 g, 1.0 mmol) and Ph$_3$P (0.39 g, 1.5 mmol) in THF (5 mL) at 0° C. was added DIAD (0.22 g, 1.1 mmol). After 10 mins at 0° C., it was added compound from Step 1c (0.32 g, 1.0 mmol) and stirred at rt for 18 h. It was concentrated and the crude was chromatographed (silica, hexanes/EtOAc) to give the desired compounds as a mixture of two diastereomers (0.22 g, 51%). ESI-MS m/z=428.07, 430.07 [M−H]$^-$.

Step 111b. A stirred solution of compounds from Step 11a (0.18 g, 0.42 mmol) in DCM (2.5 mL) at 0° C. was added mCPBA (0.28 g 77%, 1.3 mmol). It was stirred at rt overnight. It was diluted with ethyl acetate and washed with a mixture of saturated aqueous NaHCO$_3$ solution, Na$_2$S$_2$O$_3$ solution, and brine. The organic was dried (Na$_2$SO$_4$) and concentrated. The crude was chromatographed (silica, hexanes/EtOAc) to give the title product (0.078 g, 40%), ESI-MS m/z=460.11, 462.11 [M−H]$^-$.

Example 112

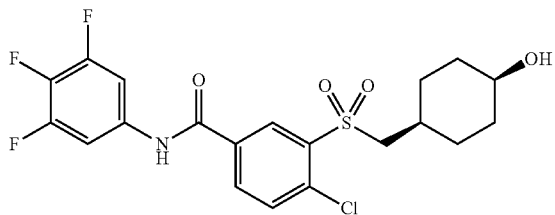 [SMILES: O=C(Nc1cc(F)c(F)c(F)c1)c1ccc(Cl)c(S(=O)(=O)C[C@H]2CC[C@@H](O)CC2)c1]

The title compound (0.028 g, 14%) was isolated from example 111. ESI-MS m/z=460.11, 462.11 [M−H]$^-$.

Example 113

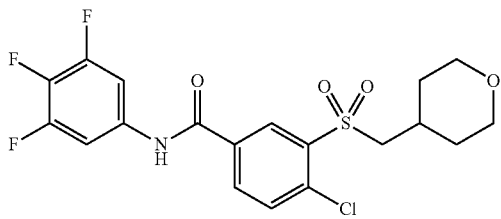 [SMILES: O=C(Nc1cc(F)c(F)c(F)c1)c1ccc(Cl)c(S(=O)(=O)CC2CCOCC2)c1]

Step 113a. A mixture of compound from Step 1c (0.075 g, 0.24 mmol), 4-bromomethyltetra-hydropyran (0.063 g, 0.35 mmol) and cesium carbonate (0.12 g, 0.37 mmol) in DMF (1.5 mL) was stirred at rt for 16 h. It was diluted with ethyl acetate and washed with water, brine. The organic was dried (Na$_2$SO$_4$), filtered and concentrated. The crude was chromatographed (silica, hexanes/EtOAc) to give the desired compound as white solid (0.098 g, 100%). ESI-MS m/z=414.05, 416.05 [M−H]$^-$.

Step 113b. Into a stirred solution of compound from Step 113a (0.10 g, 0.24 mmol) in DCM (2.5 mL) at 0° C. was added mCPBA (77%, 0.18 g, 0.80 mmol). It was stirred at rt overnight.

It was diluted with ethyl acetate and washed with a mixture of sat. aqueous NaHCO$_3$ solution, Na$_2$S$_2$O$_3$ solution, and brine. The organic was dried (Na$_2$SO$_4$) and concentrated. The crude was chromatographed (silica, hexanes/EtOAc) to give the title compound (0.076 g, 74%). ESI-MS m/z=446.04, 448.04 [M−H]$^-$.

Example 114

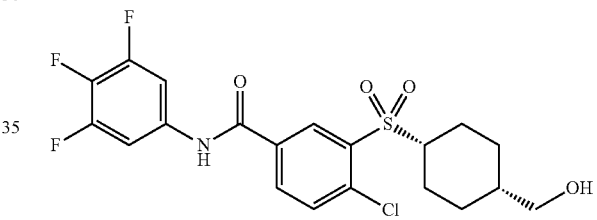

Into a stirred mixture of compound of Example 104 (0.025 g, 0.056 mmol) in THF (0.5 mL) at 0° C. was added BH$_3$-DMS (2M in THF, 0.070 mL, 0.14 mmol). After 2 h at rt, water (0.5 mL) and NaBO$_3$·4H$_2$O (0.15 g, 1.0 mmol) were added and it was stirred at rt overnight. It was extracted with ethyl acetate and washed with water, brine. The organic was dried (Na$_2$SO$_4$) and concentrated. The crude was chromatographed (silica hexanes/EtOAc) to give the title product (8.7 mg, 33%), ESI-MS m/z=460.11, 462.11 [M−H]$^-$.

Example 115

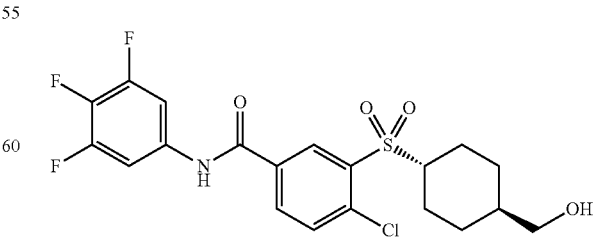

The title compound (6.5 mg, 25%) was isolated from example 114. ESI-MS m/z=460.11, 462.11 [M−H]$^-$.

Example 116

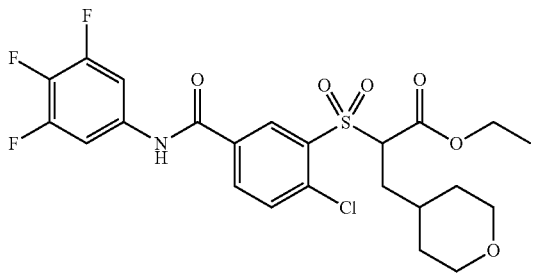 [SMILES: CCOC(=O)C(CC1CCOCC1)S(=O)(=O)c1cc(C(=O)Nc2cc(F)c(F)c(F)c2)ccc1Cl]

Into a stirred mixture of compound of Example 77 (0.065 g, 0.15 mmol) and NaH (60%, 9.0 mg, 0.23 mmol) in DMF (1.5 mL) at rt was added 4-bromomethyltetrahydropyran (0.032 g, 0.18 mmol). It was stirred at 80° C. for 24 h. It was quenched with sat. aqueous NH$_4$Cl at rt. It was extracted with ethyl acetate and washed with water, brine. The organic was dried (Na$_2$SO$_4$) and concentrated. The crude was chromatographed (silica, hexanes/EtOAc) to give the title compound (0.041 g, 51%). ESI-MS m/z=532.08, 534.08 [M−H]$^-$.

Example 119

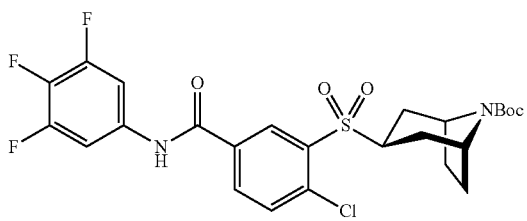

Step 119a. To a solution of tert-butyl (1R,3r,5S)-3-hydroxy-8-azabicyclo[3.2.1]octane-8-carboxylate (670 mg, 2.95 mmol) and DIAD (764 µl, 3.93 mmol) in THF (4.9 mL) was added triphenylphosphine (1.289 g, 4.91 mmol) and 4-chloro-3-mercapto-N-(3,4,5-trifluorophenyl)-benzamide (312 mg, 0.982 mmol). It was heated to and remained at 65° C. for 18 hours. It was partitioned between EtOAc and brine. The organic was dried (Na$_2$SO$_4$), filtered and concentrated. The residue was chromatographed (silica, hexanes/EtOAc) to give the desired compound (303 mg, 58% yield) as a white solid. ESI-MS m/z=525.12, 527.12[M−H]$^-$.

Step 119b. To a stirred solution of compound from Step 119a (531 mg, 1.00 mmol) in DCM (10 mL) at 0° C. was added mCPBA (77%, 904 mg, 4.00 mmol). It was stirred at rt overnight.

It was diluted with ethyl acetate and washed with a mixture of sat. aqueous NaHCO$_3$ solution, Na$_2$S$_2$O$_3$ solution, and brine. The organic was dried (Na$_2$SO$_4$) and concentrated. The crude was chromatographed (silica, hexanes/EtOAc) to give the title compound (379 mg, 67%). ESI-MS m/z=557.11, 559.11[M−H]$^-$.

Example 120

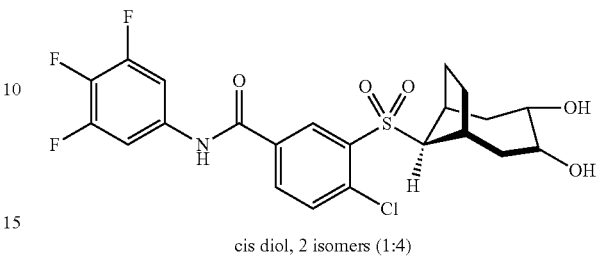

cis diol, 2 isomers (1:4)

Step 120a. To solution of buta-1,3-diene (11.36 g, 210 mmol) and 2-chlorocyclopentan-1-one (2.49 g, 21 mmol) in trifluoroethanol (21 ml) at −30° C. was added sodium 2,2,2-trifluoroethanolate (1M, 42 ml, 42 mmol) over 4 h. The resulting mixture was stirred at −25° C. for 18 h. It was partitioned between DCM and 1M HCl. The organic was dried (Na$_2$SO$_4$), filtered and concentrated. The crude product was used without further purification.

Step 120b. A solution of the compound from step 120a (550 mg, 3.63 mmol) in THF (30 mL) was cooled to −78° C. followed by addition of LiAlH$_4$ (1M in THF, 4.36 mL, 4.36 mmol). After being stirred for 30 minutes, it was quenched by water (0.5 mL), NaOH (1M, 0.5 mL) and water (1.5 mL). The organic was dried (Na$_2$SO$_4$), filtered over Celite and concentrated to give the crude desired compound (502 mg, 99%), which was used for the following step.

Step 120c. Into a solution of compound from step 120b (131 mg, 0.944 mmol) and Ph$_3$P (413 mg, 1.574 mmol) in THF (1.6 ml) was added DIAD (245 µl, 1.259 mmol) and 4-chloro-3-mercapto-N-(3,4,5-trifluorophenyl)benzamide (100 mg, 0.315 mmol). It was heated to and remained at 65° for 18 hours. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the desired compound (51 mg, 0.116 mmol, 37% yield) as a white solid. ESI-MS m/z=436.08, 438.07[M−H]$^-$.

Step 120d. The compound from Step 120c (30 mg, 0.069 mmol) was dissolved in acetone (2 ml) and water (0.1 ml) at rt followed by addition of osmium tetroxide (2.5% in tBuOH, 0.086 ml, 0.007 mmol) and NMO (20 mg, 0.171 mmol). It was stirred for 3 h at rt. It was diluted with ethyl acetate and washed with NaHCO$_3$ and brine. The organic was dried (Na$_2$SO$_4$), filtered and concentrated. The organic was dried (Na$_2$SO$_4$), filtered over Celite and concentrated to give the crude desired compound (32 mg, 0.068 mmol, 99%), which was used for the following step.

Step 120e. To a solution of the compound from Step 120d (32 mg, 0.068 mmol) in acetone (2 ml) and water (0.1 ml) was added m-CPBA (77%, 53 mg, 0.237 mmol) at 0° C. The mixture was warmed to rt and stirred 18 h. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the title compound (22 mg, 0.116 mmol, 64% yield) as a white solid. ESI-MS m/z=502.07, 504.07[M−H]$^-$.

Example 121

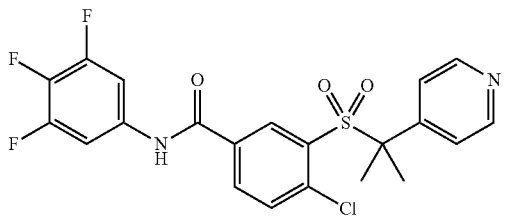 [SMILES: CC(C)(c1ccncc1)S(=O)(=O)c1cc(C(=O)Nc2cc(F)c(F)c(F)c2)ccc1Cl]

Step 121a. To a solution of the compound from Step 80c (48.0 mg, 0.141 mmol) and iodomethane (35.2 μl, 0.565 mmol) in THF (4.7 mL) at −40° C. was added a solution of 0.5 M KHMDS (1130 μl, 0.565 mmol), then the mixture was kept at −40° C. for 10 minutes. It was partitioned between EtOAc and brine. The organic was dried ($Na_2SO_4$), filtered and concentrated. The residue was chromatographed (silica, hexanes/EtOAc) to give the desired compound (31 mg, 62% yield) as a white solid. ESI-MS m/z=354.06, 356.06[M−H]⁻.

Step 121b. To a solution of the compound from Step 121a (29.1 mg, 0.082 mmol) and 3,4,5-trifluoroaniline (36.3 mg, 0.247 mmol) in toluene (2.7 mL) at rt was added trimethylaluminum (164 μl, 0.329 mmol). It was heated at 90° C. and kept for 1 h. It was partitioned between EtOAc and Rochelle's solution. The organic was dried ($Na_2SO_4$), filtered and concentrated. The residue was chromatographed (silica, hexanes/acetone) to give the title compound (21.7 mg, 56% yield) as a white solid. ESI-MS m/z=469.06, 471.06 [M−H]⁻.

Example 124

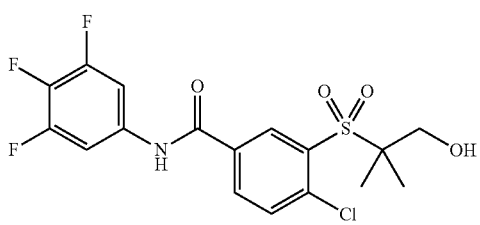 [SMILES: CC(C)(CO)S(=O)(=O)c1cc(C(=O)Nc2cc(F)c(F)c(F)c2)ccc1Cl]

To a solution of compounds from example 92 (48 mg, 0.11 mmol) in THE (1.0 mL) at 0° C. was added $LiBH_4$ (7.0 mg, 0.32 mmol). The resulting reaction mixture was stirred at rt for 16 h. The reaction was quenched with aqueous $NH_4Cl$ and the mixture was extracted with MBTE, washed with water, brine. The organic layer was dried ($Na_2SO_4$), filtered and concentrated. The crude product was chromatographed (silica, hexanes/EtOAc) to give the desired compound as white solid (33 mg, 73%). ESI-MS m/z 420.03, 422.02 [M−H]⁻.

Example 125

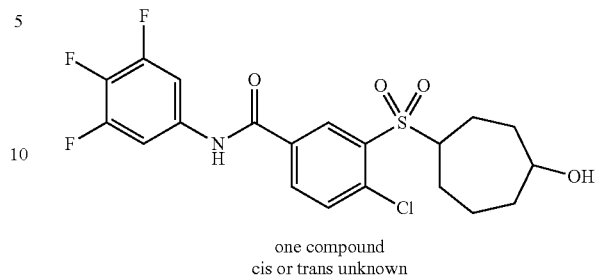

one compound
cis or trans unknown

Step 125a. A mixture of compound from step 63a (4.4 g, 31.38 mmol,), imidazole (6.41 g, 94.15 mmol) and TBSCI (5.2 g, 34.50 mmol) was stirred overnight at room temperature. The reaction was concentrated under vacuum. The residue was chromatographed (silica, petroleum ether) to give the desired compound as colorless oil (7.65 g, 96%). ¹H NMR (400 MHz, DMSO-$d_6$) δ: 5.83 (m, 2H), 4.99 (m, 4H), 3.72 (m, 2H), 2.06 (m, 4H), 1.50 (m, 4H), 0.88 (s, 9H), 0.05 (s, 6H).

Step 125b. A mixture of compound from step 125a (8.25 g, 32.42 mmol) and Grubbs cat (827 mg, 0.97 mmol) in DCM (80 mL) under nitrogen was stirred overnight at room temperature. The mixture was concentrated. The residue was chromatographed (silica, petroleum ether) to give the desired compound as colorless oil (7.3 g, 99%). ¹H NMR (400 MHz, DMSO-$d_6$) δ: 5.80 (m, 2H), 3.91 (m, 1H), 2.30 (m, 2H), 1.87 (m, 3H), 1.55 (m, 2H), 1.30 (m, 1H), 0.92 (s, 9H), 0.09 (s, 6H).

Step 125c. A mixture of compound from step 125b (7.3 g, 32.24 mmol) and m-CPBA (16.69 g, 96.71 mmol) in DCM (70 mL) under nitrogen was stirred for 1 hour at room temperature. The reaction was concentrated under vacuum. The residue was diluted with petroleum ether (70 mL) and the solids were filtered out. The filtrate was evaporated in vacuum and chromatographed (silica, ethyl acetate/petroleum ether) to give the desired compound as yellow oil (4.67 g, 60%). ESIMS m/z=243.00 [M+H]*.

Step 125d. Into the mixture of $LiAlH_4$ (2.195 g, 57.84 mmol) and $AlCl_3$ (2.57 g, 19.27 mmol) were added portionwise compound from step 125c (4.674 g, 19.28 mmol) in THE (100 mL) at 0° C. The resulting solution was stirred for 1 hour at room temperature. The reaction was quenched with water (20 mL), filtered and extracted with ethyl acetate (200 mL). The organic layer was washed with saturated $NaHCO_3$ solution (3×200 mL), dried over anhydrous $Na_2SO_4$, filtered and concentrated under vacuum to give the desired crude compound as yellow oil (3.0 g, 64%). This material was used directly in the next step with our further purification.

Step 125e. $Et_3N$ (3.4 mL) and MsCl (1.2 mL) was added drop-wise into the solution of compound from step 125d (3 g, 12.27 mmol) in DCM (50 mL) at 0° C. The resulting solution was stirred for 1 hour at room temperature. The reaction was diluted with DCM (50 mL) and washed with brine (100 mL). The organic layer was dried over anhydrous $Na_2SO_4$, filtered and concentrated under vacuum. The residue was chromatographed (silica, ethyl acetate/petroleum ether) to give the desired compound as yellow oil (625 mg, 16%).

Step 125f. A mixture of compounds from step 1c (421 mg, 1.33 mmol), from step 125e (513 mg, 1.59 mmol) and $K_2CO_3$ (366 mg, 2.63 mmol) in DMF (8 mL) was stirred for 2 hours at 100° C. The reaction was diluted with DCM (100 mL) and washed with water (100 mL) and brine (3×100 mL). The organic layer was dried over anhydrous Na₂SO₄, filtered and concentrated under vacuum. The residue was chromatographed (silica, ethyl acetate/petroleum ether) to give the desired compound as yellow oil (240 mg, 33%). ESIMS m/z=544.40 [M+H]⁺.

Step 125 g. A mixture of compound from 125f (200 mg, 0.37 mmol) and m-CPBA (77% w/w, 254 mg, 1.47 mmol) in DCM (4 mL) was stirred for 2 hours at rt. The reaction was diluted with DCM (50 mL) and washed with saturated NaHCO₃ solution (50 mL). The organic layer was dried over anhydrous Na₂SO₄, filtered and concentrated under vacuum. The residue was chromatographed (Pre-TLC, ethyl acetate/petroleum ether) and further purified by Pre-HPLC (MeCN/H₂O, containing 0.1% NH₄HCO₃) to give the desired compound as white solid (45 mg, 21%). ESIMS m/z=576.40 [M+H]⁺.

Example 128

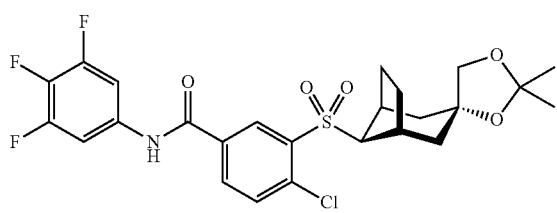 [SMILES: CC1(C)OC[C@@]2(CC3CC[C@@H](C2)[C@H]3S(=O)(=O)c2cc(C(=O)Nc3cc(F)c(F)c(F)c3)ccc2Cl)O1]

To a solution of the title compound from Example 60 (452 mg, 0.897 mmol) in THF (4.5 mL) was added 2,2-dimethoxypropane (5 ml, 40.7 mmol) and PPTS (45.1 mg, 0.179 mmol), then the mixture was heated to 60° C. and kept for 3 h. It was partitioned between EtOAc and NaHCO₃ aqueous solution. The organic was dried (Na₂SO₄), filtered and concentrated. The residue was chromatographed (silica, hexanes/acetone) to give the title compound (457 mg, 94% yield) as a white solid. ESI-MS m/z=542.10, 544.10 [M–H]⁻.

Example 129

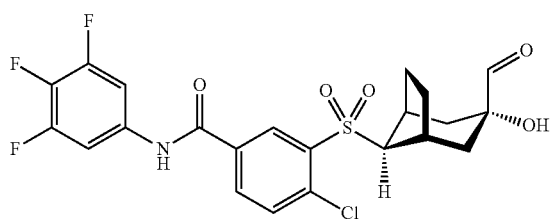

To a mixture of compound from step 60 (2.00 g, 3.97 mmol), DIPEA (3.47 mL, 19.84 mmol), and DMSO (6.2 ml, 87 mmol) in DCM (12 ml) was added SO₃ pyridine complex (1.895 g, 11.9 mmol). The reaction was stirred at rt for 3 h. It was diluted with EtOAc and washed with 1M HCl and brine. The organic was dried (Na₂SO₄), filtered and concentrated. The residue was chromatographed (silica, hexanes/acetone) to give the title compound (1.59 g, 3.18 mmol, 80% yield). ESI-MS m/z=500.055, 502.053 [M–H]⁻.

Example 130

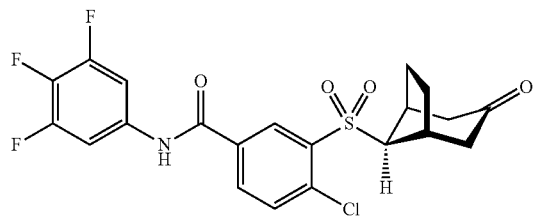

To a mixture of compound from step 60 (1.70 g, 3.37 mmol), and NaHCO₃(1M, 3.37 ml, 3.37 mmol) in DCM (17 ml) and THF (17 mL) was added NaIO₄ (1.443 g, 6.75 mmol). The reaction was stirred at rt for 1 h. It was diluted with EtOAc and filtered. The filtrate was washed with water and brine. The organic was dried (Na₂SO₄), filtered and concentrated. The residue was crystalized (hot methanol) to give the title compound (1.45 g, 3.07 mmol, 91% yield). ESI-MS m/z=470.045, 472.042 [M–H]⁻.

Example 131

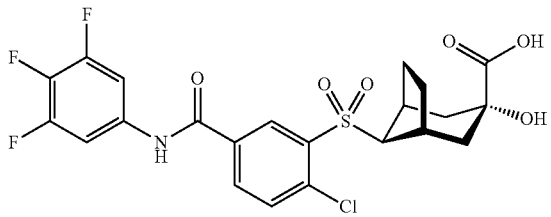

To a mixture of compound from step 129 (45 mg, 0.09 mmol), m KH₂PO₄ (85 mg, 0.628 mmol) and 2-methyl-2-butene (0.237 ml, 2.24 mmol) in t-BuOH (1.0 ml) and water (0.33 mL) was added sodium chloride (80%, 91 mg, 0.807 mmol). The reaction was stirred at rt for 18 h. It was diluted with EtOAc and extracted into the aquious layer with 0.5 M NaOH. Acidify with 1M HCl to pH 2 then extract with EtOAc. The organic was dried (Na₂SO₄), filtered and concentrated to give the title compound (26 mg, 0.050 mmol, 56% yield). ESI-MS m/z=516.082, 517.9 [M–H]⁻.

Example 132

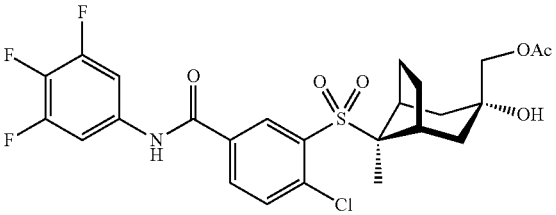

To a solution of compounds from example 128 (123 mg, 0.226 mmol) in acetic acid/water (1.6/0.4 mL) was stirred at 95° C. for 60 h. It was extracted with EtOAc, washed with water, brine. The organic layer was dried (Na₂SO₄), filtered and concentrated. The crude product was chromatographed (silica, hexanes/EtOAc) to give the desired compound as white solid (12 mg, 10%). ESI-MS m/z=544.08, 546.08.

Example 133

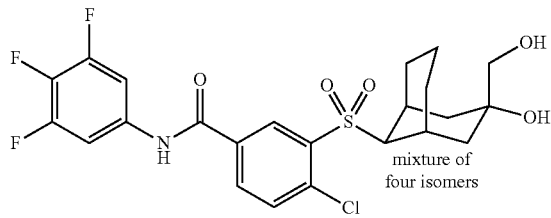 [SMILES: O=C(Nc1cc(F)c(F)c(F)c1)c1ccc(Cl)c(S(=O)(=O)C2C3CCCC2CC(O)(CO)C3)c1]

Step 133a. A mixture of 2-methylenepropane-1,3-diyl diacetate (0.781 g, 4.53 mmol), Pd(OAc)$_2$ (0.061 g, 0.272 mmol), Ph$_3$P (0.285 g, 1.088 mmol), and 1-(cyclohex-1-en-1-yl)-pyrrolidine (1.0 ml, 6.35 mmol) in acetonitrile (26 ml) was heated to and remained at 65° C. for 3 hours. Water (13 ml) was added and the reaction mixture was stirred for 1 hour at 65° C. Saturated brine was added and it was extracted with MTBE. The organic phase was dried (Na$_2$SO$_4$), filtered and concentrated. The residue was chromatographed (silica, hexanes/MTBE) to give the desired compound (0.545 g, 80% yield) as a colorless oil.

Step 133b. A solution of the compound from step a (545 mg, 3.63 mmol) in THF (18 mL) was cooled to −78° C. followed by addition of LiAlH$_4$ (1M in THF, 4.35 mL, 4.35 mmol). After being stirred for 10 minutes, it was quenched by water (0.2 mL), NaOH (1M, 0.2 mL) and water (0.6 mL). The organic was dried (Na$_2$SO$_4$), filtered over Celite and concentrated to give the crude desired compound (440 mg, 80%), as a mixture of diastereomers which was used for the following step.

Step 133c. Into a solution of compound from step b (96 mg, 0.630 mmol) and Ph$_3$P (413 mg, 1.574 mmol) in THF (1.6 ml) was added DIAD (245 µl, 1.259 mmol) and 4-chloro-3-mercapto-N-(3,4,5-trifluorophenyl)benzamide (100 mg, 0.315 mmol). It was heated to and remained at 65° for 18 hours. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the desired compound (125 mg, 0.277 mmol, 88% yield) as a mixture of diastereomers.

Step 133d. Into a solution of compound from step c (54 mg, 0.119 mmol) in DMF (1.4 mL) and water (0.075 mL) was added OsO$_4$ (2.5% in t-BuOH, 0.075 mL, 5.97 µmol) and NMO (70 mg, 0.597 mmol). The reaction was stirred at rt for 18 h. It was diluted with EtOAc and washed with 0.1M HCl and brine. The organic was dried (Na$_2$SO$_4$), filtered and concentrated to give the crude desired compound (62 mg) as a mixture of diastereomers, which was used for the following step.

Step 133e. To a solution of compound from step d (62 mg, 0.128 mmol) in DMF (1 mL) and water (0.05 mL) was added m-CPBA (77%, 143 mg, 0.638 mmol). The reaction was stirred at rt for 18 h. It was diluted with EtOAc and washed with sat. aq. NaHCO$_3$ and brine. The organic was dried (Na$_2$SO$_4$), filtered and concentrated. The residue was chromatographed (silica, hexanes/acetone) to give the title compound (20 mg, 0.042 mmol, 33% yield) as a mixture of diastereomers. ESI-MS m/z=516.09, 518.09 [M−H]$^-$.

Example 134

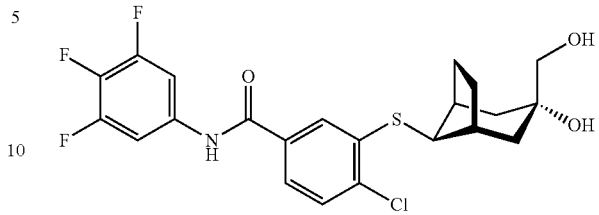

Step 134a. To a solution of compound from step 39b (7.7 g, 77.18% in THF, 43 mmol) in anhydrous dichloromethane (20 mL) at 0° C. was added DBU (7.9 g, 5.2 mmol) and 1,1,2,2,3,3,4,4,4-nonafluorobutane-1-sulfonyl fluoride (14.4 g, 48 mmol). The reaction was kept at 0° C. for 0.5 h before it was concentrated to dryness. The residue was dissolved in hexane (70 mL). The solution was washed with HCl (0.5 M), water, NaHCO$_3$, brine and dried (Na$_2$SO$_4$). It was filtered through a layer of silica gel, washed with hexane (300 mL) and concentrated to give colorless oil (16.8 g 92%). $^1$HNMR (400 MHz, CDCl$_3$) δ 5.13 (t, 1H), 4.85 (s, 2H), 2.67 (d, 2H), 2.46 (brs, 2H), 2.04 (dd, 2H), 1.72 (m, 2H), 1.58 (m, 2H).

Step 134b. A mixture of compound from step 134a (2.101 g, 5 mmol) and 4-methylmorpho-line 4-oxide (0.703 g, 6.00 mmol) in acetone-water (4.5 mL/0.5 mL) at rt was added osmium(VIII) oxide (0.628 ml, 2.5% in t-BuOH) and stirred at rt o/n. Na$_2$S$_2$O$_3$ (1.58 g, 10 mmol) and water (2 mL) was added stirred at rt for 30 mins. It was partitioned (EtOAc/water). The organic was washed with 1N HCl, aq. NaHCO$_3$, brine and dried (Na$_2$SO$_4$). After filtered, the crude was concentrated to give the desired product (2.24 g, 99%). $^1$HNMR (400 MHz, CDCl$_3$) δ 5.03 (t, 1H), 3.60 (s, 2H), 2.44 (brs, 2H), 1.99 (ddd, 4H), 1.82 (m, 4H), 1.61 (m, 2H).

Step 134c. To a suspension of the compounds from step 134b (1.84 g, 5.81 mmol), triphenylphophine (0.063 g, 0.024 mmol) in THF (4 mL) at rt was degassed followed by addition of potassium t-butoxide (1M in THF, 5.32 mL, 5.32 mmol). In 5 minutes, the compound from step 1c (2.2 g, 4.84 mmol) in THF (9 mL) was added, and stirred at 60° C. for 24 h. After being cooled, it ws diluted with MBTE (60 mL), filtered and washed with MTBE. The combined solution was washed with 0.5 N NaOH, brine and dried (Na$_2$SO$_4$). It was filtered through a short silica plug (10 g silica gel) and washed with EtOAc (50 mL). The combined organic was concentrated under vacuum to give crude and recrytalized from MeOH to give the title compound (1.91 g, 84%). ESI-MS m/z=470.08, 472.08.

Example 135

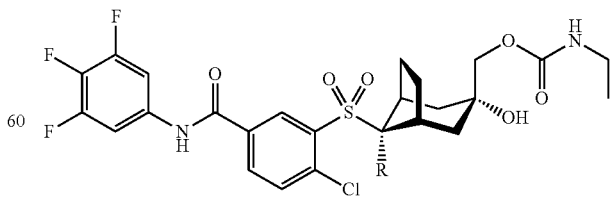

To a mixture of compound from step 60 (50 mg, 0.099 mmol), DIPEA (87 µl, 0.496 mmol) and DBU (50 µL, 0.332 mmol) in DMF (0.5 ml) was added ethylisocyanate (78 µL, 0.992 mmol). The reaction was stirred at 80° C. for 18 h. It was diluted with EtOAc and washed with water and brine. The organic was dried (Na$_2$SO$_4$), filtered and concentrated. The residue was chromatographed (silica, hexanes/acetone) to give the title compound (5 mg, 8.70 μmol, 33% yield). ESI-MS m/z=573.11, 575.11 [M–H]$^-$.

Example 136

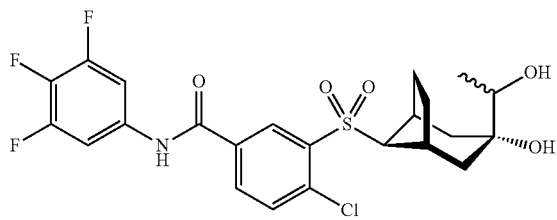

To a mixture of compound from step 129 (14 mg, 0.027 mmol) in THF (0.3 ml) at −78° C. was added methylmagnesium bromide (3M in Et$_2$O, 50 μL, 0.15 mmol). The reaction was stirred at rt for 1 h. It was diluted with EtOAc and washed with sat. aq. NH$_4$Cl and brine. The organic was dried (Na$_2$SO$_4$), filtered and concentrated. The residue was chromatographed (silica, hexanes/acetone) to give the title compound (10 mg, 0.019 mmol, 71% yield). ESI-MS m/z=516.09, 518.09 [M–H]$^-$.

Example 137

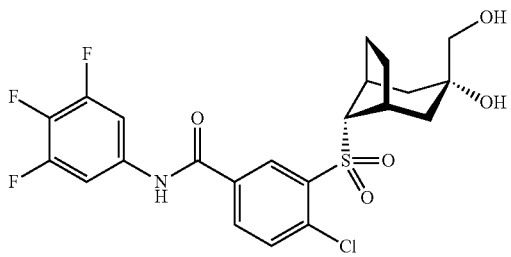

Step 137a. Into a solution of compound from step 39b (1.00 g, 7.24 mmol), Ph$_3$P (3.23 g, 12.30 mmol) and 4-nitrobenzoic acid (1.814 g, 10.85 mmol) in toluene (14.5 ml) was added DIAD (2.11 ml, 10.85 mmol). It was heated to and remained at 90° for 18 hours. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the desired compound (1.795 g, 6.25 mmol, 86% yield).

Step 137b. Into a solution of compound from step 137a (1.795 g, 6.25 mmol) in MeOH (30 mL) DCM (10 mL) was added K$_2$CO$_3$ (0.863 g, 6.25 mmol). The reaction was stirred at rt for 2 h. It was diluted with MTBE and washed with water and brine. The organic was dried (Na$_2$SO$_4$), filtered and concentrated. The residue was chromatographed (silica, hexanes/MTBE) to give the desired compound (688 g, 4.98 mmol, 80% yield) as a white solid.

Step 137c. Into a solution of compound from step 137b (0.688 g, 4.98 mmol) and 4-chloro-3-mercapto-N-(3,4,5-trifluorophenyl)benzamide (1.582 g, 4.98 mmol) in toluene (12.4 ml) was added 2-(tributyl-15-phosphanylidene)acetonitrile (1.567 ml, 5.97 mmol). It was heated to and remained at 105° for 18 hours. The crude reaction mixture was concentrated. The residue was chromatographed (silica, hexanes/MTBE) to give the desired compound (0.673 g, 1.54 mmol, 31% yield).

Step 137d. Into a solution of compound from step 137c (100 mg, 0.228 mmol) in acetone (0.95 mL) and water (0.05 mL) was added OsO$_4$ (2.5% in t-BuOH, 0.072 mL, 5.71 μmol) and NMO (134 mg, 1.142 mmol). The reaction was stirred at rt for 18 h. It was diluted with EtOAc and washed with 0.1 M HCl and brine. The organic was dried (Na$_2$SO$_4$), filtered and concentrated to give the crude desired compound (115 mg), which was used for the following step.

Step 137e. To a solution of compound from step 137d (115 mg, 0.236 mmol) in DMF (1 mL) was added m-CPBA (77%, 264 mg, 1.178 mmol). The reaction was stirred at rt for 18 h. It was diluted with EtOAc and washed with sat. aq. NaHCO$_3$ and brine. The organic was dried (Na$_2$SO$_4$), filtered and concentrated. The residue was chromatographed (silica, hexanes/acetone) to give the title compound (80 mg, 0.159 mmol, 67% yield). ESI-MS m/z=502.12, 504.07 [M–H]$^-$.

Example 138

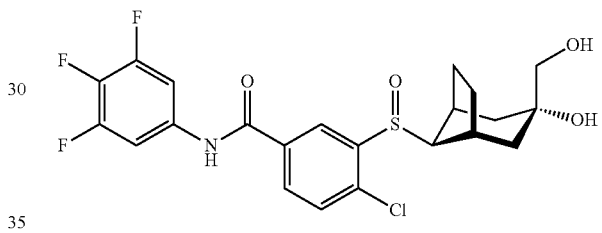

Step 138a. To a solution of compound from step 39b (7.7 g, 77.18% in THF, 43 mmol) in anhydrous dichloromethane (20 mL) at 0° C. was added DBU (7.9 g, 5.2 mmol) and 1,1,2,2,3,3,4,4,4-nonafluorobutane-1-sulfonyl fluoride (14.4 g, 48 mmol). The reaction was kept at 0° C. for 0.5 h before it was concentrated to dryness. The residue was dissolved in hexane (70 mL). The solution was washed with HCl (0.5 M), water, NaHCO$_3$, brine and dried (Na$_2$SO$_4$). It was filtered through a layer of silica gel, washed with hexane (300 mL) and concentrated to give colorless oil (16.8 g 92%). $^1$HNMR (400 MHz, CDCl$_3$) δ 5.13 (t, 1H), 4.85 (s, 2H), 2.67 (d, 2H), 2.46 (brs, 2H), 2.04 (dd, 2H), 1.72 (m, 2H), 1.58 (m, 2H).

Step 138b. A mixture of compound from step 138a (2.101 g, 5 mmol) and 4-methylmorpho-line 4-oxide (0.703 g, 6.00 mmol) in acetone-water (4.5 mL/0.5 mL) at rt was added osmium(VIII) oxide (0.628 ml, 2.5% in t-BuOH) and stirred at rt o/n. Na$_2$S$_2$O$_3$ (1.58 g, 10 mmol) and water (2 mL) was added stirred at rt for 30 mins. It was partitioned (EtOAc/water). The organic was washed with 1N HCl, aq. NaHCO$_3$, brine and dried (Na$_2$SO$_4$). After filtered, the crude was concentrated to give the desired product (2.24 g, 99%). $^1$HNMR (400 MHz, CDCl$_3$) δ 5.03 (t, 1H), 3.60 (s, 2H), 2.44 (brs, 2H), 1.99 (ddd, 4H), 1.82 (m, 4H), 1.61 (m, 2H).

Step 138c. To a suspension of the compounds from step 138b (1.84 g, 5.81 mmol), triphenylphophine (0.063 g, 0.024 mmol) in THF (4 mL) at rt was degassed followed by addition of Potassium t-butoxide (1M in THF, 5.32 mL, 5.32 mmol). In 5 minutes, the compound from step 1c (2.2 g, 4.84 mmol) in THF (9 mL) was added, and stirred at 60° C. for 24 h. After being cooled, it ws diluted with MBTE (60 mL), filtered and washed with MTBE.

The combined solution was washed with 0.5 N NaOH, brine and dried (Na₂SO₄). It was filtered through a short silica plug (10 g silica gel) and washed with EtOAc (50 mL). The combined organic was concentrated under vacuum to give crude 2.5 g (110%).

Step 138d. To the solution of the compound from step 138c (20 mg, 0.042 mmol) NBS (15 mg, 0.085 mmol) was added. It was stirred at rt o/n before aq. NaS₂O₃ (3 mL) was added. The white solid was collected under vacuum and washed with aq. NaHCO₃, water and MTBE. This mixture was further recrystallized from hot MeOH to give the title compound (7.7 mg, 37%). ESI-MS m/z=486.08, 488.08 [M−H]⁻.

Example 139

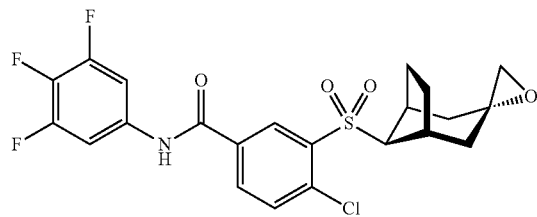

To a solution of compound from example 60 (3.02 g, 6.0 mmol) and DBU (1.83 g, 12.0 mmol) in anhydrous THF (40 mL) at 0° C. was added 1,1,2,2,3,3,4,4,4-nonafluorobutane-1-sulfonyl fluoride (3.26 g, 10.8 mmol) slowly over 30 minutes. The reaction was stirred at rt for 1 h before it was concentrated to dryness. This crude was chromatographed (silica, acetone/hexanes) to give the title compound (2.55 g, 88%), ESI-MS m/z=484.08, 486.06 [M−H]⁻.

Example 140

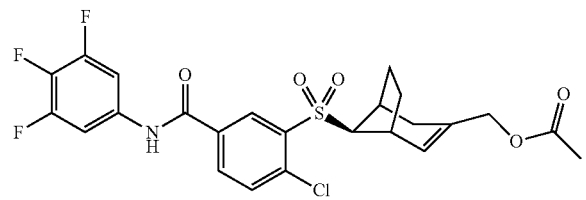 [SMILES: CC(=O)OCC1=CC2CCC(C1)[C@@H]2S(=O)(=O)c1cc(C(=O)Nc2cc(F)c(F)c(F)c2)ccc1Cl]

The title compound (2.4 mg, 2%) was isolated from example 132. ESI-MS m/z=526.08, 528.08 [M−H]⁻.

Example 141

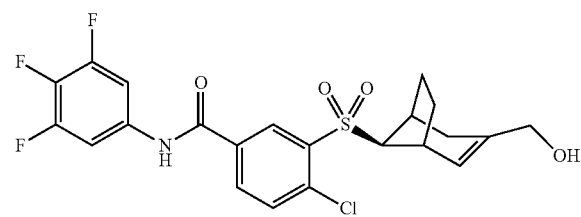 [SMILES: O=C(Nc1cc(F)c(F)c(F)c1)c1ccc(Cl)c(S(=O)(=O)[C@@H]2C3C=C(CO)CC2CC3)c1]

To a solution of the title compound from Example 60 (113 mg, 0.224 mmol) in toluene (11 mL) was added ((1S,4R)-7,7-dimethyl-2-oxobicyclo[2.2.1]heptan-1-yl)methanesulfonic acid (26.0 mg, 0.112 mmol), then it was heated to 90° C. and kept for overnight. It was partitioned between EtOAc and brine. The organic was dried (Na₂SO₄), filtered and concentrated. The residue was chromatographed (silica, hexanes/EtOAc) to give the title compound (11 mg, 10% yield) as a white solid. MS-ESI, M/Z=484.06, 486.06 [M−H]⁻.

Example 142

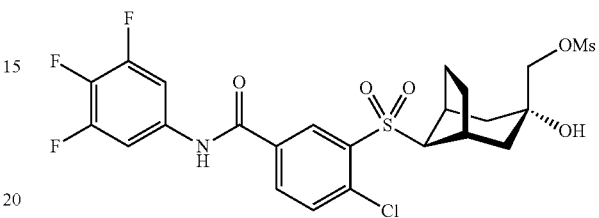

To a mixture of compound from step 60 (1.00 g, 1.984 mmol), DIPEA (1.04 ml, 5.95 mmol) and DMAP (0.97 g, 7.94 mmol) in DMF (10 ml) at rt was added methanesulfonic anhydride (0.691 g, 3.97 mmol). The reaction was stirred at rt for 1 h. It was diluted with EtOAc and washed with water and brine. The organic was dried (Na₂SO₄), filtered and concentrated. The residue was chromatographed (silica, hexanes/acetone) to give the title compound (452 mg, 0.777 mmol, 39% yield). ESI-MS m/z=580.05, 582.05 [M−H]⁻.

Example 143

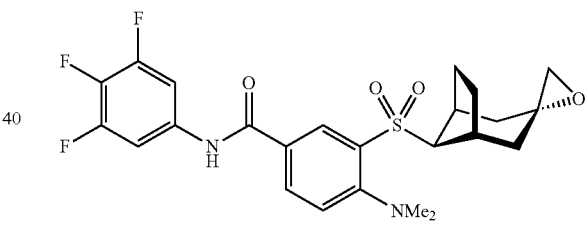

To a mixture of compound from step 139 (20 mg, 0.041 mmol) in ethanol (0.9 ml) at rt was added dimethylamine (2M in THF, 103 µL, 0.206 mmol) The reaction was stirred at 70° C. for 18 h. The crude reaction was concentrated. The residue was chromatographed (silica, hexanes/acetone) to give the title compound (8 mg, 0.016 mmol, 39% yield). ESI-MS m/z=493.14, 494.15 [M−H]⁻.

Example 144

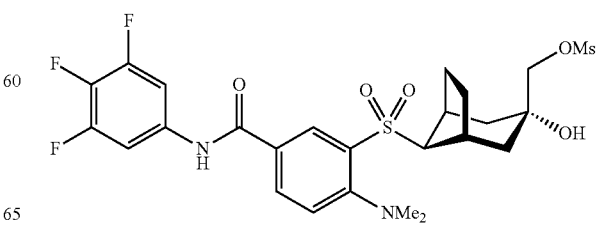

To compound from example 142 (21 mg, 0.036 mmol) was added dimethylamine (2M in THF, 540 µL, 1.08 mmol). The reaction was stirred at 70° C. for 18 h. The crude reaction was concentrated. The residue was chromatographed (silica, hexanes/acetone) to give the title compound (10 mg, 0.017 mmol, 47% yield). ESI-MS m/z=589.14, 590.13 [M−H]⁻.

Example 146

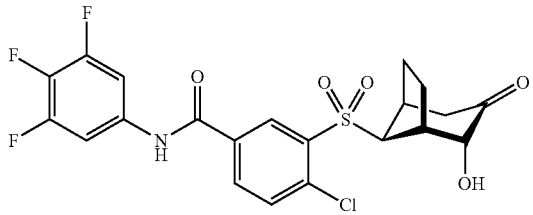

Step 146a. To a solution of the title compound (209 mg, 0.444 mmol) from Example 130 in CH₂Cl₂ (15 mL) at 0° C. was added iPr₂NEt (574 mg, 4.44 mmol) and TBSOTf (661 mg, 2.66 mmol), then the mixture was kept at 0° C. for 1 h. It was partitioned between EtOAc and brine. The organic was dried (Na₂SO₄), filtered and concentrated. The residue was chromatographed (silica, hexanes/EtOAc) to give the desired compound (218 mg, 84%) as a white solid. MS-ESI, M/Z=584.13, 586.13 [M−H]⁻.

Step 146b. To a mixture of the compound from Step 146a (73.6 mg, 0.126 mmol) in acetone (3.5 mL) and water (0.70 mL) at rt was added NMO (44.1 mg, 0.377 mmol) and osmium tetroxide (31.5 µl, 2.51 µmol). The solution was kept at rt for overnight. It was partitioned between CH₂C₁₂ and Na₂S₂O₃ aqueous solution. The organic was dried (Na₂SO₄), filtered and concentrated. The residue was chromatographed (silica, hexanes/acetone) to give the title compound (47 mg, 77%) as a white solid. MS-ESI, M/Z=486.04, 488.04 [M−H]⁻.

Example 150

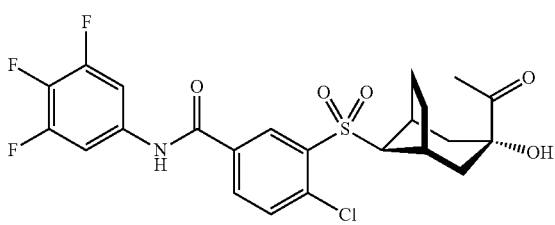

To a mixture of compound from example 136 (75 mg, 3.97 mmol), DIPEA (0.132 mL, 0.753 mmol), and DMSO (0.439 ml, 3.19 mmol) in DCM (0.439 ml) at 0° C. was added SO₃ pyridine complex (71 mg, 0.449 mmol). The reaction was stirred at rt for 3 h. It was diluted with EtOAc and washed with 1M HCl and brine. The organic was dried (Na₂SO₄), filtered and concentrated. The residue was chromatographed (silica, hexanes/acetone) to give the title compound (44 mg, 0.085 mmol, 59%). ESI-MS m/z=514.07, 516.07 [M−H]⁻.

Example 151

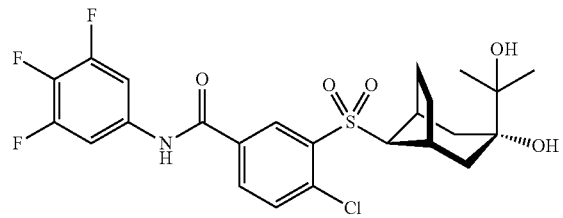

To a mixture of compound from example 150 (42 mg, 0.081 mmol) in THF (1.0 ml) at −78° C. was added methylmagnesium bromide (3M in Et₂O, 0.136 mL, 0.407 mmol). The reaction was stirred at rt for 1 h. It was diluted with EtOAc and washed with sat. aq. NH₄Cl and brine. The organic was dried (Na₂SO₄), filtered and concentrated. The residue was chromatographed (silica, hexanes/acetone) to give the title compound (40 mg, 0.075 mmol, 93% yield). ESI-MS m/z=530.10, 532.11 [M−H]⁻.

Example 152

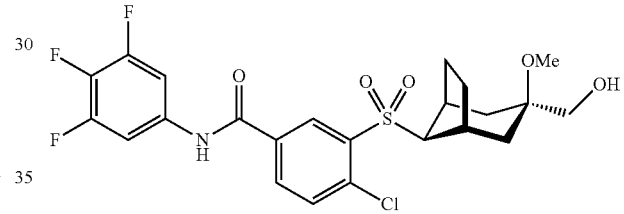

To a mixture of compound from example 139 (30 mg, 0.062 mmol) in THF (0.5 ml) and MeOH (1.0 mL) at rt was added TFA (0.1 mL, 1.298 mmol). The reaction was stirred at rt for 18 h. It was diluted with EtOAc and washed with sat. aq. NaHCO₃ and brine. The organic was dried (Na₂SO₄), filtered and concentrated. The residue was chromatographed (silica, hexanes/acetone) to give the title compound (20 mg, 0.039 mmol, 63% yield). ESI-MS m/z=516.09, 518.09 [M−H]⁻.

Example 153

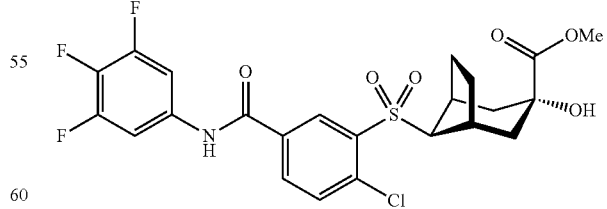

To a mixture of compound from example 131 (10 mg, 0.019 mmol) in THF (0.5 ml) and MeOH (1.0 mL) at rt was added HCl (4M in dioxane, 0.05 mL, 0.20 mmol). The reaction was stirred at rt for 2 h. It was diluted with EtOAc and washed with sat. aq. NaHCO₃ and brine. The organic was dried (Na₂SO₄), filtered and concentrated to give the title compound (8 mg, 0.015 mmol, 78% yield). ESI-MS m/z=530.08, 532.07 [M–H]⁻.

Example 154

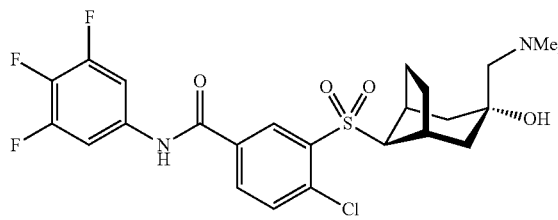

To a mixture of compound from example 129 (100 mg, 0.199 mmol) and dimethylamine (2M in THF, 0.1 mL, 0.20 mmol) in THE (3 ml) at rt was added sodium triacetoxyborohydride (68 mg, 0.319 mmol). The reaction was stirred at rt for 1 h. It was diluted with EtOAc and washed with sat. aq. NaHCO₃ and brine. The organic was dried (Na₂SO₄), filtered and concentrated. The residue was chromatographed (silica, hexanes/acetone) to give the title compound (20 mg, 0.038 mmol, 19% yield). ESI-MS m/z=529.12, 531.12 [M–H]⁻.

Example 155

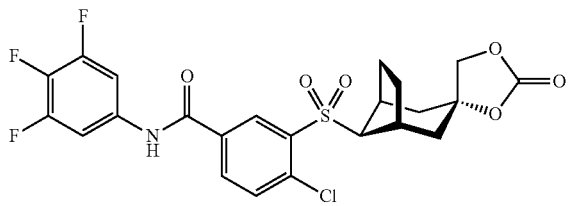

To a mixture of compound from example 60 (50 mg, 0.099 mmol), DIPEA (0.035 mL, 0.198 mmol) and DMAP (2.4 mg, 0.198 mmol) in THE (1 ml) at rt was added triphosgene (35 mg, 0.119 mmol). The reaction was stirred at rt for 5 min. It was diluted with EtOAc and washed with sat. aq. NaHCO₃ and brine. The organic was dried (Na₂SO₄), filtered and concentrated.

The residue was chromatographed (silica, hexanes/acetone) to give the title compound (15 mg, 0.028 mmol, 29% yield). ESI-MS m/z=528.05, 530.05 [M–H]⁻.

Example 157

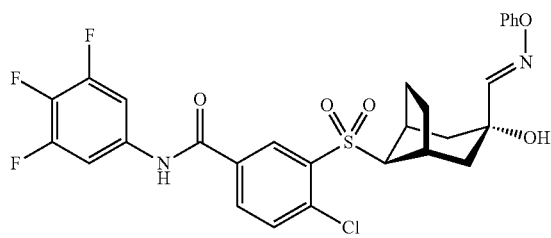

To a mixture of compound from Example 129 (50 mg, 0.10 mmol) in pyridine (1 ml) at rt was added O-phenylhydroxylamine hydrochloride (22 mg, 0.149 mmol). The reaction was stirred at rt for 4 h. The reaction was then concentrated. The residue was chromatographed (silica, hexanes/acetone) to give the title compound (16 mg, 0.027 mmol, 27%). ESI-MS m/z=591.10, 593.10 [M–H]⁻.

Example 159

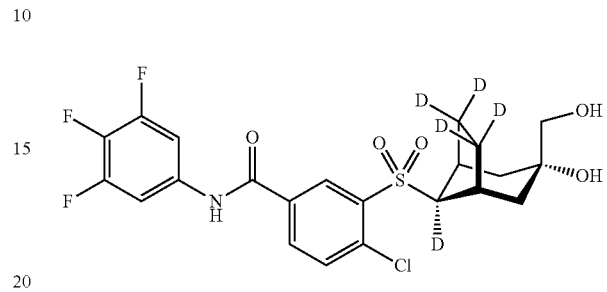

Step 159a. Cyclopentanone-3,3,4,4-d₄ (10 g, 113 mmol), pyrrolidine (10.36 mL, 8.84 g, 124 mmol) and toluene (30 mL) were added into a 100 mL RBF equipped with a Dean-Stark water separator. p-TsOH·H₂O (0.107 g, 0.565 mmol) was then added. The reaction mixture was then stirred at 118° C. for 4 h. after condensed to half the volume under reduced pressure. The mixture distilled under vacuum (93-98° C./22-26 mbar) to give the desired product as a colorless oil (8.1 g, 50%). ¹HNMR (400 MHz, CDCl₃) δ 4.22 (s, 1H), 2.80 (t, 4H), 2.36 (s, 2H), 1.51 (t, 4H).

Step 159b. Into the mixture of 2-methylenepropane-1,3-diyl diacetate (10.96 g, ~90% w/w, 9.87 g, 57.3 mmol), Ph₃P (301 mg, 1.147 mmol) and palladium diacetate (129 mg, 0.573 mmol, the compound from step 159a (8.1 g, 57.3 mmol) was added. The reaction was degassed and refilled with nitrogen and heated at 65° C. for 2 h. HCl (0.5 M, 20 mL) was added slowly. It was stirred at 65° C. for 2 h before being cooled. It was partitioned (Water/hexane). The aqueous phase was extracted twice with Hexanes. The organic was washed with HCl (0.5 M), water and brine and dried (Na₂SO₄). After being filtered and concentrated, the residue was distilled (b.p. 75-82° C./10 mbar), to afford the desired product as colorless oil (4.1 g, 51%). ¹HNMR (400 MHz, CDCl₃) δ 4.99 (s, 2H), 2.72 (dd, 2H), 2.45 (dd, 2H), 2.25 (t, 2H).

Step 159c. The desired compound was synthesized from compound from step 159b and LiAlD₄ by following the conditions described in step 39b and was used directly in the next step.

Step 159d. The title compound was prepared from compound from step 159c by following the sequences from step 138a to 138c, then the conditions in step 133e. ESI-MS m/z=507.10, 509.10 [M–H]⁻.

Example 160

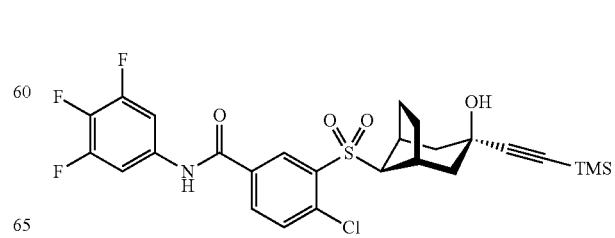

To a solution of ethynyltrimethylsilane (0.15 mL, 1.06 mmol) in THF (1 mL) at −78° C. was added n-BuLi (1.6M in hexane, 0.66 mL, 1.06 mmol). This was maintained at −78° C. for 1 h. To this a solution of compound from example 129 (100 mg, 0.212 mmol) in THF (1 ml) at rt was added. The reaction was warmed to rt and maintained for 2 h. It was diluted with EtOAc and washed with sat. aq. NH₄Cl and brine. The organic was dried (Na₂SO₄), filtered and concentrated. The residue was chromatographed (silica, hexanes/acetone) to give the title compound (46 mg, 0.028 mmol, 38% yield). ESI-MS m/z=568.11, 570.10 [M−H]⁻.

Example 161

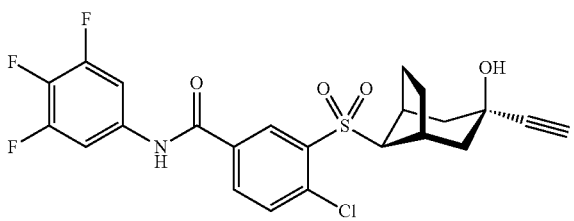

Step 161. To a mixture of compound from step 160 (42 mg, 0.074 mmol) in THF (1 ml) and MeOH (1 ml) at rt was added K₂CO₃ (20 mg, 0.147 mmol). The reaction was stirred at rt for 4 h. It was diluted with EtOAc and washed with water and brine. The organic was dried (Na₂SO₄), filtered and concentrated. The residue was chromatographed (silica, hexanes/acetone) to give the title compound (33 mg, 0.066 mmol, 90% yield). ESI-MS m/z=496.10, 498.06 [M−H]⁻.

Example 162

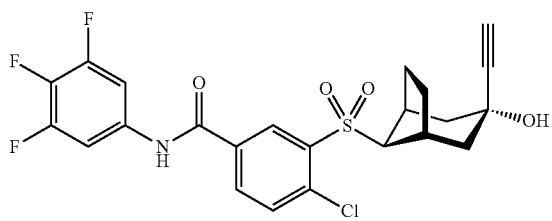

Step 162. To a solution of compound from example 129 (175 mg, 0.349 mmol) and dimethyl (1-diazo-2-oxopropyl) phosphonate (0.105 ml, 0.697 mmol) in THF (4 ml) and MeOH (2 ml) at 0° C. was added Cs₂CO₃ (454 mg, 1.395 mmol). The reaction was stirred at 0° C. for 2 h. It was diluted with EtOAc and washed with water and brine. The organic was dried (Na₂SO₄), filtered and concentrated. The residue was chromatographed (silica, hexanes/acetone) to give the title compound (74 mg, 0.149 mmol, 43% yield). ESI-MS m/z=496.06, 498.06 [M−H]⁻.

Example 163

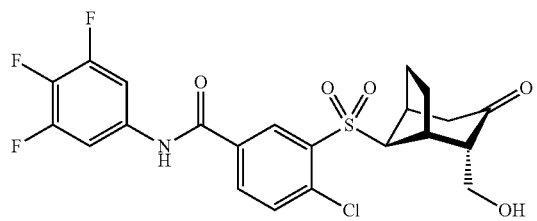

Step 163. To a solution of iodomethyl pivalate (0.1 mL, 0.642 mmol) in THF (1 ml) at −78° C. was added isopropylmagnesium chlorid-lithium chloride complex (1.3M in THF, 0.6 ml, 0.771 mmol). After stirring for 15 minutes a solution of compound from step EP-025336 (121 mg, 0.257 mmol) in THF (1.5 ml) was added. The reaction was warmed to rt and stirred for 2 h. It was diluted with EtOAc and washed with sat. aq. NH₄Cl and brine. The organic was dried (Na₂SO₄), filtered and concentrated. The residue was chromatographed (silica, hexanes/acetone) to give the title compound (25 mg, 0.049 mmol, 19% yield). ESI-MS m/z=500.06, 502.05 [M−H]⁻.

Example 164

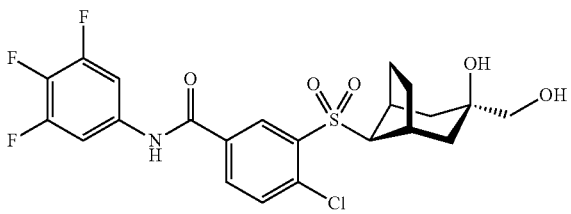

To a solution of compound from step EP-025538 (48 mg, 0.098 mmol) in THF (1 ml) and water (1 ml) at rt was added TFA (0.1 ml, 1.298 mmol). The reaction was stirred at rt for 18 h.

It was diluted with EtOAc and washed with aq. Sat. NaHCO₃ and brine. The organic was dried (Na₂SO₄), filtered and concentrated. The residue was chromatographed (silica, hexanes/acetone) to give the title compound (33 mg, 0.064 mmol, 66% yield). ESI-MS m/z=502.08, 504.07 [M−H]⁻.

Example 165

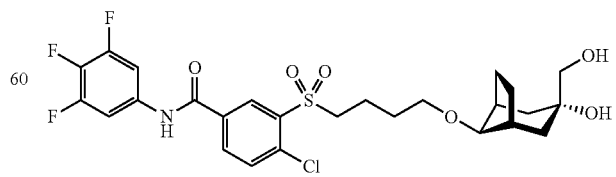

The title compound was isolated from Example 60 (Method B). ESI-MS m/z=574.13, 576.13 [M−H]⁻.

Example 167

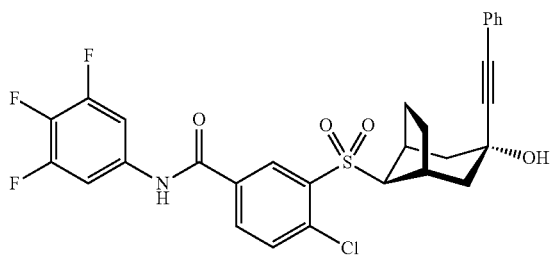

To a solution of compound from example 162 (20 mg, 0.040 mmol), DIPEA (0.1 ml, 0.702 mmol), and iodobenzene (9 µl, 0.08 mmol) in DMF (0.4 ml) at rt was added PdCl$_2$(PPh$_3$)$_2$ (2.8 mg, 4.0 µmol), CuI (1.5 mg, 8.0 mol), and PPh$_3$ (8.0 µmol). The reaction was stirred at 50° C. for 18 h. It was diluted with EtOAc and washed with aq. Sat. NaHCO$_3$ and brine. The organic was dried (Na$_2$SO$_4$), filtered and concentrated. The residue was chromatographed (silica, hexanes/acetone) to give the title compound (11 mg, 0.019 mmol, 48% yield). ESI-MS m/z=572.09, 574.10 [M−H]$^−$.

Example 173

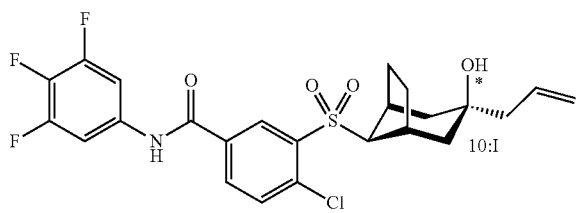

To a solution of example 130 (50 mg, 0.106 mmol) in THF (1 ml) at 0° C. was added allylmagneisum bromide solution (1 M in THF, 0.5 mL, 0.5 mmol). The reaction was warmed to rt and stirred for 1 h. It was diluted with EtOAc and washed with sat. aq. NH$_4$Cl and brine. The organic was dried (Na$_2$SO$_4$), filtered and concentrated. The residue was purified by prep-HPLC (acetonitrile/water) to give the title compound (24 mg, 44% yield). ESI-MS m/z=[M−H]$^−$.

Example 177

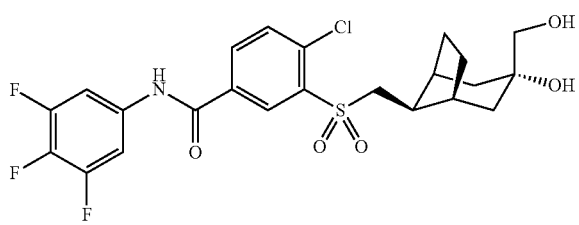 [SMILES: O=C(Nc1cc(F)c(F)c(F)c1)c1ccc(Cl)c(S(=O)(=O)C[C@H]2C3CC[C@H]2C[C@](O)(CO)C3)c1]

Step 177a. To a suspension of (methoxymethyl)triphenylphosphonium chloride (3.89 g, 11.3 mmol) THF (5.0 mL) at 0° C. was added t-BuOK (1.70 g, 15.1 mmol). The resulting reaction mixture was stirred at rt for 30 mins. A solution of compound from step 39a (1.03 g, 7.56 mmol) was added and stirred at rt for 16 h. The reaction was quenched with aqueous NH$_4$C$_1$ and the mixture was extracted with EtOAc, washed with water, brine. The organic layer was dried (Na$_2$SO$_4$), filtered and concentrated. The crude product was chromatographed (silica, hexanes/MBTE) to give the desired compound as white solid (1.21 g, 97%).

Step 177b. A solution of compound from step 177a (1.21 g, 7.37 mmol) in THF (10 mL) at rt was added HCl (3 mL 3 N, 9.0 mmol) and stirred at rt for 2 h. It was concentrated under vacuum to remove majority of THF and the residue was extracted with EtOAc. The organic phase was washed with water, 10% K$_2$CO$_3$, brine, dried over Na$_2$SO$_4$, filtered, concentrated to give a mixture of two diasteromers (~2.5/1) (0.97 g, 88%).

Step 177c. To a solution of compounds from step 177b (0.97 g, 6.46 mmol) in MeOH (10 mL) at 0° C. was added NaBH$_4$ (0.24 g, 6.46 mmol). The resulting reaction mixture was stirred at rt for 1 h. The reaction was quenched with aqueous NH$_4$Cl and the mixture was extracted with EtOAc, washed with water, brine. The organic layer was dried (Na$_2$SO$_4$), filtered and concentrated to give a mixture of two diasteromers (0.98 g, 100%).

Step 177d. To a stirred solution of the compound from Step 1c (0.856 g, 2.69 mmol) and compounds from step 177c (0.41 g, 2.69 mmol) in toluene-THF (5.0 ml/5.0 mL) was added 2-(tributyl-15-phosphanylidene)acetonitrile (0.78 g, 3.23 mmol), and the mixture was stirred at 65° C. for 16 h. It was cooled to rt, diluted with MBTE, washed with NaOH (0.5 N), brine, dried over Na$_2$SO$_4$, filtered, concentrated, silica column to desired products as a mixture of two diasteromers (1.02 g, 84%). ESI-MS m/z=450.09, 452.09 [M−H]$^−$.

Step 177e. To a suspension of compounds from step 177d (0.88 g, 1.95 mmol), NMO (1.14 g, 9.74 mmol) in acetone-water (7.0 mL/1.0 mL) at rt was added osmium tetroxide (0.76 ml 2.5% solution in t-BuOH, 0.049 mmol) and the mixture was stirred at rt for 24 h. It was quenched with aqueous Na$_2$SO$_3$, extracted with EtOAc, washed with water, 3NHCl, NaHCO$_3$, brine, dried over Na$_2$SO$_4$, filtered, concenrated and chromatographed (silica, hexanes/EtOAc) to give a mixture of two diasteromers as white solid (0.85 g, 84%) and two diasteromers (100 mg) were separated by prep-HPLC using a C18 column and acetonitrile/water as eluent to give title compound (0.024 g). ESI-MS m/z=516.08, 518.08 [M−H]$^−$.

Example 178

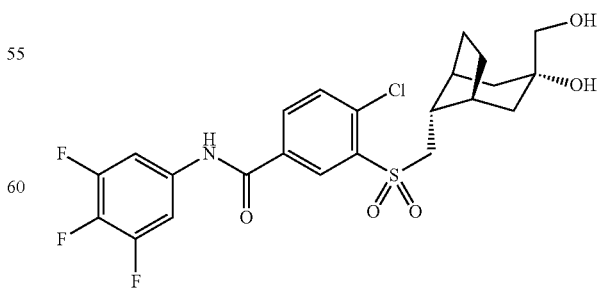

The title compound (0.061 g) was isolated from example 177. ESI-MS m/z=516.08, 518.08 [M−H]$^−$.

Example 179

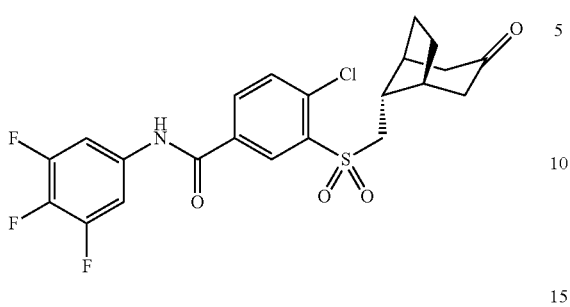

The compounds from example 177 and 178 (0.75 g, 1.448 mmol) in THF-water (20 mL/5.0 ml) was added sodium periodate (0.619 g, 2.90 mmol) and stirred at rt for 16 h. It was extracted with EtOAc, washed with water, brine, dried over Na$_2$SO$_4$, filtered, concentrated, chromatographed (silica, hexanes/EtOAc) to give a mixture of two diasteromers as white solid (0.67 g, 95%) and two diasteromers (100 mg) were separated by prep-HPLC using a C$_{18}$ column and acetonitrile/water as eluent to give title compound (0.0 59 g). ESI-MS m/z=484.06, 486.06 [M–H]$^-$.

Example 180

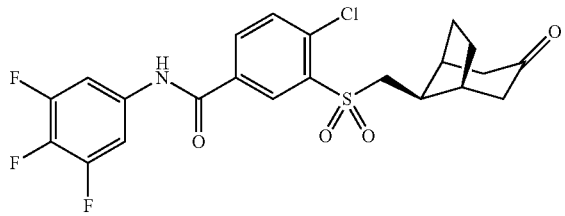 [SMILES: O=C1CC2CC[C@@H](C1)[C@H]2CS(=O)(=O)c1cc(C(=O)Nc2cc(F)c(F)c(F)c2)ccc1Cl]

The title compound (0.024 g) was isolated from example 179. ESI-MS m/z=484.06, 486.06 [M–H]$^-$.

Example 181

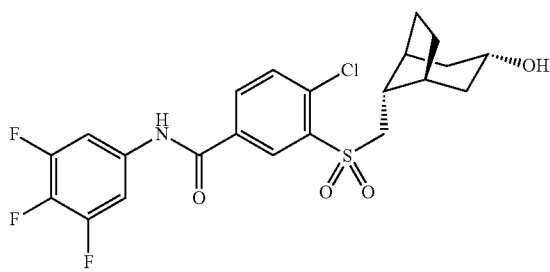 [SMILES: O=C(Nc1cc(F)c(F)c(F)c1)c1ccc(Cl)c(S(=O)(=O)C[C@@H]2C3CC[C@H]2C[C@@H](O)C3)c1]

To a stirred mixture of compound from Example 179 (50 mg, 0.10 mmol) in MeOH (2.0 mL) at 0° C. was added NaBH$_4$ (7.8 mg, 0.21 mmol) and the mixture was stirred at 0° C. for 30 minutes. The reaction was quenched with aqueous NH$_4$Cl solution, and extracted with ethyl acetate and washed with water, brine. The organic was dried (Na$_2$SO$_4$) and concentrated. The residue was separated by prep-HPLC using a C18 column and acetonitrile/water as eluent to give title compound (24 mg, 48%). ESI-MS m/z=486.07, 488.07 [M–H]$^-$.

Example 183

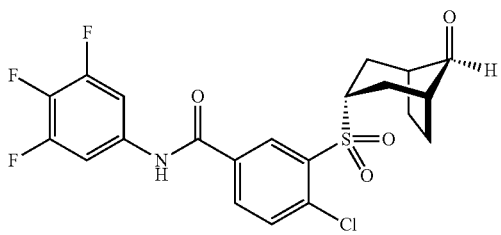

To the compound of example 191 (0.32 g, 0.72 mmol) in THF (3.0 mL) was added mCPBA (0.45 g 77%, 2.0 mmol) and stirred at rt overnight. Aqueous Na$_2$S$_2$O$_3$, NaHCO$_3$ and few drops of Et$_3$N was added and stirred at rt for 1 h. It was extracted with EtOAc, washed with water, brine, dried over Na$_2$SO$_4$, filtered, concentrated and recrystalized from methanol to give the title compound (0.26 g, 75%). ESI-MS m/z=472.06, 474.06 [M–H]$^-$.

Example 184

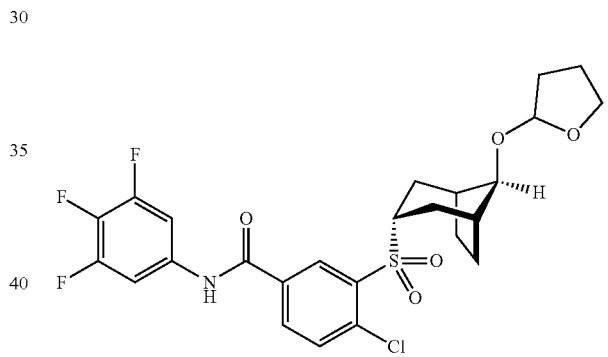

The title compound was isolated from example 183. ESI-MS m/z=542.10, 544.10 [M–H]$^-$.

Example 185

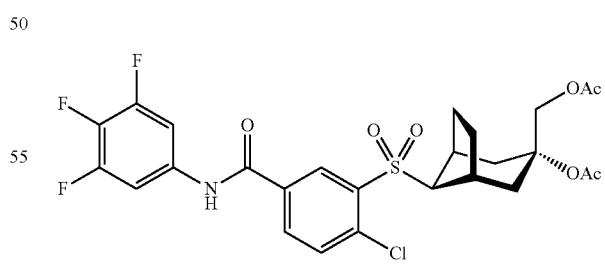

To a solution of the compound from Example 60 (213 mg, 0.423 mmol) in CH$_2$Cl$_2$ (4.2 mL) at 0° C. was added iPr$_2$EtN (369 μl, 2.11 mmol), Ac$_2$O(120 μl, 1.27 mmol) and DMAP (51.6 mg, 0.423 mmol), then the mixture was warmed to rt and kept for overnight. It was partitioned between EtOAc and brine. The organic was dried (Na$_2$SO$_4$), filtered and concentrated. The residue was chromatographed (silica, hexanes/EtOAc) to give the title compound (79 mg, 32% yield) as a white solid. MS-ESI, M/Z=586.09, 588.09 [M–H]⁻.

Example 188

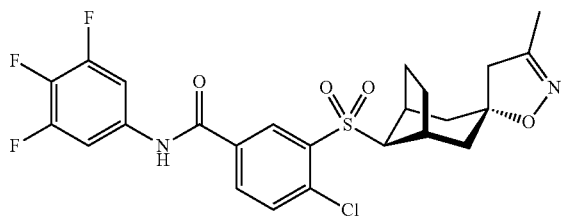 [SMILES: CC1=NO[C@@]2(C1)CC1CC[C@@H](C2)[C@H]1S(=O)(=O)c1cc(C(=O)Nc2cc(F)c(F)c(F)c2)ccc1Cl]

Step 188a: To a solution of step 39c (200 mg, 0.106 mmol), ethyl nitrate (45 mg, 0.60 mmol) and 3 drops TEA in benzene, phenyl isocynate was added dropwise and stirred 2 h at rt before being concentrated. The crude was chromatographed (silica, hexanes/acetone) to give the title compound (22 mg, 10%). ESI-MS m/z=493.09, 495.09 [M–H]⁻.

Step 188b: Into the solution of the compound from step 188a (22 mg, 0.044 mmol) in NMP (1 mL), m-CPBA (77% w/w, 50 mg, 0.22 mmol) and stirred at rt for o/n. The crude was directly purified on prep-HPLC (20 nm NH₄HCO₃ buffer and ACN) to give the title compound (17 mg, 73%) as a white solid. ESI-MS m/z=525.08, 527.08 [M–H]⁻.

Example 189

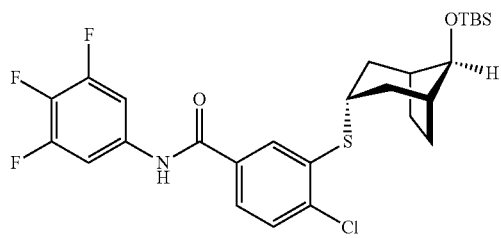

To a stirred solution of the compound from Step Ic (2.478 g, 7.80 mmol) polar diastereomer from step 191c (2.0 g, 7.80 mmol) in toluene (50 ml) was added 2-(tributyl-15-phosphanylidene)acetonitrile (4.09 ml, 15.60 mmol), and the mixture was stirred at 85° C. for 16 h. It was cooled to rt, diluted with MBTE, washed with NaOH (0.5 N), brine, dried over Na₂SO₄, filtered, concentrated, silica column desired compound (3.9 g, 90%). ESI-MS m/z=554.15, 556.15 [M–H]⁻.

Example 190

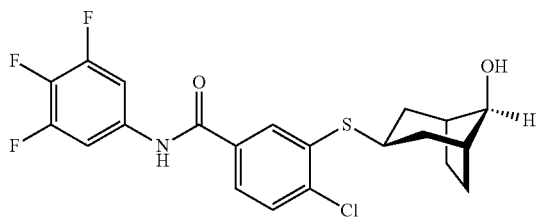

A suspension of compound from example 189 (7.1 g, 12.77 mmol) in MeOH (300 mL) at rt was added con HCl (30 mL) and stirred at rt for 60 h. It was concentrated under vacuum to remove majority of MeOH and the residue was extracted with EtOAc. The organic phase was washed with water, 10% K₂CO₃, brine, dried over Na₂SO₄, filtered, concentrated and recrystallized from EtOAc/hexanes to give desired product as a white solid (4.52 g, 80%). ESI-MS m/z=440.07, 442.07 [M–H]⁻.

Example 191

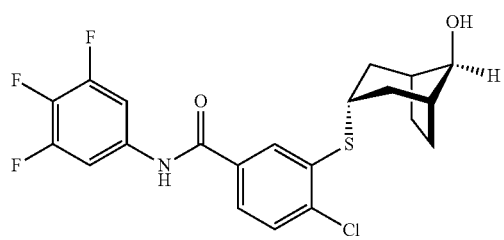

Step 191a. To a stirred compound from step 39b (4.22 g, 23.5 mmol) and imidazole (4.00 g, 58.8 mmol) in DMF (45 mL) at 0° C. was added TBSCI (4.25 g, 28.2 mmol). The resulting reaction mixture was stirred at rt for 16 h. The reaction was diluted with MBTE and the mixture was washed with water, brine. The organic layer was dried (Na₂SO₄), filtered and concentrated. The crude product was chromatographed (silica, hexanes/MBTE) to give the desired compound as white solid (5.94 g, 100%).

Step 191b. A suspension compound from step 191a (5.94 g, 23.53 mmol) in dioxane-water (72 ml/24 mL) at rt was added 2,6-dimethylpyridine (5.48 ml, 47.1 mmol), osmium (VIII) oxide (5.91 ml, 0.471 mmol) and sodium periodate (20.13 g, 94 mmol) and the mixture was stirred at rt for 20 h. It was quenched with aqueous Na₂S₂O₃, extracted with MBTE, washed with water, brine, dried over Na₂SO₄, filtered, concentrated, and chromatographed on a silica column to give desired product as white solid (5.03 g, 84%).

Step 191c. To a solution of the compound of step 191b (5.0 g, 19.7 mmol) in MeOH (50 mL) at 0° C. was added NaBH₄ (1.12 g, 29.6 mmol). The resulting reaction mixture was stirred at rt for 1 h. The reaction was quenched with aqueous NH₄Cl and the mixture was extracted with MBTE, washed with water, brine. The organic layer was dried (Na₂SO₄), filtered and concentrated. The crude product was chromatographed (silica, hexanes/MBTE) to give the less polar diastereomer (1.83 g, 36%) and another diastereomer as white solids (2.0 g, 39%).

Step 191d. To a stirred solution of the less polar diastereomer from step 191c (315 mg, 1.23 mmol) and compound from step 1c (390 mg, 1.23 mmol) in toluene (5 ml) was added 2-(tributyl-15-phosphanylidene)acetonitrile (0.81 ml, 3.07 mmol), and the mixture was stirred at 100° C. for 60 h. It was cooled to rt, diluted with MBTE, washed with NaOH (0.5 N), brine, dried over Na₂SO₄, filtered, concentrated, silica column to desired compound (362 mg, 53%). ESI-MS m/z=554.15, 556.15 [M–H]⁻.

Step 191e. A suspension of compound from step 191d (0.53 g, 0.95 mmol) in MeOH (11 mL) at rt was added con HCl (1.0 mL) and stirred at rt for 24 h. It was concentrated under vacuum to remove majority of MeOH and the residue was extracted with EtOAc. The organic phase was washed with water, 10% K₂CO₃, brine, dried over Na₂SO₄, filtered, concentrated and recrystallized from EtOAc/hexanes to give desired product as a white solid (0.33 g, 78%). ESI-MS m/z=440.07, 442.07 [M−H]⁻.

Example 192

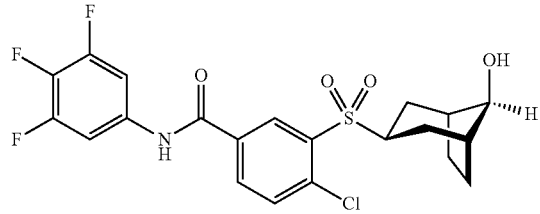

To a solution of compound from example 190 (0.32 g, 0.72 mmol) NMP (3.0 mL) was added mCPBA (0.45 g 77%, 2.0 mmol) and stirred at rt 20 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and recrystalized from methanol to give the title compound (0.26 g, 75%). ESI-MS m/z=472.06, 474.06 [M−H]⁻.

Example 193

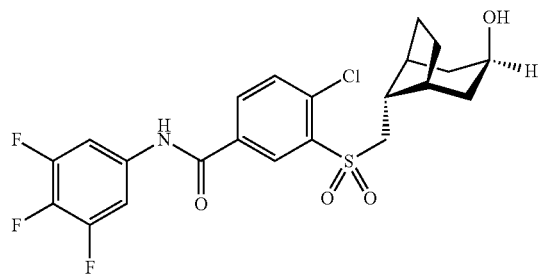 [SMILES: O=C(Nc1cc(F)c(F)c(F)c1)c1ccc(Cl)c(S(=O)(=O)C[C@@H]2C3CC[C@H]2C[C@H](O)C3)c1]

The title compound (18 mg, 36%) was isolated from example 181. ESI-MS m/z=484.06, 486.06 [M−H]⁻.

Example 194

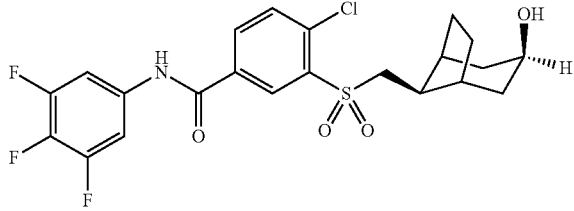 [SMILES: O=C(Nc1cc(F)c(F)c(F)c1)c1ccc(Cl)c(S(=O)(=O)C[C@H]2C3CCC2C[C@H](O)C3)c1]

The title compound was isolated from example 182. ESI-MS m/z=484.06, 486.06 [M−H]⁻.

Example 195

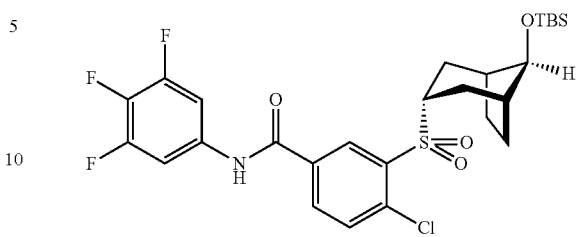

To a solution of compound from example 189 in (96 mg, 0.172 mmol) THF (2.0 mL) was added mCPBA (0.11 g 77%, 0.48 mmol) and stirred at rt for 2 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and recrystalized from methanol to give the title compound (65 mg, 68%). ESI-MS m/z=586.15, 588.15 [M−H]⁻.

Example 197

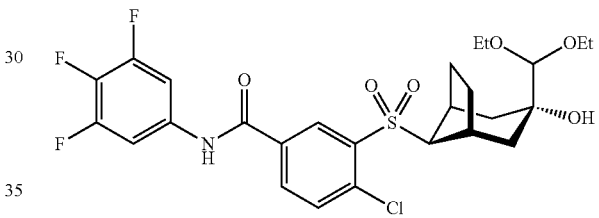

A solution of example 129 (35 mg, 0.07 mmol), N-methylhydroxylamine (6 mg, 0.07 mmol) in EtOH (3 mL), was stirred 2 h at 55° C. before being concentrated. The crude was chromatographed (silica, hexanes/acetone) to give the title compound (11 mg, 30%). ESI-MS m/z=574.12, 576.12 [M−H]⁻.

Example 200

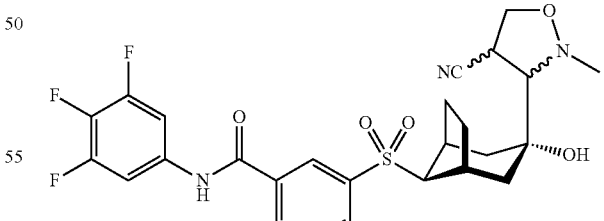

A solution of compound from example 196 (30 mg, 0.057 mmol) and methyl acrylate (0.5 ml, 5.55 mmol) in toluene (2 ml) was heated at 80° C. for 3 h. The crude reaction mixture was concentrated. The residue was chromatographed (silica, hexanes/acetone) to give the title compound (19 mg, 0.031 mmol, 55% yield). ESI-MS m/z=582.16, 584.16 [M−H]⁻.

Example 206

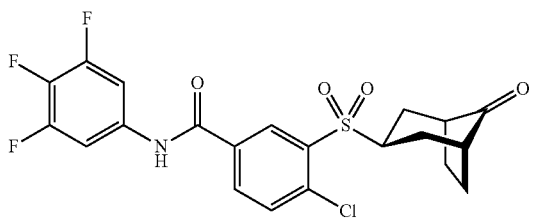

A solution of compound from example 183 (1.8 g, 3.8 mmol) in DMSO (10 mL) at rt was added IBX (4.3 g, 15.3 mmol) and the mixture was stirred at 45° C. for 20 h. Aqueous $Na_2S_2O_3NaHCO_3$ and few drops of $Et_3N$ was added and stirred at rt for 1 h. It was extracted with EtOAc, washed with water, brine, dried over $Na_2SO_4$, filtered and concentrated to give the title compound (1.65 g, 92%). ESI-MS m/z=470.04, 472.04 [M−H]⁻.

Example 207

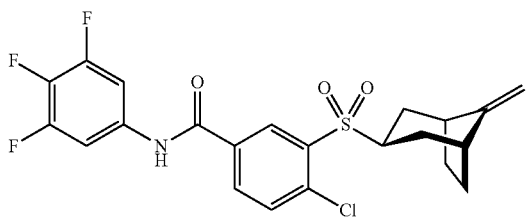

To a suspension of methyltriphenylphosphonium bromide (0.47 g, 1.3 mmol) THE (1.1 mL) at 0° C. was added t-BuOK (0.20 g, 1.8 mmol). The resulting reaction mixture was stirred at rt for 30 mins. A solution of compound from example 206 (0.21 g, 0.44 mmol) in THE (3.0 mL) was added and stirred at rt for 20 h. The reaction was quenched with aqueous $NH_4Cl$ and the mixture was extracted with EtOAc, washed with water, brine. The organic layer was dried ($Na_2SO_4$), filtered and concentrated. The crude product was chromatographed (silica, hexanes/EtOAc) to give the desired compound as white solid (90 mg, 43%). ESI-MS m/z=468.06.08, 470.06 [M−H]⁻.

Example 208

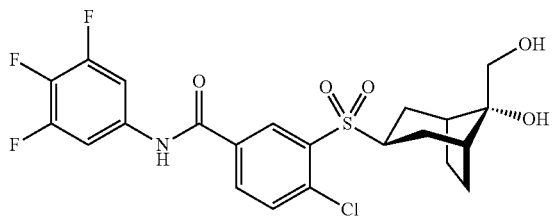

To a suspension of compound from example 207 (89 mg, 0.19 mmol) and NMO (67 mg, 0.57 mmol) in acetone-water (3 mL/0.5 mL) at rt was added osmium tetroxide (0.24 ml 2.5% solution in t-BuOH, 0.019 mmol) and the mixture was stirred at rt for 24 h. It was quenched with aqueous $Na_2SO_3$, extracted with EtOAc, washed with water, 3NHCl, $NaHCO_3$, brine, dried over $Na_2SO_4$, filtered, concenrated and recrystalized from MeOH to give the title compound (40 mg, 42%). ESI-MS m/z=502.07, 504.07 [M−H]⁻.

Example 211

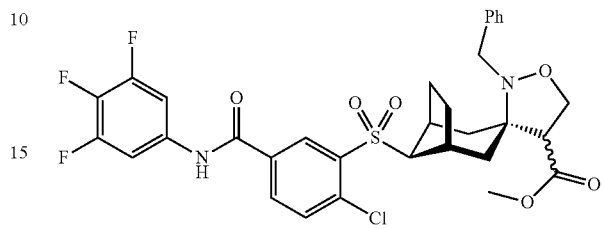

The solution of example 130 (100 mg, 0.21 mmol) and N-benzylhydroxylamine HCl (68 mg, 0.42 mmol) was stirred in pyridine for 3 hours before it was concentrated and kept under vacuum o/n/. To this mixture, methyl acrylate (91 mg, 1.05 mmol) and toluene (2 mL) was added. It was heated at 90° C. for 3 hours before it was concentrated. The crude was chromatographed (silica, aectoen/hexanes) to give the tithe compound (11 mg, 30%). ESI-MS m/z=661.14, 663.13 [M−H]⁻.

Example 212

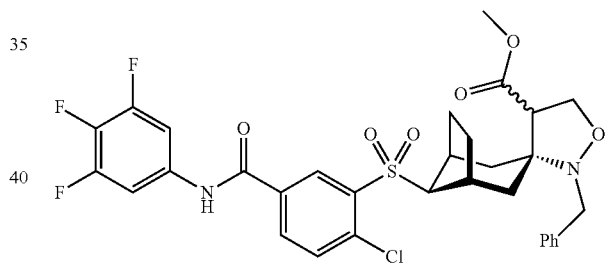

The title compound was isolated from the same reaction of preparation of Example 211. ESI-MS m/z=661.13, 663.13 [M−H]⁻.

Example 220

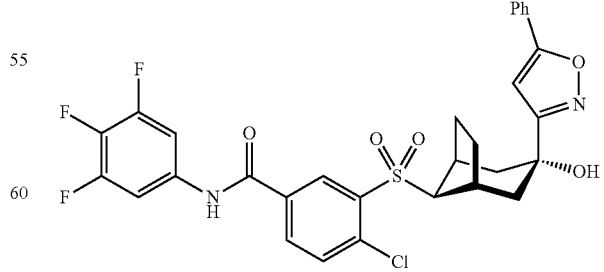

Into the solution example 129 (38 mg, 0.074 mmol) and phenyl acetylene (0.5 mL) in MeOH (1 mL) water (0.2 mL) and THF (0.5 mL), phenyl-13-iodanediyl bis(2,2,2-trifluoroacetate) was added. It was stirred at rt for 1.5 h before it was concentrated. The crude was chromatographed (silica, acetone/hexanes) to give the title compound (12 mg, 26). ESI-MS m/z=615.09, 617.09 [M–H]⁻.

Example 221

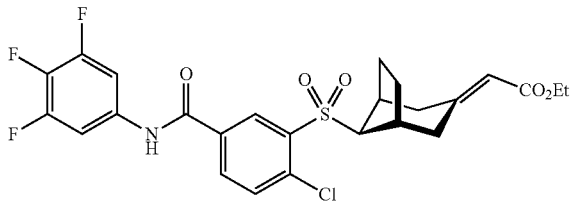

Into the solution of ethyl 2-(diethoxyphosphoryl)acetate (100 mg, 0.64 mmol) in THF (2 mL), NaH (60% w/w, 26 mg, 0.64 mmol) was added and stirred 30 minutes. Example 130 (100 mg, 0.21 mmol) was added and stirred 0/n at rt. It was diluted with EtOAc and washed with aq. NH₄Cl and brine. The organic was dried (Na₂SO₄), filtered and concentrated. The residue was chromatographed (silica, hexanes/acetone) to give the title compound (73 mg, 63%). ESI-MS m/z=540.08, 542.08 [M–H]⁻.

Example 223

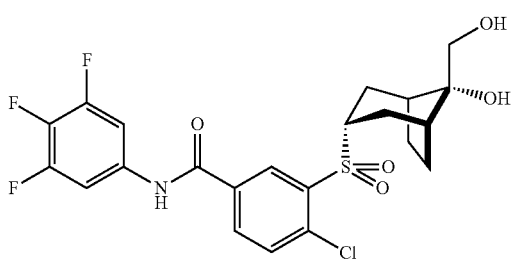

Step 223a. A solution of compound from example 190 (4.52 g, 10.2 mmol) in DMSO (30 mL) at rt was added IBX (4.3 g, 15.3 mmol) and the mixture was stirred at rt for 24 h. Aqueous Na₂S₂O₃NaHCO₃ and few drops of Et₃N was added and stirred at rt for 1 h. It was extracted with EtOAc, washed with water, brine, dried over Na₂SO₄, filtered and concentrated to give the desired ketone (4.42 g, 98%). ESI-MS m/z=438.05, 440.05 [M–H]⁻.

Step 223b. To a suspension of methyltriphenylphosphonium bromide (0.24 g, 0.67 mmol) THF (1.0 mL) at 0° C. was added t-BuOK (0.11 g, 1.0 mmol). The resulting reaction mixture was stirred at rt for 30 mins. A solution of compound from step 223 a (0.15 g, 0.34 mmol) in THF (1.0 mL) was added and stirred at rt for 24 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (1.36 g, 75%). ESI-MS m/z=436.08, 438.07 [M–H]⁻.

Step 223c. To a suspension of compound from step 223b (0.14 g, 0.298 mmol) and NMO (0.209 g, 1.788 mmol) in acetone-water (3 mL/0.5 mL) at rt was added osmium tetroxide (0.374 ml, 0.030 mmol) and the mixture was stirred at rt for 3 days. It was quenched with aqueous Na₂SO₃, extracted with EtOAc, washed with water, 3NHCl, NaHCO₃, brine, dried over Na₂SO₄, filtered, concenrated to give a mixture of sulfone and sulfoxide. To a mixture of sulfone and sulfoxide in NMP (2 mL) was added mCPBA (0.16 g 77%, 0.72 mmol) and stirred at rt for 20 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and recrystalized from methanol to give the title compound (78 mg, 54%). ESI-MS m/z=502.07, 504.07 [M–H]⁻.

Example 225

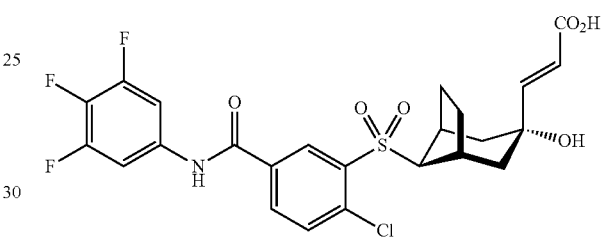

Into the solution of example 222 (27 mg, 0.047 mmol) in THF (1 mL), aq. LiOH (1 M, 1 mL) was added and stirred at rt o/n. It was diluted with EtOAc and washed with 1 M HCl and brine. The organic was dried (Na₂SO₄), filtered and concentrated. The residue was purified by prep-HPLC (acetonitrile/water) to give the title compound (7 mg, 27%). ESI-MS m/z=542.06, 544.06 [M–H]⁻.

Example 227

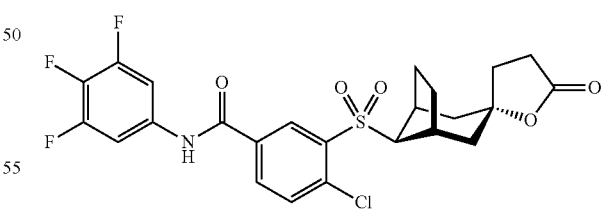

Into the solution of example 222 (17.5 mg, 0.03 mmol) in MeOH (2 mL), Pd/C (10% w/w, 3 mg) was added. The mixture was stirred at rt under the atmosphere of hydrogen (balloon) o/n.

It was filtered through a pad of celite. The filtrate was concentrated and purified by prep-HPLC (acetonitrile/water) to afford the title compound (11 mg, 63%). ESI-MS m/z=492.11 [M–H]⁻.

Example 239

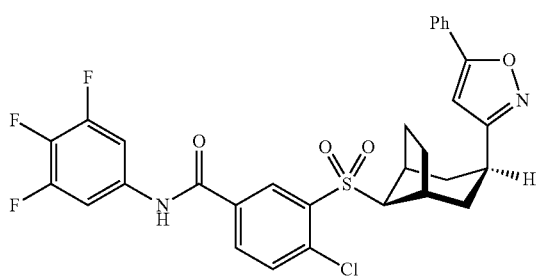 [SMILES: O=C(Nc1cc(F)c(F)c(F)c1)c1ccc(Cl)c(S(=O)(=O)[C@H]2C3CC[C@H]2C[C@H](c2cc(-c4ccccc4)on2)C3)c1]

Step 239a. Into the solution of example step 106 (500 mg, 1.0 mmol) in THF, DMP (522 mg, 1.2 mmol) was added. It was stirred at rt for 2 hours before addition of EtOAc and water. The resulted mixture was filtered and washed with EtOAc. The filtrate was partitioned (EtOAc/water). The organic was washed with aq. NaHCO$_3$, brine and dried (Na$_2$SO$_4$). After concentration, the crude product was chromatographed (silica, acetone/hexanes) to give the desired compound (410 mg, 82%).

Step 239b. Into the solution of example step 239a (310 mg, 0.64 mmol) in pyridine, hydoxylamine HCl (89 mg, 1.28 mmol) was added. It was stirred at rt for 1 h before it was concentrated. The crude product was chromatographed (silica, acetone/hexanes) to give the desired compound (45 mg, 14%). ESI-MS m/z=499.07, 501.07 [M–H]$^-$.

Step 239c. Into the solution step 239b (38 mg, 0.074 mmol) and phenyl acetylene (0.5 mL) in MeOH (1 mL) water (0.2 mL) and THE (0.5 mL), phenyl-13-iodanediyl bis(2,2,2-trifluoroacetate) (64 mg, 0.15 mmol) was added. It was stirred at rt for 1.5 h before it was concentrated. The crude was chromatographed (silica, acetone/hexanes) to give the title compound (9 mg, 21%). ESI-MS m/z=599.10, 601.10[M–H]$^-$.

Example 241

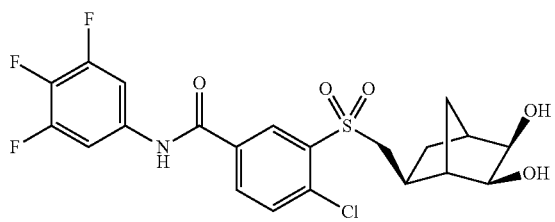 [SMILES: O=C(Nc1cc(F)c(F)c(F)c1)c1ccc(Cl)c(S(=O)(=O)C[C@H]2CC3CC2[C@H](O)[C@@H]3O)c1]

Step 241a. (Bicyclo[2.2.1]hept-5-en-2-yl)methyl methanesulfonate (1.6 g, 7.91 mmol) and NMO (1.85 g, 15.82 mmol) in acetone-water (12 ml/3 ml) was added osmium tetroxide (4.97 ml 2.5% solution in t-BuOH, 0.396 mmol) and stirred at rt for 20 h. It was quenched with aqueous Na$_2$S$_2$O$_3$, extracted with EtOAc, washed with 1N HCl, aqueous sat·NaHCO$_3$, brine, dried over Na$_2$SO$_4$, filtered, concentrated to give ((1S,4S,5S,6R)-5,6-dihydroxybicyclo[2.2.1]heptan-2-yl)methyl methanesulfonate (1.4 g, 75% yield).

Step 241b. To a stirred solution of the compounds from step Ic (0.89 g, 2.8 mmol) and step 241a (0.63 g, 2.7 mmol) in THE (6.0 mL) was added KOt-Bu (0.33 g, 2.9 mmol). The mixture was stirred at rt for 24 h. It was quenched with aqueous sat. NaHCO$_3$, extracted with EtOAc, washed with 0.5 N NaOH, brine, dried over Na$_2$SO$_4$, filtered, con, column to desired compound (1.07 g, 88%). ESI-MS m/z=456.06, 458.06 [M–H]$^-$.

Step 241c. To a solution of compound from step 241b (0.36 g, 0.78 mmol) in NMP (4.0 mL) was added mCPBA (0.49 g 77%, 2.2 mmol) and stirred at rt for 53 h. Aqueous Na$_2$S$_2$O$_3$, NaHCO$_3$ and few drops of Et$_3$N was added and stirred at rt for 1 h. It was extracted with EtOAc, washed with water, brine, dried over Na$_2$SO$_4$, filtered, concentrated and prep-HPLC to give title compound (36 mg, 9.3%). ESI-MS m/z=488.05, 490.05 [M–H]$^-$.

Example 242

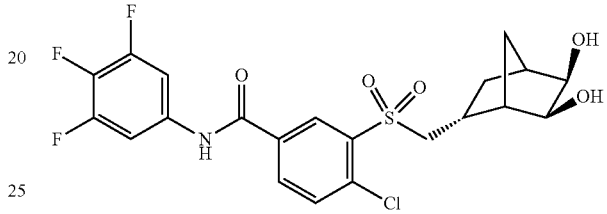

The title compound (128 mg, 33%) was isolated from example 241. ESI-MS m/z=488.05, 490.05 [M–H]$^-$.

Example 243

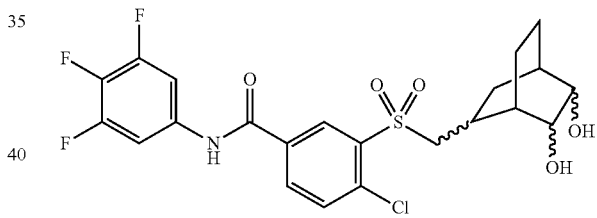

The title compound which structure was tentatively assigned was synthesized using procedures similar to that described in example 241. ESI-MS m/z=502.07, 504.07 [M–H]$^-$.

Example 245

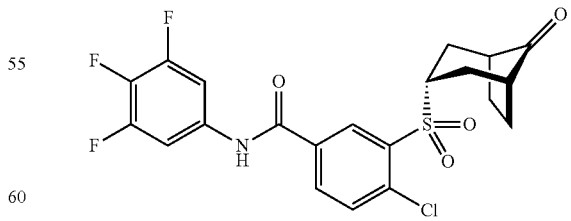

A solution of compound from example 192 (1.8 g, 3.8 mmol) in DMSO (10 mL) at rt was added IBX (4.3 g, 15.3 mmol) and the mixture was stirred at 45° C. for 20 h. Aqueous Na$_2$S$_2$O$_3$, NaHCO$_3$ and few drops of Et$_3$N was added and stirred at rt for 1 h. It was extracted with EtOAc, Example 246

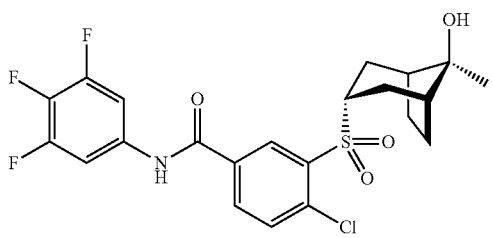

Step 246a. To a solution of compound from example 245 (0.17 g, 0.36 mmol) and trimethylsulfoxonium iodide (0.24 g, 1.1 mmol) in DMSO (2.0 mL) at 0° C. was added t-BuOK (0.12 g, 1.1 mmol). The resulting reaction mixture was stirred at rt for 1 h. The reaction was quenched with aqueous NH$_4$Cl and the mixture was extracted with EtOAc, washed with water, brine. The organic layer was dried (Na$_2$SO$_4$), filtered and concentrated. The crude product was chromatographed (silica, hexanes/EtOAc) to give the two diastereomers (0.12 g, 69%). ESI-MS m/z=484.06, 486.06 [M–H]$^-$.

Step 246b. To a solution of compound from step 264b (60 mg, 0.12 mmol) THF (1.0 mL) at 0° C. was added superhydride (0.48 mL 1M solution in THF, 0.48 mmol). The resulting reaction mixture was stirred at rt for 1 h. A solution of 50% H$_2$O$_2$ (0.40 g, 5.9 mmol) was added and the mixture was stirred at rt for 30 mins. It was diluted with EtOAc, washed with water, aqueous Na$_2$SO$_3$ and brine. The organic layer was dried (Na$_2$SO$_4$), filtered and concentrated. The crude product was purified by Prep-TLC (silica, hexanes/EtOAc) to give the desired compound as white solid (23 mg, 38%). ESI-MS m/z=486.07, 488.07 [M–H]$^-$.

Example 247

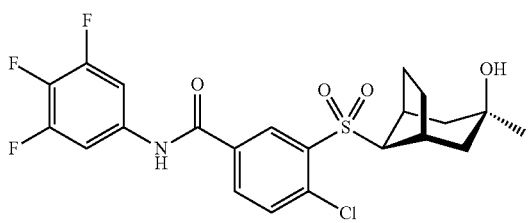 [SMILES: C[C@@]1(O)CC2CC[C@@H](C1)[C@H]2S(=O)(=O)c1cc(C(=O)Nc2cc(F)c(F)c(F)c2)ccc1Cl]

The title compound was isolated from example 106. ESI-MS m/z=486.09, 488.09 [M–H]$^-$.

Example 249

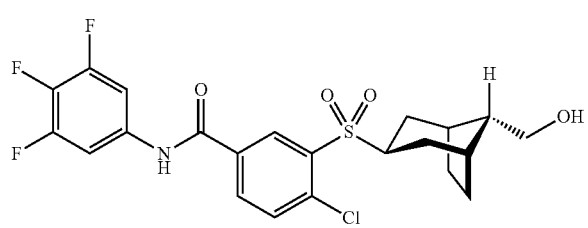

Step 249a. To a suspension of (methoxymethyl)triphenylphosphonium chloride (0.47 g, 1.36 mmol) THF (2.0 mL) at 0° C. was added t-BuOK (0.23 g, 2.03 mmol). The resulting reaction mixture was stirred at rt for 30 mins. A solution of compound from example 206 (0.32 g, 0.68 mmol) in THF (4.0 mL) was added and stirred at rt for 20 h and 60° C. for 5 h. The reaction was quenched with aqueous NH$_4$Cl and the mixture was extracted with EtOAc, washed with water, brine. The organic layer was dried (Na$_2$SO$_4$), filtered and concentrated. The crude product was chromatographed (silica, hexanes/EtOAc) to give the desired compound as white solid (0.17 g, 50%). ESI-MS m/z=498.08, 500.07 [M–H]$^-$.

Step 249b. A solution of compound from step 249 a (0.12 g, 0.24 mmol) in THF (5.0 mL) at rt was added HCl (2 mL 3 N, 6.0 mmol) and stirred at rt for 2 h. It was concentrated under vacuum to remove majority of THF and the residue was extracted with EtOAc. The organic phase was washed with water, 10% K$_2$CO$_3$, brine, dried over Na$_2$SO$_4$, filtered, and concentrated to give two diastereomers (0.114 g, 98%). ESI-MS m/z=484.06, 486.06 [M–H]$^-$.

Step 249c. To a solution of compounds from step 249b (76 mg, 0.16 mmol) in THF-MeOH (3.0/1.0 mL) at 0° C. was added NaBH$_4$ (12 mg, 0.32 mmol). The resulting reaction mixture was stirred at rt for 1 h. The reaction was quenched with aqueous NH$_4$Cl and the mixture was extracted with EtOAc, washed with water, brine. The organic layer was dried (Na$_2$SO$_4$), filtered and concentrated. The crude product was purified by Prep-HPLC using a C18 column and acetonitrile/water as eluent (8.0 mg, 10%). ESI-MS m/z=486.08, 488.07 [M–H]$^-$.

Example 250

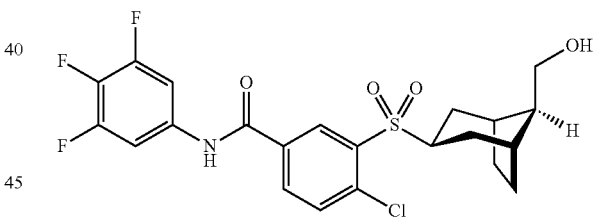

The title compound (27 mg, 34%) was isolated from example 249. ESI-MS m/z=486.07, 488.07 [M–H]$^-$.

Example 251

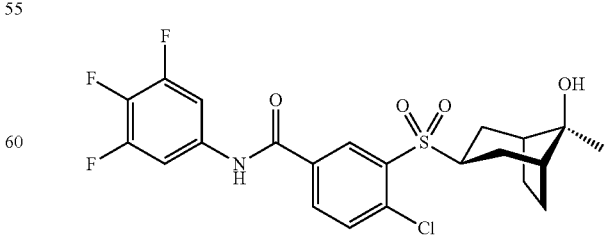

The title compound (18 mg, 30%) was isolated from example 246. ESI-MS m/z=486.07, 488.07 [M–H]$^-$.

Example 252

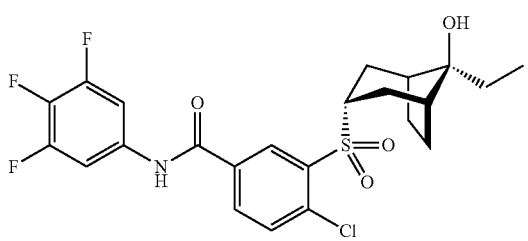

Step 252a. To a solution of compounds from step 223a (44 mg, 0.10 mmol) in THF (1.0 mL) at 0° C. was added EtMgBr (0.14 mL 3M solution in ether, 0.42 mmol). The resulting reaction mixture was stirred at rt for 0.5 h. The reaction was quenched with aqueous NH$_4$Cl and the mixture was extracted with EtOAc, washed with water, brine. The organic layer was dried (Na$_2$SO$_4$), filtered and concentrated. The crude product was chromatographed (silica, hexanes/EtOAc) to give the desired compound as white solid (20 mg, 43%). ESI-MS m/z=468.10, 470.10 [M−H]$^-$.

Step 252b. To a solution of compound from step 252a (20 mg, 0.043 mmol) NMP (1.0 mL) was added mCPBA (34 mg 77%, 0.15 mmol) and stirred at rt for 20 h. Aqueous Na$_2$S$_2$O$_3$, NaHCO$_3$ and few drops of Et$_3$N was added and stirred at rt for 1 h. It was extracted with EtOAc, washed with water, brine, dried over Na$_2$SO$_4$, filtered, concentrated and purified by Prep-HPLC using a C18 column and acetonitrile/water as eluent to give the title compound (12 mg, 56%). ESI-MS m/z=500.09, 502.09 [M−H]$^-$.

Example 253

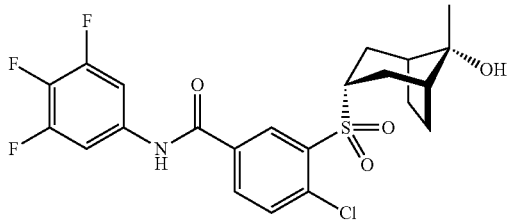

Step 253a. To a solution of compound from example 223 (72 mg, 0.14 mmol) and DMAP (69 mg, 0.56 mmol) in DMF (1.0 mL) at 0° C. was added methanesulfonic anhydride (49 mg, 0.28 mmol). The resulting reaction mixture was stirred at rt for 2 h. The reaction was diluted with EtOAc and the mixture was washed with water, 1N HCl and brine. The organic layer was dried (Na$_2$SO$_4$), filtered and concentrated, which is used in next step without purification. ESI-MS m/z=580.05, 582.04 [M−H]$^-$.

Step 253b. A solution of compound from step 253a (83 mg, 0.14 mmol) and Cs$_2$CO$_3$ (0.19 g, 0.56 mmol) in DMF (1.0 mL) was stirred at rt for 2 h. The reaction was diluted with EtOAc and the mixture was washed with water and brine. The organic layer was dried (Na$_2$SO$_4$), filtered and concentrated, which is used in next step without purification. ESI-MS m/z=484.06, 486.06 [M−H]$^-$.

Step 253c. To a solution of compound from step 253b (60 mg, 0.12 mmol) THF (1.0 mL) at 0° C. was added superhydride (0.48 mL 1M solution in THF, 0.48 mmol). The resulting reaction mixture was stirred at rt for 1 h. A solution of 50% H$_2$O$_2$ (0.40 g, 5.9 mmol) was added and the mixture was stirred at rt for 30 mins. It was diluted with EtOAc, washed with water, aqueous Na$_2$SO$_3$ and brine. The organic layer was dried (Na$_2$SO$_4$), filtered and concentrated. The crude product was purified by Prep-HPLC using a C18 column and acetonitrile/water as eluent to give the title compound as white solid (29 mg, 48%). ESI-MS m/z=486.07, 488.07 [M−H]$^-$.

Example 255

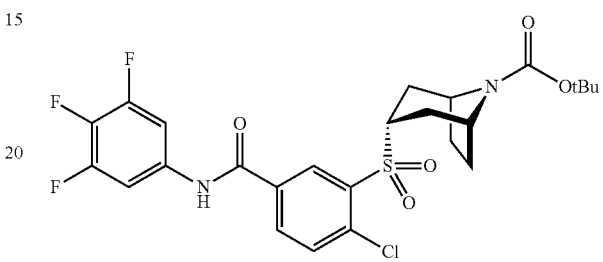

The title compound was prepared from the compound of Step 1c using procedures similar to that described in Example 139. ESI-MS m/z=557.11, 559.11[M−H]$^-$.

Example 256

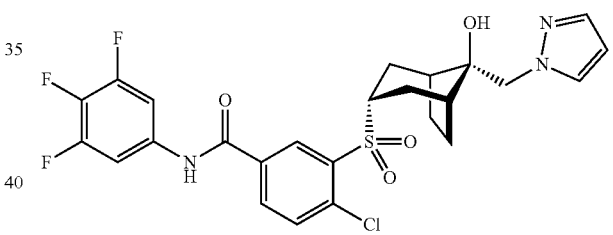

Step 256a. To a solution of compound from step 223a (1.76 g, 4.0 mmol) and trimethyl-sulfoxonium iodide (1.76 g, 8.0 mmol) in DMSO (20 mL) at 0° C. was added t-BuOK (1.12 g, 10 mmol). The resulting reaction mixture was stirred at rt for 1 h. The reaction was quenched with aqueous NH$_4$Cl and the mixture was extracted with EtOAc, washed with water, brine.

The organic layer was dried (Na$_2$SO$_4$), filtered and concentrated. The crude product was chromatographed (silica, hexanes/EtOAc) to give the desired compound as white solid (1.36 g, 75%). ESI-MS m/z=452.07, 454.07 [M−H]$^-$.

Step 256b. To a solution of pyrazole (0.136 g, 2.0 mmol) in DMF (1.0 mL) was added NaH (56 mg 60%, 1.4 mmol) and stirred at rt for 15 mins. A solution of compound from step 256a (91 mg, 0.20 mmol) in DMF (0.5 mL) was added and stirred 60° C. for 1 h. The reaction was quenched with aqueous NH$_4$Cl and the mixture was extracted with EtOAc, washed with water, brine. The organic layer was dried (Na$_2$SO$_4$) and concentrated. The crude product was chromatographed (silica, hexanes/EtOAc) to give the desired compound as white solid (94 mg, 90%). ESI-MS m/z=520.11, 522.11 [M−H]$^-$.

Step 256c. To a solution of compound from step 256b (13 mg, 0.025 mmol) NMP (0.3 mL) was added mCPBA (33 mg 77%, 0.15 mmol) and stirred at rt O/N. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated purified by prep-HPLC using a C18 column and acetonitrile/water as eluent to give title compound (8.2 mg, 59%). ESI-MS m/z=552.09, 554.09 [M−H]⁻.

Example 257

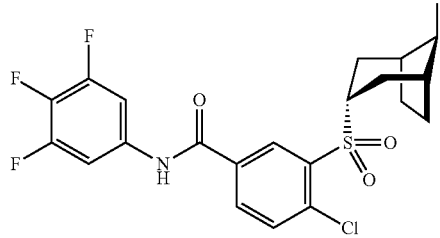

Step 257a. To a stirred solution of compound from step 256a (78 mg, 0.17 mmol) in DMF (2.5 mL) was added NH₄Cl (17 mg, 0.32 mmol) and NaN₃ (44 mg, 0.67 mmol) then stirred at 60° C. for 24 h. It was diluted with EtOAc, washed with water, brine, dried over Na₂SO₄, filtered, Con, chromatographed (silica, hexanes/EtOAc) to give the desired compound as white solid (73 mg, 88%). ESI-MS m/z=495.08, 497.08 [M−H]⁻.

Step 257b. To a solution of compound from step 257a (0.20 g, 0.40 mmol) in NMP (2.0 mL) was added mCPBA (0.27 g 77%, 1.2 mmol) and stirred at rt O/N. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and chromatographed (silica, hexanes/EtOAc) to give the desired compound as white solid (0.21 g, 98%). ESI-MS m/z=527.07, 529.07 [M−H]⁻.

Example 259

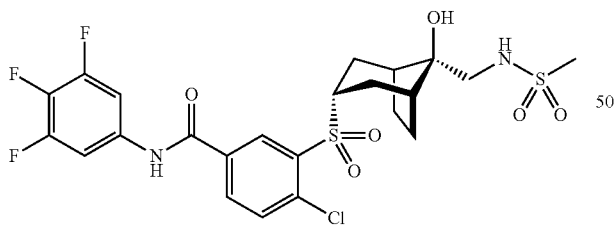

Step 259a. To a solution of compound from step 257b (70 mg, 0.13 mmol) in THE-water (1.0/0.1 ml) at rt was added trimethylphosphine (0.40 ml 1M solution in THF, 0.4 mmol) and stirred at rt for 1 h. It was concentrated under vacuum and used in next step without purification ESI-MS m/z=501.08, 503.08 [M−H]⁻.

Step 259b. To a solution of compound from step 259a (33 mg, 0.066 mmol) and DMAP (60 mg, 0.49 mmol) in THE-water (1.0/0.1 ml) at rt was added MsCl (38 mg, 0.33 mmol) and stirred at rt for 1 h. It was concentrated under vacuum and purified by prep-HPLC using a C18 column and acetonitrile/water as eluent to give title compound (11 mg, 29%). ESI-MS m/z=579.06, 581.06 [M−H]⁻.

Example 260

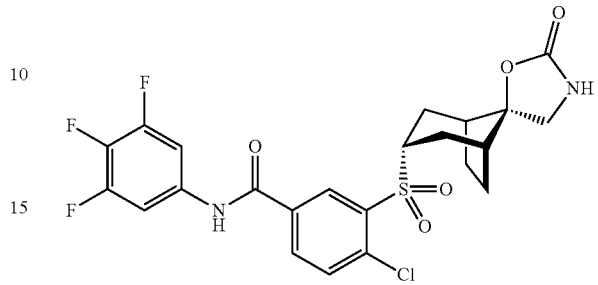

To a solution of compound from step 259a (33 mg, 0.066 mmol) in THE (2.0 mL) at rt was added CDI (32 mg, 0.20 mmol) and stirred at rt for 16 h. It was concentrated under vacuum and purified by prep-HPLC using a C18 column and acetonitrile/water as eluent to give title compound (12 mg, 34%). ESI-MS m/z=527.06, 529.06 [M−H]⁻.

Example 262

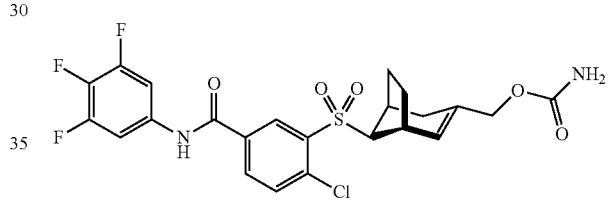

Into the solution example 139 (100 mg, 0.20 mmol) in THE (2 mL) in a dry ice/acetone bath, a solution of chlorosulfonylisocyanate (36 mg 0.23 mmol) in THE (1 mL), was added drop-wise. It was raised to rt and stirred 2 hours before it was diluted with EtOAc and washed with aq HCl (1 M), water, brine. The organic was dried (Na₂SO₄) and concentrated. The crude was chromatographed (silica, acetone/hexanes) to give the title compound (9 mg, 21%). ESI-MS m/z=527.06, 529.06 [M−H]⁻.

Example 263

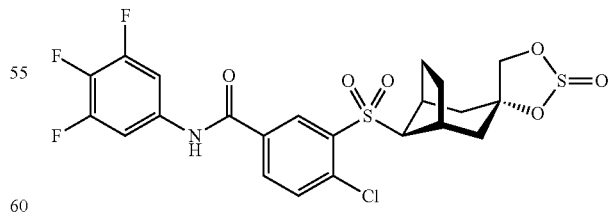

Step 263. To a solution of Example 60 (3.000 g, 5.95 mmol) in THE (90 ml) at 0° C. was added triethylamine (2.489 ml, 17.86 mmol), followed by thionyl chloride (0.521 ml, 7.14 mmol). The mixture was stirred at 0° C. for 1 h before being quenched with water. The organic layer was washed with brine (*2), dried over Na₂SO₄ (s), filtered and concentrated to ~5 ml. It was allowed to settle down. The top clear solution was decanted. The wet solid in the flask was washed with THF (3 ml). The top clear solution was again decanted. The residual white solid was dried under vacuum to afford the title compound as a white solid (2.430 g, 74%). ESI-MS m/z=548.02, 550.02 [M–H]⁻.

Example 266

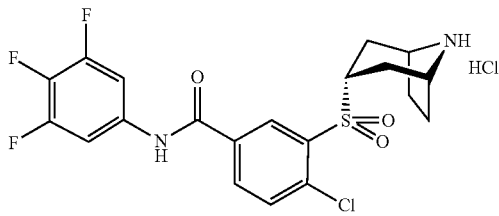

To a solution of the title compound (131 mg, 0.234 mmol) from Example 255 was added 4N HCl in dioxane at rt, then the mixture was kept at rt for 4 h. The solution was concentrated to give the title compound (107 mg, 99%) as a while solid. ESI-MS m/z=457.06, 459.06 [M–HCl—H]⁻.

Example 267

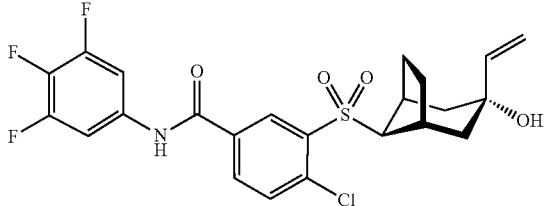

A solution of compound from step 162 (25 mg, 0.05 mmol) and Lindlar's Catalyst (3 mg) in ethyl acetate (3 ml) was flushed with nitrogen, evacuated with vacuum then added a hydrogen balloon. The reaction was stirred at rt for 2 h. It was diluted with EtOAc and filtered through celite. The filtrate was concentrated. The residue was chromatographed (prep-HPLC, acetonitrile/water) to give the title compound 267 (5 mg, 0.01 mmol, 20% yield). ESI-MS m/z=497.6, 499.6 [M–H]⁻.

Example 268

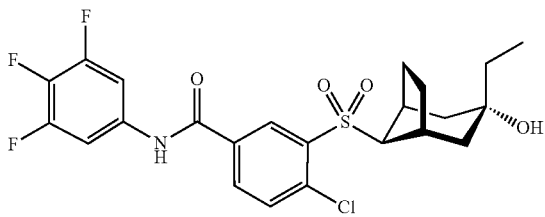

The title compound was isolated from example 267 ESI-MS m/z=499.6, 501.6 [M–H]⁻.

Example 269

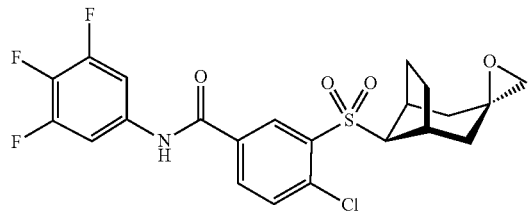 [SMILES: O=C(Nc1cc(F)c(F)c(F)c1)c1ccc(Cl)c(S(=O)(=O)[C@H]2C3CC[C@H]2C[C@@]2(CO2)C3)c1]

Into the solution of dimethylmethanesulfinic iodide (330 mg, 1.5 mmol) in DMSO (3 mL), potassium tert-butoxide (250 mg, 2.22 mmol) was added. It was stirred 15 minutes at rt before a solution of example 130 (350 mg, 0.74 mmol) in DMSO (3 mL) was added. In two hours, it was diluted with EtOAc and washed with aq NH₄Cl, water, brine. The organic was dried (Na₂SO₄) and concentrated. The crude was chromatographed (silica, acetone/hexanes) to give the title compound (160 mg, 45%). ESI-MS m/z=484.05, 486.05 [M–H]⁻.

Example 270

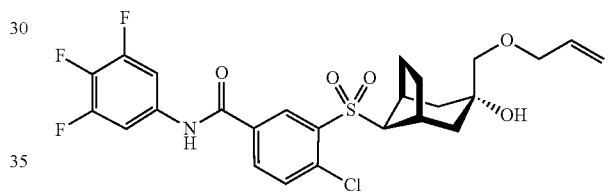

To a mixture of compound from step 60 (5.0 g, 9.92 mmol) in DMF (50 ml) at 0° C. was added sodium hydride (60%, 0.794 g, 19.84 mmol). Immediately allyl bromide (1.03 mL, 11.91 mmol) was added. The reaction was warmed to rt and stirred for 2 h. It was diluted with EtOAc and washed with sat. aq. NH₄Cl and brine. The organic was dried (Na₂SO₄), filtered and concentrated. The residue was chromatographed (silica, hexanes/acetone) to give the title compound (2.485 g, 4.57 mmol, 46% yield). ESI-MS m/z=542.14, 544.13 [M–H]⁻.

Example 271

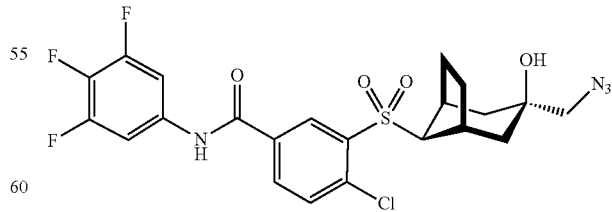

A mixture of example 269 (100 mg, 0.21 mmol) and NaN₃ (27 mmg, 0.42 mmol) in DMF (3 mL) was heated at 60° C. for 15 hours before being cooled. It was diluted with EtOAc and washed with water*2, brine and dried (Na₂SO₄). After concentrated, the crude was chromatographed (silica, EtOAc/hexanes) to give the title compound (46 mg, 42%). ESI-MS m/z=527.07, 529.07 [M−H]⁻.

Example 275

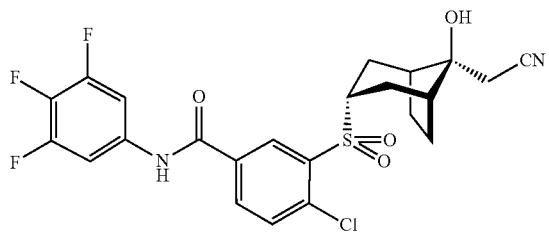

Step 275a. To a stirred solution of compound from step 256a (104 mg, 0.23 mmol) in DMF (20 mL) was added NH₄Cl (25 mg, 0.46 mmol) and KCN (60 mg, 0.92 mmol) then stirred at 80° C. for 24 h. It was diluted with EtOAc, washed with water, brine, dried over Na₂SO₄, filtered, and concentrated to give the desired compound as white solid (104 mg, 100%). ESI-MS m/z=479.08, 481.08 [M−H]⁻.

Step 257b. To a solution of compound from step 275a (53 mg, 0.11 mmol) in NMP (1.0 mL) was added mCPBA (74 mg 77%, 0.33 mmol) and stirred at rt for 20 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and chromatographed (silica, hexanes/EtOAc) to give the title compound as white solid (47 mg, 83%). ESI-MS m/z=511.12, 513.12 [M−H]⁻.

Example 276

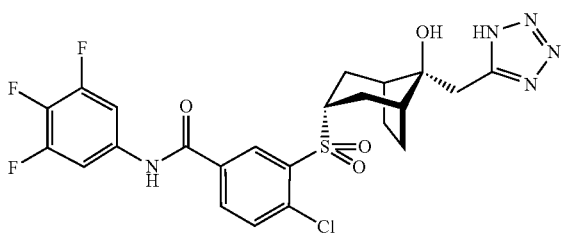

Step 276a. A suspension of compound from step 275a (180 mg, 0.37 mmol), triethylamine hydrochloride (258 mg, 1.87 mmol) and NaN₃ (122 mg, 1.87 mmol) in DMF (3.0 mL) was stirred at 140° C. for 24 h. It was diluted with EtOAc, washed with 1N HCl, brine, dried over Na₂SO₄, filtered, Concentrated and chromatographed (silica, EtOAc/MeOH) to give the desired compound as white solid (180 mg, 92%). ESI-MS m/z=522.15, 524.15 [M−H]⁻.

Step 276b. To a solution of compound from step 276a (18 mg, 0.034 mmol) NMP (1.5 mL) was added mCPBA (23 mg 77%, 0.10 mmol) and stirred at rt for 24 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated purified by prep-HPLC using a C18 column and acetonitrile/water as eluent to give title compound (5.6 mg, 29%). ESI-MS m/z=554.14, 556.14 [M−H]⁻.

Example 277

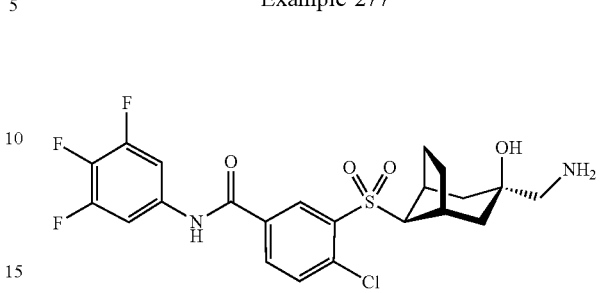

Step 277a. A solution of compound from step 269 (500 mg, 1.029 mmol), sodium azide (134 mg, 2.058 mmol) and ammonium chloride (220 mg, 4.12 mmol) in DMF (10 ml) was heated to 60° C. for 18 h. It was diluted with ethyl acetate and washed with water and brine. The organic was dried (Na₂SO₄), filtered and concentrated. The residue was chromatographed (silica, hexanes/acetone) to give the desired compound as white solid (0.410 g, 75%).

Step 277b. To a solution of compound from step 277a (390 mg, 0.737 mmol) in THF (6.7 ml) and water (0.7 ml) was added trimethylphosphine (1M, 2.2 ml, 2.2 mmol). The reaction was stirred for 1 h at rt. It was diluted with THF and MTBE and washed with water and brine. The organic was dried (Na₂SO₄), filtered and concentrated. The residue was chromatographed (silica, hexanes/acetone) to give the title compound as white solid (0.410 g, 75%). ESI-MS m/z=502.8, 504.8, 556.14 [M+H]⁺.

Example 281

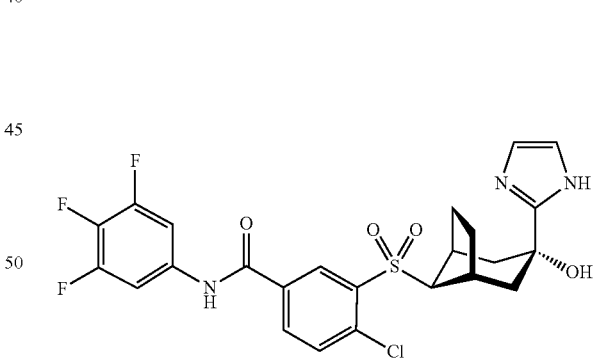

To a solution of Example 129 (0.150 g, 0.299 mmol) in DMSO (3 ml) and 7 N ammonia in methanol (0.854 ml, 5.98 mmol) at 0° C. was added glyoxal (40% in water, 0.051 ml, 0.448 mmol). The resulting solution was allowed to warm up gradually to rt and stirred at rt overnight. More glyoxal (40% in water, 0.017 ml, 0.149 mmol) were added. The solution was stirred at rt overnight before being freed of ammonia and methanol with a stream of N₂. The remaining solution was directly purified by HPLC (35~90% CH₃CN in H₂O) to afford the title compound as a white solid (62.0 mg, 38%). ESI-MS m/z=538.14, 540.14 [M−H]⁻.

Example 282

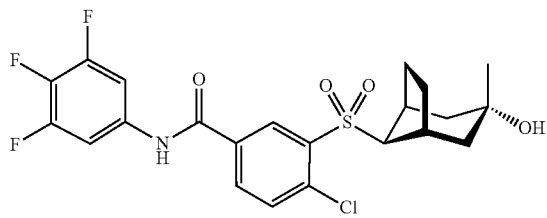

Step 282a. To a solution of the compound from step 286a (80 mg, 0.176 mmol) in THF (2 mL) at rt was added lithium triethylborohydride (1.0 M in THF, 0.352 mL, 0.352 mmol) dropwise. The colorless solution was stirred at rt for 2 h. More lithium triethylborohydride (1.0 M in THF, 0.352 mL, 0.352 mmol) was added at rt. The solution was stirred at rt for 2 h. 3 N HCl (0.23 ml) was added to quench the reaction with ice-bath cooling. The mixture was diluted with EtOAc and saturated NaHCO₃aq. The organic layer was washed with brine (*2), dried over Na₂SO₄ (s), filtered and concentrated. The residue was purified by flash column chromatography (silica, Hexanes/EtOAc) to afford the desired product as a white solid (72.0 mg, 90%). ESI-MS m/z=454.09, 456.08 [M–H]⁻.

Step 282b. To a solution of the compound from step 282a (72 mg, 0.158 mmol) in NMP (2 ml) at rt was added m-CPBA (142 mg, 0.632 mmol). The colorless solution was stirred at rt overnight. Saturated NaHCO₃ solution (~2 ml) was added along with 2 drops of Et₃N. The suspension was stirred at rt for 5 min before being filtered. The solid was washed with water (*1), MeOH (*1), EtOAc (*1) and then dried under vacuum to afford the title compound as a white solid (70.0 mg, 91%). ESI-MS m/z=486.12, 488.12 [M–H]⁻.

Example 283

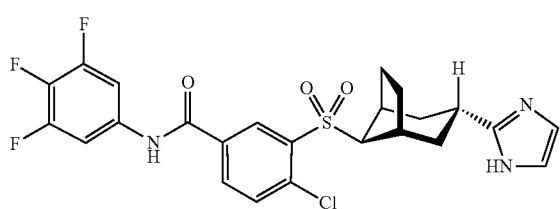

To a solution of the compound from step 239a (0.150 g, 0.309 mmol) in DMSO (3 ml) and 7 N ammonia in methanol (0.882 ml, 6.17 mmol) at 0° C. was added glyoxal (40% in water, 0.071 ml, 0.617 mmol). The mixture was allowed to warm up gradually to rt and stirred at rt overnight. It was freed of ammonia and methanol with a stream of N₂. The remaining solution was directly purified by HPLC (35~90% CH₃CN in H₂O) to afford the title compound as a white solid (55.0 mg, 34%). ESI-MS m/z=522.14, 524.14 [M–H]⁻.

Example 284

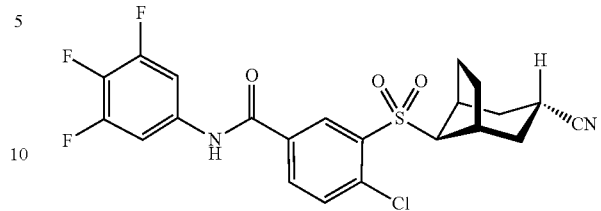

To a solution of the compound from step 239a (20.0 mg, 0.041 mmol) in DMSO (0.5 ml) at rt was added hydroxylamine hydrochloride (5.72 mg, 0.082 mmol). The resulting mixture was stirred at 100° C. for 40 min using a microwave reactor before being filtered. The filtrate was directly purified by HPLC (35~90% CH₃CN in H₂O) to afford the title compound as a white solid (8.5 mg, 43%). ESI-MS m/z=481.11, 483.11 [M–H]⁻.

Example 286

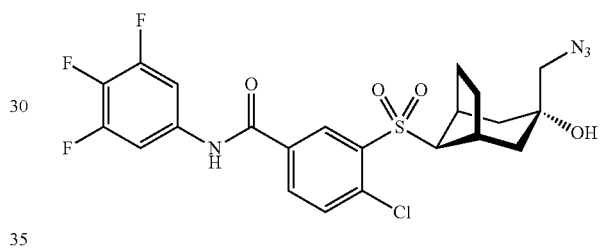

Step 286a. To a solution of compound from example 138c (500 mg, 1.0 mmol) and DBU (325 mg, 2.0 mmol) in anhydrous THF (10 mL) at 0° C. was added 1,1,2,2,3,3,4,4-nonafluorobutane-1-sulfonyl fluoride (580 mg, 1.9 mmol) slowly over 30 minutes. The reaction was stirred at rt for 1 h before it was concentrated to dryness. This crude was chromatographed (silica, EtOAc/hexanes) to give the title compound (480 mg, 100%), ESI-MS m/z=484.08, 486.06 [M–H]⁻.

Step 286b. The desired compound was synthesized from compound of step 286a by conditions similar to that described in example 271, ESI-MS m/z=495.08, 497.08 [M–H]⁻.

Step 286c. The title compound was synthesized from compound from step 286b by conditions similar to that described in step 188b, ESI-MS m/z=527.07, 529.09 [M–H]⁻.

Example 287

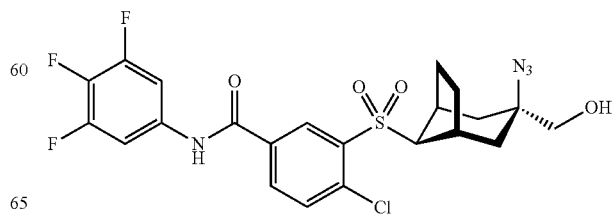

The title compound was synthesized from a minor isomer isolated from step 286b by conditions similar to that described in step 188b, ESI-MS m/z=527.12, 529.12 [M–H]⁻.

Example 289

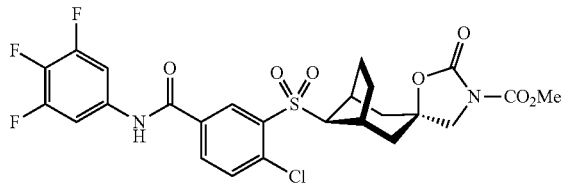

To a solution of compound from step 277 (21 mg, 0.042 mmol) and DIPEA (0.022 ml, 0.125 mmol) in THF (1 ml) was added methyl chloroformate (10 μl, 0.12 mmol). The reaction was stirred at rt for 2 h. It was diluted with EtOAc and washed with sat. aq. NH₄Cl and brine. The organic was dried (Na₂SO₄), filtered and concentrated. The residue was chromatographed (silica, hexanes/acetone) to give the title compound (12 mg, 0.02 mmol, 49% yield). ESI-MS m/z=584.8, 586.8 [M–H]⁻.

Example 290

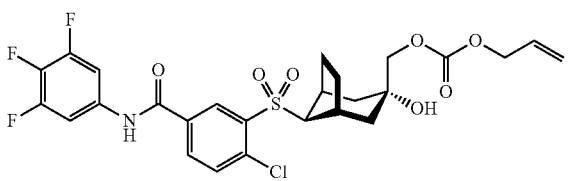

To a solution of compound from step 60 (0.98 g, 1.945 mmol) and pyridine (0.236 ml, 2.92 mmol) in THF (19.5 ml) at 0° C. was added allyl chloroformate (0.249 ml, 2.334 mmol). The reaction was warmed to rt and stirred for 4 h. It was diluted with EtOAc and washed with sat. aq. NH₄Cl and brine. The organic was dried (Na₂SO₄), filtered and concentrated. The residue was chromatographed (silica, hexanes/acetone) to give the title compound (0.85 g, 1.446 mmol, 74% yield). ESI-MS m/z=585.8, 587.8 [M–H]⁻.

Example 291

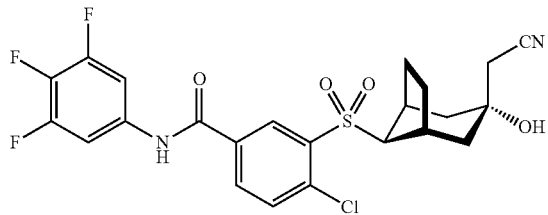

Into the solution example 139 (258 mg, 0.53 mmol) in THF (3 mL) at 60° C., Me₂AlCN (1 M in toluene, 1.10 mL, 1.10 mmol) was added drop-wise. It was stirred 1 h at such temperature before being cooled. Aq. potassium-sodium tartrate was added and extracted with EtOAc twice. The organic was washed with brine and dried (Na₂SO₄). After being concentrated, the crude was chromatographed (silica, acetone/hexanes), then by prap-HPLC (C-18, acetonitrel/water) to give the title compound as white solid (10 mg, 4%). ESI-MS m/z=511.12, 513.12 [M–H]⁻.

Example 292

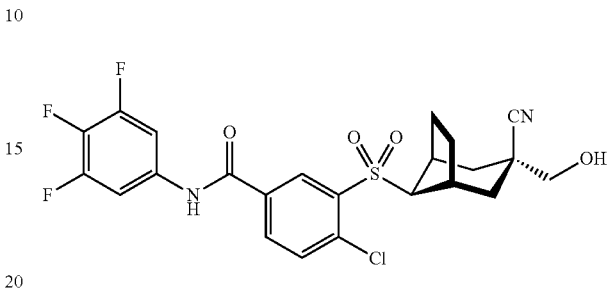

The title compound was isolated from example 291. ESI-MS m/z=511.12, 513.12 [M–H]⁻.

Example 293

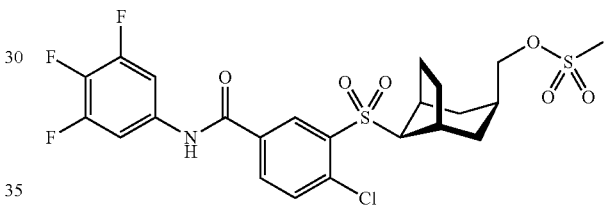

A solution of the compound of example 106 (244 mg, 0.5 mmol) and DIPEA (0.18 mL, 1 mmol) in THF (3 mL) at rt was treated with MeSO₂Cl (0.06 mL, 0.75 mmol) for 3 hours before being concentrated. The crude was chromatographed (silica, acetone/hexanes) to afford the title compound as white solid (240 mg, 85%). ESI-MS m/z=564.05, 566.05 [M–H]⁻.

Example 297

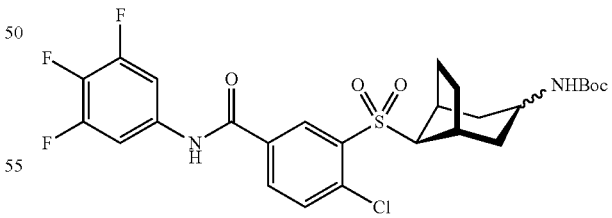

Step 297a. To a mixture of compound from step 219 (358 mg, 0.735 mmol), ammonium acetate (850 mg, 11.03 mmol), and sodium cyanoborohydride (462 mg, 7.35 mmol) in THF (7.4 ml) and MeOH (7.4 ml) was added TiCl₃ (20% in 3% HCl, 2.4 ml, 3.68 mmol). The reaction was stirred at rt for 4 h. It was poured onto conc. Aq. NaHCO₃ then extracted with THF/MTBE 1:1 and washed with brine. The organic was dried (Na₂SO₄), filtered and concentrated. The residue was used crude (348 mg, 0.735 mmol).

Step 297b. To a mixture of compound from step 297a (348 mg, 0.735 mmol) and DIPEA (0.257 ml, 1.47 mmol) in THF (7.4 ml) was added boc anhydride (0.193 g, 0.883 mmol). The reaction was stirred at rt for 1 h. It was diluted with THF/MTBE 1:1 and washed with water and brine. The organic was dried (Na₂SO₄), filtered and concentrated. The residue was chromatographed (silica, hexanes/acetone) to give the title compound (0.146 g, 0.255 mmol, 34% yield). ESI-MS m/z=571.13, 573.13[M-H]⁻.

Example 301

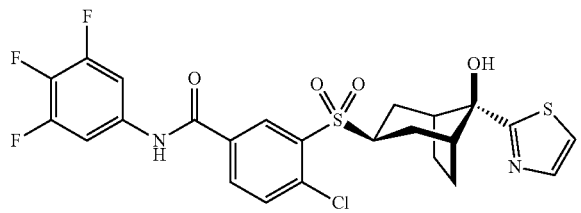

To a solution of thiazole (128 mg, 1.5 mmol) in THF (3.0 mL) at −78° C. was added BuLi (0.94 ml 1.6 M in hexanes, 1.50 mmol) and stirred at −78° C. for 1 h. A solution of compound from example 245 (142 mg, 0.30 mmol) in THF (1.0 mL) was added and slowly rose to rt and stirred at rt for 5 mins. It was quenched with Sat. aqueous NH₄Cl, extracted with EtOAc, washed with water, brine, dried over Na₂SO₄, filtered, concentrated and chromatographed (silica, EtOAc/MOH) to give the desired compound (36 mg, 22%). ESI-MS m/z=555.04, 557.04 [M-H]⁻.

Example 302

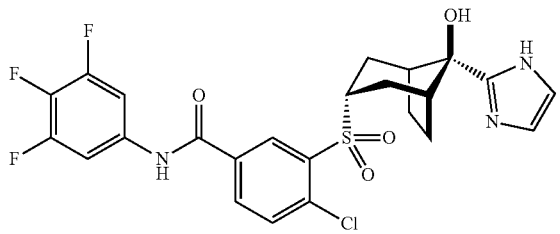

Step 302a. To a solution of 1-(Diethoxymethyl)imidazole (0.20 ml, 1.2 mmol) in THF (3.0 mL) at −78° C. was added BuLi (0.75 ml 1.6 M in hexanes, 1.20 mmol) and stirred at −78° C. for 1 h. A solution of compound from step 223a in (132 mg, 0.30 mmol) in THF (1.0 mL) was added and slowly rose to rt and stirred at rt for 5 mins. It was quenched with Sat. aqueous NH₄Cl, extracted with EtOAc, washed with water, brine, dried over Na₂SO₄, filtered, concentrated and chromatographed (silica, EtOAc/MOH) to give the desired compound (0.16 g, 87%). ESI-MS m/z=495.08, 497.08 [M-H]⁻.

Step 302b. To a solution of compound from step (70 mg, 0.138 mmol) and CSA (48 mg, 0.21 mmol) in NMP (2.0 mL) at rt was added mCPBA (124 mg 77%, 0.55 mmol) and stirred at rt for 24 h. Aqueous Na₂S₂O₃, NaHCO₃ and few drops of Et₃N was added and stirred at rt for 1 h.

It was extracted with EtOAc, washed with water, brine, dried over Na₂SO₄, filtered, concentrated purified by prep-HPLC using a C18 column and acetonitrile/water as eluent to give title compound (14 mg, 19%). ESI-MS m/z=538.08, 540.08 [M-H]⁻.

Example 303

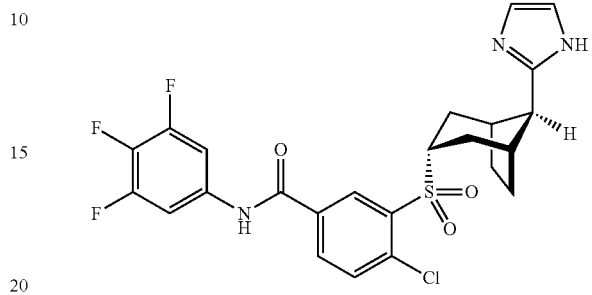

Step 303a. To a suspension of (methoxymethyl)triphenylphosphonium chloride (3.43 g, 10 mmol) THF (16 mL) at 0° C. was added t-BuOK (1.68 g, 15 mmol). The resulting reaction mixture was stirred at rt for 30 mins. A solution of compound from step 223a (2.2 g, 5.0 mmol) in THF (4.0 mL) was added and stirred at rt for 20 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (2.08 g, 89%). ESI-MS m/z=466.13, 468.13 [M-H]⁻.

Step 303b. A solution of the compound from step 303a (1.1 g, 2.35 mmol) in THF (10 mL) at rt was added Con. HCl (1.5 mL) and stirred at rt for 2 h. It was concentrated under vacuum to remove majority of THF and the residue was extracted with EtOAc. The organic phase was washed with water, 10% K₂CO₃, brine, dried over Na₂SO₄, filtered, and concentrated to give desired compound (0.95 g, 89%). ESI-MS m/z=452.07, 454.07 [M-H]⁻.

Step 303c. A solution of compound from (204 mg, 0.45 mmol), glyoxal (0.11 mL 8.8 M solution in water, 0.90 mmol) and ammonia (1.28 mL 7M in MeOH, 9.0 mmol) was stirred at rt for 24 h. The mixture was extracted with EtOAc, washed with water, brine. The organic layer was dried (Na₂SO₄), filtered and concentrated. The crude product was chromatographed (silica, EtOAc/MeOH) to give the desired compound as white solid (195 mg, 88%). ESI-MS m/z=490.10, 492.10 [M-H]⁻.

Step 303d. To a solution of compound from step (130 mg, 0.26 mmol) and CSA (92 mg, 0.39 mmol) in NMP (2.0 mL) at rt was added mCPBA (237 mg 77%, 1.06 mmol) and stirred at rt for 24 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated purified by prep-HPLC using a C18 column and acetonitrile/water as eluent to give title compound (51 mg, 37%). ESI-MS m/z 522.08, 524.08 [M-H]⁻.

Example 308

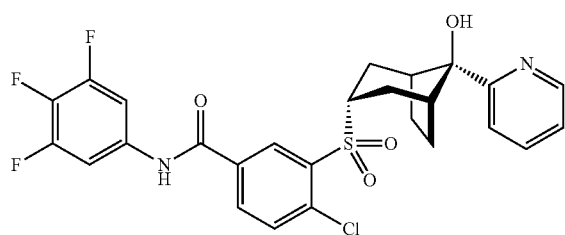

Step 308a. To a solution of 2-bromopyridine (189 mg, 1.19 mmol) in THF (2 mL) at −78° C. was added n-BuLi (746 μl, 1.19 mmol). It was kept at −78° C. for 0.5 h, then a solution of 4-chloro-3-(((1R,3r,5S)-8-oxobicyclo[3.2.1]octan-3-yl)thio)-N-(3,4,5-trifluorophenyl)-benzamide (150 mg, 0.341 mmol) in THF (1.41 mL) was added and kept for 1 h. It was partitioned between EtOAc and brine. The organic was dried (Na$_2$SO$_4$), filtered and concentrated. The residue was chromatographed (silica, hexanes/EtOAc) to give the desired compound (126 mg, 71% yield) as a white solid. MS-ESI, M/Z=517.09, 519.09 [M−H]$^-$.

Step 308b. To a solution of the compound from Step 308a (78 mg, 0.15 mmol) in CH$_2$C$_{12}$ (3.0 mL) at rt was added Ts-OH (42.9 mg, 0.225 mmol) and mCPBA (101 mg, 0.451 mmol), then the mixture was kept at rt for overnight. It was partitioned between EtOAc and Na$_2$S$_{2O3}$ aqueous solution. The organic was dried (Na$_2$SO$_4$), filtered and concentrated. The residue was chromatographed (silica, hexanes/EtOAc) to give the title compound (71 mg, 86% yield) as a white solid. MS-ESI, M/Z=595.09, 597.09 [M+HCO$_2$H—H]$^-$.

Example 309

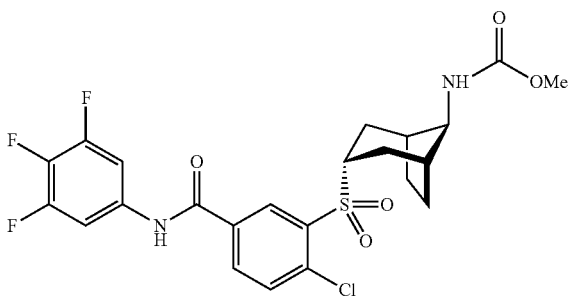

Step 309a. To a solution of 4-chloro-3-(((1R,3r,5S)-8-oxobicyclo[3.2.1]octan-3-yl)thio)-N-(3,4,5-trifluorophenyl)benzamide (0.394 g, 0.896 mmol) in pyridine (8.96 ml) was added hydroxylamine hydrochloride (0.093 g, 1.3 mmol) at rt. The mixture was kept at rt for overnight. It was concentrated and the resulting crude product was chromatographed (silica, hexanes/EtOAc) to give the desired compound (341 mg, 84% yield) as a white solid. MS-ESI, M/Z=453.06, 455.06[M−H]$^-$.

Step 309b. To a solution of the compound from Step 309a (341 mg, 0.750 mmol) in MeOH (7.5 mL) was added ammonium acetate (867 mg, 11.2 mmol), titanium(III) chloride (2.89 g, 3.75 mmol) and sodium cyanoborohydride (471 mg, 7.50 mmol) at rt, the mixture was kept at rt for overnight. It was partitioned between EtOAc and brine. The organic was dried (Na$_2$SO$_4$), filtered and concentrated. The residue was chromatographed (silica, hexanes/EtOAc) to give the desired compound (101 mg, 31% yield) as a white solid. MS-ESI, M/Z=485.08, 487.08 [M+HCO$_2$H—H]$^-$.

Step 309c. To a solution of the compound from Step 309b (37 mg, 0.084 mmol) in CH$_2$C$_{12}$ (1.7 mL) at rt was added iPr$_2$EtN (44.0 μl, 0.252 mmol) and methyl carbonochloridate (11.9 mg, 0.126 mmol), then the mixture was kept at rt for 3 h. It was partitioned between EtOAc and brine. The organic was dried (Na$_2$SO$_4$), filtered and concentrated. The residue was chromatographed (silica, hexanes/EtOAc) to give the desired compound (26.3 mg, 63% yield) as a white solid. MS-ESI, M/Z=543.09, 545.09[M+HCO$_2$H-H]$^-$.

Step 309d. To a solution of the compound from Step 309c (26.3 mg, 0.053 mmol) in CH$_2$C$_{12}$ (2.6 mL) at rt was added 3-chlorobenzoperoxoic acid (47.3 mg, 0.211 mmol). It was kept at rt for overnight. It was partitioned between EtOAc and brine. The organic was dried (Na$_2$SO$_4$), filtered and concentrated. The residue was chromatographed (silica, hexanes/EtOAc) to give the title compound (23.4 mg, 84% yield) as a white solid. MS-ESI, M/Z=575.08, 577.08 [M+HCO$_2$H—H]$^-$.

Example 315

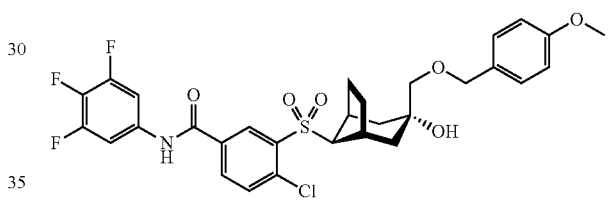

A solution of the compound of example 60 (504 mg, 1.0 mmol) and 1-(chloromethyl)-4-methoxybenzene (157 mg, 1.0 mmol) in DMF (5 mL) at rt was treated with NaH (60% w/w, 80 mg 2.0 mmol) for 3 hours. Aq. NH$_4$Cl was added slowly, followed by EtOAc and water.

The aqueous phase was extracted with EtOAc. The organic was washed with brine and dried (Na$_2$SO$_4$). After being concentrated, the crude was chromatographed (silica, acetone/hexanes) to afford the title compound as a white solid (240 mg, 38%). ESI-MS m/z=622.12, 624.12 [M−H]$^-$.

Example 318

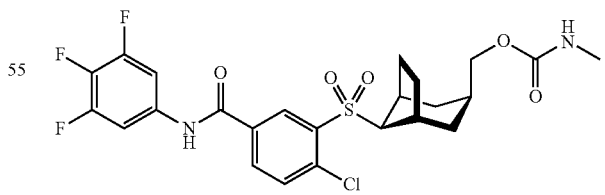

Into the solution of example 106 (50 mg, 0.10 mmol) and DIPEA (40 mg, 0.30 mmol) in THF (1 mL) at rt was added methylcarbamic chloride (15 mg, 0.15 mmol). It was stirred 2 hours before DIPEA (40 mg, 0.30 mmol) and methylcarbamic chloride (15 mg, 0.15 mmol) were added. It was stirred 3 hours before being concentrated. The crude was purified by prep-HPLC (C-18, acetonitrile/water) to afford the title compound as a white solid (24 mg, 43%). ESI-MS m/z=543.09, 545.09 [M–H]⁻.

Example 324

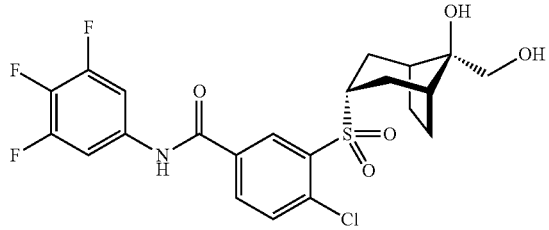

Step 324a. A solution of the compound from step 256a (214 mg, 0.47 mmol) in THF/water (3.0/1.0 mL) at rt was treated with TFA (0.40 mL) at rt for 6 h. It was concentrated under vacuum to remove majority of THF and the residue was extracted with EtOAc. The organic phase was washed with water, 10% K₂CO₃, brine, dried over Na₂SO₄, filtered, and concentrated to give the desired compound (0.20 g, 90%). ESI-MS m/z=470.08, 502.08 [M–H]⁻.

Step 324b. To solution of compound from step 324a (86 mg, 0.18 mmol) in NMP (2 mL) was added mCPBA (0.20 g 77%, 0.90 mmol) and stirred at rt for 20 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and recrystalized from methanol to give the title compound (65 mg, 70%). ESI-MS m/z=502.07, 504.07 [M–H]⁻.

Example 326

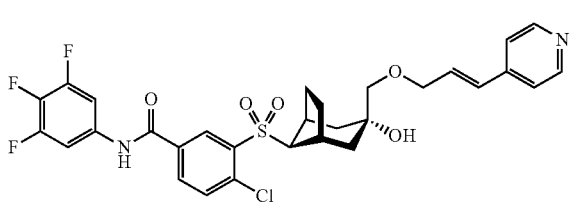

A solution of compound from step 270 (46 mg, 0.085 mmol), DIPEA (0.06 ml, 0.338 mmol), Pd(OAc)₂ (3.8 mg, 0.017 mmol), tri-m-tolylphosphine (10.3 mg, 0.034 mmol) and 4-iodo-pyridine (52 mg, 0.254 mmol) in acetonitrile (2 ml) was charged into a sealed vial. It was heated to 90° C. for 18 h. The reaction was diluted with EtOAc, filtered through celite and concentrated. The crude was purified by prep-HPLC (C-18, acetonitrile/water) to afford the title compound as a white solid (5 mg, 9.5%). ESI-MS m/z=629.13, 631.13 [M–H]⁻.

Example 329

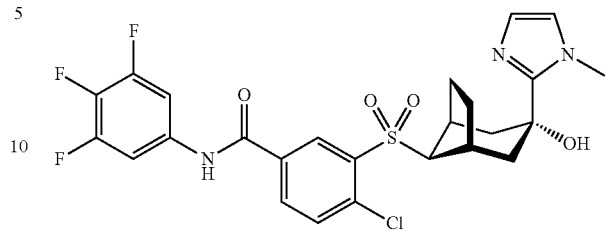

To a solution of Example 281 (10 mg, 0.019 mmol) in DMF (0.3 ml) at rt was added DIPEA (9.70 µl, 0.056 mmol), followed by iodomethane (1.390 µl, 0.022 mmol). The mixture was heated at 90° C. in a sealed tube overnight. More DIPEA (9.70 µl, 0.056 mmol) and iodomethane (2.780 µl, 0.044 mmol) were added. The yellow clear solution was heated at 90° C. overnight. Another bath of DIPEA (9.70 µl, 0.056 mmol) and iodomethane (2.780 µl, 0.044 mmol) was added. The yellow clear solution was heated at 90° C. overnight before being filtered. The filtrate was freed of volatiles with a stream of N₂. The residue was dissolved in DMSO (1.5 ml) and purified by HPLC (35~95% CH₃CN in H₂O) to afford the title compound as a white solid (3.5 mg, 34%). ESI-MS m/z=552.10, 554.10 [M–H]⁻.

Example 330

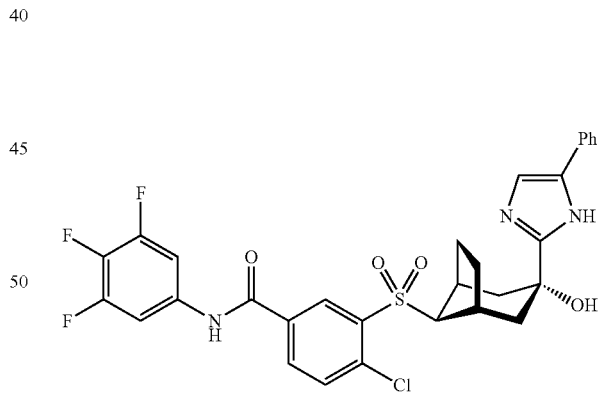

To a solution of Example 129 (0.150 g, 0.299 mmol) in DMSO (3 ml) and 7N ammonia in methanol (0.854 ml, 5.98 mmol) at 0° C. was added phenylglyoxal hydrate (0.068 g, 0.448 mmol). The resulting clear yellow solution was allowed to warm up to rt and stirred at rt overnight. The mixture was freed of ammonia and methanol by rotavapor. The remaining solution was filtered and directly purified by HPLC (40~90% CH₃CN in H₂O) to afford the title compound as a white solid (54.0 mg, 29%). ESI-MS m/z=614.11, 616.11 [M–H]⁻.

Example 333

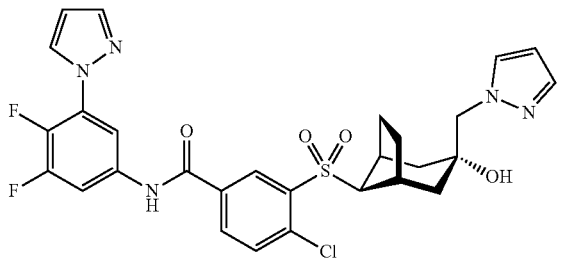

The title compound was isolated from Example 314. ESI-MS m/z=600.12, 602.12 [M–H]⁻.

Example 334

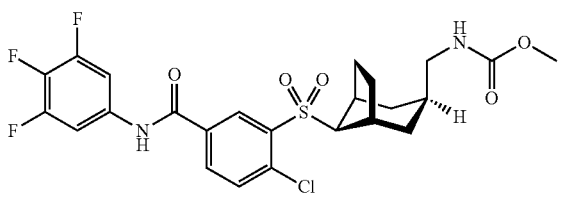

Step 334a. Into the solution of example 286b (240 mg, 0.5 mmol) in MeOH (2 mL) was added Raney nickel (~20 mg, washed with MeOH). A hydrogen balloon was introduced and stirred at rt for 1 hour. It was filtered through a pad of celite and concentrated to give the crude desired product as a white solid (240 mg, 100%). ESI-MS m/z=453.09, 455.09 [M–H]⁻. This material was used directly in the next step without further purification.

Step 334b. Into the solution of example 334a (45 mg, 0.10 mmol) and DIPEA (40 mg, 0.30 mmol) in THF (1 mL) at rt was added chloromethylformate (11 mg, 0.2 mmol). It was stirred 2 hours and concentrated to afford the crude desired product ESI-MS m/z=511.10, 513.10 [M–H]⁻. This material was used directly in the next step without further purification.

Step 334c. The title compound was synthesized from compound from step 334b by following the conditions of step 188b. ESI-MS m/z=543.09, 545.09[M–H]⁻.

Example 335

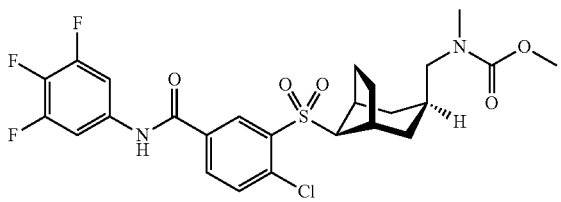

The title compound was isolated from example 334 as a minor, ESI-MS m/z=557.11, 559.11 [M–H]⁻.

Example 336

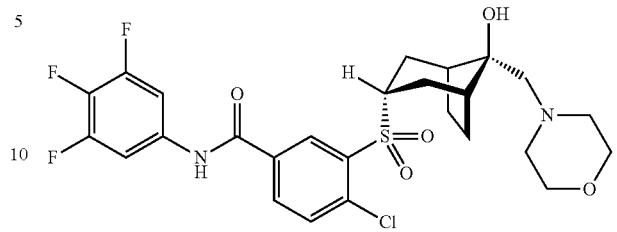

Step 336a. Into the solution of compound of step 256a (45 mg, 0.1 mmol) in DMF (1 mL) was added morpholine (50 mg, 5 mmol). It was heated at 80° C. o/n. It was concentrated to give the crude desired product as a white solid. ESI-MS m/z=539.13, 541.13[M–H]⁻. This material was used directly in the next step without further purification.

Step 336b. Into the solution of step 336a (0.1 mmol at most) in DCM (1 mL) was added CSA (70 mg, 3 mmol). It was stirred 30 minutes before m-CPBA (104 mg, 0.6 mmol) was added and stirred o/n. Aq. Na₂S₂O₃ was added and stirred 1 h. It was extracted with EtOAc twice.

The organic was washed with brine and dried (Na₂SO₄). After being concentrated, the crude was purified on prep-HPLC (C-18, Acetonitrile/water) to afford the title compound as a white solid (20 mg, 35%). ESI-MS m/z=571.13, 573.13 [M–H]⁻.

Example 338

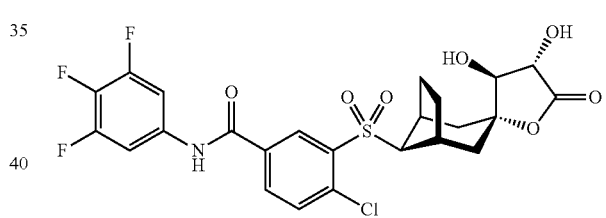

To a solution of example 222 (0.190 g, 0.34 mmol) in acetone/water (5:1, 3 ml) and NMO (0.049 g, 0.41 mmol) was added osmium tetraoxide (4% in water, 0.05 ml, 0.0068 mmol). It was stirred at rt overnight. It was diluted with ethyl acetate and washed with aq. Na₂S₂O₃, aq. NaHCO₃ and brine. The organic was dried (Na₂SO₄), filtered and concentrated. The crude was purified on prep-HPLC (C-18, acetonitrile/water) to give the title compound (35 mg, 18%) as a white solid and diastereomeric mixture of anti-diols. ESI-MS m/z=558.06, 560.06 [M–H].

Example 339

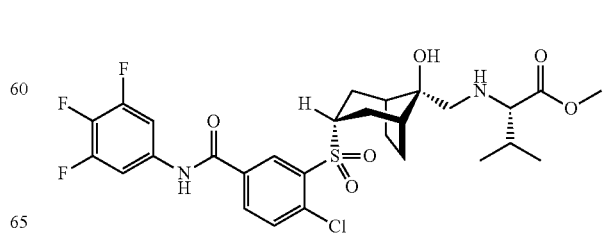

Step 339a. L-valine methyl ester HCl salt 200 mg, $K_2CO_3$ 300 mg was shaken in water 2 mL to give a solution. It was extracted with $Et_2O$ (10 mL*2), dried ($Na_2SO_4$) and concentrated to give a colorless oil. This colorless oil (26 mg, 0.20 mmol) and the compound of step 256a (45 mg, 0.1 mmol) was dissolved in EtOH (2 mL). To it, $Al(OTf)_3$ (2.4 mg, 0.005 mmol) was added and was heated at 80° C. o/n. It was concentrated to give the crude desired product as a white solid. ESI-MS m/z=583.16, 585.16 and 597.18, 599.18 (ethyl ester) [M−H]⁻. This material was used directly in the next step without further purification.

Step 339b. Into the solution of step 339a (0.1 mmol at most) in DCM (1 mL) was added CSA (70 mg, 3 mmol). It was stirred 30 minutes before m-CPBA (104 mg, 0.6 mmol) was added and stirred o/n. Aq. $Na_2S_2O_3$ was added and stirred 1 h. It was extracted with EtOAc twice.

The organic was washed with brine and dried ($Na_2SO_4$). After being concentrated, the crude was purified on prep-HPLC (C-18, Acetonitrile/water) to afford the title compound as a white solid (20 mg, 32%). ESI-MS m/z=615.15, 617.15 [M−H]⁻.

Example 340

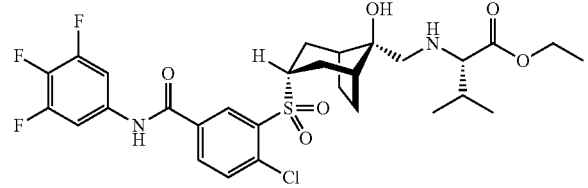

The title compound was isolated from example 339. ESI-MS m/z=629.16, 631.16 [M−H]⁻.

Example 344

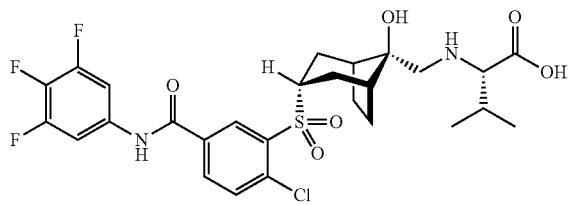

Into the solution of example 339 (15 mg, 0.024 mmol) in THF (0.5 mL) was added aq LiOH (1 M, 0.2 mL). It was stirred 40 hours at 45° C. After being cooled, HCl (1 M) was added to bring the pH to 2. It was extracted with EtOAc. The organic was washed with brine and dried ($Na_2SO_4$). After being concentrated, the crude was purified on prep-HPLC (C-18, Acetonitrile/water) to afford the title compound as a white solid (4 mg, 27%). ESI-MS m/z=601.13, 603.13 [M−H]⁻.

Example 345

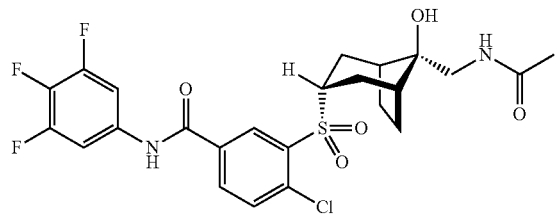

Into the solution of example 347 (19 mg, 0.038 mmol) in THF (0.5 mL) was added TEA (0.02 mL, 15 mmol), followed by acetic anhydride (7.8 mg, 0.076 mmol). It was stirred 2 hours at rt. and concentrated, the crude was purified on prep-HPLC (C-18, Acetonitrile/water) to afford the title compound as a white solid (2.5 mg, 12%). ESI-MS m/z=543.09, 545.09 [M−H].

Example 346

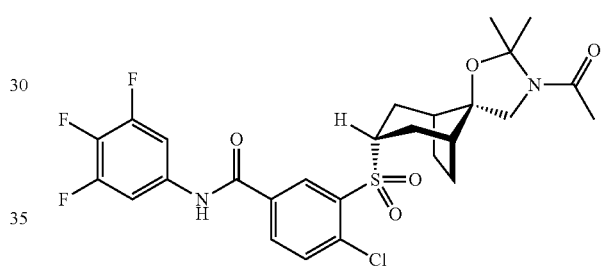

The title compound was isolated from example 345 if acetone present in reaction mixture. ESI-MS m/z=583.12, 585.12 [M−H]⁻.

Example 347

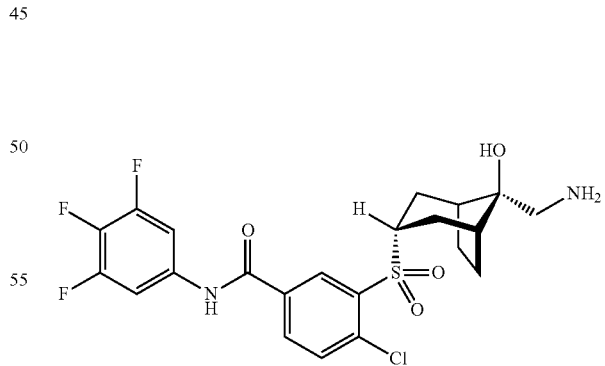

Into the solution of example 257 (540 mg, 1.02 mmol) in MeOH (2 mL) and THF (1 mL), Raney nickel (washed with MeOH, 50 mg) was added. A balloon filled with hydrogen was introduced. It was stirred 2 hours at rt. The mixture was filtered through a pad of celite, washed with MeOH. The filtrated was concentrated to give the title compound (440 mg, 86%). ESI-MS m/z=501.08, 503.08 [M−H]⁻.

Example 348

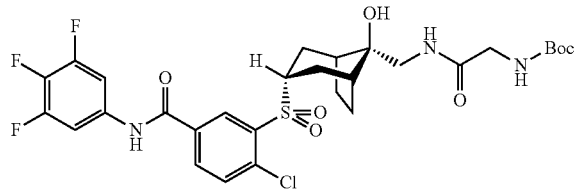

Into the solution of example 347 (50 mg, 0.10 mmol) and (tert-butoxycarbonyl)glycine (26.1 mg, 0.15 mmol) in DMF (1 mL) was added DIPEA (0.051 mL, 0.30 mmol) and HATU (76 mg, 0.2 mL). It was stirred 2 hours at rt. It was concentrated and the crude was purified on prep-HPLC (C-18, Acetonitrile/water) to afford the title compound as a white solid (28 mg, 47%). ESI-MS m/z=658.16, 660.16 [M−H]−.

Example 350

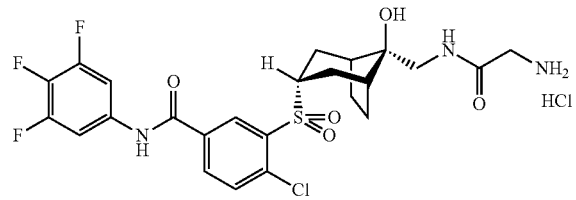

Into the solution of example 348 (20 mg, 0.03 mmol) in THF (0.5 mL) was added HCl (4M in dioxane, 0.5 mL, 2 mmol). It was stirred 2 hours at rt and concentrated to afford the title compound as a white solid (14 mg, 83%). ESI-MS m/z=558.10, 560.10 [M−H]−.

Example 352

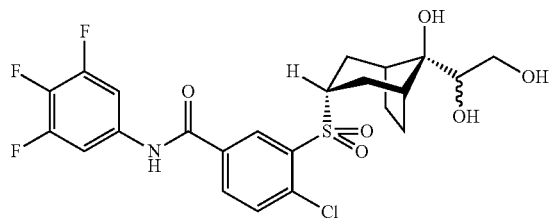

Step 352a. Into the solution of step 223a (220 mg, 0.5 mmol) in THF (1 mL) vinylmag-nesium bromide (1 M in THF, 1.2 mmol, 1.2 mmol) was added. It was stirred 30 minutes at rt. Aq. NH4Cl was added. It was extracted with EtOAc twice. The organic was washed with brine and dried (Na2SO4). After being concentrated, the crude was chromatographed (silica, EtOAc/hexanes) to afford the desired compound as a white solid (32 mg, 13.50%). ESI-MS m/z=466.08, 468.08 [M−H]−.

Step 352b. The title compound was prepared from the compound of step 352a by following the conditions described in step 223c. ESI-MS m/z=532.08, 534.08 [M−H]−.

Example 355

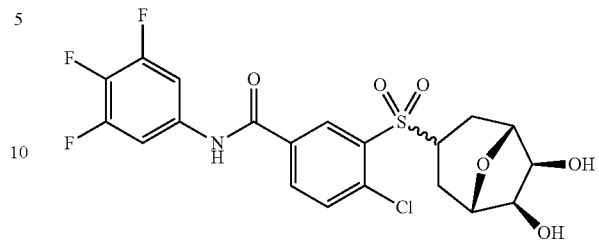

Step 355a. To a solution of 8-oxabicyclo[3.2.1]oct-6-en-3-one (500 mg, 4.03 mmol) in THF (8 ml) at 0° C. was added LAH (1M, 1.2 ml, 1.20 mmol). This was stirred 30 min followed by addition of water (0.5 ml), then NaOH (1M, 0.5 ml), then water (1.5 ml). Dried organic with Na2SO4, filter and evaporate to give crude product (0.5 g) as a 1.6:1 mixture of diastereomers.

Step 355b. To a solution of compound from Step 355a (0.5 g, 3.96 mmol) and compound from Step 1c (1.259 g, 3.96 mmol) in toluene was added PPh3 (1.455 g, 5.55 mmol) and DIAD (1.0 ml, 5.15 mmol). It was heated to and remained at 90° C. for 18 hours. It was diluted with EtOAc and washed with sat. aq. NaHCO3 and brine. The organic was dried (Na2SO4), filtered and concentrated. The residue was chromatographed (silica, hexanes/EtOAc) to give the desired product (950 mg, 2.31 mmol, 56% yield) as a 3:1 mixture of diastereomers.

Step 355c. The compound from Step 355b (300 mg, 0.704 mmol) was dissolved in acetone (5.0 ml) and water (1 ml) at rt followed by addition of osmium tetroxide (4% in water, 0.276 ml, 0.035 mmol) and NMO (413 mg, 3.52 mmol). The reaction was stirred at rt for 18 h. It was diluted with EtOAc and washed with sat. aq. NaHCO3 and brine. The organic was dried (Na2SO4), filtered and concentrated to give crude product (300 mg).

Step 355d. To compound from Step 355c (300 mg, 0.652 mmol) in NMP (6.5 ml) was added m-CPBA (563 mg, 2.51 mmol, 77%). The reaction was stirred at rt for 4 h. It was diluted with EtOAc and washed with sat. aq. NaHCO3 and brine. The organic was dried (Na2SO4), filtered and concentrated. The residue was chromatographed (silica, hexanes/acetone) to give the title compound (150 mg, 0.305 mmol, 47% yield) as a 2:1 mixture of diastereomers. ESI-MS m/z=558.10, 560.10 [M−H]−.

Example 356

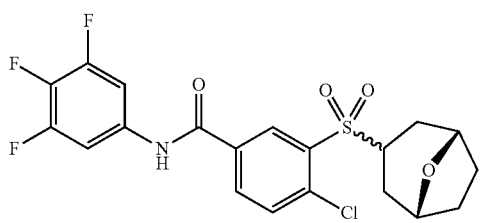 [SMILES: O=C(Nc1cc(F)c(F)c(F)c1)c1ccc(Cl)c(S(=O)(=O)C2C[C@H]3CC[C@@H](C2)O3)c1]

Step 356a. To compound from Step 355b (100 mg, 0.234 mmol) and Pd—C(12 mg) in ethyl acetate (5 ml) was flushed with nitrogen, evacuated with vacuum then added a hydrogen balloon. The reaction was stirred at rt for 2 h. It was diluted with EtOAc and filtered through celite. The filtrate was concentrated. Crude product was used without further purification.

Step 356b. To compound from Step 356a (100 mg, 0.134 mmol) in NMP (2.3 ml) was added m-CPBA (202 mg, 0.901 mmol, 77%). The reaction was stirred at rt for 4 h. It was diluted with EtOAc and washed with sat. aq. NaHCO$_3$ and brine. The organic was dried (Na$_2$SO$_4$), filtered and concentrated. The residue was chromatographed (prep-HPLC, acetonitrile/water) to give the title compound (15 mg, 0.305 mmol, 15% yield) as a 2.8:1 mixture of diastereomers. ESI-MS m/z=458.05, 460.04 [M−H]$^-$.

Example 357

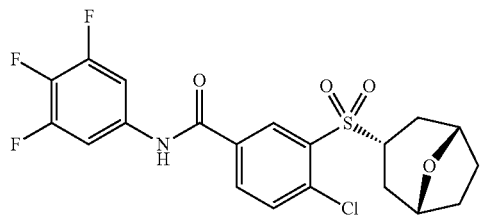 [SMILES: O=C(Nc1cc(F)c(F)c(F)c1)c1ccc(Cl)c(S(=O)(=O)[C@H]2C[C@H]3CC[C@@H](C2)O3)c1]

The title compound was isolated from Example 356 (1 mg). ESI-MS m/z=458.05, 460.04 [M−H]$^-$.

Example 359

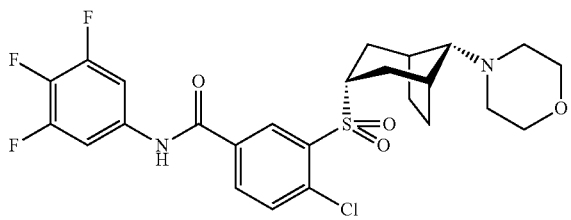

Step 359a. To a solution of compound from example 190 (1.07 g, 2.42 mmol) in anhydrous dichloromethane (20 mL) at 0° C. was added DBU (0.474 mL, 3.15 mmol) and 1,1,2,2,3,3,4,4,4-nonafluorobutane-1-sulfonyl fluoride (0.805 g, 2.66 mmol). The reaction was kept at 0° C. for 0.5 h before it was concentrated to dryness. The residue was dissolved in hexane (70 mL). The solution was washed with HCl (0.5 M), water, NaHCO$_3$, brine and dried (Na$_2$SO$_4$), filtered and concentrated. The crude product was chromatographed (silica, hexanes/EtOAc) to give the desired compound as white solid (1.6 g, 91%). ESI-MS m/z=722.01, 724.01 [M−H]$^-$.

Step 359b. To a mixture of compound from step (136 mg, 0.188 mmol) in DMF (0.8 ml) at rt was added morpholine (164 mg, 1.88 mmol) and stirred at 60° C. for 24 h. It was diluted with EtOAc and washed with water and brine. The organic was dried (Na$_2$SO$_4$), filtered and concentrated. The residue was chromatographed (silica, hexanes/EtOAc) to give the desired compound (12 mg, 13% yield). ESI-MS m/z=509.13, 511.13 [M−H]$^-$.

Step 359c. To a solution of compound from step (12 mg, 0.023 mmol) and CSA (10.9 mg, 0.047 mmol) in NMP (1.5 mL) at rt was added mCPBA (26.3 mg 77%, 0.117 mmol) and stirred at rt for 24 h. Aqueous Na$_2$S$_2$O$_3$, NaHCO$_3$ and few drops of Et$_3$N was added and stirred at rt for 1 h. It was extracted with EtOAc, washed with water, brine, dried over Na$_2$SO$_4$, filtered, concentrated purified by prep-HPLC using a C18 column and acetonitrile/water as eluent to give title compound (7.2 mg, 56%). ESI-MS m/z=541.11, 543.11 [M−H]$^-$.

Example 360

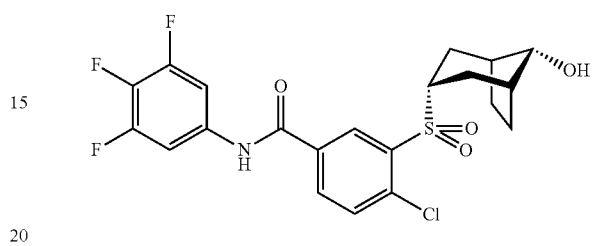

Step 360a. The desired compound (65 mg, 78% yield) was isolated from step 359b. ESI-MS m/z=440.08, 442.08 [M−H]$^-$.

Step 360b. To a solution of compound from step 360a (60 mg, 0.136 mmol) in NMP (2.0 mL) at rt was added mCPBA (152 mg 77%, 0.279 mmol) and stirred at rt for 24 h. Aqueous Na$_2$S$_2$O$_3$, NaHCO$_3$ and few drops of Et$_3$N was added and stirred at rt for 1 h. It was extracted with EtOAc, washed with water, brine, dried over Na$_2$SO$_4$, filtered, concentrated purified by prep-HPLC using a C18 column and acetonitrile/water as eluent to give title compound (42 mg, 65.3%). ESI-MS m/z=472.06, 474.06 [M−H]$^-$.

Example 361

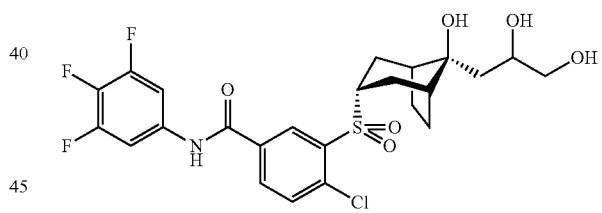

Step 361a. To a solution of compounds from step 223a (220 mg, 0.50 mmol) in THF (3.0 mL) at 0° C. was added allyl magnesium bromide (2.0 mL 1M solution in ether, 2.0 mmol).

The resulting reaction mixture was stirred at rt for 0.5 h. The reaction was quenched with aqueous NH$_4$Cl and the mixture was extracted with EtOAc, washed with water, brine. The organic layer was dried (Na$_2$SO$_4$), filtered and concentrated. The crude product was chromatographed (silica, hexanes/EtOAc) to give the desired compound as white solid (200 mg, 82%). ESI-MS m/z=[M−H]$^-$.

Step 361b. To a suspension of compound from step 361a (0.20 g, 0.415 mmol) and NMO (0.243 g, 2.075 mmol) in acetone-water (9 mL/1 mL) at rt was added osmium tetroxide (0.326 ml 4% in water, 0.041 mmol) and the mixture was stirred at rt for 3 days. It was quenched with aqueous Na$_2$SO$_3$, extracted with EtOAc, washed with water, 3N HCl, NaHCO$_3$, brine, dried over Na$_2$SO$_4$, filtered, concentrated to give a mixture of sulfone and sulfoxide. To a mixture of sulfone and sulfoxide in NMP (2 mL) was added mCPBA (0.558 g 77%, 2.49 mmol) and stirred at rt for 20 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and purified by prep-HPLC using a C18 column and acetonitrile/water as eluent to give the title compound (152 mg, 66%). ESI-MS m/z=546.09, 548.09 [M−H]⁻.

Example 363

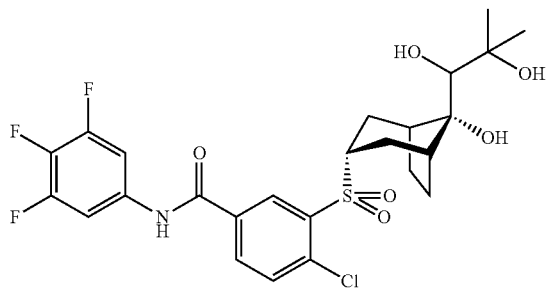

Step 363a. To a solution of triethyl phosphonoacetate (0.520 ml, 2.60 mmol) THF (5.0 mL) at 0° C. was added NaH (0.104 g 60%, 2.6 mmol). The resulting reaction mixture was stirred at 0° C. for 30 mins. A solution of compound from step 223 a (0.15 g, 0.34 mmol) in THF (2.0 mL) was added and stirred at rt for 2 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (0.50 g, 98%). ESI-MS m/z=508.10, 510.10 [M−H]⁻.

Step 363b. To a solution of compounds from step 363a (100 mg, 0.196 mmol) in THF (2.0 mL) at 0° C. was added MeLi (0.55 mL 1.6 M solution in ether, 0.882 mmol). The resulting reaction mixture was stirred at 0° C. for 10 mins. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (57 mg, 58%). ESI-MS m/z=494.11, 496.11 [M−H]⁻.

Step 363c. To a mixture of compound from step 363b (57 mg, 0.115 mmol) and NMO (81 mg, 0.69 mmol) in acetone (2.0 mL) at rt was added osmium tetroxide (0.73 ml 400 in water, 0.115 mmol) and the mixture was stirred at rt for 2 days. It was quenched with aqueous Na₂SO₃, extracted with EtOAc, washed with water, 3N HCl, NaHCO₃, brine, dried over Na₂SO₄, filtered, concentrated and purified by prep-HPLC using a C18 column and acetonitrile/water as eluent to give title compound (22 mg, 34%). ESI-MS m/z=560.11, 562.11 [M−H]⁻.

The following examples were prepared using procedures similar to those described above:

| Example | Structure | ESIMS (M − H)⁻ or (M + H)⁺ |
|---------|-----------|----------------------------|
| 11 | 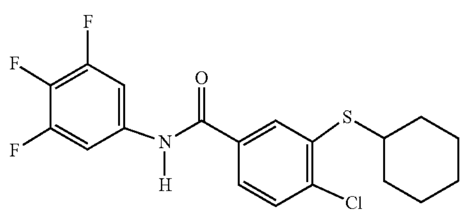 [SMILES: O=C(Nc1cc(F)c(F)c(F)c1)c1ccc(Cl)c(SC2CCCCC2)c1] | 398.13, 400.06 |
| 12 | 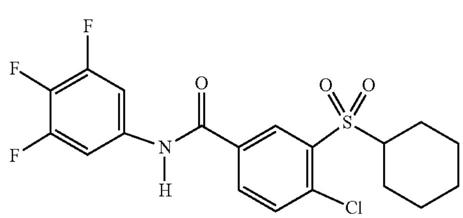 [SMILES: O=C(Nc1cc(F)c(F)c(F)c1)c1ccc(Cl)c(S(=O)(=O)C2CCCCC2)c1] | 430.06, 432.05 |
| 13 | 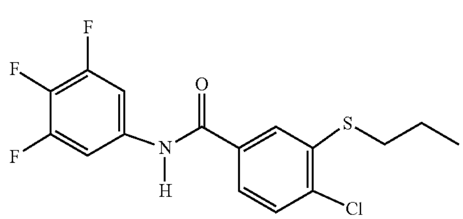 [SMILES: CCCSc1cc(C(=O)Nc2cc(F)c(F)c(F)c2)ccc1Cl] | 358.10, 360.03 |

| Example | Structure | ESIMS (M − H)⁻ or (M + H)⁺ |
|---|---|---|
| 15 | 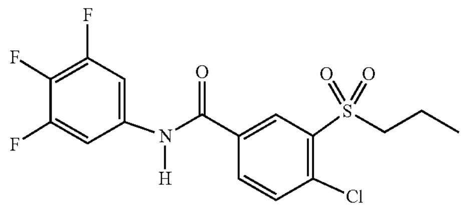 [SMILES: CCCS(=O)(=O)c1cc(C(=O)Nc2cc(F)c(F)c(F)c2)ccc1Cl] | 390.08, 392.02 |
| 26 | 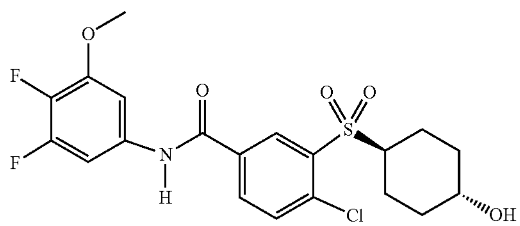 [SMILES: COc1cc(NC(=O)c2ccc(Cl)c(S(=O)(=O)[C@H]3CC[C@H](O)CC3)c2)cc(F)c1F] | 440.08, 442.08 |
| 27 | 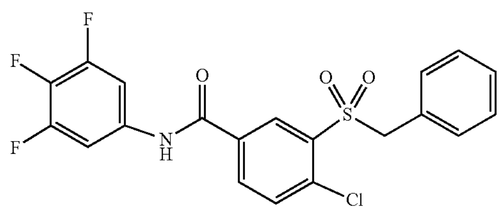 [SMILES: O=C(Nc1cc(F)c(F)c(F)c1)c1ccc(Cl)c(S(=O)(=O)Cc2ccccc2)c1] | 438.03, 440.02 |
| 28 | 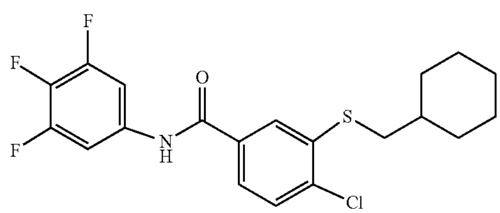 [SMILES: O=C(Nc1cc(F)c(F)c(F)c1)c1ccc(Cl)c(SCC2CCCCC2)c1] | 412.08, 414.07 |
| 29 | 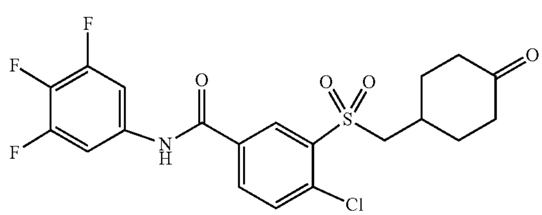 [SMILES: O=C1CCC(CS(=O)(=O)c2cc(C(=O)Nc3cc(F)c(F)c(F)c3)ccc2Cl)CC1] | 444.03, 446.03 |
| 32 | 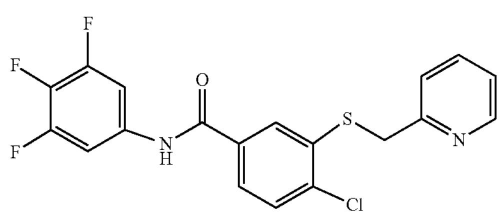 [SMILES: O=C(Nc1cc(F)c(F)c(F)c1)c1ccc(Cl)c(SCc2ccccn2)c1] | 409.05, 411.04 |
| 33 | 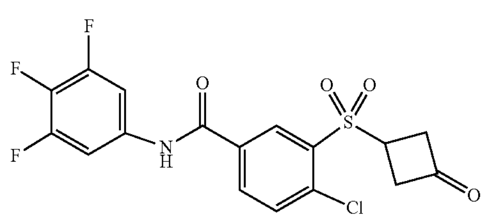 [SMILES: O=C1CC(S(=O)(=O)c2cc(C(=O)Nc3cc(F)c(F)c(F)c3)ccc2Cl)C1] | 416.00, 418.00 |

-continued

| Example | Structure | ESIMS (M − H)⁻ or (M + H)⁺ |
|---|---|---|
| 34 | 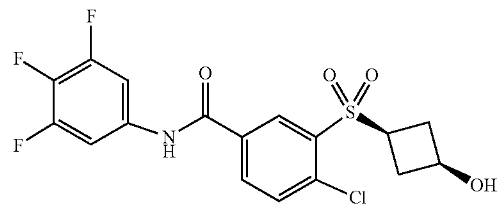 [SMILES: O=C(Nc1cc(F)c(F)c(F)c1)c1ccc(Cl)c(S(=O)(=O)[C@H]2C[C@@H](O)C2)c1] | 418.02, 420.01 |
| 35 | 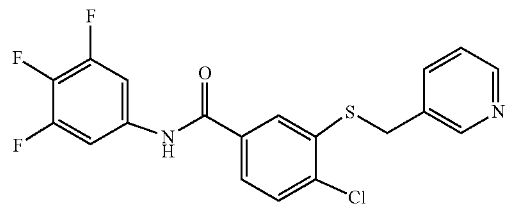 [SMILES: O=C(Nc1cc(F)c(F)c(F)c1)c1ccc(Cl)c(SCc2cccnc2)c1] | 409.05, 411.04 |
| 36 | 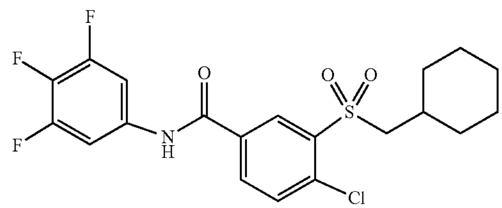 [SMILES: O=C(Nc1cc(F)c(F)c(F)c1)c1ccc(Cl)c(S(=O)(=O)CC2CCCCC2)c1] | 444.08, 446.06 |
| 38 | 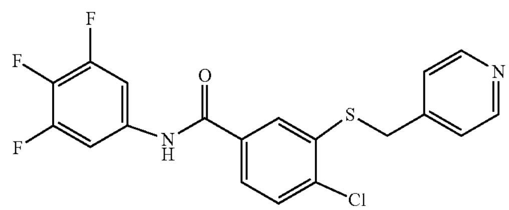 [SMILES: O=C(Nc1cc(F)c(F)c(F)c1)c1ccc(Cl)c(SCc2ccncc2)c1] | 409.05, 411.04 |
| 40 | 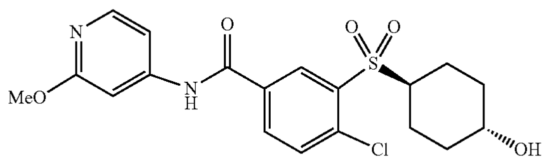 [SMILES: COc1cc(NC(=O)c2ccc(Cl)c(S(=O)(=O)[C@H]3CC[C@H](O)CC3)c2)ccn1] | 423.08, 425.07 |
| 41 | 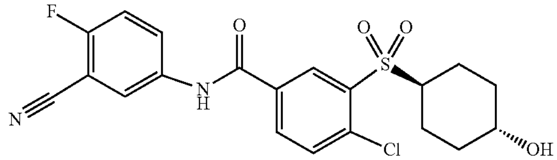 [SMILES: N#Cc1cc(NC(=O)c2ccc(Cl)c(S(=O)(=O)[C@H]3CC[C@H](O)CC3)c2)ccc1F] | 435.08, 437.06 |
| 42 | 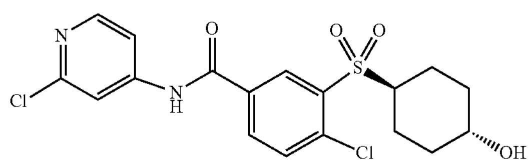 [SMILES: O=C(Nc1ccnc(Cl)c1)c1ccc(Cl)c(S(=O)(=O)[C@H]2CC[C@H](O)CC2)c1] | 427.05, 429.03 |
| 43 | 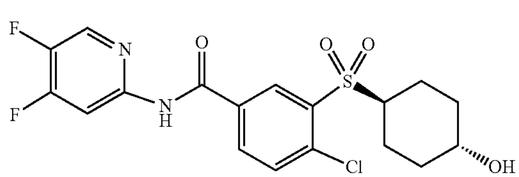 [SMILES: O=C(Nc1cc(F)c(F)cn1)c1ccc(Cl)c(S(=O)(=O)[C@H]2CC[C@H](O)CC2)c1] | 429.05, 431.05 |

-continued

| Example | Structure | ESIMS (M − H)⁻ or (M + H)⁺ |
|---|---|---|
| 45 | 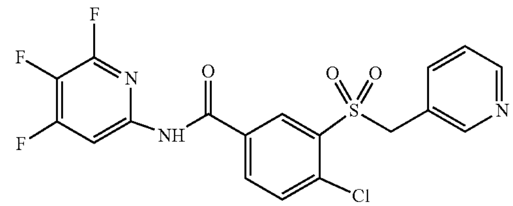 [SMILES: O=C(Nc1cc(F)c(F)c(F)n1)c1ccc(Cl)c(S(=O)(=O)Cc2cccnc2)c1] | 441.03, 443.02 |
| 46 | 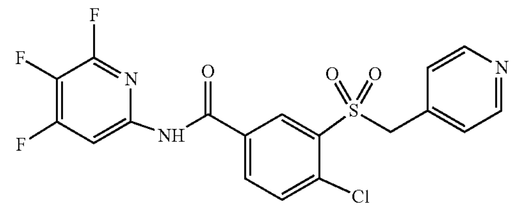 [SMILES: O=C(Nc1cc(F)c(F)c(F)n1)c1ccc(Cl)c(S(=O)(=O)Cc2ccncc2)c1] | 441.03, 443.02 |
| 47 | 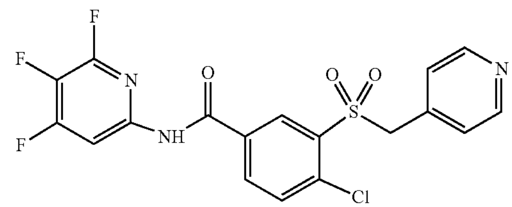 [SMILES: O=C(Nc1cc(F)c(F)c(F)n1)c1ccc(Cl)c(S(=O)(=O)Cc2ccncc2)c1] | 425.04, 427.03 |
| 48 | 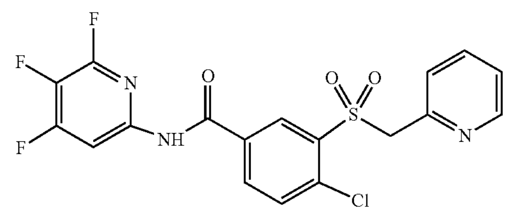 [SMILES: O=C(Nc1cc(F)c(F)c(F)n1)c1ccc(Cl)c(S(=O)(=O)Cc2ccccn2)c1] | 439.02, 441.01 |
| 51 | 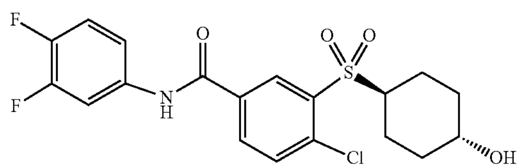 | 428.07, 430.05 |
| 52 | 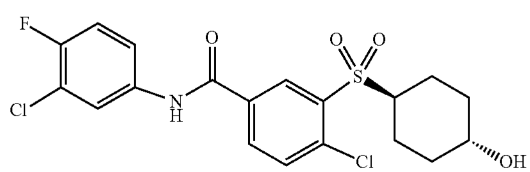 [SMILES: O=C(Nc1ccc(F)c(Cl)c1)c1ccc(Cl)c(S(=O)(=O)[C@H]2CC[C@H](O)CC2)c1] | 444.03, 446.02 |
| 56 | 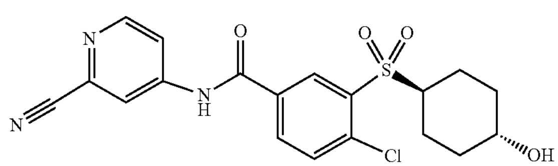 [SMILES: N#Cc1cc(NC(=O)c2ccc(Cl)c(S(=O)(=O)[C@H]3CC[C@H](O)CC3)c2)ccn1] | 418.08, 420.06 |
| 57 | 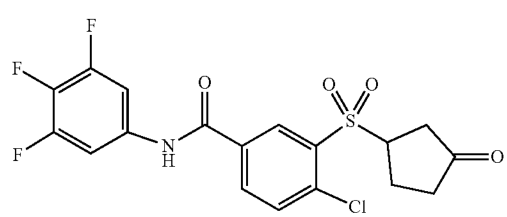 [SMILES: O=C1CCC(S(=O)(=O)c2cc(C(=O)Nc3cc(F)c(F)c(F)c3)ccc2Cl)C1] | 430.01, 432.01 |

-continued
| Example | Structure | ESIMS (M − H)⁻ or (M + H)⁺ |
|---|---|---|
| 58 | 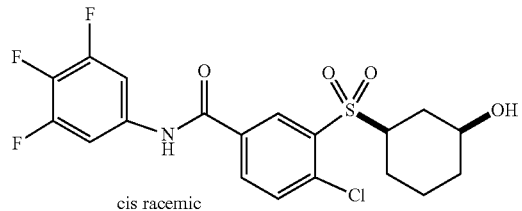 cis racemic | 446.05, 448.04 |
| 59 | 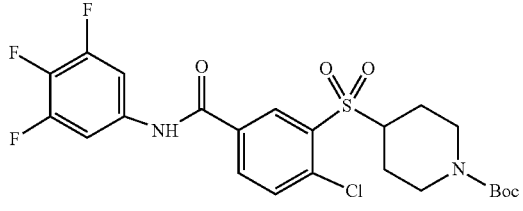 [SMILES: CC(C)(C)OC(=O)N1CCC(S(=O)(=O)c2cc(C(=O)Nc3cc(F)c(F)c(F)c3)ccc2Cl)CC1] | 531.10, 533.10 |
| 65 | 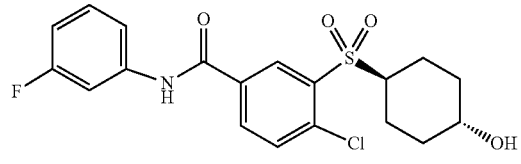 [SMILES: O=C(Nc1cccc(F)c1)c1ccc(Cl)c(S(=O)(=O)[C@H]2CC[C@H](O)CC2)c1] | 412.13, 414.13 |
| 66 | 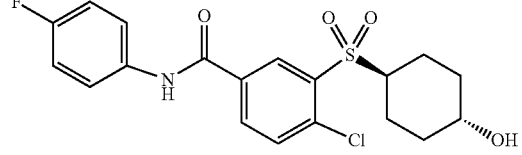 | 412.14, 414.14 |
| 67 | 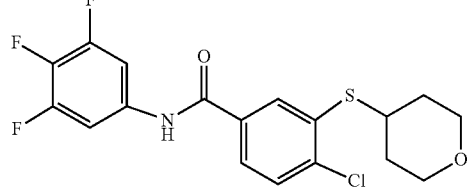 | 400.01, 402.04 |
| 68 | 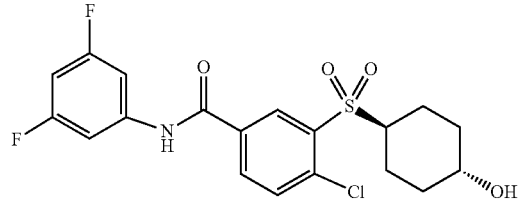 [SMILES: O=C(Nc1cc(F)cc(F)c1)c1ccc(Cl)c(S(=O)(=O)[C@H]2CC[C@H](O)CC2)c1] | 428.06, 430.05 |
| 69 | 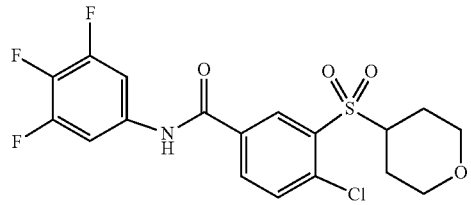 [SMILES: O=C(Nc1cc(F)c(F)c(F)c1)c1ccc(Cl)c(S(=O)(=O)C2CCOCC2)c1] | 432.05, 434.03 |

-continued

| Example | Structure | ESIMS (M − H)⁻ or (M + H)⁺ |
|---|---|---|
| 74 | 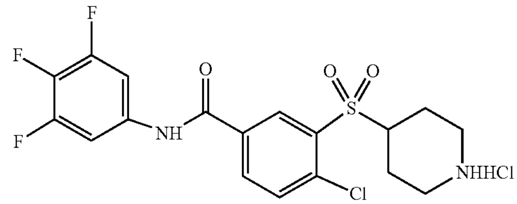 | 431.12, 433.12 |
| 85 | diol cis to each other<br>sulfone vs diol: de 5:1 | 494.02, 496.02<br>(M + HCO₂) |
| 93 | 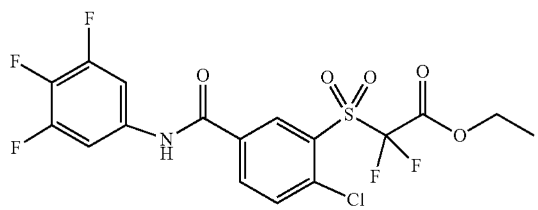 [SMILES: CCOC(=O)C(F)(F)S(=O)(=O)c1cc(C(=O)Nc2cc(F)c(F)c(F)c2)ccc1Cl] | 469.99, 471.99 |
| 94 | 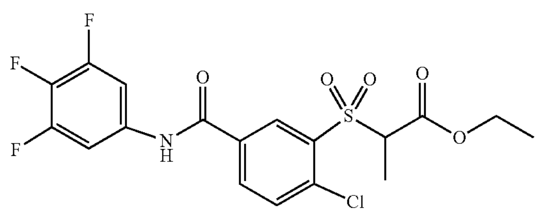 [SMILES: CCOC(=O)C(C)S(=O)(=O)c1cc(C(=O)Nc2cc(F)c(F)c(F)c2)ccc1Cl] | 448.02, 450.02 |
| 96 | 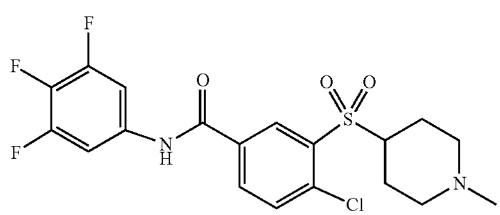 [SMILES: CN1CCC(S(=O)(=O)c2cc(C(=O)Nc3cc(F)c(F)c(F)c3)ccc2Cl)CC1] | 447.07-, 449.07- |
| 102 | diol cis to each other<br>sulfone vs diol cis:trans = 1:3 | 462.04, 464.04 |

| Example | Structure | ESIMS (M − H)⁻ or (M + H)⁺ |
|---|---|---|
| 105 | 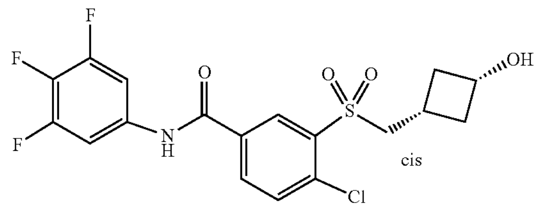 [SMILES: O=C(Nc1cc(F)c(F)c(F)c1)c1ccc(Cl)c(S(=O)(=O)C[C@H]2C[C@@H](O)C2)c1] | 432.03, 434.03 |
| 117 | 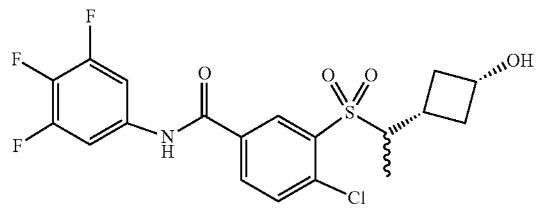 [SMILES: CC([C@H]1C[C@@H](O)C1)S(=O)(=O)c1cc(C(=O)Nc2cc(F)c(F)c(F)c2)ccc1Cl] | 446.05, 448.04 |
| 118 | 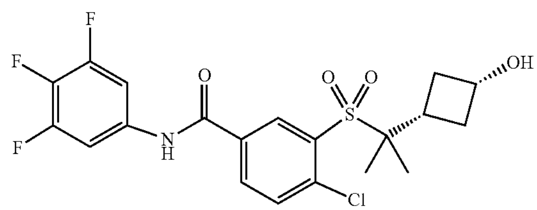 [SMILES: CC(C)([C@H]1C[C@@H](O)C1)S(=O)(=O)c1cc(C(=O)Nc2cc(F)c(F)c(F)c2)ccc1Cl] | 460.06, 462.06 |
| 122 | 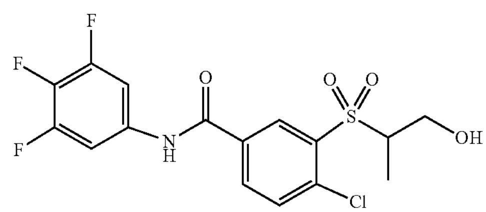 [SMILES: CC(CO)S(=O)(=O)c1cc(C(=O)Nc2cc(F)c(F)c(F)c2)ccc1Cl] | 469.99, 471.99 |
| 123 | 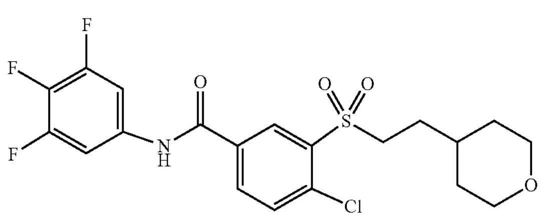 [SMILES: O=C(Nc1cc(F)c(F)c(F)c1)c1ccc(Cl)c(S(=O)(=O)CCC2CCOCC2)c1] | 460.06, 462.06 |
| 126 | 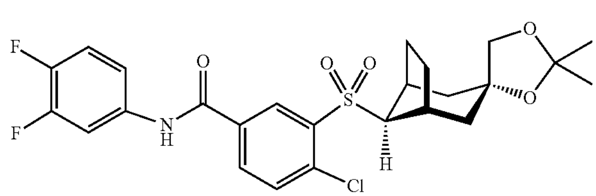 [SMILES: CC1(C)OC[C@@]2(CC3CC[C@@H](C2)[C@H]3S(=O)(=O)c2cc(C(=O)Nc3ccc(F)c(F)c3)ccc2Cl)O1] | 524.11, 526.11 |
| 127 | 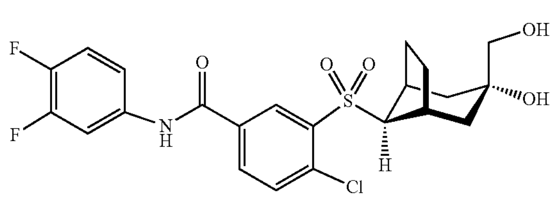 [SMILES: O=C(Nc1ccc(F)c(F)c1)c1ccc(Cl)c(S(=O)(=O)[C@H]2C3CC[C@H]2C[C@](O)(CO)C3)c1] | 484.06, 486.06 |

-continued

| Example | Structure | ESIMS (M − H)⁻ or (M + H)⁺ |
|---|---|---|
| 145 | 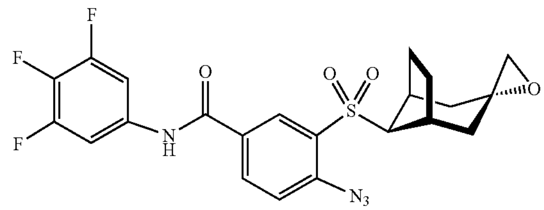 | 491.11, 492.10 |
| 147 | 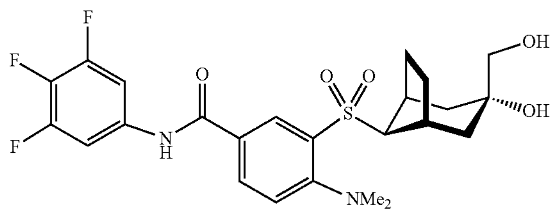 | 557.16, 558.16 |
| 148 | 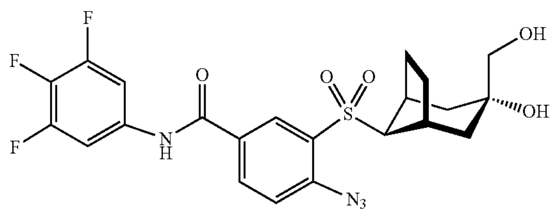 | 555.13, 556.12 |
| 149 | 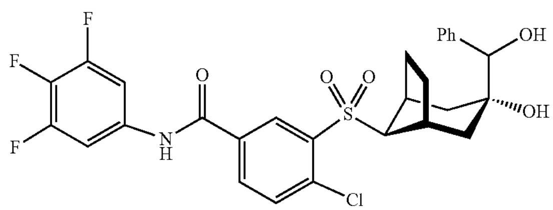 | 624.11, 626.11 |
| 156 | 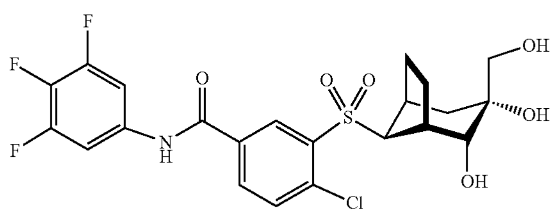 | 518.06, 520.064 |
| 158 | 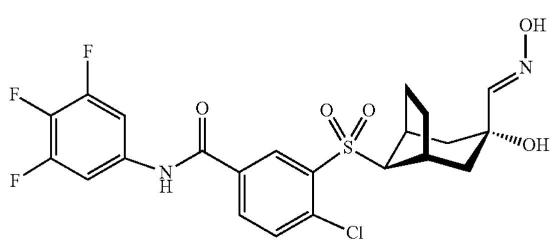 | 515.07, 517.08 |
| 166 | 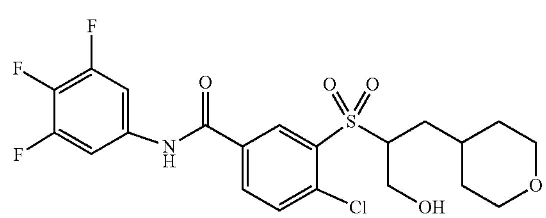 [SMILES: O=C(Nc1cc(F)c(F)c(F)c1)c1ccc(Cl)c(S(=O)(=O)C(CO)CC2CCOCC2)c1] | 490.07, 492.07 |

-continued
| Example | Structure | ESIMS (M − H)⁻ or (M + H)⁺ |
|---|---|---|
| 168 | 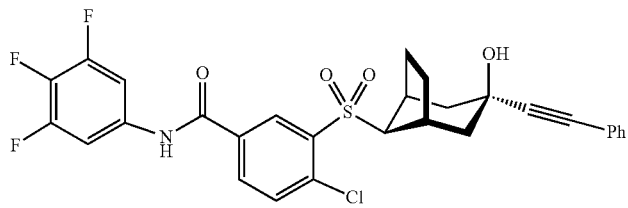 | 572.09, 574.10 |
| 169 | 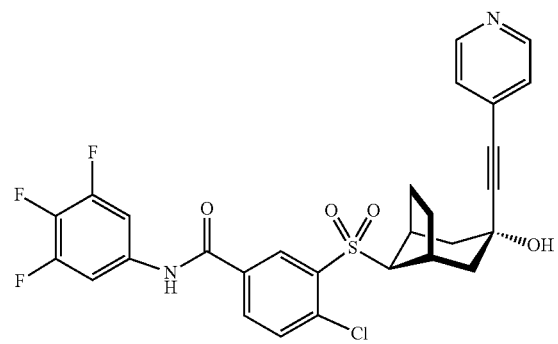 | 573.09, 575.08 |
| 170 | 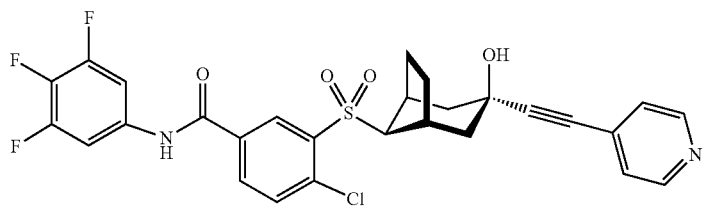 | 573.09, 575.08 |
| 171 | 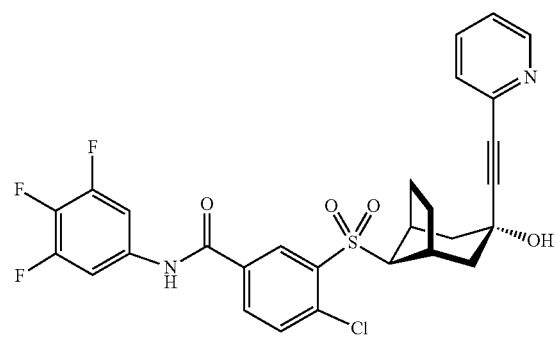 | 573.09, 575.09 |
| 172 | 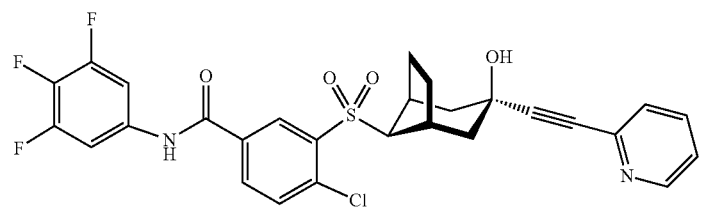 | 573.09, 575.08 |
| 174 | 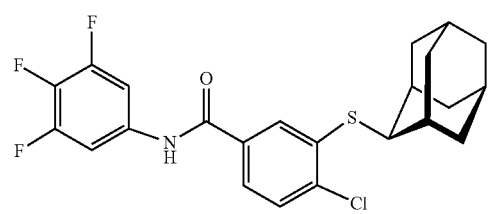 [SMILES: O=C(Nc1cc(F)c(F)c(F)c1)c1ccc(Cl)c(S[C@H]2C3CC4C[C@H](C3)C[C@@H]2C4)c1] | 450.09, 452.08 |

-continued

| Example | Structure | ESIMS (M − H)⁻ or (M + H)⁺ |
|---|---|---|
| 175 | 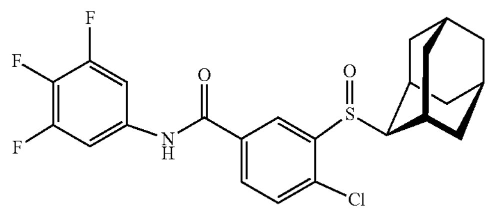 [SMILES: O=C(Nc1cc(F)c(F)c(F)c1)c1ccc(Cl)c(S(=O)[C@H]2C3C[C@@H]4C[C@H](C3)C[C@@H]2C4)c1] | 466.08, 468.08 |
| 176 | 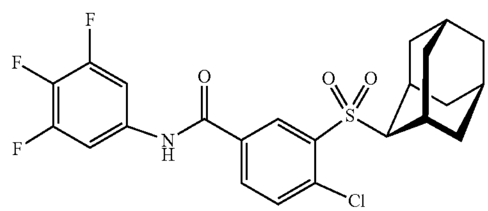 [SMILES: O=C(Nc1cc(F)c(F)c(F)c1)c1ccc(Cl)c(S(=O)(=O)[C@H]2C3C[C@@H]4C[C@H](C3)C[C@@H]2C4)c1] | 482.08, 484.07 |
| 182 | 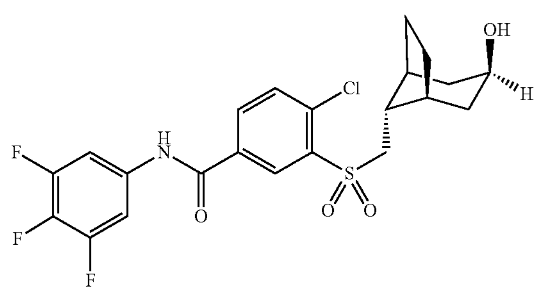 [SMILES: O=C(Nc1cc(F)c(F)c(F)c1)c1ccc(Cl)c(S(=O)(=O)C[C@@H]2C3CC[C@H]2C[C@H](O)C3)c1] | 486.07, 488.07 |
| 186 | 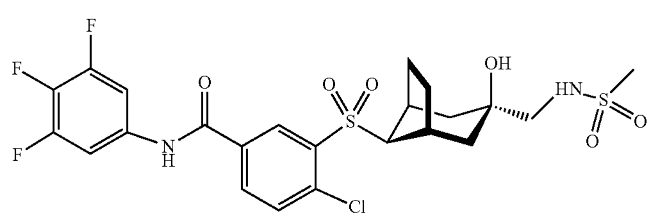 | 579.12, 581.12 |
| 187 | 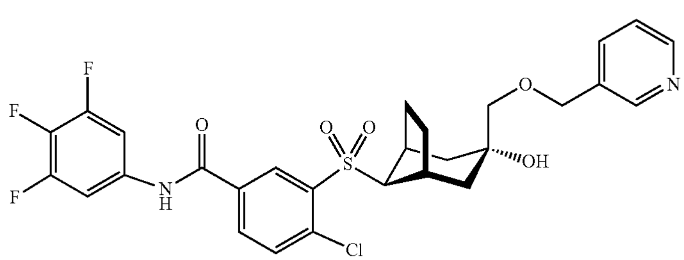 | 593.11, 595.10 |
| 196 | 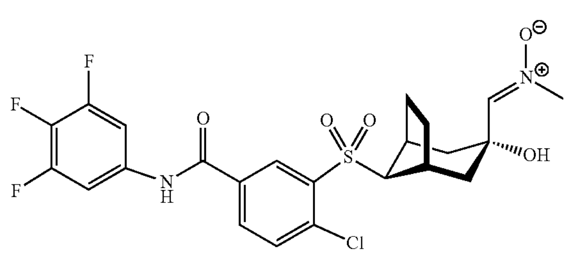 | 529.08, 531.08 |

-continued

| Example | Structure | ESIMS (M − H)⁻ or (M + H)⁺ |
|---|---|---|
| 198 | 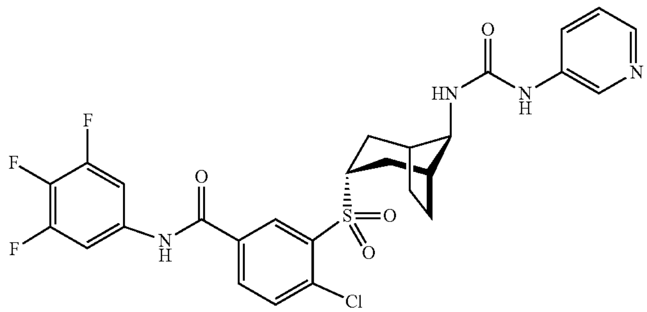 | 637.11, 639.11 (M + HCO2H − H) |
| 199 | 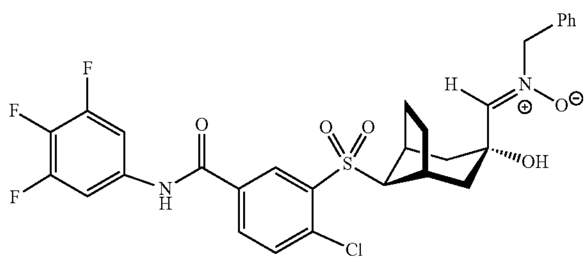 | 605.11, 607.11 |
| 201 | 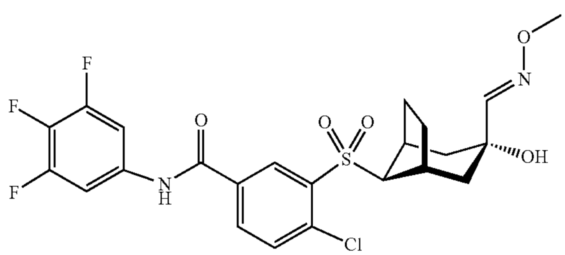 [SMILES: CO/N=C/[C@]1(O)CC2CC[C@@H](C1)[C@H]2S(=O)(=O)c1cc(C(=O)Nc2cc(F)c(F)c(F)c2)ccc1Cl] | 529.14, 531.18 |
| 202 | 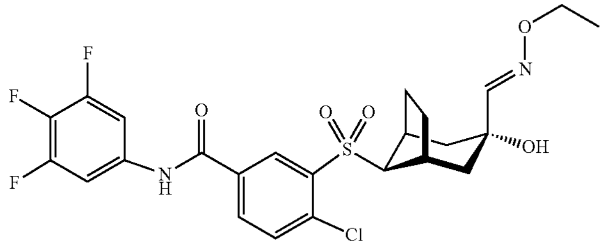 [SMILES: CCO/N=C/[C@]1(O)CC2CC[C@@H](C1)[C@H]2S(=O)(=O)c1cc(C(=O)Nc2cc(F)c(F)c(F)c2)ccc1Cl] | 543.11, 545.23 |
| 203 | 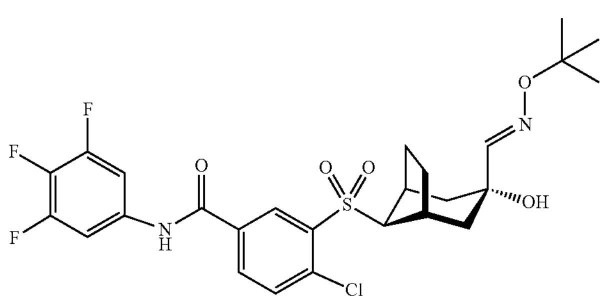 [SMILES: CC(C)(C)O/N=C/[C@]1(O)CC2CC[C@@H](C1)[C@H]2S(=O)(=O)c1cc(C(=O)Nc2cc(F)c(F)c(F)c2)ccc1Cl] | 571.18, 573.20 |

-continued

| Example | Structure | ESIMS (M − H)⁻ or (M + H)⁺ |
|---|---|---|
| 204 | 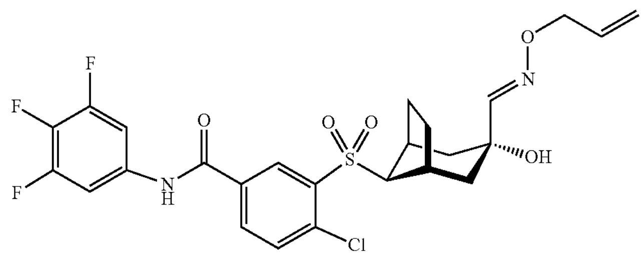 [SMILES: C=CCO/N=C/[C@]1(O)CC2CC[C@@H](C1)[C@H]2S(=O)(=O)c1cc(C(=O)Nc2cc(F)c(F)c(F)c2)ccc1Cl] | 555.15, 557.16 |
| 205 | 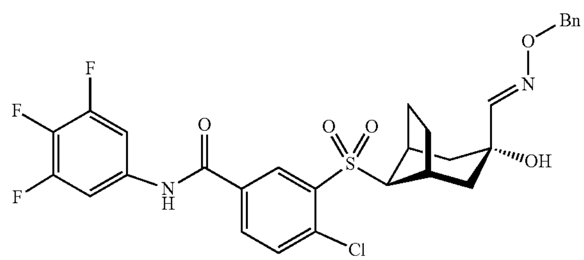 [SMILES: O=C(Nc1cc(F)c(F)c(F)c1)c1ccc(Cl)c(S(=O)(=O)[C@H]2C3CC[C@H]2C[C@](O)(/C=N/OCc2ccccc2)C3)c1] | 605.19, 607.18 |
| 209 | 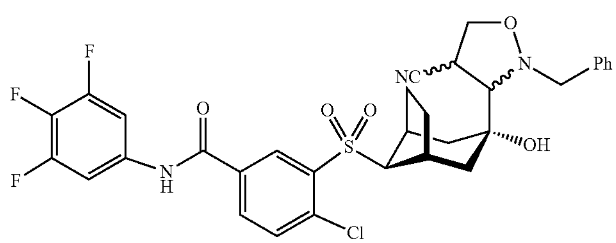 [SMILES: N#CC1CON(Cc2ccccc2)C1[C@]1(O)CC2CC[C@@H](C1)[C@H]2S(=O)(=O)c1cc(C(=O)Nc2cc(F)c(F)c(F)c2)ccc1Cl] | 658.13, 660.13 |
| 210 | 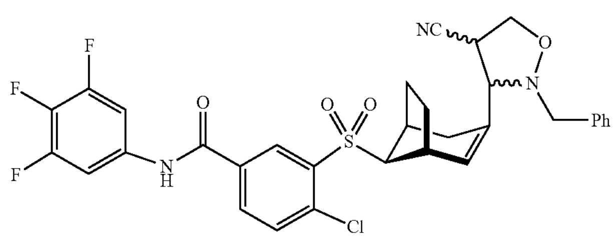 [SMILES: N#CC1CON(Cc2ccccc2)C1C1=C[C@@H]2CCC(C1)[C@@H]2S(=O)(=O)c1cc(C(=O)Nc2cc(F)c(F)c(F)c2)ccc1Cl] | 640.13, 642.12 |
| 213 | 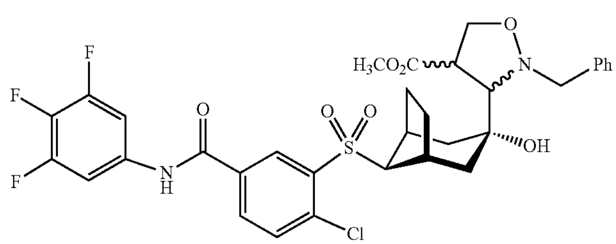 [SMILES: COC(=O)C1CON(Cc2ccccc2)C1[C@]1(O)CC2CC[C@@H](C1)[C@H]2S(=O)(=O)c1cc(C(=O)Nc2cc(F)c(F)c(F)c2)ccc1Cl] | 691.15, 693.15 |
| 214 | 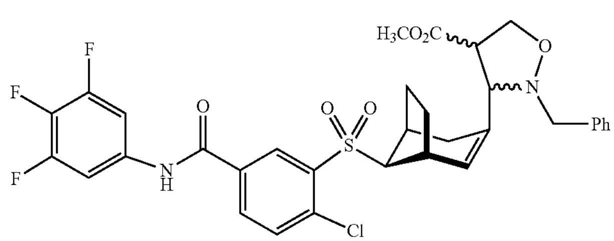 [SMILES: COC(=O)C1CON(Cc2ccccc2)C1C1=C[C@@H]2CCC(C1)[C@@H]2S(=O)(=O)c1cc(C(=O)Nc2cc(F)c(F)c(F)c2)ccc1Cl] | 673.13, 675.13 |

-continued

| Example | Structure | ESIMS (M − H)⁻ or (M + H)⁺ |
|---|---|---|
| 215 | 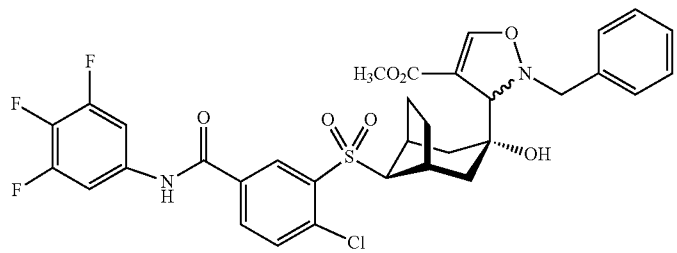 [SMILES: COC(=O)C1=CON(Cc2ccccc2)C1[C@]1(O)CC2CC[C@@H](C1)[C@H]2S(=O)(=O)c1cc(C(=O)Nc2cc(F)c(F)c(F)c2)ccc1Cl] | 689.13, 691.13 |
| 216 | 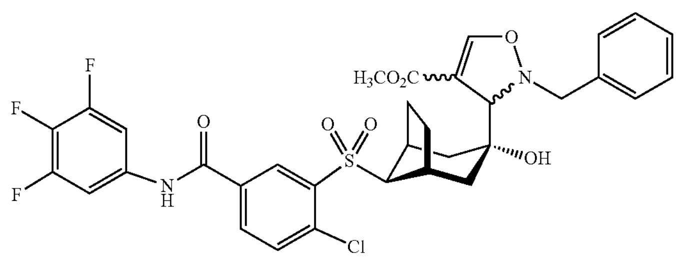 [SMILES: COC(=O)C1=CON(Cc2ccccc2)C1[C@]1(O)CC2CC[C@@H](C1)[C@H]2S(=O)(=O)c1cc(C(=O)Nc2cc(F)c(F)c(F)c2)ccc1Cl] | 689.13, 691.13 |
| 217 | 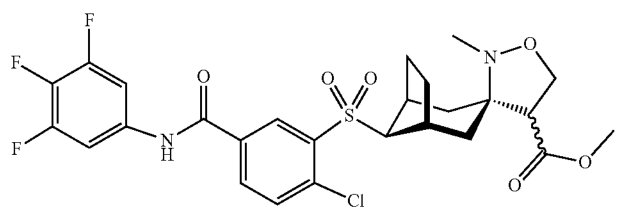 | 585.10, 587.10 |
| 218 | 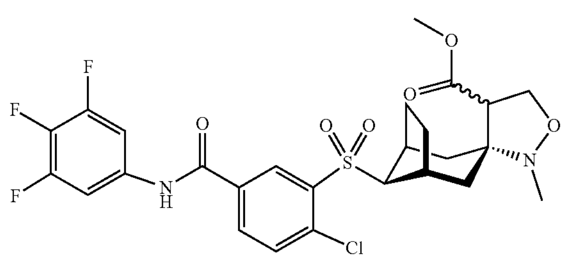 | 585.10, 587.10 |
| 219 | 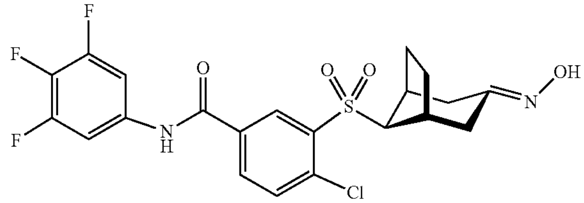 | 485.05, 487.05 |
| 222 | 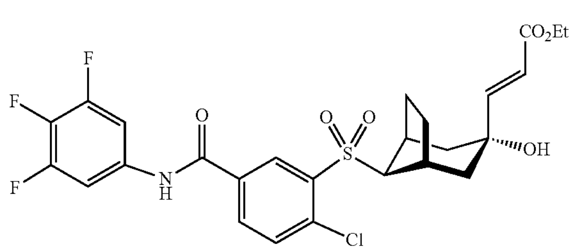 [SMILES: CCOC(=O)/C=C/[C@]1(O)CC2CC[C@@H](C1)[C@H]2S(=O)(=O)c1cc(C(=O)Nc2cc(F)c(F)c(F)c2)ccc1Cl] | 570.09, 572.09 |

| Example | Structure | ESIMS (M − H)⁻ or (M + H)⁺ |
|---|---|---|
| 224 | 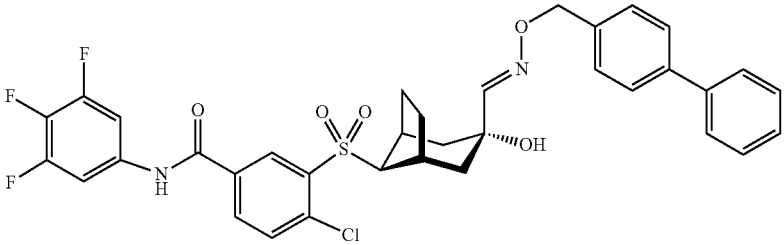 [SMILES: O=C(Nc1cc(F)c(F)c(F)c1)c1ccc(Cl)c(S(=O)(=O)[C@H]2C3CC[C@H]2C[C@](O)(/C=N/OCc2ccc(-c4ccccc4)cc2)C3)c1] | 681.15, 683.15 |
| 226 | 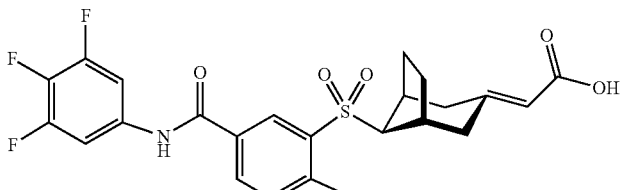 | 512.05, 514.05 |
| 228 | 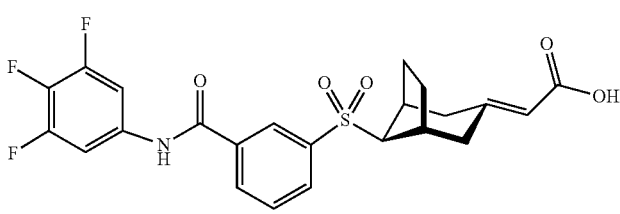 | 506.12 |
| 229 | 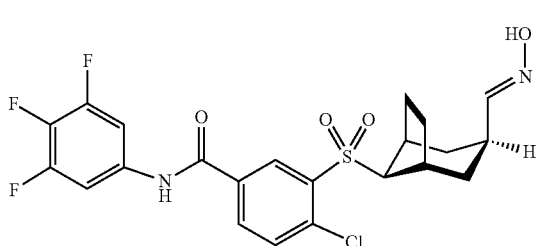 | 499.07, 510.06 |
| 230 | 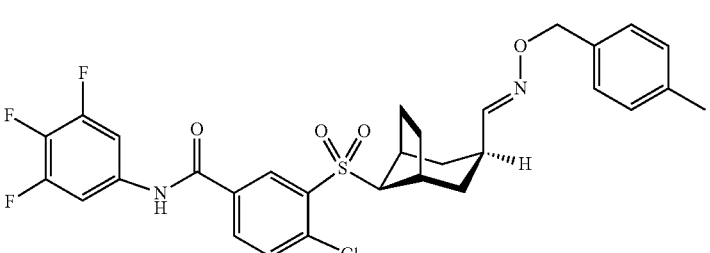 | 619.2, 621.2 |
| 231 | 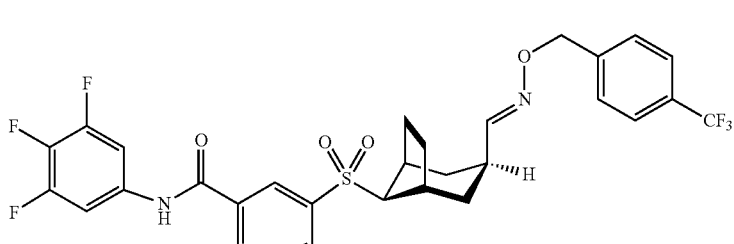 | 673.0, 675.0 |

| Example | Structure | ESIMS (M − H)⁻ or (M + H)⁺ |
|---|---|---|
| 232 | 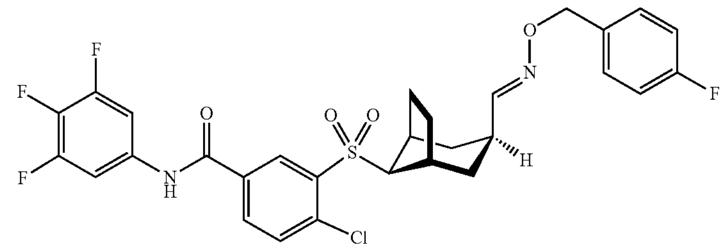 | 623.1, 625.0 |
| 233 | 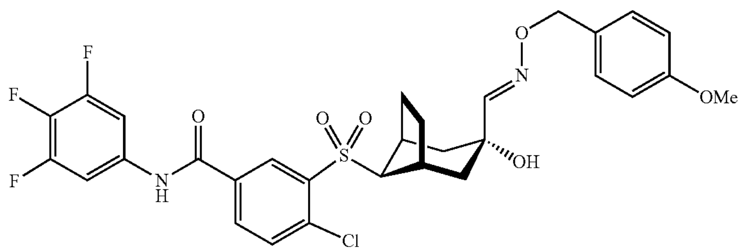 | 635.1, 636.9 |
| 234 | 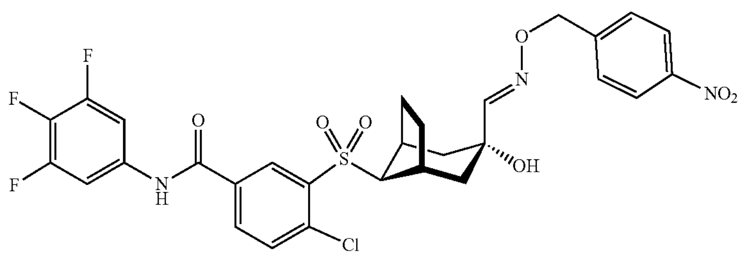 | 650.0, 652.0 |
| 235 | 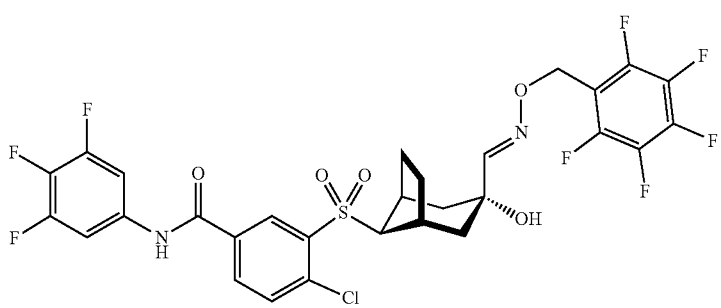 | 695.0, 697.0 |
| 236 | 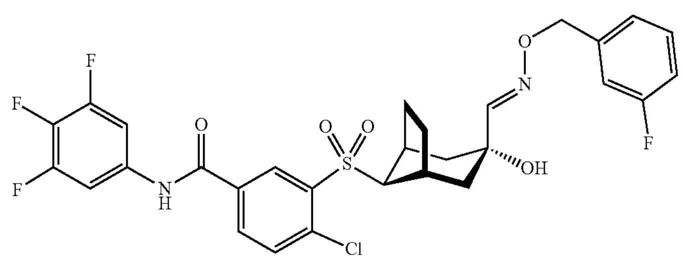 | 623.1, 625.0 |
| 237 | 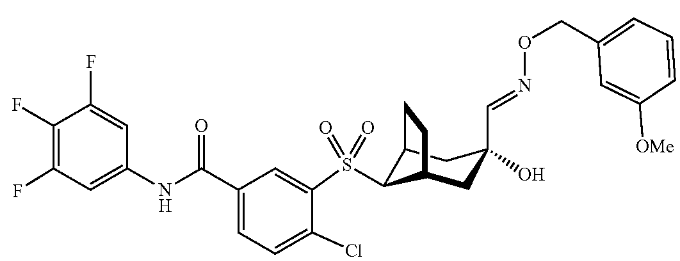 | 635.1, 636.9 |

-continued
| Example | Structure | ESIMS (M − H)⁻ or (M + H)⁺ |
|---------|-----------|------------------------------|
| 238 | 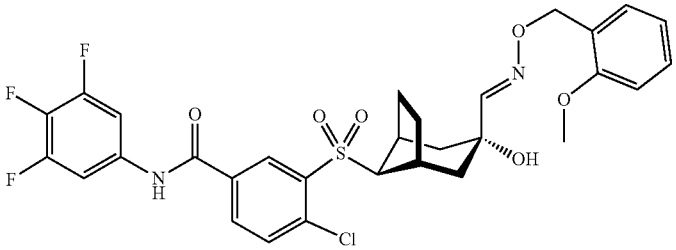 | 635.1, 636.9 |
| 240 | 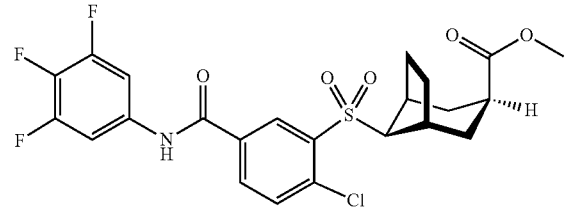 | 514.07, 516.06 |
| 244 | 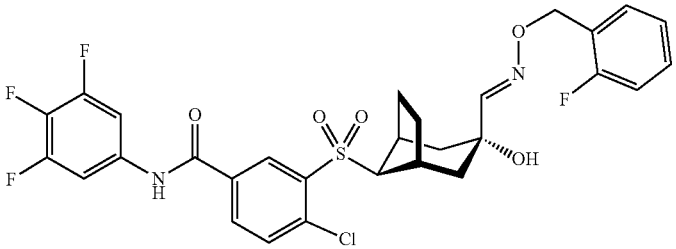 | 623.1, 625.0 |
| 248 | 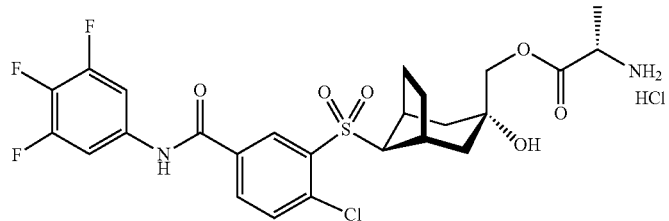 | 572.7, 574.8 |
| 254 | 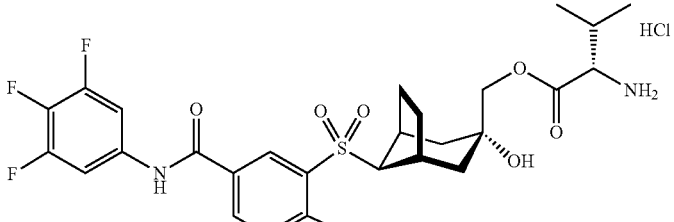 | 602.9, 605.0 |
| 258 | 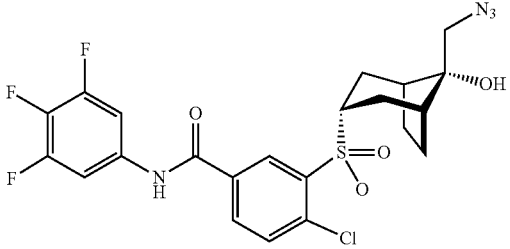 | 527.09, 529.09 |

-continued
| Example | Structure | ESIMS (M − H)⁻ or (M + H)⁺ |
|---|---|---|
| 261 | 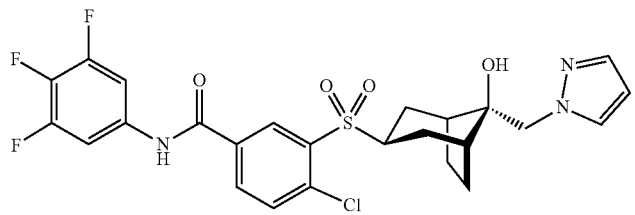 | 552.09, 554.09 |
| 264 | 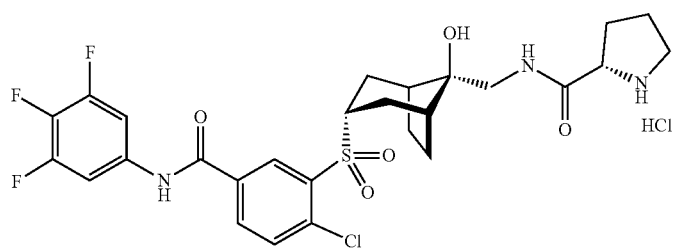 | 598.14, 600.14 |
| 265 | 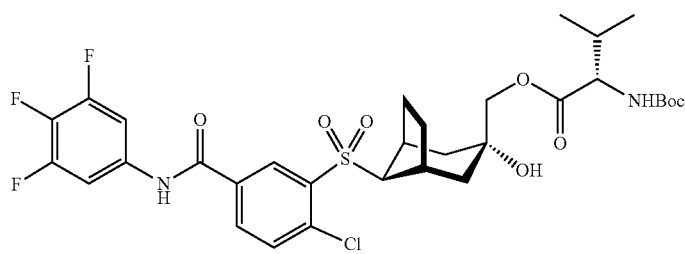 | 700.9, 702.9 |
| 272 | 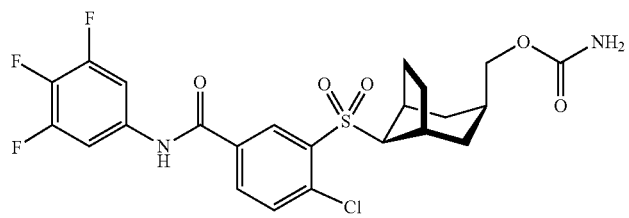 | 529.08, 531.08 |
| 273 | 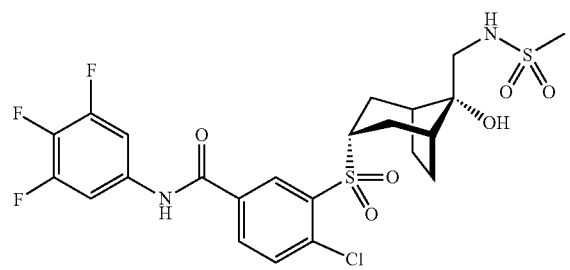 | 579.06, 581.06 |
| 274 | 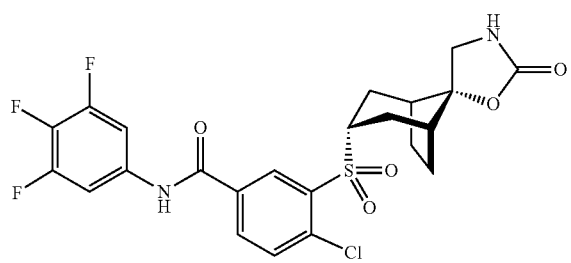 | 527.06, 529.06 |

-continued

| Example | Structure | ESIMS (M − H)⁻ or (M + H)⁺ |
|---|---|---|
| 278 | 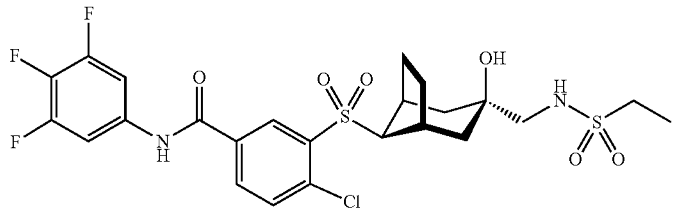 | 592.8, 594.8 |
| 279 | 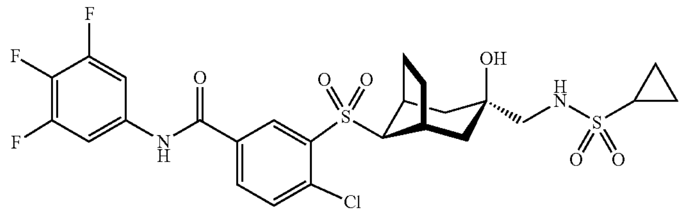 | 604.6, 606.6 |
| 280 | 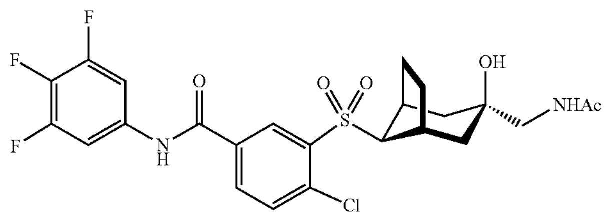 | 542.8, 544.7 |
| 285 | 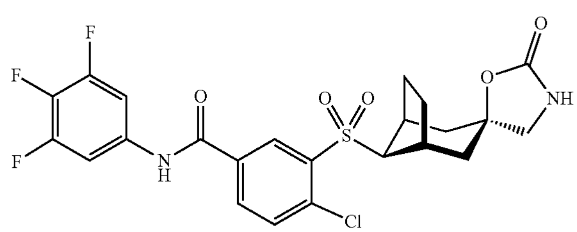 [SMILES: O=C1NC[C@]2(CC3CC[C@@H](C2)[C@H]3S(=O)(=O)c2cc(C(=O)Nc3cc(F)c(F)c(F)c3)ccc2Cl)O1] | 527.12, 529.12 |
| 288 | 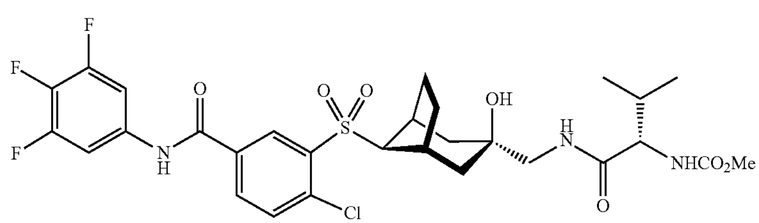 | 657.7, 659.8 |
| 294 | 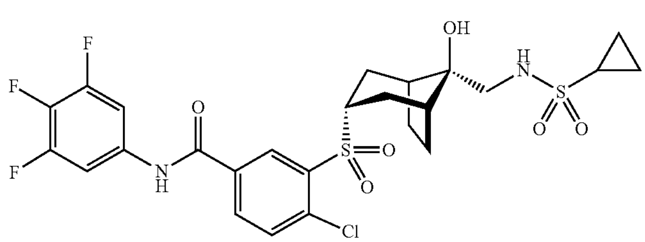 | 605.08, 607.08 |

-continued

| Example | Structure | ESIMS (M − H)⁻ or (M + H)⁺ |
|---|---|---|
| 295 | 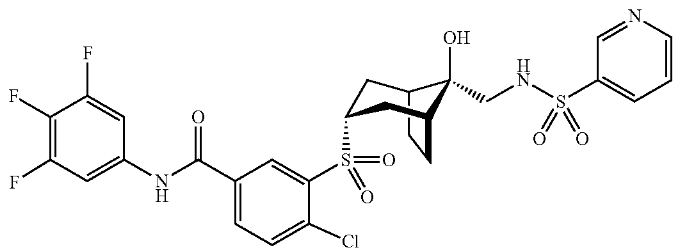 | 642.07, 644.07 |
| 296 | 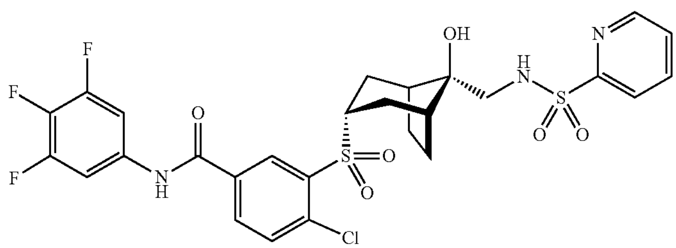 | 642.07, 644.07 |
| 298 | 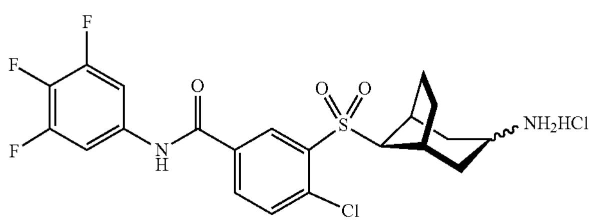 | 471.09, 473.08 |
| 299 | 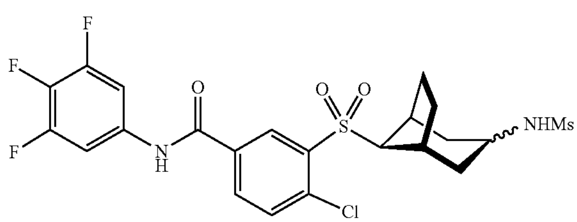 | 549.05, 551.05 |
| 300 | 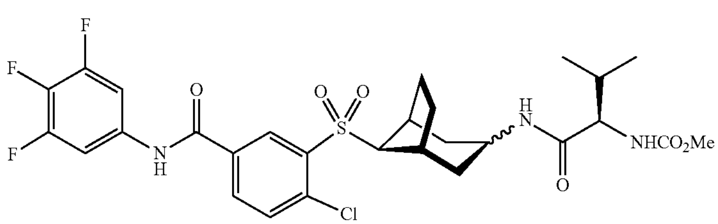 | 628.14, 630.15 |
| 304 | 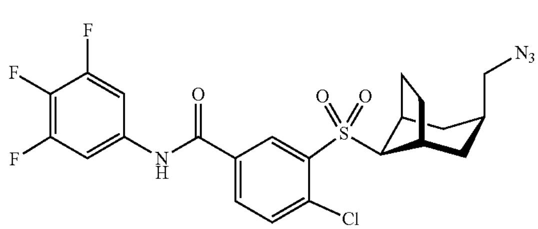 [SMILES: [N-]=[N+]=NC[C@@H]1CC2CC[C@@H](C1)[C@H]2S(=O)(=O)c1cc(C(=O)Nc2cc(F)c(F)c(F)c2)ccc1Cl] | 511.3, 513.3 |

-continued
| Example | Structure | ESIMS (M − H)⁻ or (M + H)⁺ |
|---|---|---|
| 305 | 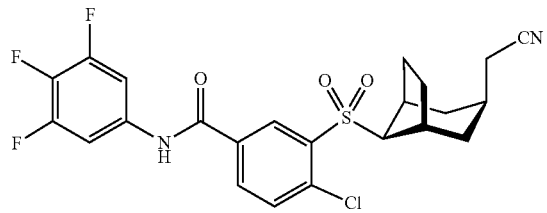 [SMILES: N#CC[C@@H]1CC2CC[C@@H](C1)[C@H]2S(=O)(=O)c1cc(C(=O)Nc2cc(F)c(F)c(F)c2)ccc1Cl] | 511.3, 513.3 |
| 306 | 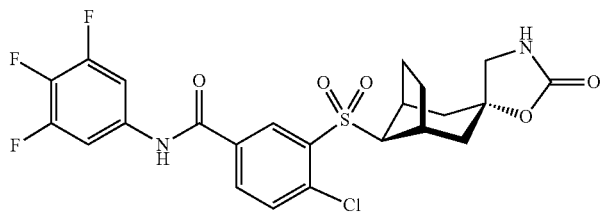 [SMILES: O=C1NC[C@@]2(CC3CC[C@@H](C2)[C@H]3S(=O)(=O)c2cc(C(=O)Nc3cc(F)c(F)c(F)c3)ccc2Cl)O1] | 527.12, 529.12 |
| 307 | 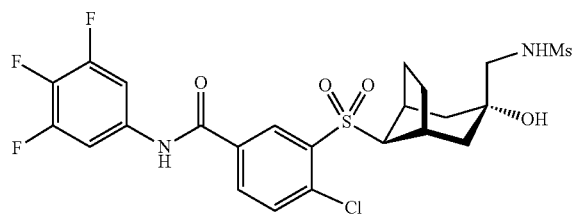 | 579.06, 581.06 |
| 310 | 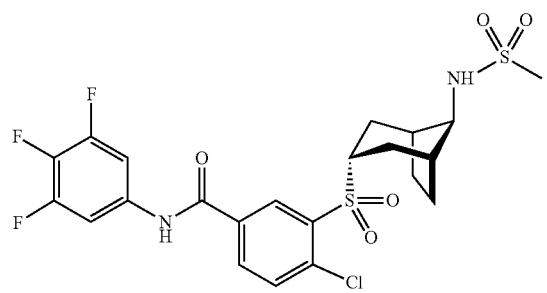 | 595.05, 597.05 |
| 311 | 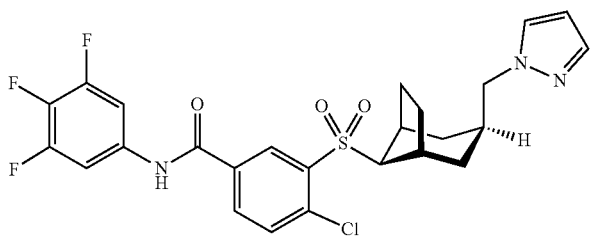 [SMILES: O=C(Nc1cc(F)c(F)c(F)c1)c1ccc(Cl)c(S(=O)(=O)[C@H]2C3CC[C@H]2C[C@H](Cn2cccn2)C3)c1] | 536.10, 538.10 |
| 312 | 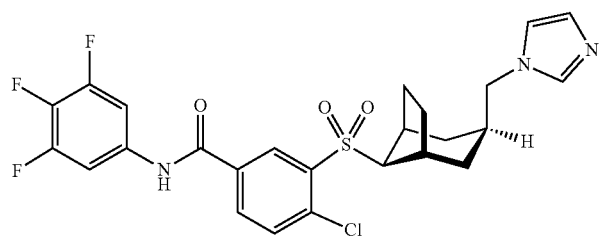 [SMILES: O=C(Nc1cc(F)c(F)c(F)c1)c1ccc(Cl)c(S(=O)(=O)[C@H]2C3CC[C@H]2C[C@H](Cn2ccnc2)C3)c1] | 536.10, 538.10 |

-continued

| Example | Structure | ESIMS (M − H)⁻ or (M + H)⁺ |
|---|---|---|
| 313 | 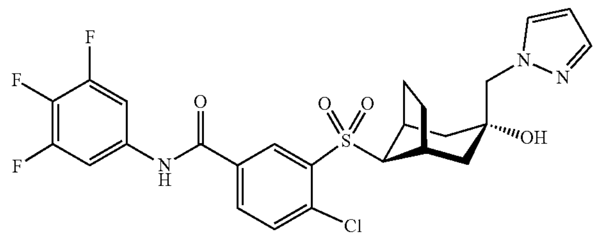 [SMILES: O=C(Nc1cc(F)c(F)c(F)c1)c1ccc(Cl)c(S(=O)(=O)[C@H]2C3CC[C@H]2C[C@](O)(Cn2cccn2)C3)c1] | 552.09, 554.09 |
| 314 | 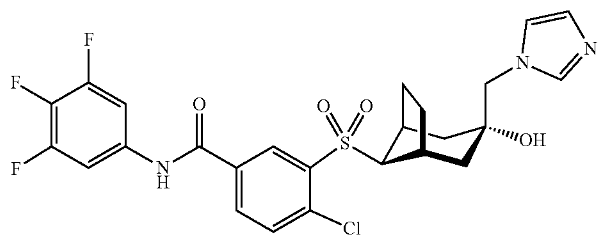 [SMILES: O=C(Nc1cc(F)c(F)c(F)c1)c1ccc(Cl)c(S(=O)(=O)[C@H]2C3CC[C@H]2C[C@](O)(Cn2ccnc2)C3)c1] | 552.09, 554.09 |
| 316 | 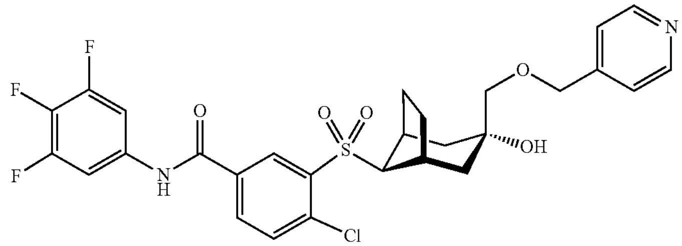 [SMILES: O=C(Nc1cc(F)c(F)c(F)c1)c1ccc(Cl)c(S(=O)(=O)[C@H]2C3CC[C@H]2C[C@](O)(COCc2ccncc2)C3)c1] | 593.11, 595.11 |
| 317 | 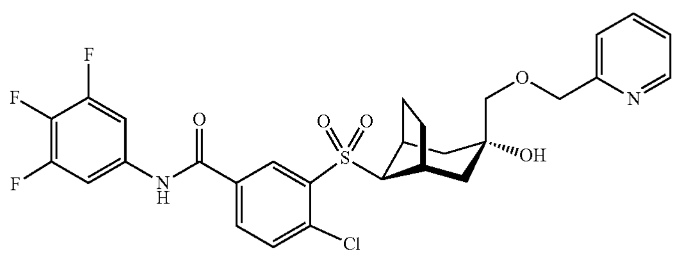 [SMILES: O=C(Nc1cc(F)c(F)c(F)c1)c1ccc(Cl)c(S(=O)(=O)[C@H]2C3CC[C@H]2C[C@](O)(COCc2ccccn2)C3)c1] | 593.11, 595.11 |
| 319 | 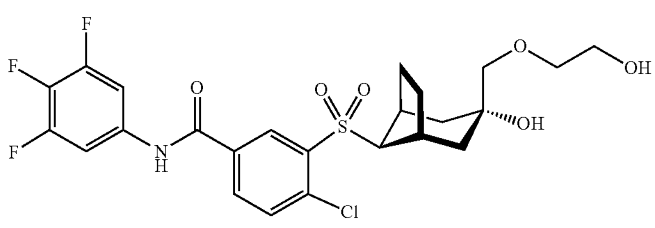 | 546.10, 548.10 |
| 320 | 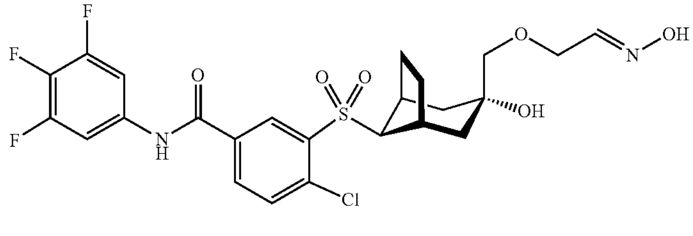 | 559.09, 651.09 |

-continued

| Example | Structure | ESIMS (M − H)⁻ or (M + H)⁺ |
|---------|-----------|----------------------------|
| 321 | 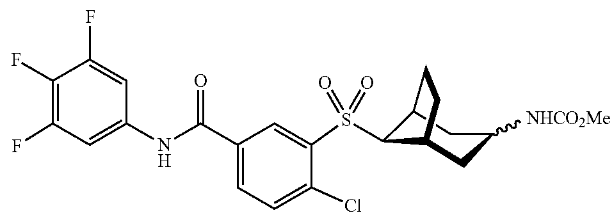 | 529.08, 531.09 |
| 322 | 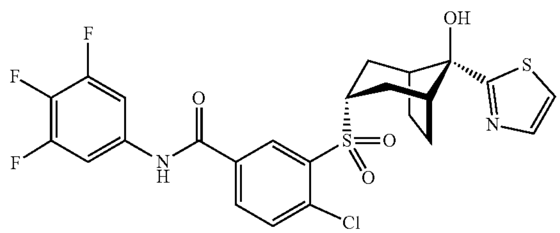 | 555.04, 557.04 |
| 323 | 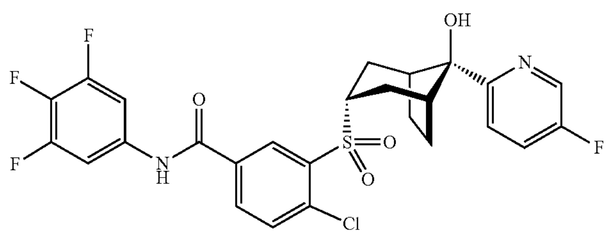 | 613.08, 615.08 [M + HCO₂H − H]− |
| 325 | 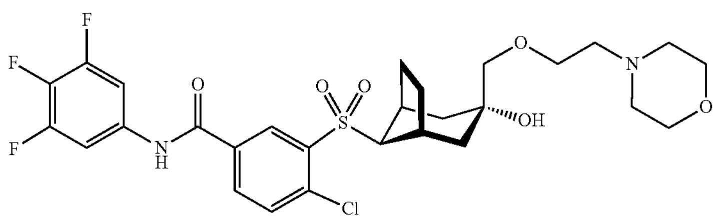 | 615.17, 617.17 |
| 327 | 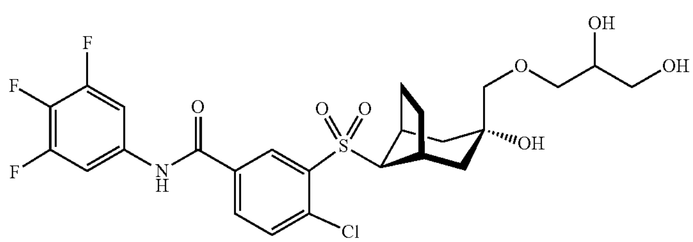 | 576.11, 578.11 |
| 328 | 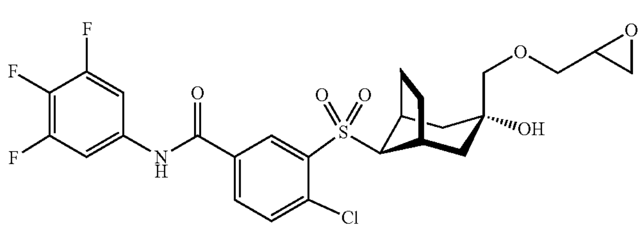 | 558.10, 560.10 |

| Example | Structure | ESIMS (M − H)⁻ or (M + H)⁺ |
|---------|-----------|----------------------------|
| 331 | 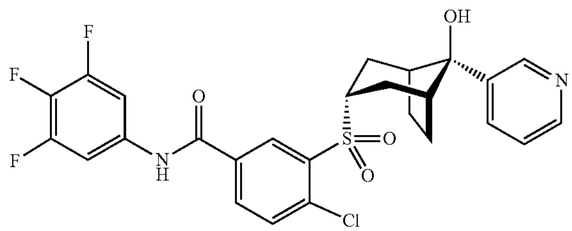 | 595.09, 597.09 |
| 332 | 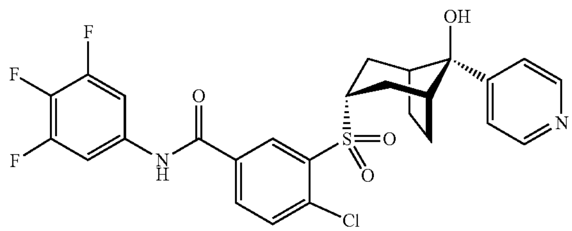 | 595.09, 597.09 |
| 337 | 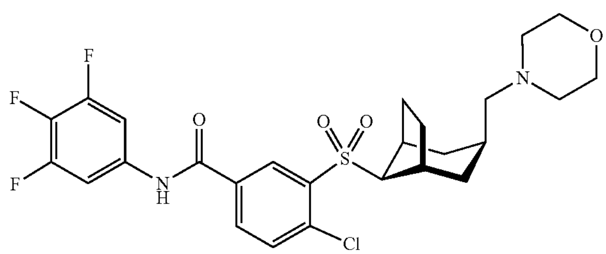 [SMILES: O=C(Nc1cc(F)c(F)c(F)c1)c1ccc(Cl)c(S(=O)(=O)[C@H]2C3CC[C@H]2C[C@H](CN2CCOCC2)C3)c1] | 555.13, 557.13 |
| 341 | 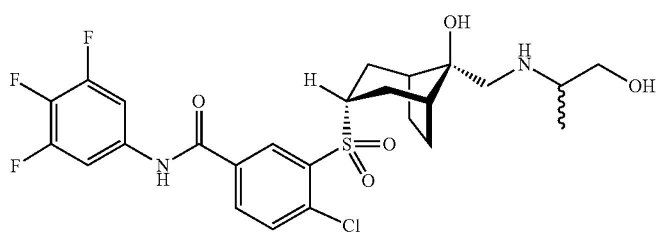 | 559.12, 561.12 |
| 342 | 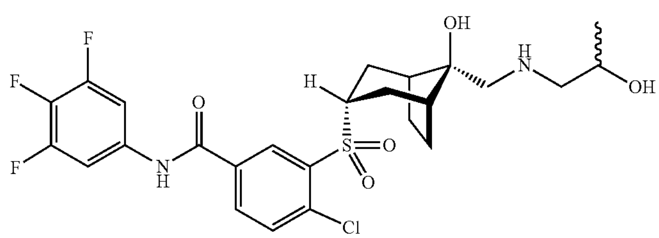 | 559.12, 561.12 |
| 343 | 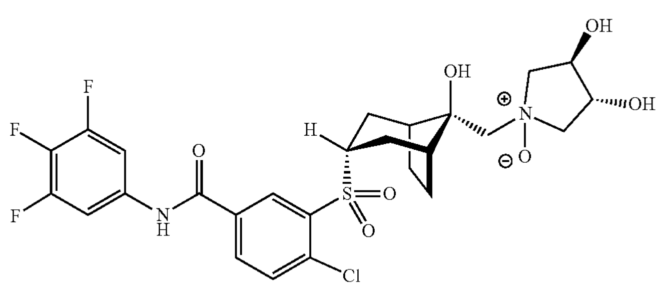 | 603.11, 605.11 |

-continued

| Example | Structure | ESIMS (M − H)⁻ or (M + H)⁺ |
|---|---|---|
| 349 | 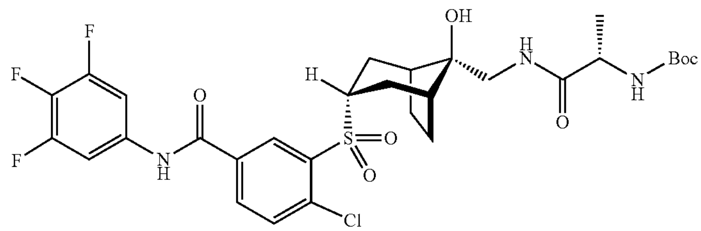 | 672.17, 674.17 |
| 351 | 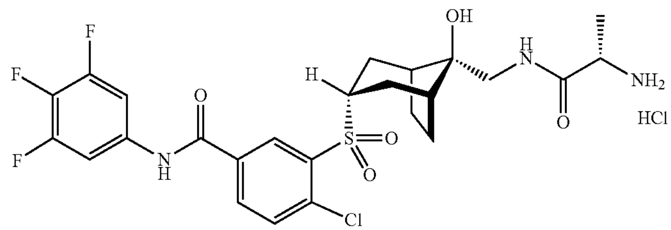 | 572.12, 574.12 |
| 353 | 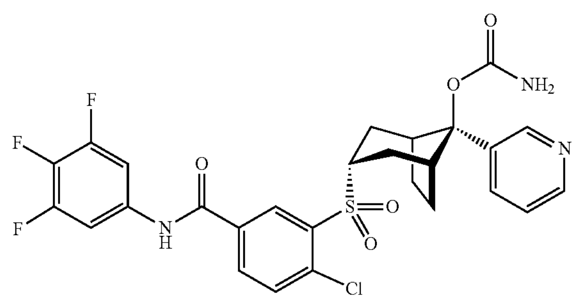 | 592.09, 594.09 |
| 354 | 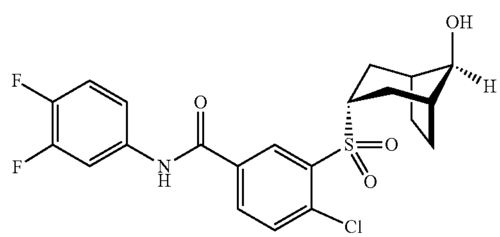 | 454.07, 456.07 |
| 358 | 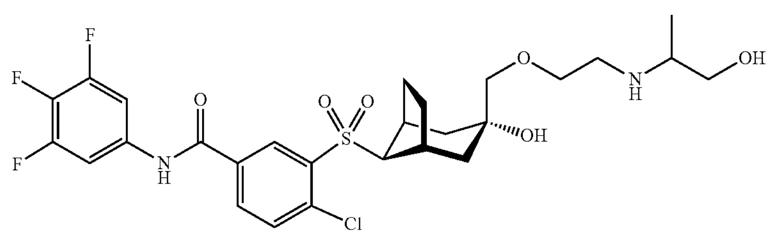 | 603.16, 605.16 |
| 362 | 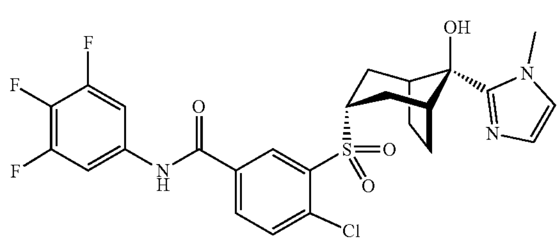 | 552.09, 554.09 |

-continued
| Example | Structure | ESIMS (M − H)⁻ or (M + H)⁺ |
|---|---|---|
| 364 | 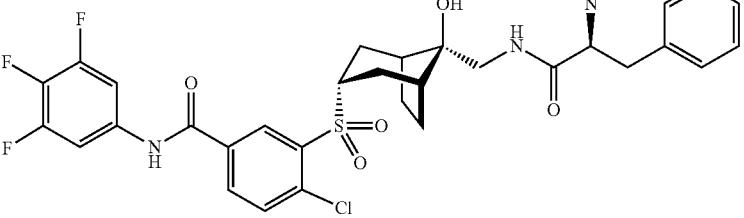 | 748.21, 750.21 |
| 365 | 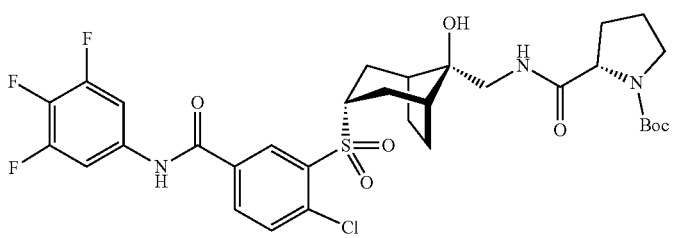 | 698.19, 700.19 |
| 366 | 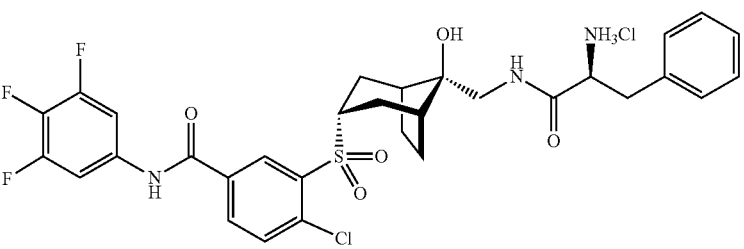 | 648.16, 650.16 |
| 367 | 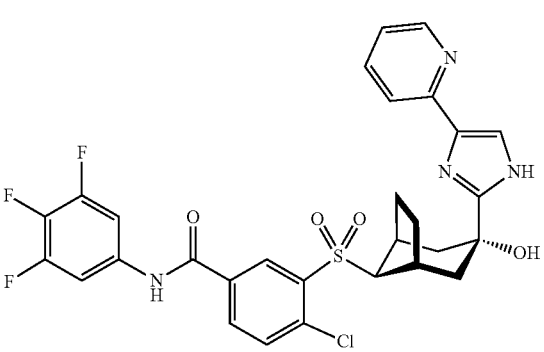 | 541.11, 543.11 |
| 368 | 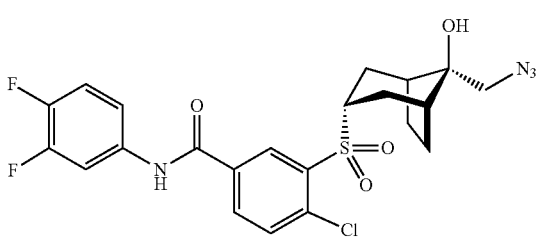 | 509.09, 511.08 |
| 369 | 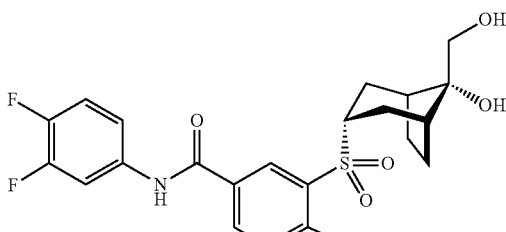 | 484.08, 486.08 |

-continued

| Example | Structure | ESIMS (M − H)⁻ or (M + H)⁺ |
|---|---|---|
| 370 | 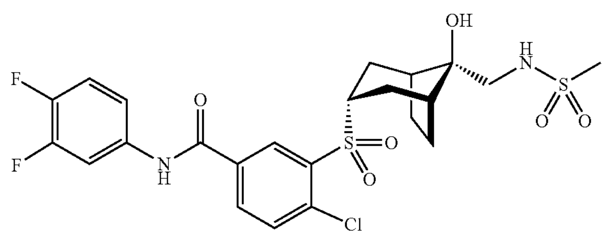 | 607.08, 609.08 [M − H + (CO₂H)]⁻ |
| 371 | 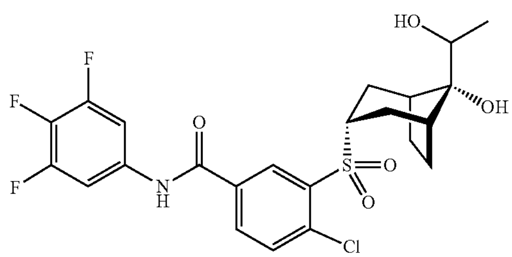 | 516.08, 518.08 |
| 372 | 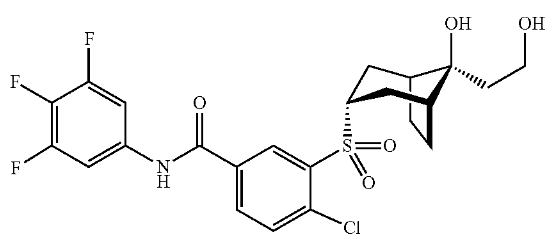 | 516.08, 518.08 |
| 373 | 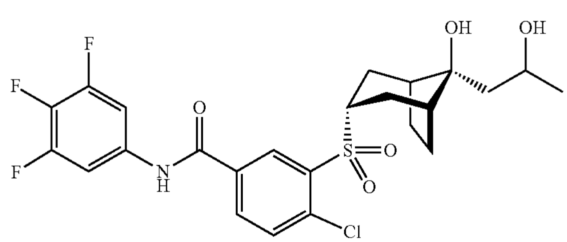 | 530.10, 532.10 |
| 374 | 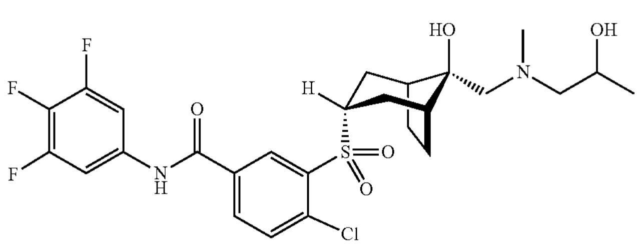 | 573.14, 575.14 |
| 375 | 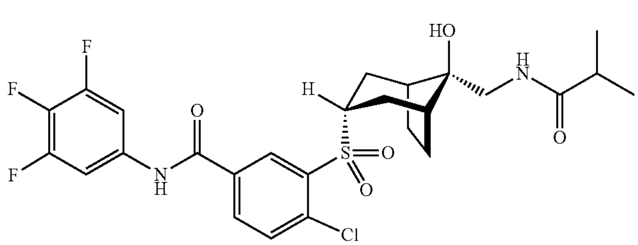 | 571.12, 573.12 |

| Example | Structure | ESIMS (M − H)⁻ or (M + H)⁺ |
|---|---|---|
| 376 | 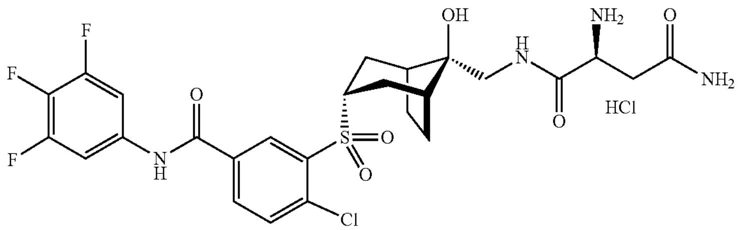 | 615.12, 617.12 |
| 377 | 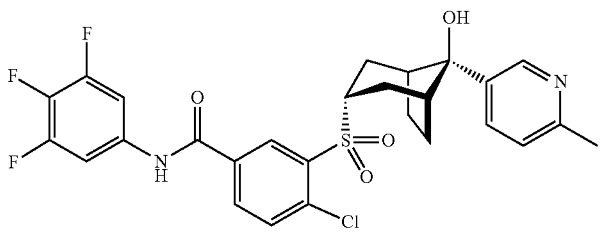 | 609.11, 611.11 (M + HCO$_2$H − H)⁻ |
| 378 | 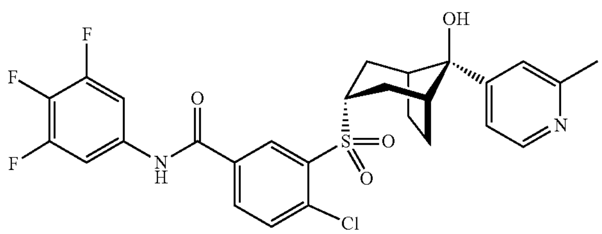 | 609.11, 611.11 (M + HCO$_2$H − H)⁻ |
The following example are prepared using procedures similar to those describe above:
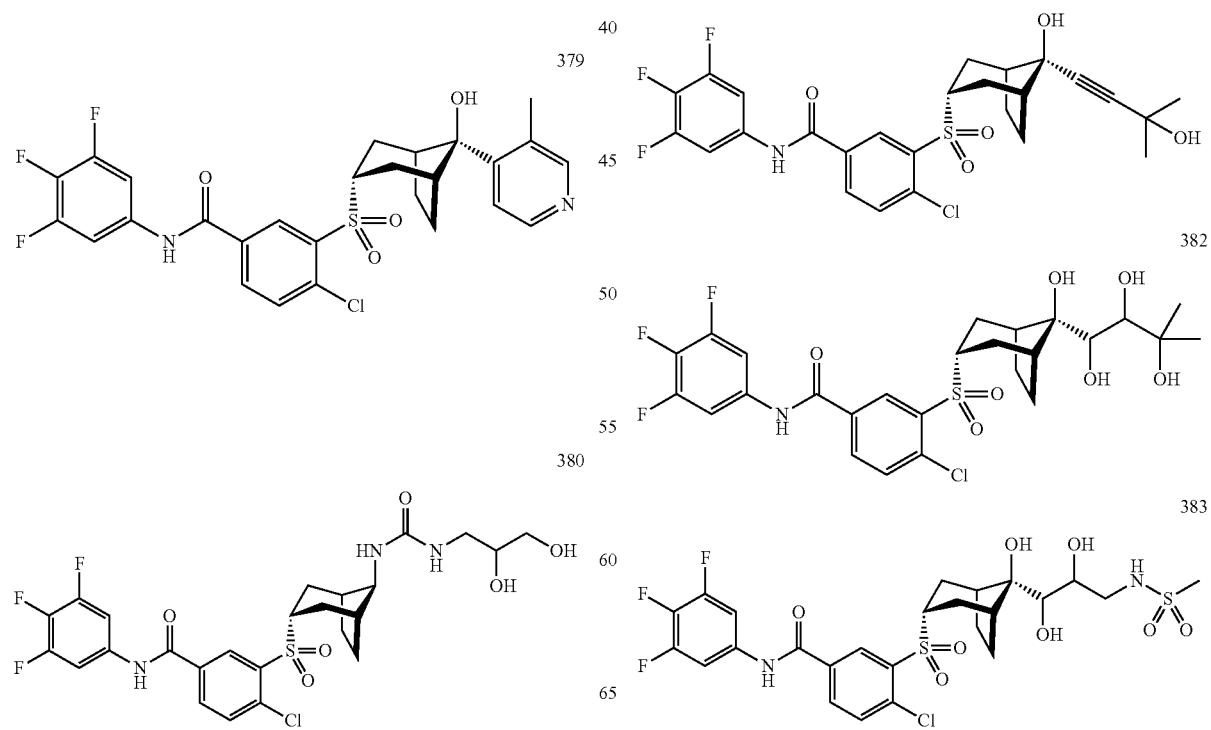

384
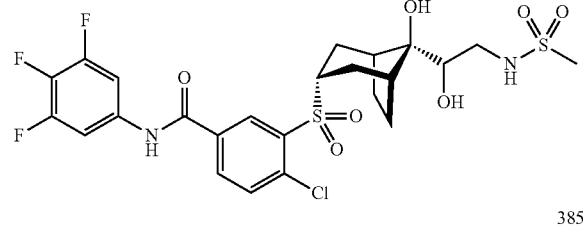
385
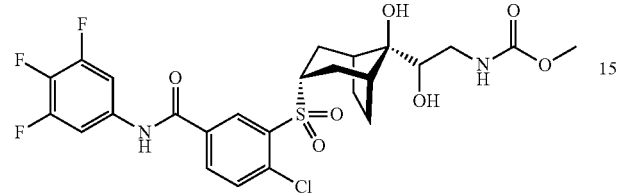
386
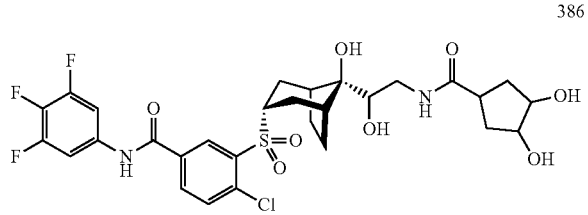
387
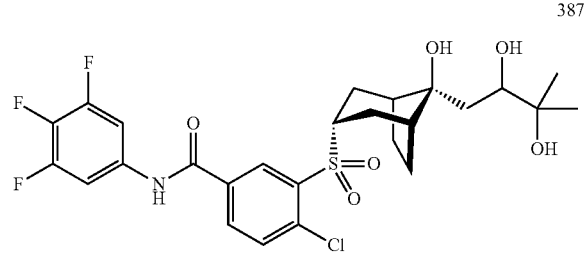
388
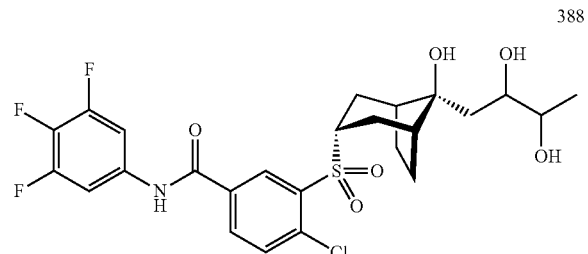
389
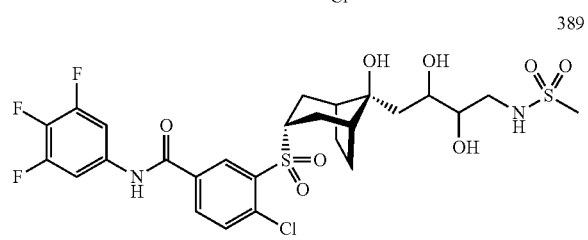
390
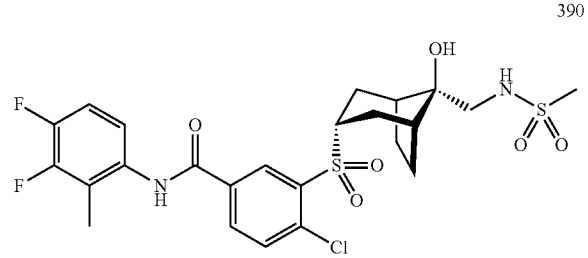
391
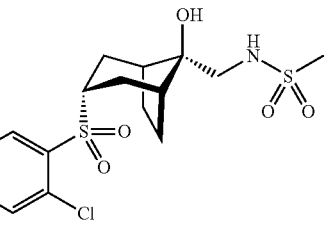
392
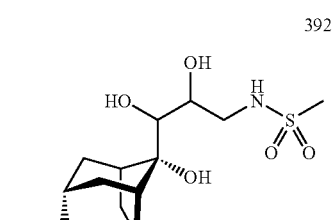
393
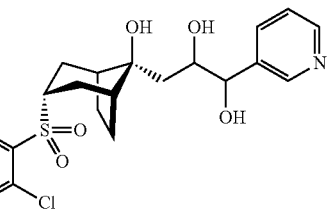
394
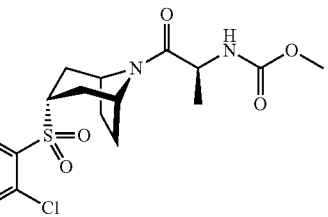
395
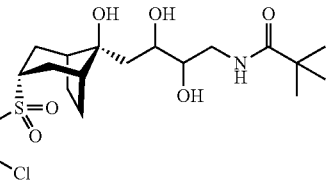
396

197
-continued
397
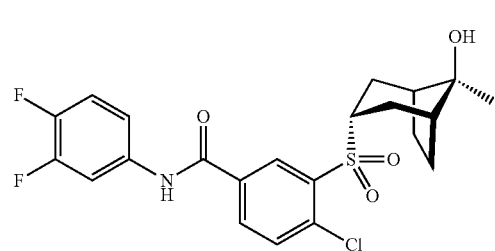
398
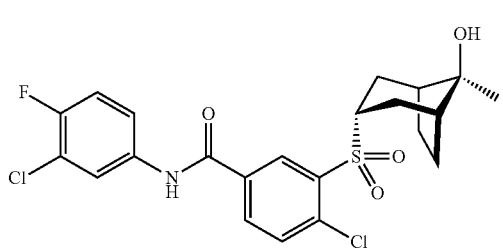
399
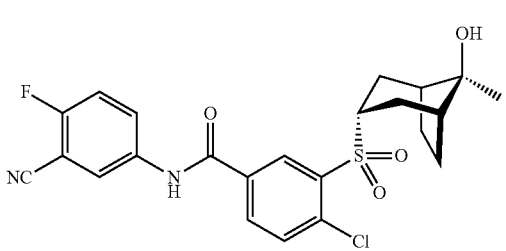
400
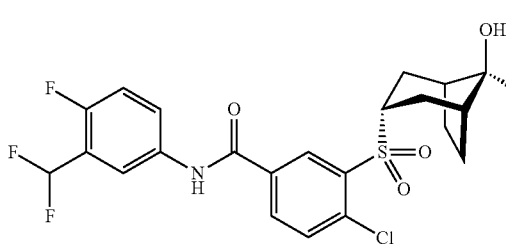
401
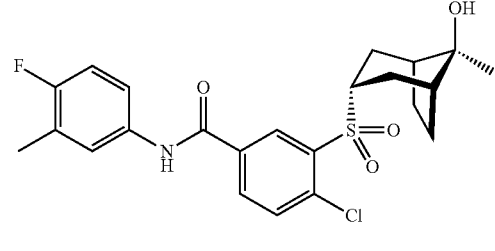
402
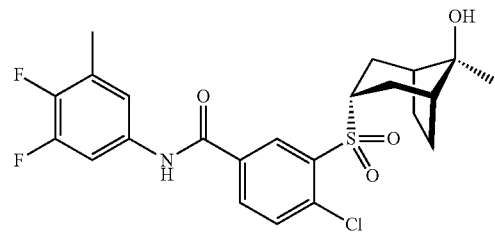
198
-continued
403
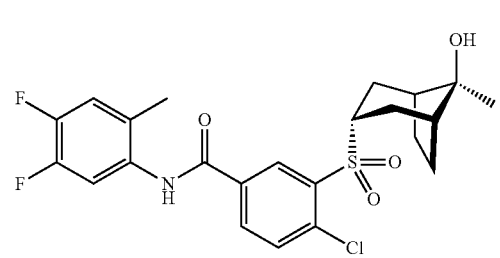
404
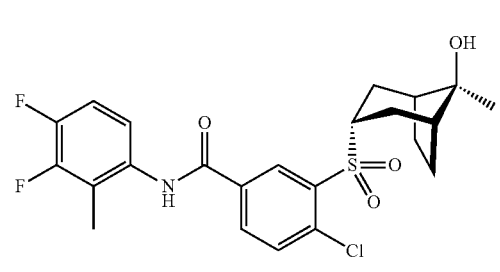
405
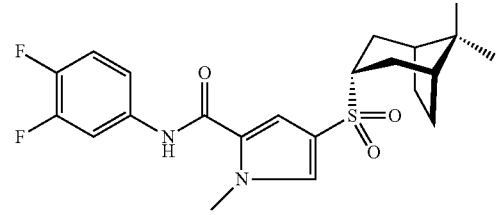
406
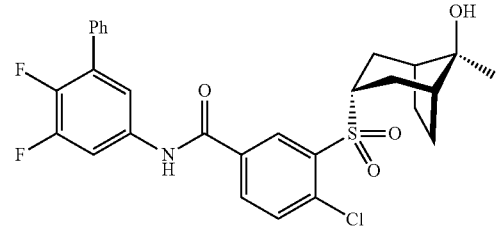
407
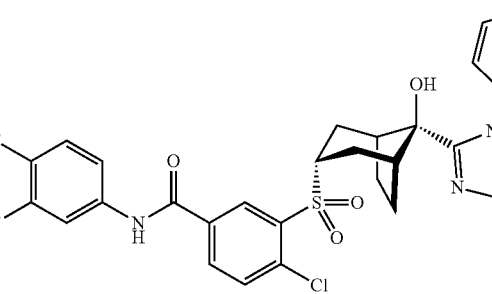
408
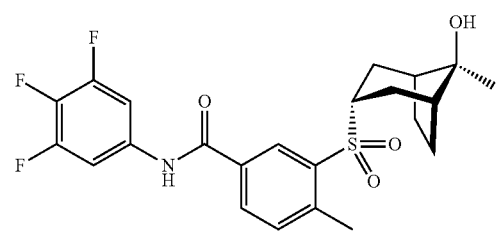

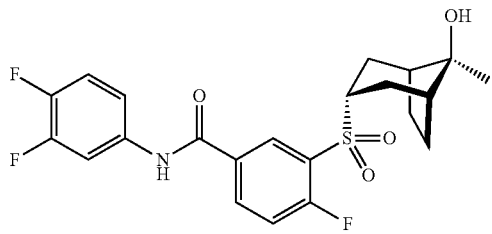

409

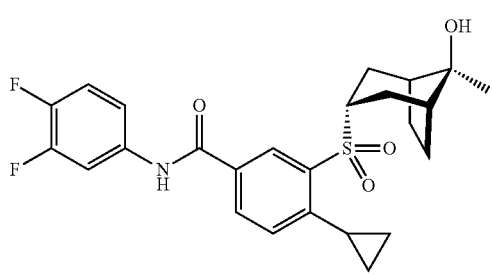

410

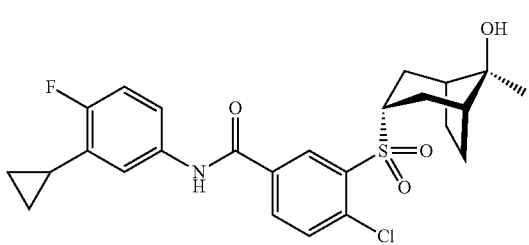

411

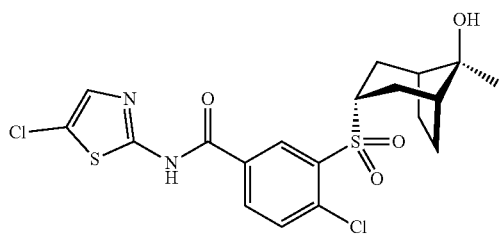

412

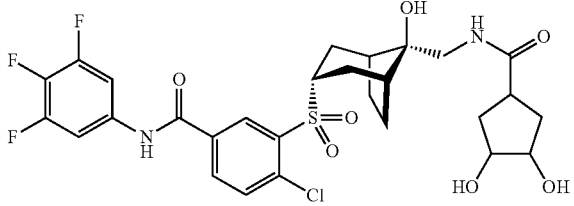

413

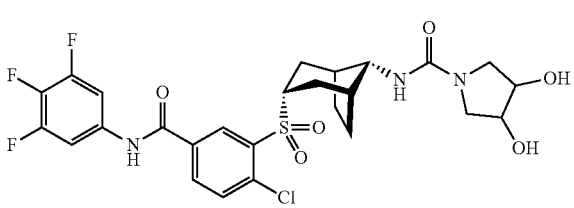

414

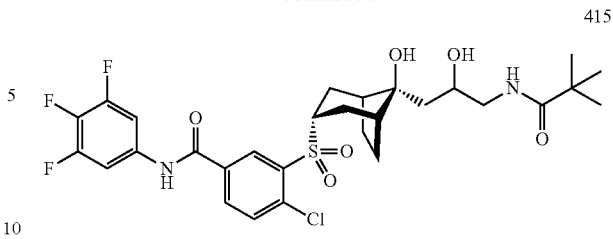

415

Biological Activity

Methods: HepAD38 cells are maintained as previously reported (Ladner et al, *Antimicrob. Agents Chemother.* 1997, 4, 1715). Briefly, cells are passaged upon attaining confluency in DMEM/F12 media in the presence of 10% FBS, Penn/Strep, 250 µg/mL G418, and 1 ug/ml tetracycline. Novel compounds are screened by first washing cells three times with PBS to remove tetracycline, and plating in 96 well plates at 35,000 cells/well. Compounds dissolved in DMSO are then diluted 1:200 into wells containing cells. Five days after compound addition, material is harvested for analysis. For an extended 8 day analysis, cells are plated and treated as described above, but media and compound are refreshed on d2 and d5 post initial treatment.

On harvest day, virion DNA is obtained by lysing with Sidestep Lysis and Stabilization Buffer and then quantified via quantitative real time PCR. Commercially available ELISA kits are used to quantitate the viral proteins HBsAg (Alpco) or HbeAg (US Biological) by following the manufacturer's recommended protocol after diluting samples to match the linear range of their respective assays. Irrespective of readout, compound concentrations that reduce viral product accumulation in the cell lysates or supernatants by 500 relative to no drug controls ($EC_{50}$) are reported; $EC_{50}$ ranges are as follows: A 0.1 µM; B 0.1-0.4 µM; C>0.4 µM.

Compound toxicity is evaluated by seeding cells at 15,000 cells/well and treating with compound as described above. Three days after compound addition, cells are treated with ATPLite reagent and compound concentrations that reduce total ATP levels in wells by 50% relative to no drug controls ($CC_{50}$) are reported; $CC_{50}$ ranges are as follows: A>25 µM; B 10-25 µM; C<10 µM.

TABLE 1

Summary of Activities

| Compd. Number | HepAD38 $EC_{50}$ (µM) | Compd. Number | HepAD38 $EC_{50}$ (µM) |
|---|---|---|---|
| 1 | B | 2 | B |
| 3 | B | 4 | B |
| 5 | B | 6 | B |
| 7 | C | 8 | B |
| 9 | B | 10 | B |
| 11 | C | 12 | B |
| 13 | C | 14 | C |
| 15 | B | 16 | B |
| 17 | B | 18 | B |
| 19 | C | 20 | B |
| 21 | B | 22 | B |
| 23 | B | 24 | C |
| 25 | C | 26 | C |
| 27 | C | 28 | C |
| 29 | C | 30 | C |
| 31 | B | 32 | C |
| 33 | C | 34 | C |
| 35 | C | 36 | C |
| 37 | C | 38 | C |
| 39 | C | 40 | C |

TABLE 1-continued

Summary of Activities

| Compd. Number | HepAD38 EC$_{50}$ (μM) | Compd. Number | HepAD38 EC$_{50}$ (μM) |
|---|---|---|---|
| 41 | C | 42 | C |
| 43 | C | 44 | B |
| 45 | B | 46 | B |
| 47 | C | 48 | C |
| 49 | B | 50 | C |
| 51 | B | 52 | B |
| 53 | C | 54 | B |
| 55 | C | 56 | C |
| 57 | C | 58 | C |
| 59 | A | 60 | A |
| 61 | C | 62 | C |
| 63 | C | 64 | C |
| 65 | C | 66 | C |
| 67 | C | 68 | B |
| 69 | B | 70 | B |
| 71 | C | 72 | C |
| 73 | C | 74 | C |
| 75 | B | 76 | B |
| 77 | C | 78 | C |
| 79 | C | 80 | A |
| 81 | C | 82 | C |
| 83 | B | 84 | A |
| 85 | B | 86 | C |
| 87 | B | 88 | C |
| 89 | B | 90 | C |
| 91 | C | 92 | C |
| 93 | C | 94 | C |
| 95 | C | 96 | C |
| 97 | C | 98 | C |
| 99 | C | 100 | C |
| 101 | C | 102 | B |
| 103 | C | 104 | B |
| 105 | B | 106 | A |
| 107 | C | 108 | C |
| 109 | B | 110 | B |
| 111 | A | 112 | A |
| 113 | B | 114 | B |
| 115 | B | 116 | C |
| 117 | B | 118 | B |
| 119 | C | 120 | A |
| 121 | C | 122 | B |
| 123 | B | 124 | B |
| 125 | B | 126 | B |
| 127 | A | 128 | B |
| 129 | A | 130 | A |
| 131 | C | 132 | A |
| 133 | B | 134 | B |
| 135 | B | 136 | A |
| 137 | B | 138 | C |
| 139 | A | 140 | B |
| 141 | B | 142 | A |
| 143 | C | 144 | C |
| 145 | B | 146 | A |
| 147 | C | 148 | C |
| 149 | A | 150 | A |
| 151 | A | 152 | A |
| 153 | C | 154 | A |
| 155 | A | 156 | A |
| 157 | A | 158 | A |
| 159 | A | 160 | B |
| 161 | A | 162 | A |
| 163 | B | 164 | A |
| 165 | C | 166 | B |
| 167 | B | 168 | C |
| 169 | A | 170 | C |
| 171 | A | 172 | B |
| 173 | A | 174 | C |
| 175 | C | 176 | C |
| 177 | A | 178 | A |
| 179 | A | 180 | A |
| 181 | A | 182 | B |
| 183 | B | 184 | C |
| 185 | A | 186 | B |
| 187 | A | 188 | A |
| 189 | B | 190 | C |
| 191 | C | 192 | B |
| 193 | B | 194 | A |
| 195 | C | 196 | A |
| 197 | B | 198 | A |
| 199 | B | 200 | B |
| 201 | A | 202 | A |
| 203 | A | 204 | A |
| 205 | A | 206 | C |
| 207 | C | 208 | C |
| 209 | C | 210 | C |
| 211 | C | 212 | C |
| 213 | C | 214 | B |
| 215 | C | 216 | C |
| 217 | C | 218 | C |
| 219 | A | 220 | A |
| 221 | B | 222 | C |
| 223 | A | 224 | B |
| 225 | C | 226 | B |
| 227 | C | 228 | C |
| 229 | A | 230 | B |
| 231 | B | 232 | A |
| 233 | A | 234 | B |
| 235 | B | 236 | B |
| 237 | B | 238 | B |
| 239 | A | 240 | B |
| 241 | A | 242 | B |
| 243 | A | 244 | A |
| 245 | B | 246 | B |
| 247 | A | 248 | A |
| 249 | B | 250 | C |
| 251 | C | 252 | A |
| 253 | A | 254 | A |
| 255 | C | 256 | A |
| 257 | A | 258 | A |
| 259 | A | 260 | A |
| 261 | C | 262 | A |
| 263 | A | 264 | A |
| 265 | B | 266 | B |
| 267 | A | 268 | B |
| 269 | A | 270 | A |
| 271 | A | 272 | A |
| 273 | A | 274 | A |
| 275 | A | 276 | C |
| 277 | B | 278 | B |
| 279 | B | 280 | B |
| 281 | A | 282 | A |
| 283 | B | 284 | A |
| 285 | B | 286 | A |
| 287 | B | 288 | B |
| 289 | B | 290 | A |
| 291 | A | 292 | A |
| 293 | A | 294 | A |
| 295 | A | 296 | A |
| 297 | A | 298 | B |
| 299 | A | 300 | A |
| 301 | C | 302 | A |
| 303 | A | 304 | B |
| 305 | A | 306 | A |
| 307 | A | 308 | A |
| 309 | A | 310 | A |
| 311 | A | 312 | A |
| 313 | A | 314 | A |
| 315 | A | 316 | B |
| 317 | A | 318 | A |
| 319 | A | 320 | A |
| 321 | A | 322 | A |
| 323 | A | 324 | A |
| 325 | A | 326 | C |
| 327 | B | 328 | A |
| 329 | A | 330 | A |
| 331 | A | 332 | A |
| 333 | C | 334 | A |
| 335 | A | 336 | A |
| 337 | B | 338 | C |
| 339 | C | 340 | C |

TABLE 1-continued

Summary of Activities

| Compd. Number | HepAD38 EC$_{50}$ (μM) | Compd. Number | HepAD38 EC$_{50}$ (μM) |
|---|---|---|---|
| 341 | B | 342 | A |
| 343 | B | 344 | C |
| 345 | A | 346 | A |
| 347 | B | 348 | A |
| 349 | A | 350 | B |
| 351 | B | 352 | A |
| 353 | A | 354 | B |
| 355 | C | 356 | B |
| 357 | B | 358 | B |
| 359 | A | 360 | A |
| 361 | A | 362 | A |
| 363 | A | 364 | A |
| 365 | A | 366 | B |

TABLE 2

Summary of Cytotoxicity

| Compd. Number | ATPlite CC$_{50}$ (μM) | Compd. Number | ATPlite CC$_{50}$ (μM) |
|---|---|---|---|
| 3 | A | 4 | A |
| 7 | A | 8 | B |
| 9 | B | 16 | A |
| 17 | A | 45 | A |
| 46 | A | 48 | A |
| 60 | A | 80 | B |
| 84 | A | 150 | B |
| 154 | C | 188 | >12.5 |
| 220 | C | 246 | B |
| 252 | >6.25 | 253 | A |
| 256 | >12.5 | 257 | A |
| 258 | >12.5 | 259 | >12.5 |
| 260 | A | 267 | A |
| 271 | >12.5 | 272 | >12.5 |
| 273 | >12.5 | 274 | A |
| 275 | A | 276 | A |
| 277 | C | 278 | A |
| 279 | A | 280 | A |
| 281 | A | 282 | A |
| 283 | C | 284 | >3.125 |
| 285 | A | 286 | B |
| 287 | A | 288 | B |
| 289 | >12.5 | 290 | A |
| 291 | B | 292 | B |
| 293 | >6.25 | 294 | >6.25 |
| 295 | >12.5 | 296 | >6.25 |
| 297 | >6.25 | 298 | B |
| 299 | A | 300 | >6.25 |
| 301 | B | 302 | B |
| 303 | C | 304 | >6.25 |
| 305 | >3.125 | 306 | >12.5 |
| 307 | A | 308 | A |
| 309 | A | 310 | A |
| 312 | B | 313 | >6.25 |
| 317 | C | 319 | A |
| 321 | A | 322 | B |
| 324 | >12.5 | 329 | >6.25 |
| 330 | C | 331 | B |
| 332 | B | | |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

X-A-Y-L-R      (I)

or a pharmaceutically acceptable salt thereof, wherein:

X is phenyl substituted with one or more substituents independently selected from fluoro, chloro, bromo, difluoromethyl, trifluoromethyl, CN and cyclopropyl;

Y is

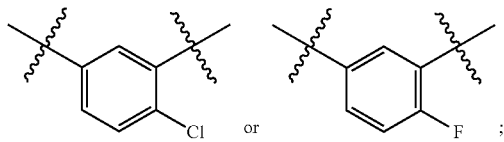 [SMILES: *c1ccc(Cl)c(*)c1 ; *c1ccc(F)c(*)c1]

A is —NHC(O)—;
L is S(O)$_2$; and
R is selected from the group consisting of

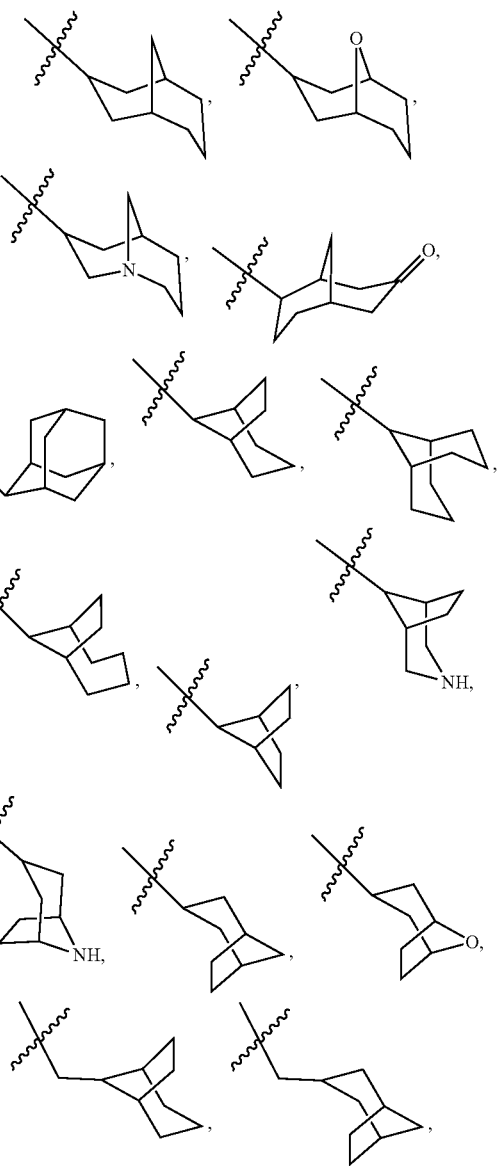

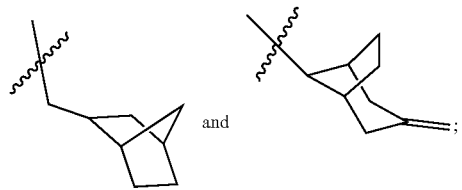
each of which is optionally substituted.
2. The compound of claim 1, wherein X is selected from the group consisting of
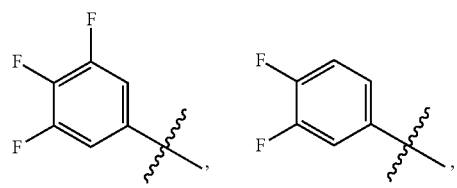
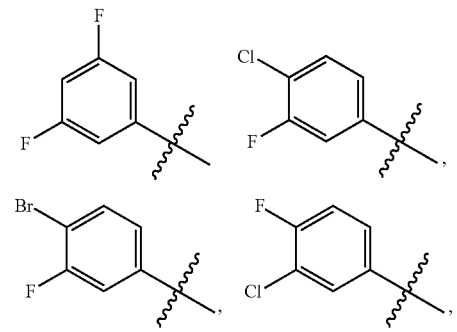
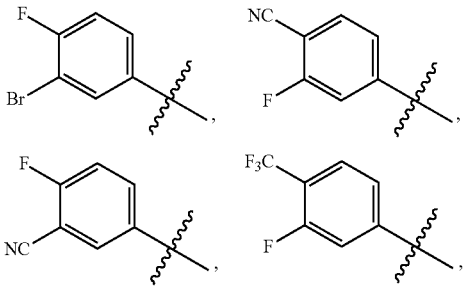
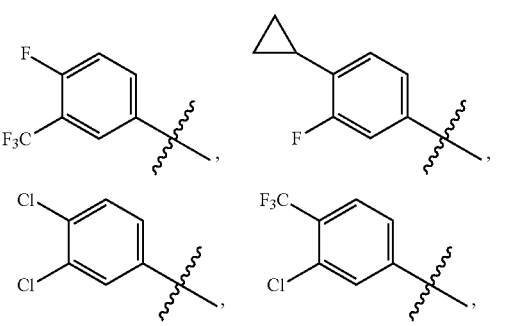
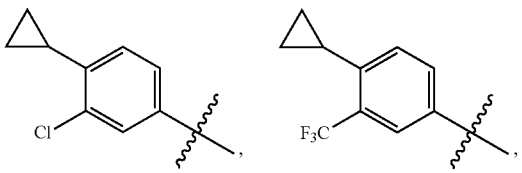
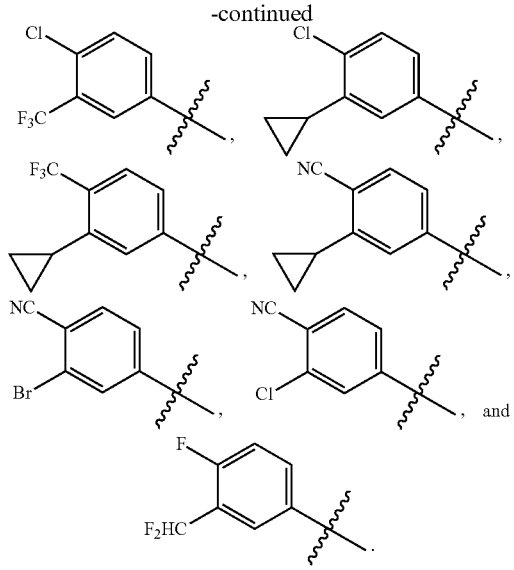
3. The compound of claim 2 wherein X is
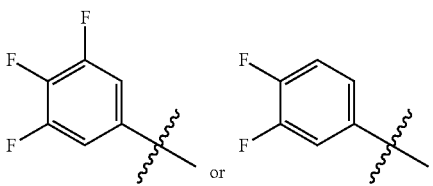
4. The compound of claim 1 wherein R is
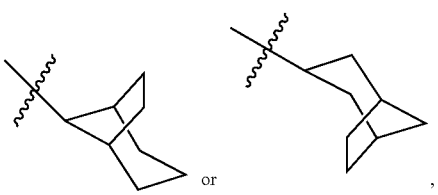
each of which is optionally substituted.
5. The compound of claim 1 wherein X is
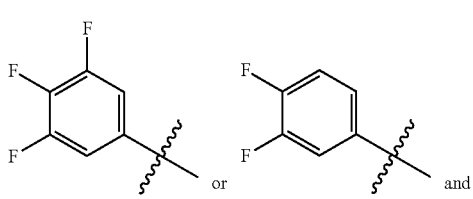
R is
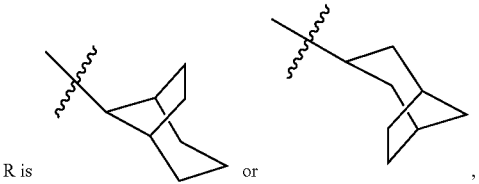
each of which is optionally substituted.

6. A pharmaceutical composition comprising a compound according to claim 1 and a pharmaceutically acceptable carrier or excipient.

7. A method of treating or preventing an HBV infection in a subject in need thereof, comprising administering to the subject a therapeutically effective amount of a compound or a combination of compounds according to claim 1.

8. The method of claim 7, further comprising administering to the subject at least one additional therapeutic agent selected from the group consisting of HBV polymerase inhibitors, interferon, viral entry inhibitors, viral maturation inhibitors, capsid assembly, core protein inhibitors, core protein modulators, reverse transcriptase inhibitors, TLR-agonists, inducers of cellular viral RNA sensor, therapeutic vaccines, RNA interference (RNAi), small interfering RNA (siRNA) and combinations thereof.

9. The method of claim 8, wherein the compound and the at least one additional therapeutic agent are co-formulated.

10. The method of claim 8, wherein the at least one additional therapeutic agent is administered at a lower dose and/or frequency than that which is therapeutically effective when said agent is administered alone.

\* \* \* \* \*